United States Patent

Yasuma et al.

(10) Patent No.: US 8,729,102 B2
(45) Date of Patent: May 20, 2014

(54) BICYCLIC COMPOUND

(75) Inventors: Tsuneo Yasuma, Osaka (JP); Tohru Yamashita, Kanagawa (JP); Takuya Fujimoto, Kanagawa (JP); Zenichi Ikeda, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 51 days.

(21) Appl. No.: 13/306,069

(22) Filed: Nov. 29, 2011

(65) Prior Publication Data

US 2012/0142714 A1 Jun. 7, 2012

(30) Foreign Application Priority Data

Nov. 30, 2010 (JP) ................. 2010/266097
Aug. 10, 2011 (JP) ................. 2011/175330

(51) Int. Cl.
*A61K 31/4439* (2006.01)
*C07D 413/04* (2006.01)

(52) U.S. Cl.
USPC ...................... 514/338; 546/271.7

(58) Field of Classification Search
USPC ...................... 546/271.7; 514/338
See application file for complete search history.

(56) References Cited

U.S. PATENT DOCUMENTS

| | | |
|---|---|---|
| 2006/0258722 A1 | 11/2006 | Yasuma et al. |
| 2007/0149608 A1 | 6/2007 | Yasuma et al. |
| 2009/0012093 A1 | 1/2009 | Fukatsu et al. |
| 2010/0004312 A1 | 1/2010 | Yasuma et al. |
| 2010/0144806 A1 | 6/2010 | Yasuma et al. |
| 2010/0197761 A1 | 8/2010 | Yasuma et al. |
| 2012/0046338 A1 | 2/2012 | Yasuma et al. |
| 2013/0267589 A1 | 10/2013 | Yasuma et al. |

FOREIGN PATENT DOCUMENTS

| | | |
|---|---|---|
| EP | 2 351 743 | 8/2011 |
| WO | 2004/106276 | 12/2004 |
| WO | 2005/063729 | 7/2005 |
| WO | 2007/013689 | 2/2007 |
| WO | 2008/001931 | 1/2008 |
| WO | 2010/050445 | 5/2010 |
| WO | 2011/136385 | 11/2011 |
| WO | 2012/108478 | 8/2012 |

OTHER PUBLICATIONS

Dorwald, Side Reactions in Organic Synthesis, 2005, Wiley: VCH Weinheim Preface, pp. 1-15 & Chapter 8, pp. 279-308.*
International Search Report issued Feb. 23, 2012 along with the Written Opinion in International (PCT) Application No. PCT/JP2011/078010.
J. W. Corbett et al., "Inhibitors of Mammalian Acetyl-CoA Carboxylase", Recent Patents on Cardiovascular Drug Discovery, vol. 2, No. 3, pp. 162-180, Nov. 1, 2007.
J. Konda et al., "6-Methoxy-2-(4-substituted phenyl)benzoxazoles as Fluorescent Chiral Derivatization Reagents for Carboxylic Acid Enantiomers", Analytical Sciences, vol. 10, Feb. 1994.
Costa Rican Opposition issued Oct. 9, 2013 in corresponding Costa Rican Application No. 2013-0281.

* cited by examiner

*Primary Examiner* — Patricia L Morris
(74) *Attorney, Agent, or Firm* — Wenderoth, Lind & Ponack, L.L.P.

(57) ABSTRACT

The present invention provides a compound having an ACC inhibitory action, which is useful as an agent for the prophylaxis or treatment of obesity, diabetes and the like, and having superior efficacy.

The present invention relates to a compound represented by the formula (I):

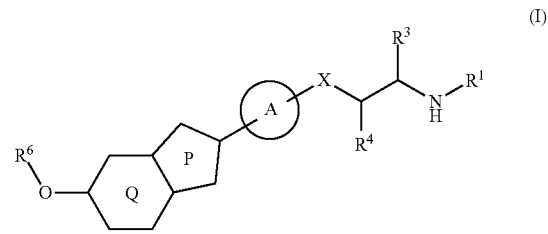

wherein each symbol is as defined in the specification, or a salt thereof.

5 Claims, No Drawings

BICYCLIC COMPOUND

TECHNICAL FIELD

The present invention relates to a bicyclic compound having an acetyl-CoA carboxylase (in the present specification, sometimes to be abbreviated as ACC) inhibitory action, which is useful for the prophylaxis or treatment of obesity, diabetes, hypertension, hyperlipidemia, cardiac failure, diabetic complications, metabolic syndrome, sarcopenia, cancer and the like.

BACKGROUND OF THE INVENTION

ACC is an enzyme that converts acetyl-CoA to malonyl-CoA, and catalyzes a rate determining reaction in fatty acid metabolism. Malonyl-CoA, which is produced by an ACC catalyst reaction, inhibits fatty acid oxidation in mitochondria based on the feedback inhibition of carnitine palmitoyl transferase-1 (CPT-1). Accordingly, ACC plays a key role in controlling the balance between use of carbohydrate and fatty acid in the liver and skeletal muscle, and further, controlling insulin sensitivity in the liver, skeletal muscle and adipose tissue.

A reduced level of malonyl-CoA by ACC inhibition can promote a promotion in fatty acid oxidation, decreased secretion of triglyceride (TG)-rich lipoprotein (VLDL) in the liver, regulation of insulin secretion in the pancreas, and further, improvement in the insulin sensitivity in the liver, skeletal muscle and adipose tissue.

In addition, long-term administration of a compound having an ACC inhibitory action can strikingly decrease the TG content of the liver and adipose tissues and selectively decrease body fat in obese test subjects taking low fat diet, by promoting fatty acid oxidation and suppressing de novo synthesis of fatty acid.

Accordingly, a compound having an ACC inhibitory action is extremely useful for the prophylaxis or treatment of metabolic syndrome, obesity, hypertension, diabetes, cardiovascular diseases associated with atherosclerosis and the like.

On the other hand, patent document 1 (WO 2010/050445) has reported the following compound.

A compound or a salt thereof represented by the formula:

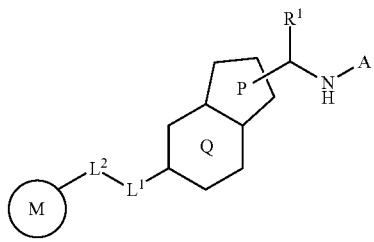

(I)

wherein
A is an acyl group or an optionally substituted 5- or 6-membered aromatic ring group;
ring M is an optionally condensed 5- to 7-membered ring which is optionally further substituted;
for ring P and ring Q
(1) ring P is an optionally further substituted 5-membered heterocycle, ring Q is an optionally further substituted 6-membered ring, and ring P and ring Q are fused to form an optionally further substituted bicyclic aromatic heterocycle, or (2) ring P is an optionally further substituted 5-membered non-aromatic ring, ring Q is an optionally further substituted 6-membered aromatic ring, and ring P and ring Q are fused to form an optionally further substituted bicyclic non-aromatic ring;
$R^1$ is an optionally substituted $C_{1-6}$ alkyl group or an optionally substituted $C_{3-6}$ cycloalkyl group; and
$L^1$ and $L^2$ are
(1) independently optionally substituted methylene, O, S, SO or $SO_2$, or
(2) $L^1$ and $L^2$ in combination form optionally substituted vinylene or ethynylene,
provided that
(a) a compound wherein A is an α-aminoisobutyroyl group; and
(b) a compound wherein A is a 5- or 6-membered aromatic ring group substituted by a group represented by the formula: —CO—$(CH_2)_3$—COOR$^{41}$ wherein R$^{41}$ is a hydrogen atom or a $C_{1-6}$ alkyl group, or a group represented by the formula: —CO—NR$^{42}$—CR$^{43}$R$^{44}$—CR$^{45}$R$^{46}$—COOR$^{47}$ wherein R$^{42}$, R$^{43}$, R$^{44}$, R$^{45}$ and R$^{47}$ are independently a hydrogen atom or a $C_{1-6}$ alkyl group; and R$^{46}$ is a hydrogen atom, a $C_{1-6}$ alkyl group or a hydroxy group.

are excluded.

In addition, non-patent document 1 (Analytical Sciences (1994), 10(1), pages 17-23) has reported the following compound.

A compound represented by the formula:

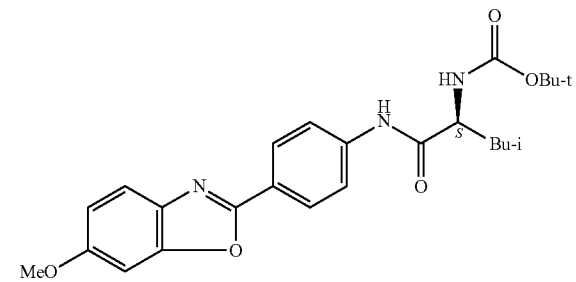

or the formula:

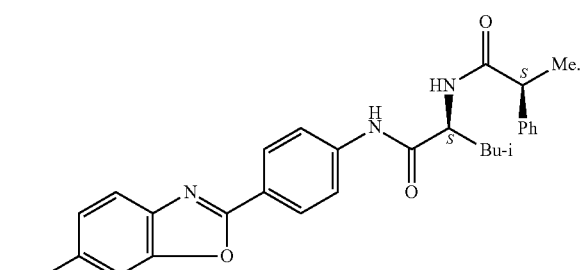

In addition, patent document 2 (WO 2011/136385) has reported the following compound.

A compound or a salt thereof represented by the formula:

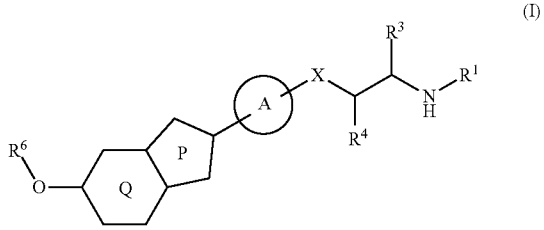

wherein
$R^1$ is a group represented by the formula: $-COR^2$ wherein $R^2$ is a hydrogen atom or a substituent, an optionally substituted 5- or 6-membered aromatic heterocyclic group or an optionally substituted phenyl group;
$R^3$ is a $C_{1-6}$ alkyl group optionally substituted by halogen atom(s), or an optionally substituted $C_{3-6}$ cycloalkyl group;
$R^4$ is a hydrogen atom or a substituent;
X is O, CO, $CR^{5a}R^{5b}$ wherein $R^{5a}$ and $R^{5b}$ are each independently a hydrogen atom, a halogen atom or an optionally substituted $C_{1-6}$ alkyl group, $NR^{5c}$ wherein $R^{5c}$ is a hydrogen atom or an optionally substituted $C_{1-6}$ alkyl group, S, SO or $S(O)_2$;
ring A is an optionally further substituted 4- to 7-membered non-aromatic ring (the ring is optionally crosslinked);
ring P is a 5-membered aromatic heterocycle, ring Q is an optionally further substituted 6-membered ring, and ring P and ring Q are condensed to form an optionally further substituted bicyclic aromatic heterocycle; and
$R^6$ is an optionally substituted $C_{1-6}$ alkyl group or an optionally substituted $C_{3-6}$ cycloalkyl group.

SUMMARY OF THE INVENTION

Problems to be Solved by the Invention

There is a demand for the development of a compound having an ACC inhibitory action, which is useful as an agent for the prophylaxis or treatment of obesity, diabetes, hypertension, hyperlipidemia, cardiac failure, diabetic complications, metabolic syndrome, sarcopenia, cancer and the like, and has superior efficacy.

Means of Solving the Problems

The present inventors have found for the first time that a compound represented by the formula (I):

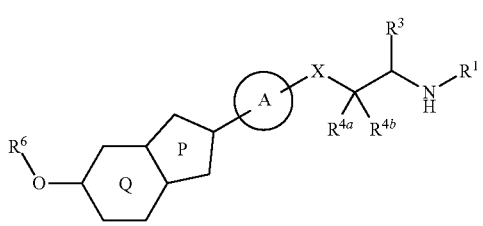

wherein
$R^1$ is a group represented by the formula: $-COR^2$ wherein $R^2$ is a hydrogen atom or a substituent, or an optionally substituted 5- or 6-membered aromatic ring group;
$R^3$ is a $C_{1-6}$ alkyl group optionally substituted by halogen atom(s), or an optionally substituted $C_{3-6}$ cycloalkyl group;
$R^{4a}$ and $R^{4b}$ are independently a hydrogen atom or a substituent;
X is O, CO, $CR^{5a}R^{5b}$ wherein $R^{5a}$ and $R^{5b}$ are independently a hydrogen atom or a substituent, $NR^{5c}$ wherein $R^{5c}$ is a hydrogen atom or an optionally substituted $C_{1-6}$ alkyl group, S, SO, or $S(O)_2$;
ring A is an optionally further substituted 5- or 6-membered aromatic ring;
for ring P and ring Q,
(1) ring P is an optionally further substituted 5-membered aromatic ring, ring Q is an optionally further substituted 6-membered ring, and ring P and ring Q are fused to form an optionally further substituted bicyclic aromatic ring, or
(2) ring P is an optionally further substituted 5-membered non-aromatic ring, ring Q is an optionally further substituted 6-membered aromatic ring, and ring P and ring Q are fused to is form an optionally further substituted bicyclic non-aromatic ring; and
$R^6$ is an optionally substituted $C_{1-6}$ alkyl group or an optionally substituted $C_{3-6}$ cycloalkyl group,
or a salt thereof [hereinafter sometimes to be referred to as compound (I)] has a superior ACC inhibitory action, which is useful for the prophylaxis or treatment of obesity, diabetes, hypertension, hyperlipidemia, cardiac failure, diabetic complications, metabolic syndrome, sarcopenia, cancer and the like, and has superior efficacy. Based on this finding, the present inventors have conducted intensive studies and completed the present invention.

Accordingly, the present invention relates to
[1] compound (I);
[2] the compound or salt of the above-mentioned [1], wherein $R^1$ is a group represented by the formula: $-COR^2$
wherein
$R^2$ is
(a) a $C_{1-6}$ alkyl group optionally substituted by 1 to 3 halogen atoms;
(b) a $C_{1-6}$ alkoxy group; or
(c) an amino group optionally mono- or di-substituted by $C_{1-6}$ alkyl group(s);
[3] the compound or salt of the above-mentioned [1] or [2], wherein the "optionally further substituted bicyclic aromatic ring" or "optionally further substituted bicyclic non-aromatic ring" formed by fusion of ring P and ring Q is

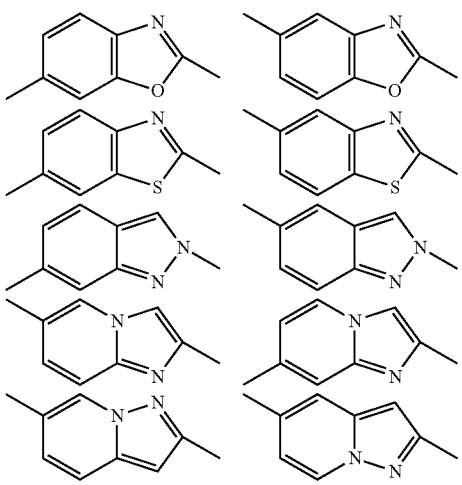

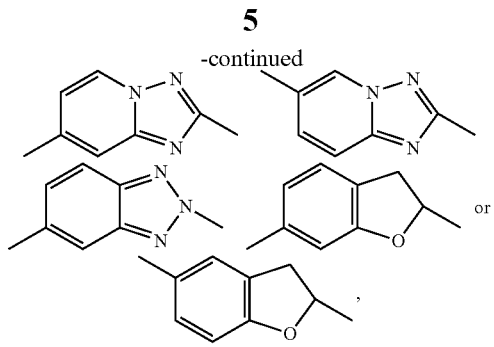

each of which is optionally further substituted by 1 to 4 substituents selected from
  (1) a halogen atom,
  (2) a $C_{1-6}$ alkyl group optionally substituted by 1 to 3 halogen atoms,
  (3) a $C_{3-6}$ cycloalkyl group optionally substituted by 1 to 3 halogen atoms, and
  (4) a cyano group;
[4] the compound or salt of the above-mentioned [1], [2] or [3], wherein $R^3$ is a $C_{1-6}$ alkyl group optionally substituted by 1 to 3 halogen atoms, and $R^{4a}$ and $R^{4b}$ are each a hydrogen atom;
[5] the compound or salt of the above-mentioned [1], [2], [3] or [4], wherein X is O, CO or $CH_2$;
[6] the compound or salt of the above-mentioned [1], [2], [3], [4] or [5], wherein $R^6$ is a $C_{1-6}$ alkyl group optionally substituted by 1 to 3 substituents selected from
  (a) a halogen atom, and
  (b) a $C_{3-6}$ cycloalkyl group optionally substituted by 1 to 3 halogen atoms;
[7] the compound or salt of the above-mentioned [1], [2], [3], [4], [5] or [6], wherein ring A is benzene, optionally oxidized pyridine, pyrimidine, pyrazole or isoxazole, each of which is optionally substituted by 1 to 3 substituents selected from
  (1) a halogen atom,
  (2) a $C_{1-6}$ alkyl group optionally substituted by 1 to 3 halogen atoms,
  (3) a $C_{1-6}$ alkoxy group, and
  (4) a $C_{7-13}$ aralkyl group;
[8] the compound or salt of the above-mentioned [1], wherein $R^1$ is a group represented by the formula: —$COR^2$
  wherein
  $R^2$ is
  (a) a $C_{1-6}$ alkyl group optionally substituted by 1 to 3 halogen atoms;
  (b) a $C_{1-6}$ alkoxy group; or
  (c) an amino group optionally mono- or di-substituted by $C_{1-6}$ alkyl group(s),
the "optionally further substituted bicyclic aromatic ring" or "optionally further substituted bicyclic non-aromatic ring" formed by fusion of ring P and ring Q is

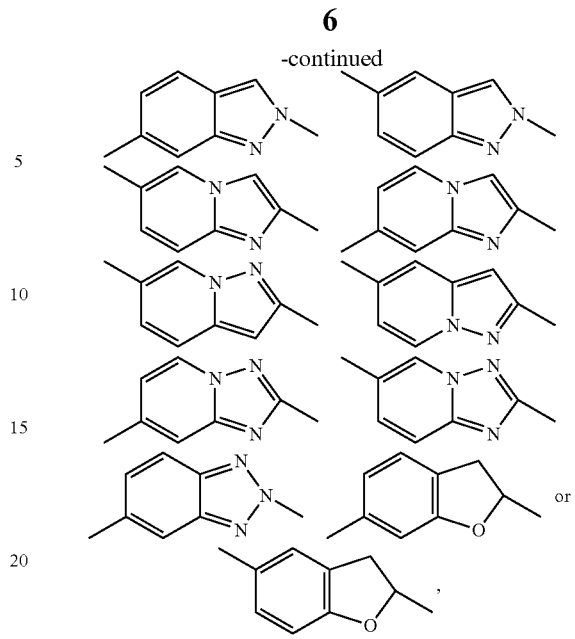

each of which is optionally further substituted by 1 to 4 substituents selected from
  (1) a halogen atom,
  (2) a $C_{1-6}$ alkyl group optionally substituted by 1 to 3 halogen atoms,
  (3) a $C_{3-6}$ cycloalkyl group optionally substituted by 1 to 3 halogen atoms, and
  (4) a cyano group,
$R^3$ is a $C_{1-6}$ alkyl group optionally substituted by 1 to 3 halogen atoms,
$R^{4a}$ and $R^{4b}$ are each a hydrogen atom,
X is O, CO or $CH_2$,
$R^6$ is a $C_{1-6}$ alkyl group optionally substituted by 1 to 3 substituents selected from
  (a) a halogen atom, and
  (b) a $C_{3-6}$ cycloalkyl group optionally substituted by 1 to 3 halogen atoms, and
ring A is benzene, optionally oxidized pyridine, pyrimidine, pyrazole or isoxazole, each of which is optionally substituted by 1 to 3 substituents selected from
  (1) a halogen atom,
  (2) a $C_{1-6}$ alkyl group optionally substituted by 1 to 3 halogen atoms,
  (3) a $C_{1-6}$ alkoxy group, and
  (4) a $C_{7-13}$ aralkyl group;
[9] N-[(1S)-2-({6-[6-(cyclopropylmethoxy)-1,3-benzoxazol-2-yl]pyridin-3-yl}oxy)-1-methylethyl]acetamide or a salt thereof;
[10] N-[(1S)-2-({6-[6-(cyclopropylmethoxy)-1,3-benzoxazol-2-yl]-5-fluoropyridin-3-yl}oxy)-1-methylethyl]acetamide or a salt thereof;
[11] N-[(1S)-2-{[6-(6-ethoxy-1,3-benzoxazol-2-yl)pyridin-3-yl]oxy}-1-methylethyl]acetamide or a salt thereof;
[11A] a prodrug of the compound or salt of the above-mentioned [1], [2], [3], [4], [5], [6], [7], [8], [9], [10] or [11];
[12] a medicament comprising the compound or salt of the above-mentioned [1], [2], [3], [4], [5], [6], [7], [8], [9], [10] or [11] or a prodrug thereof;
[13] the medicament of the above-mentioned [12], which is an acetyl-CoA carboxylase inhibitor;
[14] the medicament of the above-mentioned [12], which is an agent for the prophylaxis or treatment of obesity or diabetes;

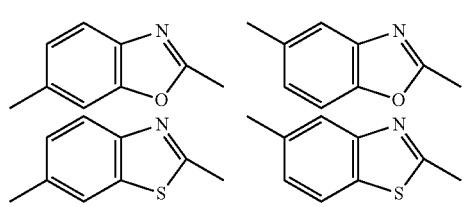

[15] a method of inhibiting acetyl-CoA carboxylase in a mammal, which comprises administering an effective amount of the compound or salt of the above-mentioned [1], [2], [3], [4], [5], [6], [7], [8], [9], [10] or [11] or a prodrug thereof to the mammal;

[16] a method for the prophylaxis or treatment of obesity or diabetes in a mammal, which comprises administering an effective amount of the compound or salt of the above-mentioned [1], [2], [3], [4], [5], [6], [7], [8], [9], [10] or [11] or a prodrug thereof to the mammal;

[17] use of the compound or salt of the above-mentioned [1], [2], [3], [4], [5], [6], [7], [8], [9], [10] or [11] or a prodrug thereof for production of an agent for the prophylaxis or treatment of obesity or diabetes;

[18] the compound or salt of the above-mentioned [1], [2], [3], [4], [5], [6], [7], [8], [9], [10] or [11] or a prodrug thereof for use in the prophylaxis or treatment of obesity or diabetes;

and the like.

Effect of the Invention

Compound (I) has an ACC inhibitory action, which is useful for the prophylaxis or treatment of obesity, diabetes, hypertension, hyperlipidemia, cardiac failure, diabetic complications, metabolic syndrome, sarcopenia, cancer and the like, and has superior efficacy.

DETAILED DESCRIPTION OF THE INVENTION

The definition of each symbol in the formula (I) is described in detail in the following.

The "halogen atom" in the present specification means, unless otherwise specified, a fluorine atom, a chlorine atom, a bromine atom or an iodine atom.

The "$C_{1-3}$ alkylenedioxy group" in the present specification means, unless otherwise specified, methylenedioxy, ethylenedioxy or the like.

The "$C_{1-6}$ alkyl group" in the present specification means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

The "$C_{1-6}$ alkoxy group" in the present specification means, unless otherwise specified, methoxy, ethoxy, propoxy, isopropoxy, butoxy, isobutoxy, sec-butoxy, tert-butoxy or the like.

The "$C_{1-6}$ alkoxy-carbonyl group" in the present specification means, unless otherwise specified, methoxycarbonyl, ethoxycarbonyl, propoxycarbonyl, tert-butoxycarbonyl or the like.

The "$C_{1-6}$ alkyl-carbonyl group" in the present specification means, unless otherwise specified, acetyl, propanoyl, butanoyl, isobutanoyl, pentanoyl, isopentanoyl, hexanoyl or the like.

$R^1$ is a group represented by the formula: —$COR^2$ wherein $R^2$ is a hydrogen atom or a substituent, or an optionally substituted 5- or 6-membered aromatic group.

Examples of the "substituent" for $R^2$ include a "halogen atom", "nitro", "cyano", an "optionally substituted hydrocarbon group", an "optionally substituted heterocyclic group", an "optionally substituted hydroxy group", an "optionally substituted amino group", an "optionally substituted mercapto group", an "acyl group" and the like.

Examples of the "hydrocarbon group" of the above-mentioned "optionally substituted hydrocarbon group" include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-13}$ aralkyl group, a $C_{8-13}$ arylalkenyl group and the like.

Examples of the $C_{1-10}$ alkyl group include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like. Of these, a $C_{1-6}$ alkyl group is preferable.

Examples of the $C_{2-10}$ alkenyl group include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like. Of these, a $C_{2-6}$ alkenyl group is preferable.

Examples of the $C_{2-10}$ alkynyl group include ethynyl, propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like. Of these, a $C_{2-6}$ alkynyl group is preferable.

Examples of the $C_{3-10}$ cycloalkyl group include cyclopropyl cyclobutyl, cyclopentyl, cyclohexyl, cycloheptyl, cyclooctyl and the like. Of these, a $C_{3-6}$ cycloalkyl group is preferable.

Examples of the $C_{3-10}$ cycloalkenyl group include 2-cyclopenten-1-yl, 3-cyclopenten-1-yl, 2-cyclohexen-1-yl, 3-cyclohexen-1-yl and the like. Of these, a $C_{3-6}$ cycloalkenyl group is preferable.

Examples of the $C_{4-10}$ cycloalkadienyl group include 2,4-cyclopentadien-1-yl, 2,4-cyclohexadien-1-yl, 2,5-cyclohexadien-1-yl and the like. Of these, a $C_{4-6}$ cycloalkadienyl group is preferable.

The above-mentioned $C_{3-10}$ cycloalkyl group, $C_{3-10}$ cycloalkenyl group and $C_{4-10}$ cycloalkadienyl group are each optionally fused with a benzene ring to form a fused ring group. Examples of the fused ring group include indanyl, dihydronaphthyl, tetrahydronaphthyl, fluorenyl and the like.

In addition, the above-mentioned $C_{3-10}$ cycloalkyl group, $C_{3-10}$ cycloalkenyl group and $C_{4-10}$ cycloalkadienyl group may be each a $C_{7-10}$ bridged hydrocarbon group. Examples of the $C_{7-30}$ bridged hydrocarbon group include bicyclo[2.2.1]heptyl (norbornyl), bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

Moreover, the above-mentioned $C_{3-10}$ cycloalkyl group, $C_{3-10}$ cycloalkenyl group and $C_{4-10}$ cycloalkadienyl group each optionally forms a spiro ring group together with a $C_{3-10}$ cycloalkane, a $C_{3-10}$ cycloalkene or a $C_{4-10}$ cycloalkadiene. Examples of the $C_{3-10}$ cycloalkane, $C_{3-10}$ cycloalkene and $C_{4-10}$ cycloalkadiene include rings corresponding to the above-mentioned $C_{3-10}$ cycloalkyl group, $C_{3-10}$ cycloalkenyl group and $C_{4-10}$ cycloalkadienyl group. Examples of the spiro ring group include spiro[4.5]decan-8-yl and the like.

Examples of the $C_{6-14}$ aryl group include phenyl, naphthyl, anthryl, phenanthryl, acenaphthylenyl, biphenylyl and the like. Of these, a $C_{6-12}$ aryl group is preferable.

Examples of the $C_{7-13}$ aralkyl group include benzyl, phenethyl, naphthylmethyl, biphenylylmethyl and the like.

Examples of the $C_{8-13}$ arylalkenyl group include styryl and the like.

The $C_{1-10}$ alkyl group, $C_{2-10}$ alkenyl group and $C_{2-10}$ alkynyl group, which are exemplified as the above-mentioned "hydrocarbon group", optionally have 1 to 7 (preferably 1 to 3) substituents at substitutable positions.

Examples of the substituent include
(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;
(4) a non-aromatic heterocyclic group (e.g., tetrahydrofuryl, morpholinyl, thiomorpholinyl, piperidyl, pyrrolidinyl, piperazinyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms,
    (d) a halogen atom, and
    (e) an oxo group;
(5) an amino group optionally mono- or di-substituted by substituent(s) selected from
    (a) a $C_{1-6}$ alkyl group optionally substituted by 1 to 3 halogen atoms,
    (b) a $C_{1-6}$ alkyl-carbonyl group optionally substituted by 1 to 3 halogen atoms,
    (c) a $C_{1-6}$ alkoxy-carbonyl group optionally substituted by 1 to 3 halogen atoms,
    (d) a $C_{1-6}$ alkylsulfonyl group (e.g., methylsulfonyl) optionally substituted by 1 to 3 halogen atoms,
    (e) a carbamoyl group optionally mono- or di-substituted by $C_{1-6}$ alkyl group(s) optionally substituted by 1 to 3 halogen atoms, and
    (f) an aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a $C_{1-6}$ alkyl-carbonyl group optionally substituted by 1 to 3 halogen atoms;
(7) a $C_{1-6}$ alkoxy-carbonyl group optionally substituted by 1 to 3 substituents selected from
    (a) a halogen atom,
    (b) a $C_{1-6}$ alkoxy group,
    (c) a $C_{6-14}$ aryl group (e.g., phenyl), and
    (d) a heterocyclic group (e.g., tetrahydrofuryl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by $C_{1-6}$ alkyl group(s) optionally substituted by 1 to 3 halogen atoms;
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a hydroxy group;
(14) a $C_{1-6}$ alkoxy group optionally substituted by 1 to 3 substituents selected from
    (a) a halogen atom,
    (b) a carboxy group,
    (c) a $C_{1-6}$ alkoxy group,
    (d) a $C_{1-6}$ alkoxy-carbonyl group optionally substituted by 1 to 3 $C_{6-14}$ aryl groups (e.g., phenyl),
    (e) an amino group optionally mono- or di-substituted by substituent(s) selected from a $C_{1-6}$ alkyl group and a $C_{1-6}$ alkoxy-carbonyl group,
    (f) a heterocyclic group (e.g., tetrahydrofuryl), and
    (g) a $C_{3-10}$ cycloalkyl group;
(15) a $C_{2-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-14}$ aryloxy group (e.g., phenyloxy, naphthyloxy);
(18) a $C_{1-6}$ alkyl-carbonyloxy group (e.g., acetyloxy, tert-butylcarbonyloxy);
(19) a $C_{6-14}$ aryl-carbonyl group (e.g., benzoyl) optionally substituted by 1 to 3 substituents selected from
    (a) a halogen atom, and
    (b) a $C_{1-6}$ alkyl group optionally substituted by 1 to 3 halogen atoms;
(20) a non-aromatic heterocyclylcarbonyl group (e.g., pyrrolidinylcarbonyl, morpholinylcarbonyl) optionally substituted by 1 to 3 $C_{1-6}$ alkyl groups optionally substituted by 1 to 3 halogen atoms;
(21) a mercapto group;
(22) a $C_{1-6}$ alkylthio group (e.g., methylthio, ethylthio) optionally substituted by 1 to 3 substituents selected from
    (a) a halogen atom, and
    (b) a $C_{1-6}$ alkoxy-carbonyl group;
(23) a $C_{7-13}$ aralkylthio group (e.g., benzylthio);
(24) a $C_{6-14}$ arylthio group (e.g., phenylthio, naphthylthio);
(25) a cyano group;
(26) a nitro group;
(27) a halogen atom;
(28) a $C_{1-3}$ alkylenedioxy group;
(29) a $C_{1-3}$ alkyleneoxy group (e.g., methyleneoxy, ethyleneoxy);
(30) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;
(31) a $C_{3-40}$ cycloalkoxy group (e.g., cyclopropoxy, cyclopentyloxy) optionally substituted by 1 to 3 substituents selected from
    (a) a halogen atom (e.g., a fluorine atom), and
    (b) a $C_{1-6}$ alkoxy group (e.g., methoxy) and the like. When the number of the substituents is not less than 2, the respective substituents may be the same or different.

The $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group and $C_{8-13}$ arylalkenyl group, which are exemplified as the above-mentioned "hydrocarbon group", optionally have 1 to 3 substituents at substitutable positions.

Examples of the substituent include
(1) the groups exemplified as the substituents for the above-mentioned $C_{1-10}$ alkyl group and the like;
(2) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group, and (f) an amino group optionally mono- or di-substituted by $C_{1-6}$ alkyl group(s);

(3) a $C_{2-6}$ alkenyl group (e.g., ethenyl, 1-propenyl) optionally substituted by 1 to 3 substituents selected from
   (a) a halogen atom,
   (b) a carboxy group,
   (c) a hydroxy group,
   (d) a $C_{1-6}$ alkoxy-carbonyl group,
   (e) a $C_{1-6}$ alkoxy group, and
   (f) an amino group optionally mono- or di-substituted by $C_{1-6}$ alkyl group(s);

(4) a $C_{7-13}$ aralkyl group (e.g., benzyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group, and
   (d) a halogen atom;

and the like. When the number of the substituents is not less than 2, the respective substituents may be the same or different.

Examples of the "heterocyclic group" of the above-mentioned "optionally substituted heterocyclic group" include an "aromatic heterocyclic group" and a "non-aromatic heterocyclic group".

Examples of the aromatic heterocyclic group include a 4- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, and the like.

Preferable examples of the aromatic heterocyclic group include monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like;

fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), thienopyridinyl (e.g., thieno[2,3-b]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl), pyridopyridinyl (e.g., pyrido[2,3-b]pyridin-3-yl), thienopyridyl (e.g., thieno[2,3-b]pyridin-3-yl) and the like; and the like.

Examples of the non-aromatic heterocyclic group include a 4- to 7-membered (preferably 5- or 6-membered) monocyclic non-aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 4- to 7-membered monocyclic non-aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, a group wherein the above-mentioned group is partially saturated, and the like.

Preferable examples of the non-aromatic heterocyclic group include monocyclic non-aromatic heterocyclic groups such as azetidinyl (e.g., 1-azetidinyl, 2-azetidinyl, 3-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like; fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like; and the like.

The "heterocyclic group" of the "optionally substituted heterocyclic group" optionally has 1 to 3 substituents at substitutable positions. Examples of the substituent include those similar to the substituents that the $C_{3-10}$ cycloalkyl group and the like exemplified as the "hydrocarbon group" of the above-mentioned "optionally substituted hydrocarbon group" optionally has. When the heterocyclic group is a "non-aromatic heterocyclic group", the substituent further includes an oxo group. When the number of the substituents is not less than 2, the respective substituents may be the same or different.

Examples of the above-mentioned "optionally substituted hydroxy group" include a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each of which is optionally substituted.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those exemplified as the "hydrocarbon group" of the above-mentioned "optionally substituted hydrocarbon group".

Examples of the heterocyclic group include those similar to the "aromatic heterocyclic group" and "non-aromatic heterocyclic group" exemplified as the "heterocyclic group" of the above-mentioned "optionally substituted heterocyclic group".

The above-mentioned $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{1-6}$ alkyl-carbonyl group and heterocyclic group optionally have 1 to 3 substituents at substitutable positions. When the number of the substituents is not less than 2, the respective substituents may be the same or different.

Examples of the substituent for the $C_{1-10}$ alkyl group, $C_{2-10}$ alkenyl group and $C_{1-6}$ alkyl-carbonyl group include those similar to the substituent that the $C_{1-10}$ alkyl group and the like exemplified as the "hydrocarbon group" of the above-mentioned "optionally substituted hydrocarbon group" optionally has.

Examples of the substituent for the $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those similar to the substituent that the $C_{3-10}$ cycloalkyl group and the like exemplified as the "hydrocarbon group" of the above-mentioned "optionally substituted hydrocarbon group" optionally has. Examples of the substituent for the heterocyclic group include those similar to the substituent that the "heterocyclic group" of the above-3 mentioned "optionally substituted heterocyclic group" optionally has.

Examples of the above-mentioned "optionally substituted mercapto group" include a mercapto group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each of which is optionally substituted.

Examples of the substituent include those exemplified as the substituents of the above-mentioned "optionally substituted hydroxy group".

Examples of the above-mentioned "optionally substituted amino group" include an amino group optionally mono- or di-substituted by substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group and a heterocyclic group, each of which is optionally substituted; an acyl group and the like.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those exemplified as the "hydrocarbon group" of the above-mentioned "optionally substituted hydrocarbon group".

Examples of the heterocyclic group include those similar to the "aromatic heterocyclic group" and "non-aromatic heterocyclic group" exemplified as the "heterocyclic group" of the above-mentioned "optionally substituted heterocyclic group". Of these, a 5- or 6-membered monocyclic aromatic heterocyclic group is preferable.

The $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group and heterocyclic group optionally have 1 to 3 substituents at substitutable positions. When the number of the substituents is not less than 2, the respective substituents may be the same or different.

Examples of the substituent for the $C_{1-10}$ alkyl group and $C_{2-10}$ alkenyl group include those similar to the substituent that the $C_{1-10}$ alkyl group and the like exemplified as the "hydrocarbon group" of the above-mentioned "optionally substituted hydrocarbon group" optionally has.

Examples of the substituent for the $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those similar to the substituent that the $C_{3-10}$ cycloalkyl group and the like exemplified as the "hydrocarbon group" of the above-mentioned "optionally substituted hydrocarbon group" optionally has. Examples of the substituent for the heterocyclic group include those similar to the substituent that the "heterocyclic group" of the above-mentioned "optionally substituted heterocyclic group" optionally has.

Examples of the "acyl group" exemplified as the substituent for the "optionally substituted amino group" include those similar to the "acyl group" below, which is exemplified as the "substituent" for $R^2$.

Examples of the "acyl group" exemplified as the "substituent" for $R^2$ include a group represented by the formula: —$COR^A$, —CO—$OR^A$, —$SO_3R^A$, —$S(O)_2R^A$, —$SOR^A$, —CO—$NR^{A'}R^{B'}$, —CS—$NR^{A'}R^{B'}$ or —$S(O)_2NR^{A'}R^{B'}$ wherein $R^A$ is a hydrogen atom, an optionally substituted hydrocarbon group or an optionally substituted heterocyclic group, $R^{A'}$ and $R^{B'}$ are the same or different and each is a hydrogen atom, an optionally substituted hydrocarbon group or an optionally substituted heterocyclic group, or $R^{A'}$ and $R^{B'}$ form, together with the adjacent nitrogen atom, an optionally substituted nitrogen-containing heterocycle, and the like.

Examples of the "optionally substituted hydrocarbon group" and "optionally substituted heterocyclic group" for $R^A$, $R^{A'}$ or $R^{B'}$ include those similar to the "optionally substituted hydrocarbon group" and "optionally substituted heterocyclic group", which are exemplified as the "substituent" for $R^2$.

Examples of the "nitrogen-containing heterocycle" of the "optionally substituted nitrogen-containing heterocycle" formed by $R^{A'}$ and $R^{B'}$ together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 5 (preferably 1 or 2) substituents at substitutable positions. Examples of the substituent include those similar to the substituent that the "heterocyclic group" of the "optionally substituted heterocyclic group", which is exemplified as the "substituent" for $R^2$, optionally has. When the number of the substituents is not less than 2, the respective substituents may be the same or different.

Preferable examples of the "acyl group" include
(1) a formyl group;
(2) a carboxy group;
(3) a $C_{1-6}$ alkyl-carbonyl group (e.g., acetyl) optionally substituted by 1 to 3 halogen atoms;
(4) a $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 halogen atoms;
(7) a carbamoyl group optionally mono- or di-substituted by substituent(s) selected from
   (a) a $C_{1-6}$ alkyl group optionally substituted by 1 to 3 substituents selected from a halogen atom, a $C_{1-6}$ alkoxy group, a $C_{1-6}$ alkoxy-carbonyl group and a carboxy group, and
   (b) an amino group optionally mono- or di-substituted by $C_{1-6}$ alkoxy-1-carbonyl group(s);
(8) a $C_{1-6}$ alkylsulfonyl group (e.g., methylsulfonyl, ethylsulfonyl, isopropylsulfonyl) optionally substituted by 1 to 3 halogen atoms;
(9) a $C_{6-14}$ arylsulfonyl group (e.g., benzenesulfonyl);
(10) a sulfamoyl group;
(11) a thiocarbamoyl group;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a non-aromatic heterocyclylcarbonyl group (e.g., tetrahydrofurylcarbonyl, pyrrolidinocarbonyl) optionally substituted by 1 to 3 substituents selected from a $C_{1-6}$ alkyl group optionally substituted by 1 to 3 halogen atoms;
and the like.

$R^2$ is preferably an optionally substituted $C_{1-6}$ alkyl group, an optionally substituted $C_{1-6}$ alkoxy group, an optionally substituted $C_{3-10}$ cycloalkyl group, an optionally substituted $C_{6-14}$ aryl group, an optionally substituted amino group, an optionally substituted aromatic heterocyclic group, an optionally substituted non-aromatic heterocyclic group or the like.

Specifically, $R^2$ is preferably
(a) a $C_{1-6}$ alkyl group (e.g., methyl, ethyl, propyl, butyl, isobutyl, isopentyl) optionally substituted by 1 to 3 substituents selected from
   (i) an amino group,
   (ii) a carboxy group,
   (iii) a $C_{1-6}$ alkoxy-carbonyl group (e.g., methoxycarbonyl, ethoxycarbonyl),
   (iv) a $C_{6-14}$ aryl group (e.g., phenyl),
   (v) a $C_{1-6}$ alkoxy group (e.g., methoxy), and
   (vi) a halogen atom (e.g., a fluorine atom);
(b) a $C_{1-6}$ alkoxy group (e.g., methoxy, tert-butoxy);
(c) a $C_{3-10}$ cycloalkyl group (e.g., cyclopropyl, cyclopentyl);
(d) a $C_{6-14}$ aryl group (e.g., phenyl);
(e) an amino group optionally mono- or di-substituted by substituent(s) selected from
   (i) a $C_{1-6}$ alkyl group (e.g., methyl, ethyl, propyl, isopropyl) optionally substituted by 1 to 3 $C_{6-14}$ aryl groups (e.g., phenyl),
   (ii) a $C_{6-14}$ aryl group (e.g., phenyl),
   (iii) a $C_{3-10}$ cycloalkyl group (e.g., cyclopentyl, cyclohexyl),
   (iv) a $C_{1-6}$ alkylsulfonyl group (e.g., methylsulfonyl), and
   (v) an aromatic heterocyclic group (e.g., pyridyl) optionally substituted by 1 to 3 $C_{1-6}$ alkyl groups (e.g., methyl);
(f) an aromatic heterocyclic group (e.g., furyl, pyrazolyl, pyridyl, isoxazolyl, thiazolyl) optionally substituted by 1 to 3 substituents selected from a $C_{1-6}$ alkyl group optionally substituted by 1 to 3 halogen atoms (e.g., a fluorine atom);
(g) a non-aromatic heterocyclic group (e.g., tetrahydropyranyl);
or the like.

$R^2$ is more preferably an optionally substituted $C_{1-6}$ alkyl group, an optionally substituted $C_{1-6}$ alkoxy group, an optionally substituted amino group or the like.

Specifically, $R^2$ is more preferably
(a) a $C_{1-6}$ alkyl group (e.g., methyl, ethyl, propyl, butyl, isobutyl, isopentyl) optionally substituted by 1 to 3 substituents selected from
   (i) an amino group,
   (ii) a carboxy group,
   (iii) a $C_{1-6}$ alkoxy-carbonyl group (e.g., methoxycarbonyl, ethoxycarbonyl),
   (iv) a $C_{6-14}$ aryl group (e.g., phenyl),
   (v) a $C_{1-6}$ alkoxy group (e.g., methoxy), and
   (vi) a halogen atom (e.g., a fluorine atom);
(b) a $C_{1-6}$ alkoxy group (e.g., methoxy, tert-butoxy);
(c) an amino group optionally mono- or di-substituted by substituent(s) selected from
   (i) a $C_{1-6}$ alkyl group (e.g., methyl, ethyl, propyl, isopropyl) optionally substituted by 1 to 3 $C_{6-14}$ aryl groups (e.g., phenyl),
   (ii) a $C_{6-14}$ aryl group (e.g., phenyl),
   (iii) a $C_{3-10}$ cycloalkyl group (e.g., cyclopentyl, cyclohexyl),
   (iv) a $C_{1-6}$ alkylsulfonyl group (e.g., methylsulfonyl), and
   (v) an aromatic heterocyclic group (e.g., pyridyl) optionally substituted by 1 to 3 $C_{1-6}$ alkyl groups (e.g., methyl);
or the like.

$R^2$ is still more preferably
(a) a $C_{1-6}$ alkyl group (e.g., methyl, ethyl, propyl, butyl, isobutyl, isopentyl) optionally substituted by 1 to 3 halogen atoms (e.g., a fluorine atom);
(b) a $C_{1-6}$ alkoxy group (e.g., methoxy, tert-butoxy);
(c) an optionally mono- or di-substituted amino group by $C_{1-6}$ alkyl group(s) (e.g., methyl, ethyl, propyl, isopropyl); or the like.

$R^2$ is particularly preferably
(a) a $C_{1-6}$ alkyl group (e.g., methyl, ethyl, propyl, butyl, isobutyl, isopentyl);
(b) a $C_{1-6}$ alkoxy group (e.g., methoxy, tert-butoxy);
(c) an amino group optionally mono- or di-substituted by $C_{1-6}$ alkyl group(s) (e.g., methyl, ethyl, propyl, isopropyl);
or the like.

The "group represented by the formula: —$COR^2$" for $R^1$ is preferably a group represented by the formula: —$COR^2$ wherein $R^2$ is an optionally substituted $C_{1-6}$ alkyl group, an optionally substituted $C_{1-6}$ alkoxy group, an optionally substituted $C_{3-10}$ cycloalkyl group, an optionally substituted $C_{6-14}$ aryl group, an optionally substituted amino group, an optionally substituted aromatic heterocyclic group, an optionally substituted non-aromatic heterocyclic group or the like.

Specifically, the "group represented by the formula: —$COR^2$" for $R^1$ is preferably a group represented by the formula: —$COR^2$
wherein
$R^2$ is
(a) a $C_{1-6}$ alkyl group (e.g., methyl, ethyl, propyl, butyl, isobutyl, isopentyl) optionally substituted by 1 to 3 substituents selected from
  (i) an amino group,
  (ii) a carboxy group,
  (iii) a $C_{1-6}$ alkoxy-carbonyl group (e.g., methoxycarbonyl, ethoxycarbonyl),
  (iv) a $C_{6-14}$ aryl group (e.g., phenyl),
  (v) a $C_{1-6}$ alkoxy group (e.g., methoxy), and
  (vi) a halogen atom (e.g., a fluorine atom);
(b) a $C_{1-6}$ alkoxy group (e.g., methoxy, tert-butoxy);
(c) a $C_{3-10}$ cycloalkyl group (e.g., cyclopropyl, cyclopentyl);
(d) a $C_{6-14}$ aryl group (e.g., phenyl);
(e) an amino group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl);
(f) an aromatic heterocyclic group (e.g., furyl, pyrazolyl, pyridyl, isoxazolyl, thiazolyl) optionally substituted by 1 to 3 substituents selected from a $C_{1-6}$ alkyl group optionally substituted by 1 to 3 halogen atoms (e.g., a fluorine atom);
(g) a non-aromatic heterocyclic group (e.g., tetrahydropyranyl);
or the like.

The "group represented by the formula: —$COR^2$" for $R^1$ is more preferably a group represented by the formula: —$COR^2$ wherein $R^2$ is an optionally substituted $C_{1-6}$ alkyl group, an optionally substituted $C_{1-6}$ alkoxy group, an optionally substituted amino group or the like.

Specifically, the "group represented by the formula: —$COR^2$" for $R^1$ is more preferably a group represented by the formula: —$COR^2$
wherein
$R^2$ is
(a) a $C_{1-6}$ alkyl group (e.g., methyl, ethyl, propyl, butyl, isobutyl, isopentyl) optionally substituted by 1 to 3 substituents selected from
  (i) an amino group,
  (ii) a carboxy group,
  (iii) a $C_{1-6}$ alkoxy-carbonyl group (e.g., methoxycarbonyl, ethoxycarbonyl),
  (iv) a $C_{6-14}$ aryl group (e.g., phenyl),
  (v) a $C_{1-6}$ alkoxy group (e.g., methoxy), and
  (vi) a halogen atom (e.g., a fluorine atom);
(b) a $C_{1-6}$ alkoxy group (e.g., methoxy, tert-butoxy);
(c) an amino group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl);
or the like.

The "group represented by the formula: —$COR^2$" for $R^1$ is still more preferably a group represented by the formula: —$COR^2$
wherein
$R^2$ is
(a) a $C_{1-6}$ alkyl group (e.g., methyl, ethyl, propyl, butyl, isobutyl, isopentyl) optionally substituted by 1 to 3 halogen atoms (e.g., a fluorine atom);
(b) a $C_{1-6}$ alkoxy group (e.g., methoxy, tert-butoxy);
(c) an amino group optionally mono- or di-substituted by $C_{1-6}$ alkyl group(s) (e.g., methyl, ethyl, propyl, isopropyl);
or the like.

The "group represented by the formula: —$COR^2$" for $R^1$ is particularly preferably a group represented by the formula: —$COR^2$
wherein
$R^2$ is
(a) a $C_{1-6}$ alkyl group (e.g., methyl, ethyl, propyl, butyl, isobutyl, isopentyl);
(b) a $C_{1-6}$ alkoxy group (e.g., methoxy, tert-butoxy);
(c) an amino group optionally mono- or di-substituted by $C_{1-6}$ alkyl group(s) (e.g., methyl, ethyl, propyl, isopropyl); or the like.

Examples of the "5- or 6-membered aromatic group" of the "optionally substituted 5- or 6-membered aromatic group" for $R^1$ include phenyl, pyrrolyl, pyrazolyl, imidazolyl, triazolyl (1,2,3-triazolyl, 1,2,4-triazolyl, 1,3,4-triazolyl), tetrazolyl, oxazolyl, isoxazolyl, triazolyl, isothiazolyl, oxadiazolyl, thiadiazolyl, furyl, thienyl, pyridyl, pyridazinyl, pyrimidinyl, pyrazinyl, triazinyl and the like.

The "5- or 6-membered aromatic group" is preferably a 5-membered aromatic heterocyclic group, phenyl or the like, more preferably pyrazolyl, oxazolyl, isoxazolyl, thiazolyl, isothiazolyl, thiadiazolyl, phenyl or the like, particularly preferably isoxazolyl.

The "5- or 6-membered aromatic group" of the "optionally substituted 5- or 6-membered aromatic group" for $R^1$ optionally has 1 to 3 substituents at substitutable positions. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has The "optionally substituted 5- or 6-membered aromatic group" for $R^1$ is preferably a 5-membered aromatic heterocyclic group (e.g., pyrazolyl, oxazolyl, isoxazolyl, thiazolyl, isothiazolyl, thiadiazolyl, preferably isoxazolyl) or phenyl, each of which is optionally substituted by 1 to 3 substituents selected from (1) a $C_{1-6}$ alkyl-carbonyl group optionally substituted by 1 to 3 halogen atoms;
(2) a $C_{1-6}$ alkoxy-carbonyl group optionally substituted by 1 to 3 substituents selected from
  (a) a halogen atom,
  (b) a $C_{1-6}$ alkoxy group, and
  (c) a $C_{6-14}$ aryl group (e.g., phenyl);
(3) a carbamoyl group optionally mono- or di-substituted by $C_{1-6}$ alkyl group(s) optionally substituted by 1 to 3 halogen atoms;
(4) a carboxy group;
(5) a hydroxy group;
(6) a halogen atom; and
(7) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group, and
  (e) a $C_{1-6}$ alkoxy group.

The "optionally substituted 5- or 6-membered aromatic group" for $R^1$ is more preferably a 5-membered aromatic heterocyclic group (e.g., pyrazolyl, oxazolyl, thiazolyl, isothiazolyl, thiadiazolyl, preferably isoxazolyl) or phenyl, each of which is optionally substituted by 1 to 3 substituents selected from (i) a halogen atom and (ii) a $C_{1-6}$ alkyl group.

The "optionally substituted 5- or 6-membered aromatic group" for $R^1$ is still more preferably a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 substituents selected from a $C_{1-6}$ alkyl group.

$R^1$ is preferably
(1) a group represented by the formula: —$COR^2$ wherein $R^2$ is an optionally substituted $C_{1-6}$ alkyl group, an optionally substituted $C_{1-6}$ alkoxy group, an optionally substituted $C_{3-10}$ cycloalkyl group, an optionally substituted $C_{6-14}$ aryl group, an optionally substituted amino group, an optionally substituted aromatic heterocyclic group, an optionally substituted non-aromatic heterocyclic group or the like; or
(2) an optionally substituted 5- or 6-membered aromatic group.

Specifically, $R^1$ is preferably
(1) a group represented by the formula: —$COR^2$
  wherein
  $R^2$ is
  (a) a $C_{1-6}$ alkyl group (e.g., methyl, ethyl, propyl, butyl, isobutyl, isopentyl) optionally substituted by 1 to 3 substituents selected from
    (i) an amino group,
    (ii) a carboxy group,
    (iii) a $C_{1-6}$ alkoxy-carbonyl group (e.g., methoxycarbonyl, ethoxycarbonyl),
    (iv) a $C_{6-14}$ aryl group (e.g., phenyl),
    (v) a $C_{1-6}$ alkoxy group (e.g., methoxy), and
    (vi) a halogen atom (e.g., a fluorine atom);
  (b) a $C_{1-6}$ alkoxy group (e.g., methoxy, tert-butoxy);
  (c) a $C_{3-10}$ cycloalkyl group (e.g., cyclopropyl, cyclopentyl);
  (d) a $C_{6-14}$ aryl group (e.g., phenyl);
  (e) an amino group optionally mono- or di-substituted by substituent(s) selected from
    (i) a $C_{1-6}$ alkyl group (e.g., methyl, ethyl, propyl, isopropyl) optionally substituted by 1 to 3 $C_{6-14}$ aryl groups (e.g., phenyl),
    (ii) a $C_{6-14}$ aryl group (e.g., phenyl),
    (iii) a $C_{3-10}$ cycloalkyl group (e.g., cyclopentyl, cyclohexyl),
    (iv) a $C_{1-6}$ alkylsulfonyl group (e.g., methylsulfonyl), and
    (v) an aromatic heterocyclic group (e.g., pyridyl) optionally substituted by 1 to 3 $C_{1-6}$ alkyl groups (e.g., methyl);
  (f) an aromatic heterocyclic group (e.g., furyl, pyrazolyl, pyridyl, isoxazolyl, thiazolyl) optionally substituted by 1 to 3 substituents selected from a $C_{1-6}$ alkyl group optionally substituted by 1 to 3 halogen atoms (e.g., a fluorine atom);
  (g) a non-aromatic heterocyclic group (e.g., tetrahydropyranyl);
  or the like, or
(2) a 5-membered aromatic heterocyclic group (e.g., pyrazolyl, oxazolyl, isoxazolyl, thiazolyl, isothiazolyl, thiadiazolyl, preferably isoxazolyl) or phenyl, each of which is optionally substituted by 1 to 3 substituents selected from
  (i) a $C_{1-6}$ alkyl-carbonyl group optionally substituted by 1 to 3 halogen atoms;
  (ii) a $C_{1-6}$ alkoxy-carbonyl group optionally substituted by 1 to 3 substituents selected from
    (a) a halogen atom,
    (b) a $C_{1-6}$ alkoxy group, and
    (c) a $C_{6-14}$ aryl group (e.g., phenyl);
  (iii) a carbamoyl group optionally mono- or di-substituted by $C_{1-6}$ alkyl group(s) optionally substituted by 1 to 3 halogen atoms;
  (iv) a carboxy group;
  (v) a hydroxy group;
  (vi) a halogen atom; and
  (vii) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group, and
    (e) a $C_{1-6}$ alkoxy group.

$R^1$ is more preferably
(1) a group represented by the formula: —$COR^2$ wherein $R^2$ is an optionally substituted $C_{1-6}$ alkyl group, an optionally substituted $C_{1-6}$ alkoxy group, an optionally substituted amino group or the like; or
(2) an optionally substituted 5- or 6-membered aromatic ring group.

Specifically, $R^1$ is more preferably
(1) a group represented by the formula: —$COR^2$
  wherein
  $R^2$ is
  (a) a $C_{1-6}$ alkyl group (e.g., methyl, ethyl, propyl, butyl, isobutyl, isopentyl) optionally substituted by 1 to 3 substituents selected from
    (i) an amino group,
    (ii) a carboxy group,
    (iii) a $C_{1-6}$ alkoxy-carbonyl group (e.g., methoxycarbonyl ethoxycarbonyl),
    (iv) a $C_{6-14}$ aryl group (e.g., phenyl),
    (v) a $C_{1-6}$ alkoxy group (e.g., methoxy), and
    (vi) a halogen atom (e.g., a fluorine atom);
  (b) a $C_{1-6}$ alkoxy group (e.g., methoxy, tert-butoxy);
  (c) an amino group optionally mono- or di-substituted by substituent(s) selected from
    (i) a $C_{1-6}$ alkyl group (e.g., methyl, ethyl, propyl, isopropyl) optionally substituted by 1 to 3 $C_{6-14}$ aryl groups (e.g., phenyl),
    (ii) a $C_{6-14}$ aryl group (e.g., phenyl),
    (iii) a $C_{3-10}$ cycloalkyl group (e.g., cyclopentyl, cyclohexyl), (iv) a $C_{1-6}$ alkylsulfonyl group (e.g., methylsulfonyl), and (v) an aromatic heterocyclic group (e.g., pyridyl) optionally substituted by 1 to 3 $C_{1-6}$ alkyl groups (e.g., methyl);

or the like; or (2) a 5-membered aromatic heterocyclic group (e.g., pyrazolyl, oxazolyl, isoxazolyl, thiazolyl, isothiazolyl, thiadiazolyl, preferably isoxazolyl) or phenyl, each of which is optionally substituted by 1 to 3 substituents selected from (i) a halogen atom and (ii) a $C_{1-6}$ alkyl group.

$R^1$ is further more preferably (1) a group represented by the formula: —$COR^2$
wherein
$R^2$ is
(a) a $C_{1-6}$ alkyl group (e.g., methyl, ethyl, propyl, butyl, isobutyl, isopentyl) optionally substituted by 1 to 3 halogen atoms (e.g., a fluorine atom);
(b) a $C_{1-6}$ alkoxy group (e.g., methoxy, tert-butoxy);
(c) an amino group optionally mono- or di-substituted by $C_{1-6}$ alkyl group(s) (e.g., methyl, ethyl, propyl, isopropyl); or the like; or (2) a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 substituents selected from a $C_{1-6}$ alkyl group.

$R^1$ is still more preferably (1) a group represented by the formula: —$COR^2$ wherein
$R^2$ is
(a) a $C_{1-6}$ alkyl group (e.g., methyl, ethyl, propyl, butyl, isobutyl, isopentyl) optionally substituted by 1 to 3 halogen atoms (e.g., a fluorine atom);
(b) a $C_{1-6}$ alkoxy group (e.g., methoxy, tert-butoxy);
(c) an amino group optionally mono- or di-substituted by $C_{1-6}$ alkyl group(s) (e.g., methyl, ethyl, propyl, isopropyl); or the like.

$R^1$ is particularly preferably (1) a group represented by the formula: —$COR^2$
wherein
$R^2$ is
(a) a $C_{1-6}$ alkyl group (e.g., methyl, ethyl, propyl, butyl, isobutyl, isopentyl);
(b) a $C_{1-6}$ alkoxy group (e.g., methoxy, tert-butoxy);
(c) an amino group optionally mono- or di-substituted by $C_{1-6}$ alkyl group(s) (e.g., methyl, ethyl, propyl, isopropyl); or the like.

For ring P and ring Q, (1) ring P is an optionally further substituted 5-membered aromatic ring, ring Q is an optionally further substituted 6-membered ring, and ring P and ring Q are fused to form an optionally further substituted bicyclic aromatic ring, or (2) ring P is an optionally further substituted 5-membered non-aromatic ring, ring Q is an optionally further substituted 6-membered aromatic ring, and ring P and ring Q are fused to form an optionally further substituted bicyclic non-aromatic ring.

The case that
"(1) ring P is an optionally further substituted 5-membered aromatic ring, ring Q is an optionally further substituted 6-membered ring, and ring P and ring Q are fused to form an optionally further substituted bicyclic aromatic ring".

Examples of the "5-membered aromatic ring" of the "optionally further substituted 5-membered aromatic ring" for ring P include pyrrole, pyrazole, imidazole, triazole (1,2,3-triazole, 1,2,4-triazole, 1,3,4-triazole), tetrazole, oxazole, isoxazole, thiazole, isothiazole, oxadiazole, thiadiazole, furan, thiophene and the like. Of these, oxazole, thiazole, pyrazole and 1,2,3-triazole are preferable, and pyrazole, oxazole and thiazole are particularly preferable.

The "5-membered aromatic ring" of the "optionally further substituted 5-membered aromatic ring" for ring P optionally has 1 or 2 substituents, besides ring A, at substitutable position. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has.

Preferable examples of additional substituent for the "5-membered aromatic ring" of the "optionally further substituted 5-membered aromatic ring" for ring P include
(1) a halogen atom (e.g., a fluorine atom, a chlorine atom, a bromine atom),
(2) a $C_{1-6}$ alkyl group (e.g., methyl) optionally substituted by 1 to 3 halogen atoms (e.g., a fluorine atom),
(3) a $C_{3-6}$ cycloalkyl group (e.g., cyclopropyl) optionally substituted by 1 to 3 halogen atoms (e.g., a fluorine atom),
(4) a cyano group
and the like.

Examples of the "6-membered ring" of the "optionally further substituted 6-membered ring" for ring Q include benzene, pyridine, pyridazine, pyrimidine, pyrazine, triazine, cyclohexa-1,3-diene, dihydropyridine and the like. Of these, benzene, 1,2-dihydropyridine and cyclohexa-1,3-diene are particularly preferable.

The "6-membered ring" of the "optionally further substituted 6-membered ring" for ring Q optionally has, besides the group —O—$R^6$, 1 to 3 substituents at substitutable positions. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has.

Preferable examples of additional substituent for the "6-membered ring" of the "optionally further substituted 6-membered ring" for ring Q include
(1) a halogen atom (e.g., a fluorine atom, a chlorine atom, a bromine atom),
(2) a $C_{1-6}$ alkyl group (e.g., methyl) optionally substituted by 1 to 3 halogen atoms (e.g., a fluorine atom),
(3) a $C_{3-6}$ cycloalkyl group (e.g., cyclopropyl) optionally substituted by 1 to 3 halogen atoms (e.g., a fluorine atom),
(4) a cyano group
and the like.

Specific examples of the "bicyclic aromatic ring" of the "optionally further substituted bicyclic aromatic ring" formed by fusion of ring P and ring Q include

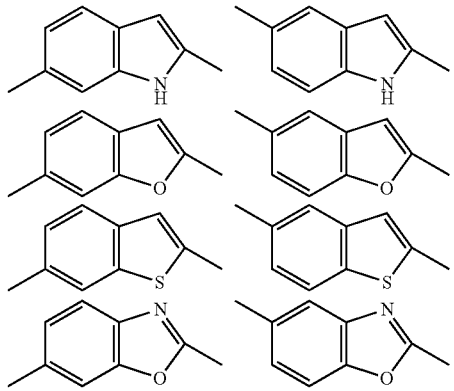

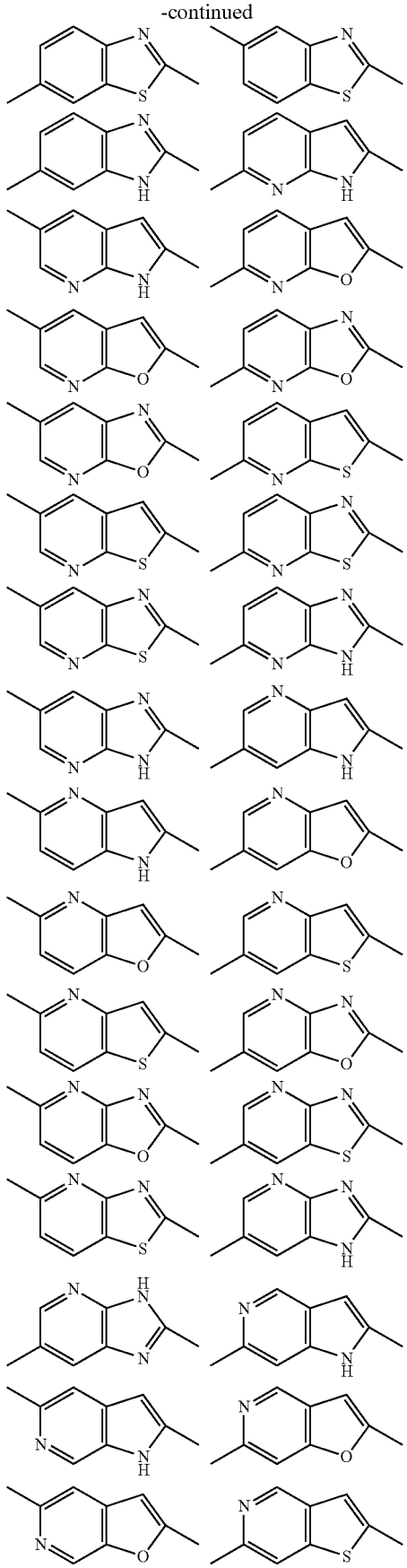
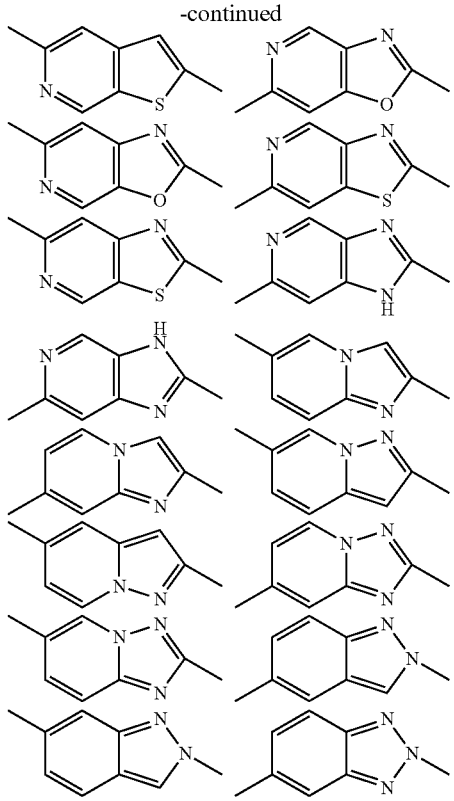

and the like.

The "bicyclic aromatic ring" of the "optionally further substituted bicyclic aromatic ring" formed by fusion of ring P and ring Q optionally has, besides the group of $R^6$—O—, 1 to 3 substituents at substitutable positions on the ring Q, and optionally has, besides ring A, 1 or 2 substituents at substitutable positions on the ring P. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has.

Preferable examples of additional substituent for the "bicyclic aromatic ring" of the "optionally further substituted bicyclic aromatic ring" formed by fusion of ring P and ring Q include (1) a halogen atom (e.g., a fluorine atom, a chlorine atom, a bromine atom), (2) a $C_{1-6}$ alkyl group (e.g., methyl) optionally substituted by 1 to 3 halogen atoms (e.g., a fluorine atom), (3) a $C_{3-6}$ cycloalkyl group (e.g., cyclopropyl) optionally substituted by 1 to 3 halogen atoms (e.g., a fluorine atom), (4) a cyano group and the like.

The "optionally further substituted bicyclic aromatic ring" formed by fusion of ring P and ring Q is preferably

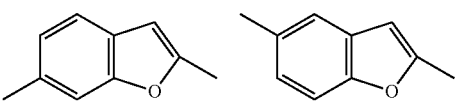

-continued

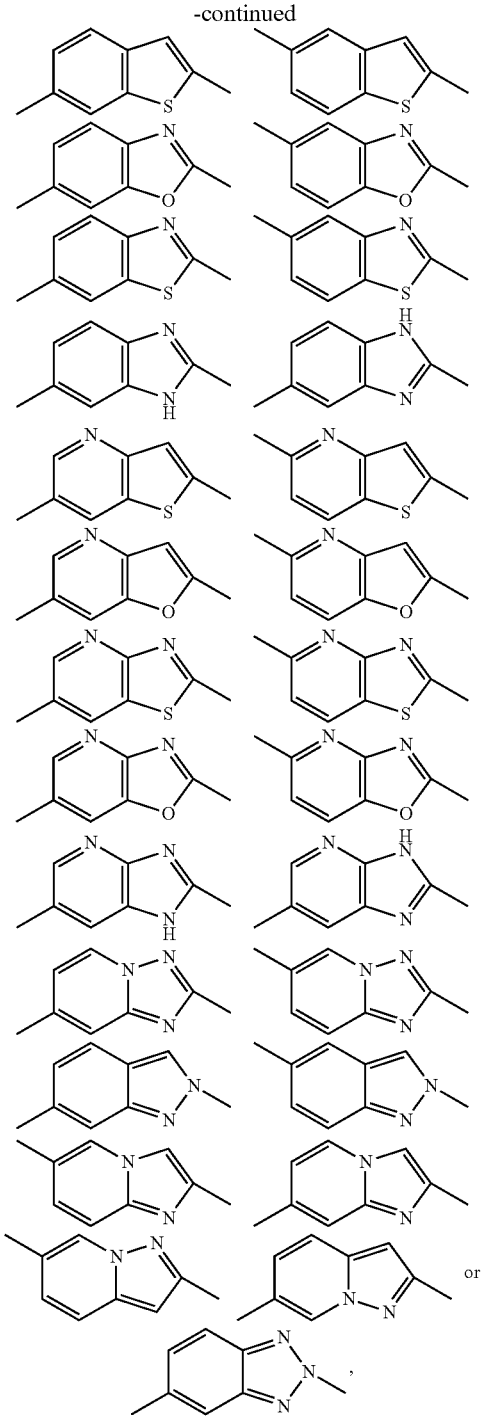

each of which is optionally substituted by 1 to 4 substituents selected from
(1) a halogen atom (e.g., a fluorine atom, a chlorine atom, a bromine atom),
(2) a $C_{1-6}$ alkyl group (e.g., methyl) optionally substituted by 1 to 3 halogen atoms (e.g., a fluorine atom),
(3) a $C_{3-6}$ cycloalkyl group (e.g., cyclopropyl) optionally substituted by 1 to 3 halogen atoms (e.g., a fluorine atom), and
(4) a cyano group.

The "optionally further substituted bicyclic aromatic heterocycle" formed by fusion of ring P and ring Q is more preferably

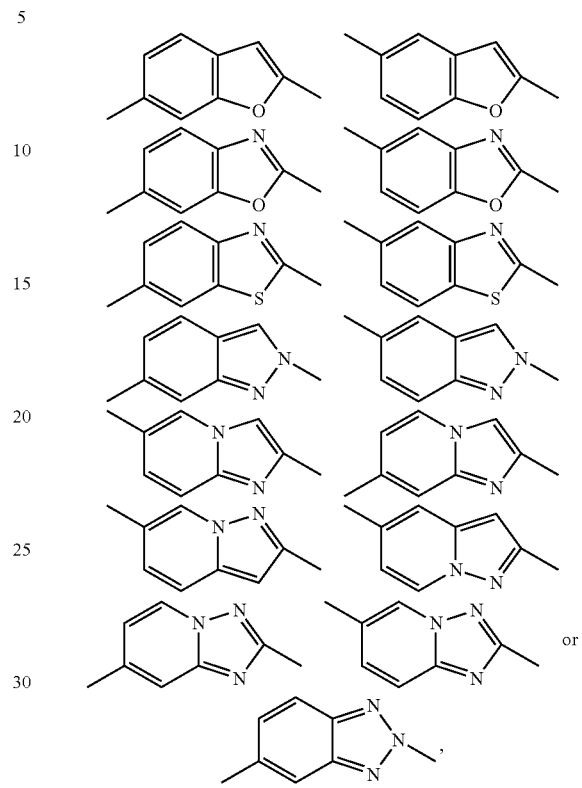

each of which is optionally substituted by 1 to 4 substituents selected from
(1) a halogen atom (e.g., a fluorine atom, a chlorine atom, a bromine atom),
(2) a $C_{1-4}$ alkyl group (e.g., methyl) optionally substituted by 1 to 3 halogen atoms (e.g., a fluorine atom),
(3) a $C_{3-6}$ cycloalkyl group (e.g., cyclopropyl) optionally substituted by 1 to 3 halogen atoms (e.g., a fluorine atom), and
(4) a cyano group.

The "optionally further substituted bicyclic aromatic heterocycle" formed by fusion of ring P and ring Q is still more preferably

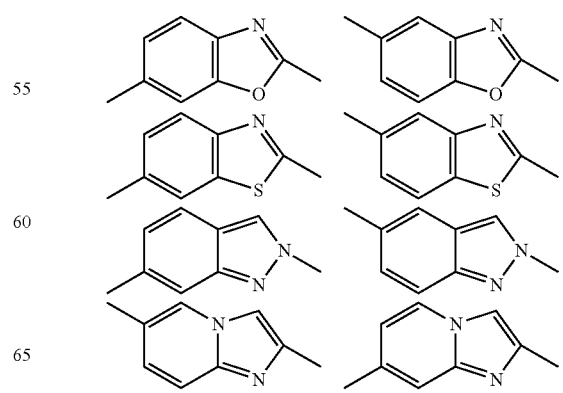

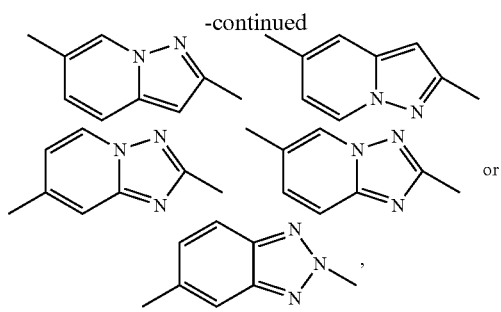

each of which is optionally substituted by 1 to 4 substituents selected from
(1) a halogen atom (e.g., a fluorine atom, a chlorine atom, a bromine atom),
(2) a $C_{1-6}$ alkyl group (e.g., methyl) optionally substituted by 1 to 3 halogen atoms (e.g., a fluorine atom),
(3) a $C_{3-6}$ cycloalkyl group (e.g., cyclopropyl) optionally substituted by 1 to 3 halogen atoms (e.g., a fluorine atom), and
(4) a cyano group.

The case that
"(2) ring P is an optionally further substituted 5-membered non-aromatic ring, ring Q is an optionally further substituted 6-membered aromatic ring, and ring P and ring Q are fused to form an optionally further substituted bicyclic non-aromatic ring".

Examples of the "5-membered non-aromatic ring" of the "optionally further substituted 5-membered non-aromatic ring" for ring P include cyclopentene, dihydrofuran, dihydrothiophene, dihydropyrrole, dihydroimidazole, dihydropyrazole, dihydrotriazole, dihydrooxazole, dihydrothiazole, dihydroisoxazole, dihydroisothiazole and the like.

The "5-membered non-aromatic ring" of the "optionally further substituted 5-membered non-aromatic ring" for ring P optionally has, besides ring A, 1 to 5 substituents at substitutable position. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has.

Preferable examples of additional substituent for the "5-membered non-aromatic ring" of the "optionally further substituted 5-membered non-aromatic ring" for ring P include
(1) a halogen atom (e.g., a fluorine atom, a chlorine atom, a bromine atom),
(2) a $C_{1-6}$ alkyl group (e.g., methyl) optionally substituted by 1 to 3 halogen atoms (e.g., a fluorine atom),
(3) a $C_{3-6}$ cycloalkyl group (e.g., cyclopropyl) optionally substituted by 1 to 3 halogen atoms (e.g., a fluorine atom),
(4) a cyano group
and the like.

Examples of the "6-membered aromatic ring" of the "optionally further substituted 6-membered aromatic ring" for ring Q include benzene, pyridine, pyridazine, pyrimidine, pyrazine, triazine and the like.

The "6-membered aromatic ring" of the "optionally further substituted 6-membered aromatic ring" for ring Q optionally has, besides the group $R^6$—O—, 1 to 3 substituents at substitutable position. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has.

Preferable examples of additional substituent for the "6-membered aromatic ring" of the "optionally further substituted 6-membered aromatic ring" for ring Q include
(1) a halogen atom (e.g., a fluorine atom, a chlorine atom, a bromine atom),
(2) a $C_{1-6}$ alkyl group (e.g., methyl) optionally substituted by 1 to 3 halogen atoms (e.g., a fluorine atom),
(3) a $C_{3-6}$ cycloalkyl group (e.g., cyclopropyl) optionally substituted by 1 to 3 halogen atoms (e.g., a fluorine atom),
(4) a cyano group
and the like.

Specific examples of the "bicyclic non aromatic ring" of the "optionally further substituted bicyclic non-aromatic ring" formed by fusion of ring P and ring Q include

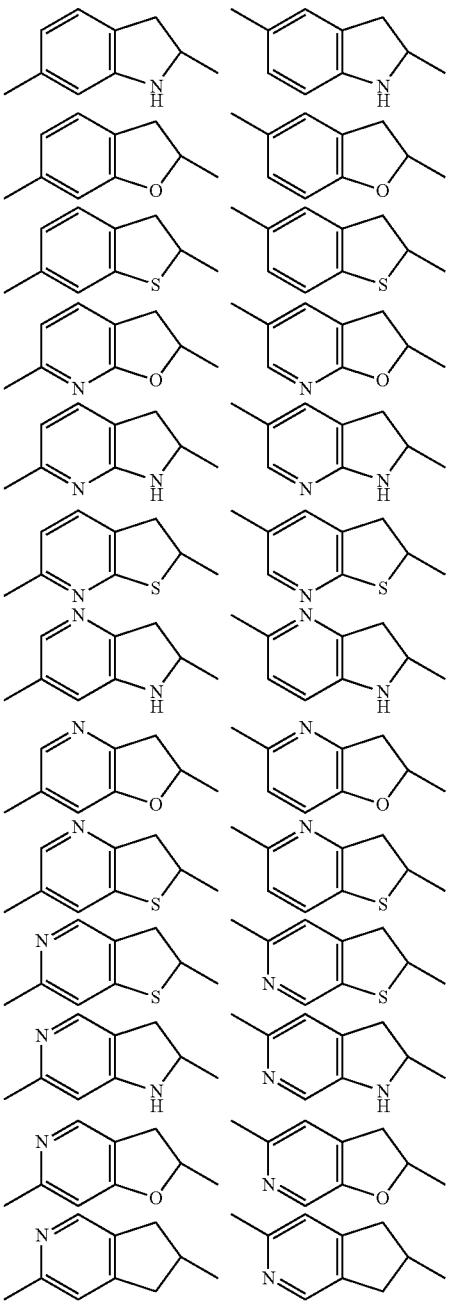

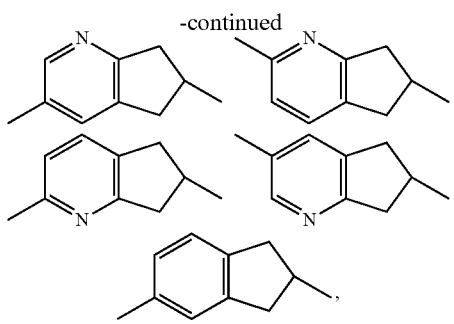

and the like.

The "bicyclic non-aromatic ring" of the "optionally further substituted bicyclic non-aromatic ring" formed by fusion of ring P and ring Q optionally has, besides ring A, 1 to 5 substituents at substitutable positions on the ring P, and optionally has, besides the group —O—R$^6$, 1 to 3 substituents at substitutable positions on the ring Q. Examples of the substituent include those similar to the substituents that the C$_{3-10}$ cycloalkyl group and the like exemplified as the "hydrocarbon group" of the "optionally substituted hydrocarbon group", which is exemplified as the "substituent" for R$^2$, optionally has.

Preferable examples of additional substituent for the "bicyclic non-aromatic ring" of the "optionally further substituted bicyclic non-aromatic ring" formed by fusion of ring P and ring Q include (1) a halogen atom (e.g., a fluorine atom, a chlorine atom, a bromine atom),
(2) a C$_{1-6}$ alkyl group (e.g., methyl) optionally substituted by 1 to 3 halogen atoms (e.g., a fluorine atom),
(3) a C$_{3-6}$ cycloalkyl group (e.g., cyclopropyl) optionally substituted by 1 to 3 halogen atoms (e.g., a fluorine atom),
(4) a cyano group
and the like.

The "optionally further substituted bicyclic non-aromatic ring" formed by fusion of ring P and ring Q is preferably

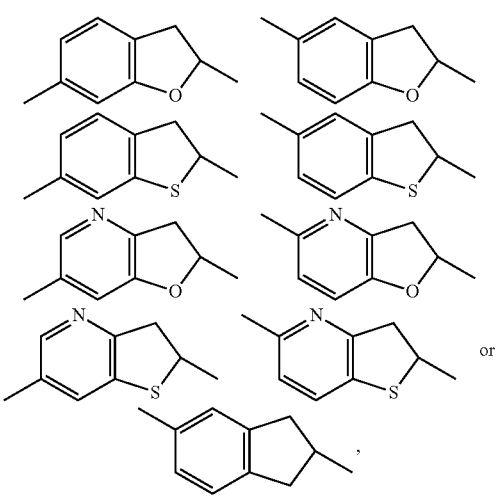

each of which is optionally substituted by 1 to 4 substituents is selected from
(1) a halogen atom (e.g., a fluorine atom, a chlorine atom, a bromine atom),
(2) a C$_{1-6}$ alkyl group (e.g., methyl) optionally substituted by 1 to 3 halogen atoms (e.g., a fluorine atom),
(3) a C$_{3-6}$ cycloalkyl group (e.g., cyclopropyl) optionally substituted by 1 to 3 halogen atoms (e.g., a fluorine atom), and
(4) a cyano group.

The "optionally further substituted bicyclic non-aromatic ring" formed by fusion of ring P and ring Q is more preferably

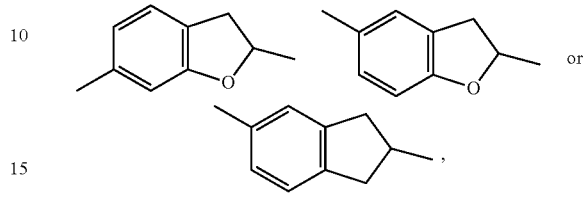

each of which is optionally substituted by 1 to 4 substituents selected from
(1) a halogen atom (e.g., a fluorine atom, a chlorine atom, a bromine atom),
(2) a C$_{1-6}$ alkyl group (e.g., methyl) optionally substituted by 1 to 3 halogen atoms (e.g., a fluorine atom),
(3) a C$_{3-6}$ cycloalkyl group (e.g., cyclopropyl) optionally substituted by 1 to 3 halogen atoms (e.g., a fluorine atom), and
(4) a cyano group.

The "optionally further substituted bicyclic non-aromatic ring" formed by fusion of ring P and ring Q is still more preferably

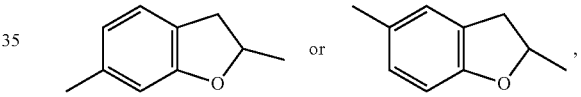

each of which is optionally substituted by 1 to 4 substituents selected from
(1) a halogen atom (e.g., a fluorine atom, a chlorine atom, a bromine atom),
(2) a C$_{1-6}$ alkyl group (e.g., methyl) optionally substituted by 1 to 3 halogen atoms (e.g., a fluorine atom),
(3) a C$_{3-6}$ cycloalkyl group (e.g., cyclopropyl) optionally substituted by 1 to 3 halogen atoms (e.g., a fluorine atom), and
(4) a cyano group.

The "optionally further substituted bicyclic aromatic heterocycle" or "optionally further substituted bicyclic non-aromatic ring" formed by fusion of ring P and ring Q is preferably

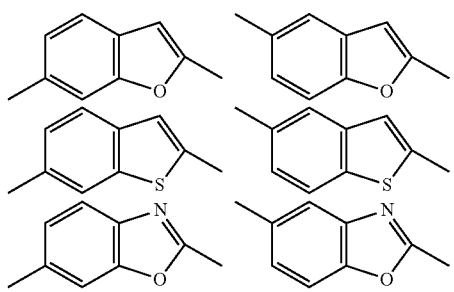

-continued

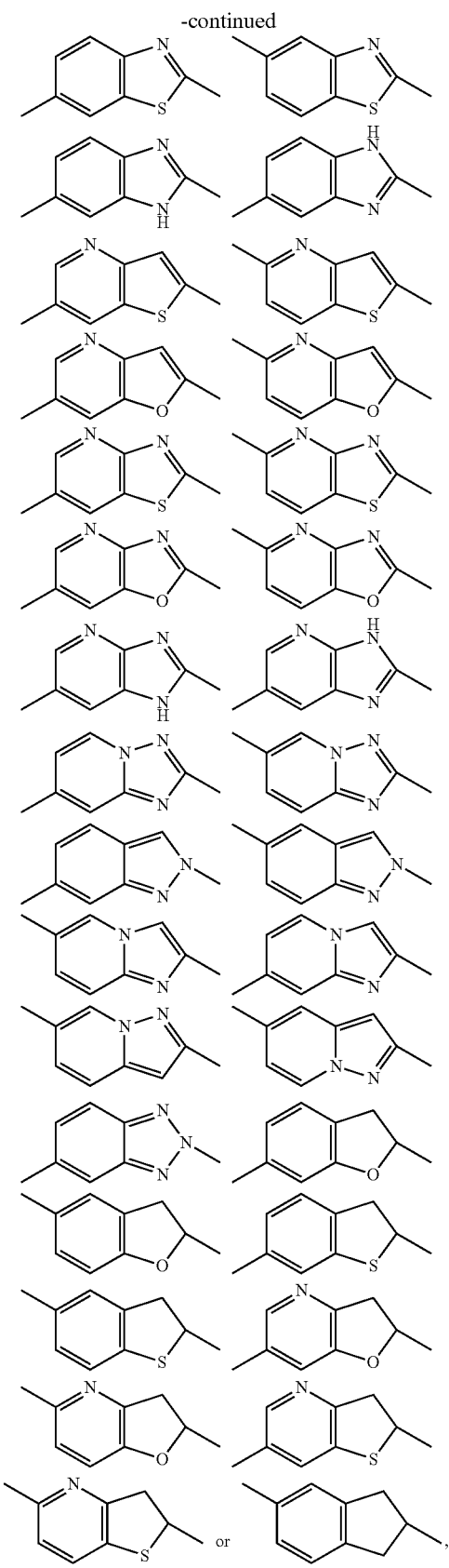

each of which is optionally substituted by 1 to 4 substituents selected from (1) a halogen atom (e.g., a fluorine atom, a chlorine atom, a bromine atom),
(2) a $C_{1-6}$ alkyl group (e.g., methyl) optionally substituted by 1 to 3 halogen atoms (e.g., a fluorine atom),
(3) a $C_{3-6}$ cycloalkyl group (e.g., cyclopropyl) optionally substituted by 1 to 3 halogen atoms (e.g., a fluorine atom), and
(4) a cyano group.

The "optionally further substituted bicyclic aromatic heterocycle" or "optionally further substituted bicyclic non-aromatic ring" formed by fusion of ring P and ring Q is more preferably

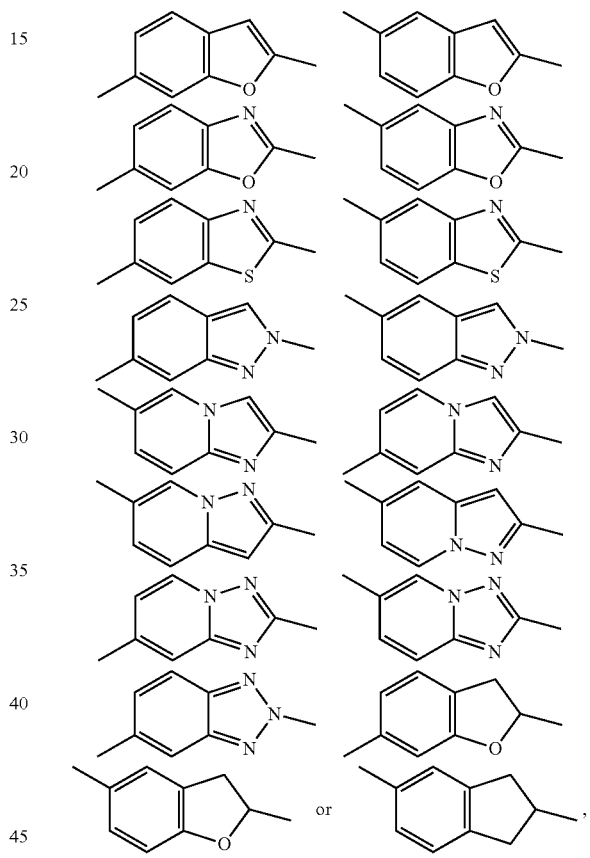

each of which is optionally substituted by 1 to 4 substituents selected from (1) a halogen atom (e.g., a fluorine atom, a chlorine atom, a bromine atom),
(2) a $C_{1-6}$ alkyl group (e.g., methyl) optionally substituted by 1 to 3 halogen atoms (e.g., a fluorine atom),
(3) a $C_{3-6}$ cycloalkyl group (e.g., cyclopropyl) optionally substituted by 1 to 3 halogen atoms (e.g., a fluorine atom), and
(4) a cyano group.

The "optionally further substituted bicyclic aromatic heterocycle" or "optionally further substituted bicyclic non-aromatic ring" formed by fusion of ring P and ring Q is still more preferably

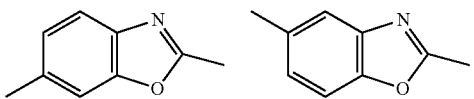

each of which is optionally substituted by 1 to 4 substituents selected from
  (1) a halogen atom (e.g., a fluorine atom, a chlorine atom, a bromine atom),
  (2) a $C_{1-6}$ alkyl group (e.g., methyl) optionally substituted by 1 to 3 halogen atoms (e.g., a fluorine atom),
  (3) a $C_{3-6}$ cycloalkyl group (e.g., cyclopropyl) optionally substituted by 1 to 3 halogen atoms (e.g., a fluorine atom), and
  (4) a cyano group.

$R^3$ is a $C_{1-6}$ alkyl group optionally substituted by halogen atom(s), or an optionally substituted $C_{3-6}$ cycloalkyl group.

The "$C_{1-6}$ alkyl group" of the "$C_{1-6}$ alkyl group optionally substituted by halogen atom(s)" for $R^3$ optionally has preferably 1 to 7, more preferably 1 to 3 halogen atoms, at substitutable positions.

Examples of the "$C_{3-6}$ cycloalkyl group" of the "optionally substituted $C_{3-6}$ cycloalkyl group" for $R^3$ include cyclopropyl, cyclobutyl, cyclopentyl and cyclohexyl.

The "$C_{3-6}$ cycloalkyl group" of the "optionally substituted $C_{3-6}$ cycloalkyl group" for $R^3$ optionally has 1 to 7 substituents at substitutable positions. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has.

$R^3$ is preferably a $C_{1-6}$ alkyl group optionally substituted by 1 to 7 (preferably 1 to 3) halogen atoms (e.g., a fluorine atom), or a $C_{3-6}$ cycloalkyl group, more preferably a $C_{1-6}$ alkyl group optionally substituted by 1 to 3 halogen atoms (e.g., a fluorine atom), still more preferably a $C_{1-6}$ alkyl group, particularly preferably methyl.

$R^{4a}$ and $R^{4b}$ are independently a hydrogen atom or a substituent.

Examples of the "substituent" for $R^{4a}$ or $R^{4b}$ include those similar to the "substituent" for $R^2$.

$R^{4a}$ is preferably a hydrogen atom or a fluorine atom, particularly preferably a hydrogen atom.

$R^{4b}$ is preferably a hydrogen atom or a fluorine atom, particularly preferably a hydrogen atom.

X is O, CO, $CR^{5a}R^{5b}$ wherein $R^{5a}$ and $R^{5b}$ are independently a hydrogen atom or a substituent, $NR^{5c}$ wherein $R^{5c}$ is a hydrogen atom or an optionally substituted $C_{1-6}$ alkyl group, S, SO or $S(O)_2$.

Examples of the "substituent" for $R^{5a}$ or $R^{5b}$ include those similar to the "substituent" for $R^2$.

The "$C_{1-6}$ alkyl group" of the "optionally substituted $C_{1-6}$ alkyl group" for $R^{5c}$ optionally has 1 to 3 substituents at substitutable positions. Examples of the substituent include those similar to the substituents that the $C_{1-10}$ alkyl group and the like exemplified as the "hydrocarbon group" of the "optionally substituted hydrocarbon group", which is exemplified as the "substituent" for $R^2$, optionally has.

X is preferably O, CO or $CR^{5a}R^{5b}$ wherein $R^{5a}$ and $R^{5b}$ are the same as above, more preferably O, CO or $CH_2$, particularly preferably O.

$R^6$ is an optionally substituted $C_{1-6}$ alkyl group or an optionally substituted $C_{3-6}$ cycloalkyl group.

The "$C_{1-6}$ alkyl group" of the "optionally substituted $C_{1-6}$ alkyl group" for $R^6$ optionally has 1 to 3 substituents at substitutable positions. Examples of the substituent include those similar to the substituents that the $C_{1-10}$ alkyl group and the like exemplified as the "hydrocarbon group" of the "optionally substituted hydrocarbon group", which is exemplified as the "substituent" for $R^2$, optionally has.

Examples of the "optionally substituted $C_{3-6}$ cycloalkyl group" for $R^6$ include those similar to the "optionally substituted $C_{3-6}$ cycloalkyl group" for $R^3$.

$R^6$ is preferably
(1) a $C_{1-6}$ alkyl group (e.g., methyl, ethyl, propyl, isopropyl, butyl) optionally substituted by 1 to 3 substituents selected from
  (a) a halogen atom (e.g., a fluorine atom), and
  (b) a $C_{3-6}$ cycloalkyl group (e.g., cyclopropyl, cyclobutyl) optionally substituted by 1 to 3 halogen atoms (e.g., a fluorine atom); or
(2) a $C_{3-6}$ cycloalkyl group (e.g., cyclopropyl).

$R^6$ is more preferably a $C_{1-6}$ alkyl group (e.g., methyl, ethyl, propyl, isopropyl, butyl) optionally substituted by 1 to 3 substituents selected from
  (a) a halogen atom (e.g., a fluorine atom), and
  (b) a $C_{3-6}$ cycloalkyl group (e.g., cyclopropyl, cyclobutyl) optionally substituted by 1 to 3 halogen atoms (e.g., a fluorine atom).

$R^6$ is still more preferably a $C_{1-6}$ alkyl group optionally substituted by 1 to 3 $C_{3-6}$ cycloalkyl groups optionally substituted by 1 to 3 halogen atoms.

In another embodiment, $R^6$ is preferably a $C_{1-6}$ alkyl group optionally substituted by 1 to 3 halogen atoms.

Ring A is an optionally further substituted 5- or 6-membered aromatic ring.

Examples of the "5- or 6-membered aromatic ring" of the "optionally further substituted 5- or 6-membered aromatic ring" for ring A include benzene, pyrrole, pyrazole, imidazole, triazole (1,2,3-triazole, 1,2,4-triazole, 1,3,4-triazole), tetrazole, oxazole, isoxazole, thiazole, isothiazole, oxadiazole (1,2,4-oxadiazole, 1,3,4-oxadiazole), thiadiazole (1,2,4-thiadiazole, 1,3,4-thiadiazole), furan, thiophene, pyridine, pyridazine, pyrimidine, pyrazine, triazine and the like.

The "5- or 6-membered aromatic ring" of the "optionally further substituted 5- or 6-membered aromatic ring" for ring A is preferably benzene, optionally oxidized pyridine, pyrimidine, pyrazole, oxazole, isoxazole, thiazole, isothiazole, oxadiazole, thiadiazole or the like, more preferably benzene, optionally oxidized pyridine, pyrimidine, pyrazole, isoxazole or oxadiazole, still more preferably benzene, optionally oxidized pyridine, pyrimidine, pyrazole or isoxazole.

The "5- or 6-membered aromatic ring" of the "optionally further substituted 5- or 6-membered aromatic ring" for ring A optionally has, besides group —X—CH($R^{4a}$)($R^{4b}$)—CH($R^3$)—NH—$R^1$ and ring P, 1 to 4 substituents (preferably 1 to 3 substituents) at substitutable positions. Examples of the substituent include those similar to the substituents that the "heterocyclic group" of the "optionally substituted heterocyclic group", which is exemplified as the "substituent" for $R^2$, optionally has.

Ring A is preferably benzene, optionally oxidized pyridine, pyrimidine, pyrazole, oxazole, isoxazole, thiazole, isothiazole, oxadiazole or thiadiazole, each of which is optionally substituted by 1 to 3 substituents selected from
(1) a halogen atom (e.g., a fluorine atom, a chlorine atom),
(2) a $C_{1-6}$ alkyl group (e.g., methyl) optionally substituted by 1 to 3 halogen atoms,
(3) a $C_{1-6}$ alkoxy group (e.g., methoxy), and
(4) a $C_{7-13}$ aralkyl group (e.g., benzyl).

Ring A is more preferably benzene, optionally oxidized pyridine, pyrimidine, pyrazole, isoxazole or oxadiazole, each of which is optionally substituted by 1 to 3 substituents selected from
(1) a halogen atom (e.g., a fluorine atom, a chlorine atom),
(2) a $C_{1-6}$ alkyl group (e.g., methyl) optionally substituted by 1 to 3 halogen atoms,
(3) a $C_{1-6}$ alkoxy group (e.g., methoxy), and
(4) a $C_{7-13}$ aralkyl group (e.g., benzyl).

Ring A is still more preferably benzene, optionally oxidized pyridine, pyrimidine, pyrazole or isoxazole, each of which is optionally substituted by 1 to 3 substituents selected from
(1) a halogen atom (e.g., a fluorine atom, a chlorine atom),
(2) a $C_{1-6}$ alkyl group (e.g., methyl) optionally substituted by 1 to 3 halogen atoms,
(3) a $C_{1-6}$ alkoxy group (e.g., methoxy), and
(4) a $C_{7-13}$ aralkyl group (e.g., benzyl).

Preferable examples of compound (I) include the following compounds.

[Compound A-1]

Compound (I) wherein $R^1$ is (1) a group represented by the formula: —$COR^2$ wherein $R^2$ is an optionally substituted $C_{1-6}$ alkyl group, an optionally substituted $C_{1-6}$ alkoxy group, an optionally substituted $C_{3-10}$ cycloalkyl group, an optionally substituted $C_{6-14}$ aryl group, an optionally substituted amino group, an optionally substituted aromatic heterocyclic group or an optionally substituted non-aromatic heterocyclic group; or (2) an optionally substituted 5- or 6-membered aromatic group;

$R^3$ is a $C_{1-6}$ alkyl group optionally substituted by 1 to 7 halogen atoms, or a $C_{3-6}$ cycloalkyl group;

$R^{4a}$ and $R^{4b}$ are independently a hydrogen atom or a fluorine atom;

X is O, CO, $CR^{5a}R^{5b}$ wherein $R^{5a}$ and $R^{5b}$ is as defined above, $NR^{5c}$ wherein $R^{5c}$ is as defined above, S, SO or $S(O)_2$;

ring A is benzene, pyridine, pyrazole, oxazole, isoxazole, thiazole, isothiazole, oxadiazole or thiadiazole, each of which is optionally substituted by
(1) a halogen atom (e.g., a fluorine atom, a chlorine atom); or
(2) a $C_{1-6}$ alkyl group (e.g., methyl) optionally substituted by 1 to 3 halogen atoms;

ring P and ring Q are fused to form

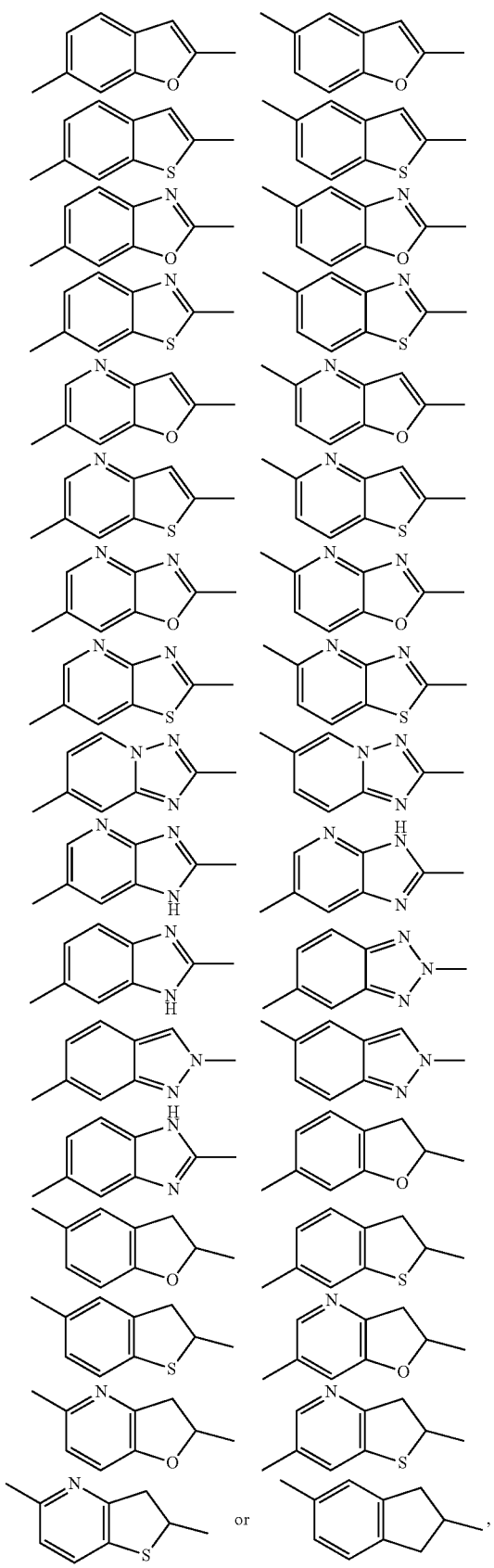

each of which is optionally substituted by 1 to 4 substituents selected from
(1) a halogen atom (e.g., a fluorine atom, a chlorine atom),
(2) a $C_{1-6}$ alkyl group optionally substituted by halogen atom(s) (e.g., methyl, trifluoromethyl), and
(3) a $C_{3-6}$ cycloalkyl group (e.g., cyclopropyl) optionally substituted by halogen atom(s); and $R^6$ is
(1) a $C_{1-6}$ alkyl group optionally substituted by 1 to 3 substituents selected from a halogen atom and a $C_{3-6}$ cycloalkyl group; or
(2) a $C_{3-6}$ cycloalkyl group (e.g., cyclopropyl).

[Compound B-1]
Compound (I) wherein
$R^1$ is
(1) a group represented by the formula: —$COR^2$
  wherein
  $R^2$ is
  (a) a $C_{1-6}$ alkyl group (e.g., methyl, ethyl, propyl, butyl, isobutyl, isopentyl) optionally substituted by 1 to 3 substituents selected from
    (i) an amino group,
    (ii) a carboxy group,
    (iii) a $C_{1-6}$ alkoxy-carbonyl group (e.g., methoxycarbonyl, ethoxycarbonyl),
    (iv) a $C_{6-14}$ aryl group (e.g., phenyl), and
    (v) a $C_{1-6}$ alkoxy group (e.g., methoxy);
  (b) a $C_{1-6}$ alkoxy group (e.g., methoxy, tert-butoxy);
  (c) an amino group optionally mono- or di-substituted by substituent(s) selected from
    (i) a $C_{1-6}$ alkyl group (e.g., methyl, ethyl, propyl, isopropyl) optionally substituted by 1 to 3 $C_{6-14}$ aryl groups (e.g., phenyl),
    (ii) a $C_{6-14}$ aryl group (e.g., phenyl),
    (iii) a $C_{3-10}$ cycloalkyl group (e.g., cyclopentyl, cyclohexyl),
    (iv) a $C_{1-6}$ alkylsulfonyl group (e.g., methylsulfonyl), and
    (v) an aromatic heterocyclic group (e.g., pyridyl) optionally substituted by 1 to 3 $C_{1-6}$ alkyl groups (e.g., methyl);
  or the like; or
(2) a 5-membered aromatic heterocyclic group (e.g., pyrazolyl, oxazolyl, isoxazolyl, thiazolyl, isothiazolyl, thiadiazolyl) or phenyl, each of which is optionally substituted by 1 to 3% substituents selected from (i) a halogen atom and (ii) a $C_{1-6}$ alkyl group;
$R^3$ is a $C_{1-6}$ alkyl group optionally substituted by 1 to 7 halogen atoms, or a $C_{3-6}$ cycloalkyl group;
$R^{4a}$ and $R^{4b}$ are independently a hydrogen atom or a fluorine atom;
X is O or $CH_2$;
ring A is benzene, pyridine, pyrazole, oxazole, isoxazole, thiazole, isothiazole, oxadiazole or thiadiazole, each of which is optionally substituted by
  (1) a halogen atom (e.g., a fluorine atom, a chlorine atom); or
  (2) a $C_{1-6}$ alkyl group (e.g., methyl) optionally substituted by 1 to 3 halogen atoms;
ring P and ring Q are fused to form

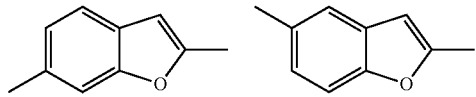

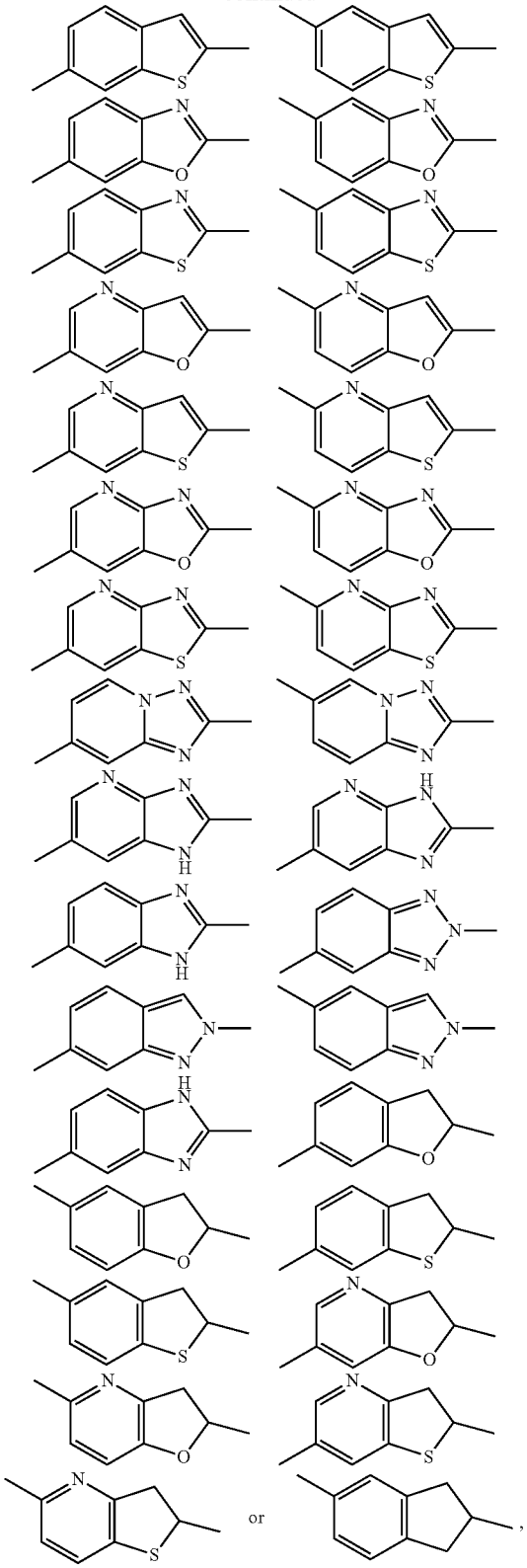

each of which is optionally substituted by 1 to 4 substituents selected from
(1) a halogen atom (e.g., a fluorine atom),
(2) a $C_{1-6}$ alkyl group optionally substituted by halogen atom(s) (e.g., methyl, trifluoromethyl), and (3) a $C_{3-6}$ cycloalkyl group (e.g., cyclopropyl) optionally substituted by halogen atom(s); and $R^6$ is (1) a $C_{1-6}$ alkyl group optionally substituted by 1 to 3 substituents selected from a halogen atom and a $C_{3-6}$ cycloalkyl group; or (2) a $C_{3-6}$ cycloalkyl group (e.g., cyclopropyl).

[Compound C-1]

Compound (I) wherein $R^1$ is (1) a group represented by the formula: —$COR^2$
wherein
$R^2$ is
(a) a $C_{1-6}$ alkyl group (e.g., methyl, ethyl, propyl, butyl, isobutyl, isopentyl);
(b) a $C_{1-6}$ alkoxy group (e.g., methoxy, tert-butoxy);
(c) an amino group optionally mono- or di-substituted by $C_{1-6}$ alkyl group(s) (e.g., methyl, ethyl, propyl, isopropyl); or the like; or (2) a 5-membered aromatic heterocyclic group (e.g., pyrazolyl, oxazolyl, isoxazolyl, thiazolyl, isothiazolyl, thiadiazolyl) optionally substituted by 1 to 3 substituents selected from a $C_{1-6}$ alkyl group;

$R^3$ is a $C_{1-6}$ alkyl group optionally substituted by 1 to 7 halogen atoms, or a $C_{3-6}$ cycloalkyl group;

$R^{4a}$ and $R^{4b}$ are independently a hydrogen atom or a fluorine atom;

X is O or $CH_2$;

ring A is benzene, pyridine, pyrazole, oxazole, isoxazole, thiazole, isothiazole, thiadiazole, oxadiazole or thiadiazole, each of which is optionally substituted by (1) a halogen atom (e.g., a fluorine atom, a chlorine atom); or (2) a $C_{1-6}$ alkyl group (e.g., methyl) optionally substituted by 1 to 3 halogen atoms;

ring P and ring Q are fused to form

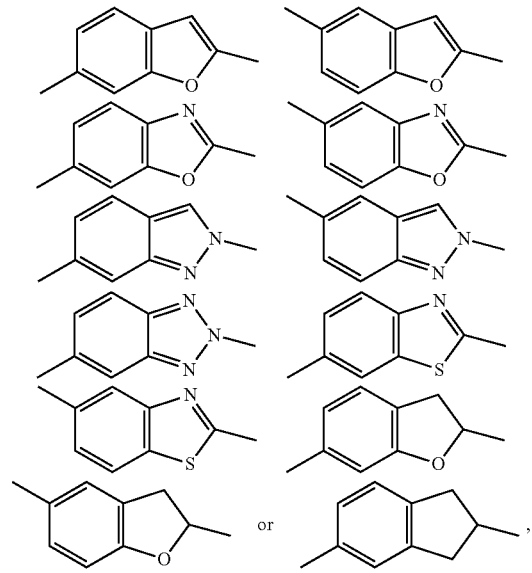

each of which is optionally substituted by 1 to 4 substituents selected from (1) a halogen atom (e.g., a fluorine atom), (2) a $C_{1-6}$ alkyl group optionally substituted by halogen atom(s) (e.g., methyl, trifluoromethyl), and (3) a $C_{3-6}$ cycloalkyl group (e.g., cyclopropyl) optionally substituted by halogen atom(s); and $R^6$ is (1) a $C_{1-6}$ alkyl group optionally substituted by 1 to 3 substituents selected from a halogen atom and a $C_{3-6}$ cycloalkyl group; or (2) a $C_{3-6}$ cycloalkyl group (e.g., cyclopropyl).

[Compound A-2]

Compound (I) wherein $R^1$ is (1) a group represented by the formula: —$COR^2$ wherein $R^2$ is an optionally substituted $C_{1-6}$ alkyl group, an optionally substituted $C_{1-6}$ alkoxy group, an optionally substituted $C_{3-10}$ cycloalkyl group, an optionally substituted $C_{6-14}$ aryl group, an optionally substituted amino group, an optionally substituted aromatic heterocyclic group or an optionally substituted non-aromatic heterocyclic group; or (2) an optionally substituted 5- or 6-membered aromatic ring group;

$R^3$ is a $C_{1-6}$ alkyl group optionally substituted by 1 to 7 halogen atoms, or a $C_{3-6}$ cycloalkyl group;

$R^{4a}$ and $R^{4b}$ are independently a hydrogen atom or a fluorine atom;

X is O, CO, $CR^{5a}R^{5b}$ wherein $R^{5a}$ and $R^{5b}$ is as defined above, $NR^{5c}$ wherein $R^{5c}$ is as defined above, S, SO, or $S(O)_2$;

ring A is benzene, pyridine, pyrazole, oxazole, isoxazole, thiazole, isothiazole, oxadiazole or thiadiazole, each of which is optionally substituted by (1) a halogen atom (e.g., a fluorine atom, a chlorine atom); or (2) a $C_{1-6}$ alkyl group (e.g., methyl) optionally substituted by 1 to 3 halogen atoms;

ring P and ring Q are fused to form

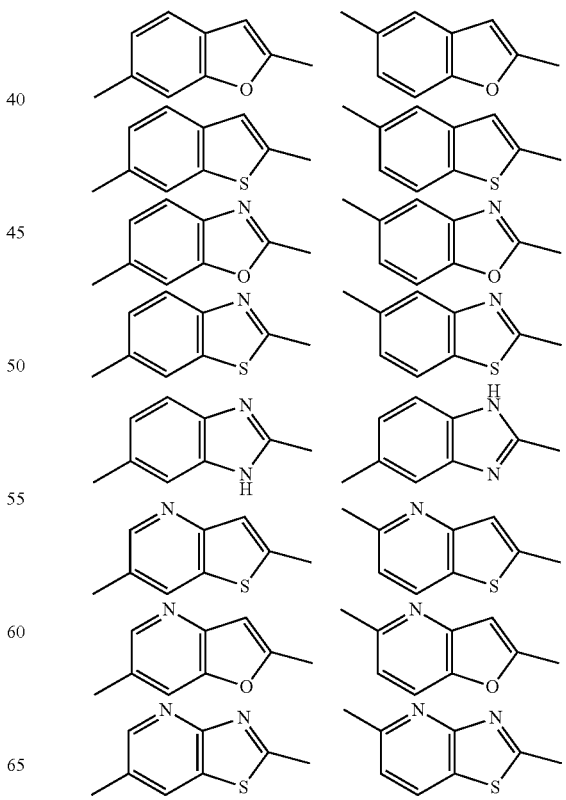

-continued

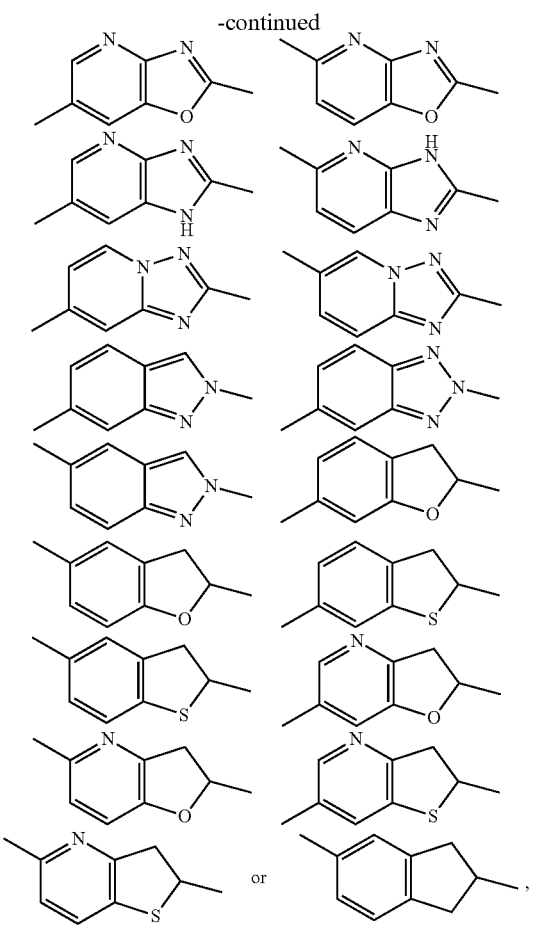

each of which is optionally substituted by 1 to 4 substituents selected from
(1) a halogen atom (e.g., a fluorine atom, a chlorine atom),
(2) a $C_{1-6}$ alkyl group optionally substituted by halogen atom(s) (e.g., methyl, trifluoromethyl), and
(3) a $C_{3-6}$ cycloalkyl group (e.g., cyclopropyl) optionally substituted by halogen atom(s); and
$R^6$ is
(1) a $C_{1-6}$ alkyl group optionally substituted by 1 to 3 substituents selected from
(a) a halogen atom, and
(b) a $C_{3-6}$ cycloalkyl group optionally substituted by 1 to 3 halogen atoms; or
(2) a $C_{3-6}$ cycloalkyl group (e.g., cyclopropyl).

[Compound B-2]
Compound (I) wherein
$R^1$ is
(1) a group represented by the formula: —$COR^2$
wherein
$R^2$ is
(a) a $C_{1-6}$ alkyl group (e.g., methyl, ethyl, propyl, butyl, isobutyl, isopentyl) optionally substituted by 1 to 3 substituents selected from
(i) an amino group,
(ii) a carboxy group,
(iii) a $C_{1-6}$ alkoxy-carbonyl group (e.g., methoxycarbonyl, ethoxycarbonyl),
(iv) a $C_{6-14}$ aryl group (e.g., phenyl), and
(v) a $C_{1-6}$ alkoxy group (e.g., methoxy);

(b) a $C_{1-6}$ alkoxy group (e.g., methoxy, tert-butoxy);
(c) an amino group optionally mono- or di-substituted by substituent(s) selected from
(i) a $C_{1-6}$ alkyl group (e.g., methyl, ethyl, propyl, isopropyl) optionally substituted by 1 to 3 $C_{6-14}$ aryl groups (e.g., phenyl),
(ii) a $C_{6-14}$ aryl group (e.g., phenyl),
(iii) a $C_{3-10}$ cycloalkyl group (e.g., cyclopentyl, cyclohexyl),
(iv) a $C_{1-6}$ alkylsulfonyl group (e.g., methylsulfonyl), and
(v) an aromatic heterocyclic group (e.g., pyridyl) optionally substituted by 1 to 3 $C_{1-6}$ alkyl groups (e.g., methyl);
or the like; or
(2) a 5-membered aromatic heterocyclic group (e.g., pyrazolyl, oxazolyl, isoxazolyl, thiazolyl, isothiazolyl, thiadiazolyl) or phenyl, each of which is optionally substituted by 1 to 3 substituents selected from (i) a halogen atom and (ii) a $C_{1-6}$ alkyl group;
$R^3$ is a $C_{1-6}$ alkyl group optionally substituted by 1 to 7 halogen atoms, or a $C_{3-6}$ cycloalkyl group;
$R^{4a}$ and $R^{4b}$ are independently a hydrogen atom or a fluorine atom;
X is O or $CH_2$;
ring A is benzene, pyridine, pyrazole, oxazole, isoxazole, thiazole, isothiazole, oxadiazole or thiadiazole, each of which is optionally substituted by
(1) a halogen atom (e.g., a fluorine atom, a chlorine atom); or
(2) a $C_{1-6}$ alkyl group (e.g., methyl) optionally substituted by 1 to 3 halogen atoms;
ring P and ring Q are fused to form

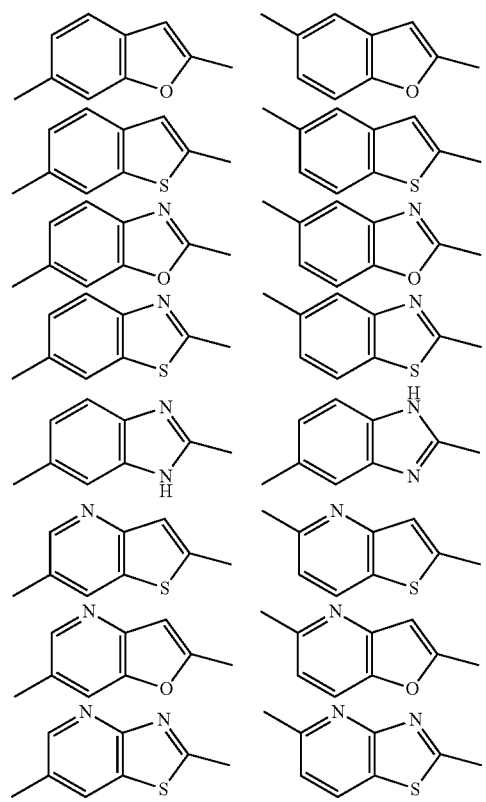

43

-continued

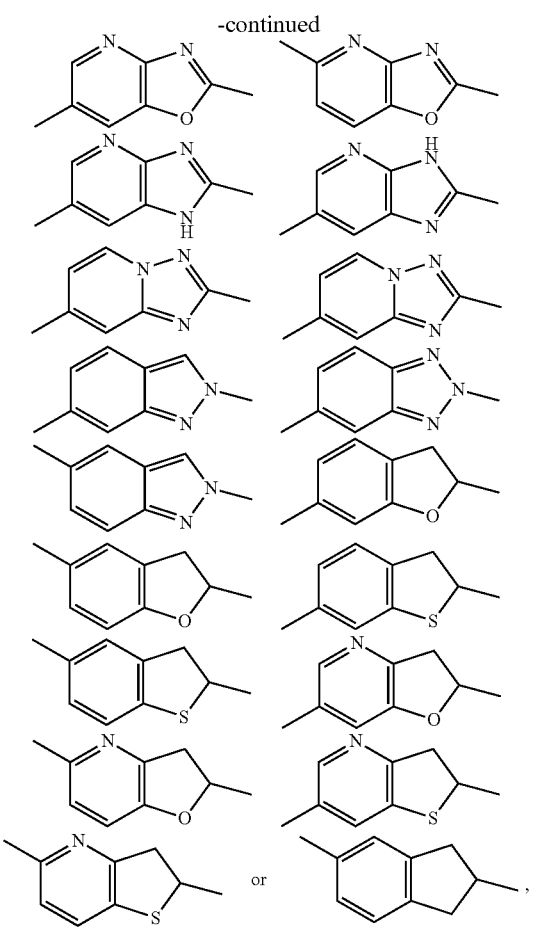

each of which is optionally substituted by 1 to 4 substituents selected from
(1) a halogen atom (e.g., a fluorine atom),
(2) a $C_{1-6}$ alkyl group optionally substituted by halogen atom(s) (e.g., methyl, trifluoromethyl), and
(3) a $C_{3-6}$ cycloalkyl group (e.g., cyclopropyl) optionally substituted by halogen atom(s); and $R^6$ is
(1) a $C_{1-6}$ alkyl group optionally substituted by 1 to 3 substituents selected from
(a) a halogen atom, and
(b) a $C_{3-6}$ cycloalkyl group optionally substituted by 1 to 3 halogen atoms; or
(2) a $C_{3-6}$ cycloalkyl group (e.g., cyclopropyl).

[Compound C-2]
Compound (I) wherein
$R^1$ is
(1) a group represented by the formula: —$COR^2$
wherein
$R^2$ is
(a) a $C_{1-6}$ alkyl group (e.g., methyl, ethyl, propyl, butyl, isobutyl, isopentyl);
(b) a $C_{1-6}$ alkoxy group (e.g., methoxy, tert-butoxy);
(c) an amino group optionally mono- or di-substituted by $C_{1-6}$ alkyl group(s) (e.g., methyl, ethyl, propyl, isopropyl); or the like; or
(2) a 5-membered aromatic heterocyclic group (e.g., pyrazolyl, oxazolyl, isoxazolyl, thiazolyl, isothiazolyl, thiadiazolyl) optionally substituted by 1 to 3 substituents selected from a $C_{1-6}$ alkyl group;

44

$R^3$ is a $C_{1-6}$ alkyl group optionally substituted by 1 to 7 halogen atoms, or a $C_{3-6}$ cycloalkyl group;
$R^{4a}$ and $R^{4b}$ are independently a hydrogen atom or a fluorine atom;
X is O or $CH_2$;
ring A is benzene, pyridine, pyrazole, oxazole, isoxazole, thiazole, isothiazole, oxadiazole or thiadiazole, each of which is optionally substituted by
(1) a halogen atom (e.g., a fluorine atom, a chlorine atom); or
(2) a $C_{1-6}$ alkyl group (e.g., methyl) optionally substituted by 1 to 3 halogen atoms;
ring P and ring Q are fused to form

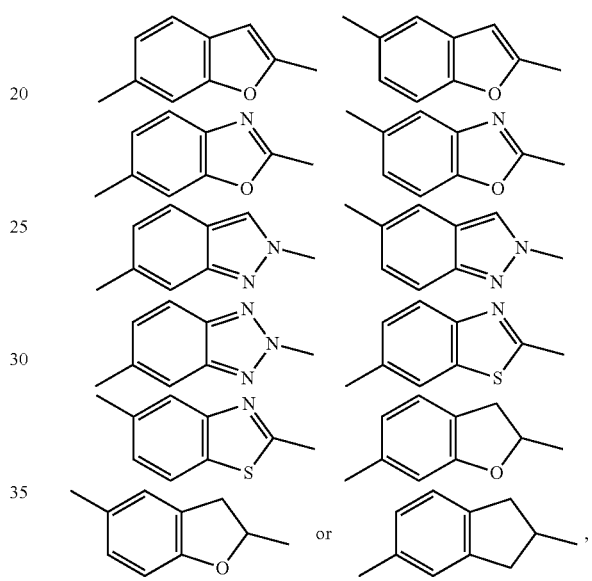

each of which is optionally substituted by 1 to 4 substituents selected from
(1) a halogen atom (e.g., a fluorine atom),
(2) a $C_{1-6}$ alkyl group optionally substituted by halogen atom(s) (e.g., methyl, trifluoromethyl), and
(3) a $C_{3-6}$ cycloalkyl group (e.g., cyclopropyl) optionally substituted by halogen atom(s); and $R^6$ is
(1) a $C_{1-6}$ alkyl group optionally substituted by 1 to 3 substituents selected from
(a) a halogen atom, and
(b) a $C_{3-6}$ cycloalkyl group optionally substituted by 1 to 3 halogen atoms; or
(2) a $C_{3-6}$ cycloalkyl group (e.g., cyclopropyl).

[Compound A-3]
Compound (I) wherein
$R^1$ is
(1) a group represented by the formula: —$COR^2$ wherein $R^2$ is an optionally substituted $C_{1-6}$ alkyl group, an optionally substituted $C_{1-6}$ alkoxy group, an optionally substituted $C_{3-10}$ cycloalkyl group, an optionally substituted $C_{6-14}$ aryl group, an optionally substituted amino group, an optionally substituted aromatic heterocyclic group or an optionally substituted non-aromatic heterocyclic group; or (2) an optionally substituted 5- or 6-membered aromatic ring group
(preferably
(1) a group represented by the formula: —COR$^2$
wherein
R$^2$ is
(a) a C$_{1-6}$ alkyl group (e.g., methyl, ethyl, propyl, butyl, isobutyl, isopentyl) optionally substituted by 1 to 3 substituents selected from
(i) an amino group,
(ii) a carboxy group,
(iii) a C$_{1-6}$ alkoxy-carbonyl group (e.g., methoxycarbonyl, ethoxycarbonyl),
(iv) a C$_{6-14}$ aryl group (e.g., phenyl),
(v) a C$_{1-6}$ alkoxy group (e.g., methoxy), and
(vi) a halogen atom (e.g., a fluorine atom);
(b) a C$_{1-6}$ alkoxy group (e.g., methoxy, tert-butoxy);
(c) a C$_{3-10}$ cycloalkyl group (e.g., cyclopropyl, cyclopentyl);
(d) a C$_{6-14}$ aryl group (e.g., phenyl);
(e) an amino group optionally mono- or di-substituted by substituent(s) selected from
(i) a C$_{1-6}$ alkyl group (e.g., methyl, ethyl, propyl, isopropyl) optionally substituted by 1 to 3 C$_{6-14}$ aryl groups (e.g., phenyl),
(ii) a C$_{6-14}$ aryl group (e.g., phenyl),
(iii) a C$_{3-10}$ cycloalkyl group (e.g., cyclopentyl, cyclohexyl),
(iv) a C$_{1-6}$ alkylsulfonyl group (e.g., methylsulfonyl), and
(v) an aromatic heterocyclic group (e.g., pyridyl) optionally substituted by 1 to 3 C$_{1-6}$ alkyl groups (e.g., methyl);
(f) an aromatic heterocyclic group (e.g., furyl, pyrazolyl, pyridyl, isoxazolyl, thiazolyl) optionally substituted by 1 to 3 substituents selected from a C$_{1-6}$ alkyl group optionally substituted by 1 to 3 halogen atoms (e.g., a fluorine atom);
(g) a non-aromatic heterocyclic group (e.g., tetrahydropyranyl);
or the like; or
(2) a 5-membered aromatic heterocyclic group (e.g., pyrazolyl, oxazolyl, isoxazolyl, thiazolyl, isothiazolyl, thiadiazolyl, preferably isoxazolyl) or phenyl, each of which is optionally substituted by 1 to 3 substituents selected from
(i) a C$_{1-6}$ alkyl-carbonyl group optionally substituted by 1 to 3 halogen atoms;
(ii) a C$_{1-6}$ alkoxy-carbonyl group optionally substituted by 1 to 3 substituents selected from
(a) a halogen atom,
(b) a C$_{1-6}$ alkoxy group, and
(c) a C$_{6-14}$ aryl group (e.g., phenyl);
(iii) a carbamoyl group optionally mono- or di-substituted by C$_{1-6}$ alkyl group(s) optionally substituted by 1 to 3 halogen atoms;
(iv) a carboxy group;
(v) a hydroxy group;
(vi) a halogen atom; and
(vii) a C$_{1-6}$ alkyl group optionally substituted by 1 to 3 substituents selected from
(a) a halogen atom,
(b) a carboxy group,
(c) a hydroxy group,
(d) a C$_{1-6}$ alkoxy-carbonyl group, and
(e) a C$_{1-6}$ alkoxy group);
R$^3$ is a C$_{1-6}$ alkyl group optionally substituted by 1 to 7 halogen atoms, or a C$_{3-6}$ cycloalkyl group;

R$^{4a}$ and R$^{4b}$ are independently a hydrogen atom or a fluorine atom;
X is O, CO, CR$^{5a}$R$^{5b}$ wherein R$^{5a}$ and R$^{5b}$ is as defined above, NR$^{5c}$ wherein R$^{5c}$ is as defined above, S, SO, or S(O)$_2$;
ring A is benzene, optionally oxidized pyridine, pyrimidine, pyrazole, oxazole, isoxazole, thiazole, isothiazole, oxadiazole or thiadiazole, each of which is optionally substituted by 1 to 3 substituents selected from
(1) a halogen atom (e.g., a fluorine atom, a chlorine atom),
(2) a C$_{1-6}$ alkyl group (e.g., methyl) optionally substituted by 1 to 3 halogen atoms,
(3) a C$_{1-6}$ alkoxy group (e.g., methoxy), and
(4) a C$_{7-13}$ aralkyl group (e.g., benzyl);
ring P and ring Q are fused to form

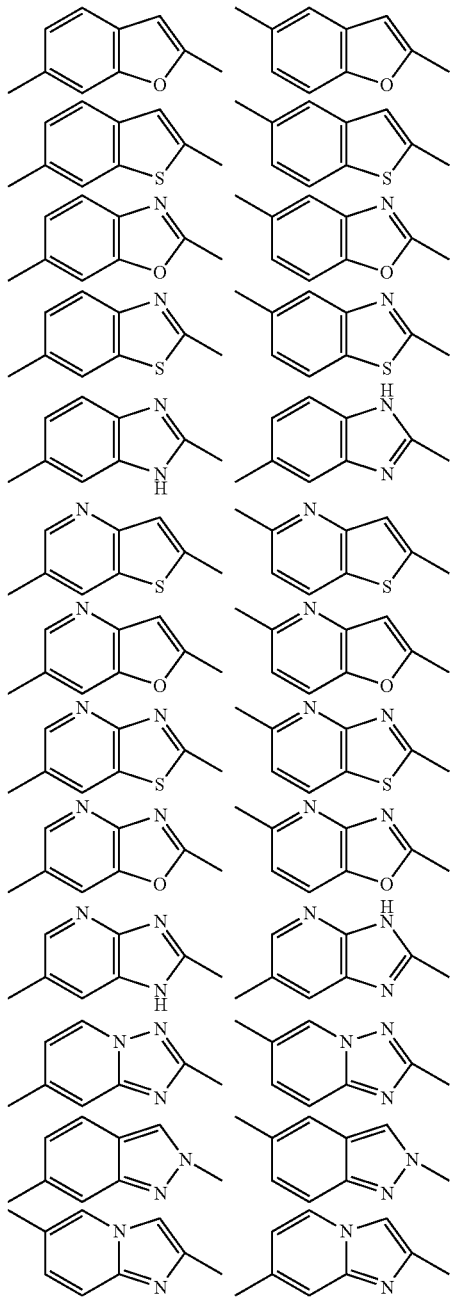

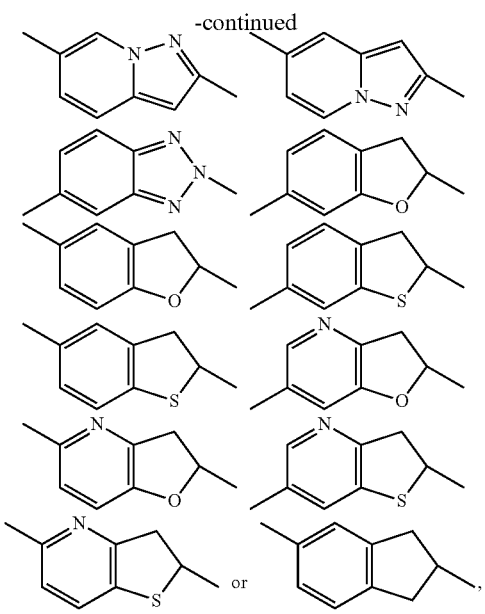

each of which is optionally substituted by 1 to 4 substituents selected from
(1) a halogen atom (e.g., a fluorine atom, a chlorine atom, a bromine atom),
(2) a $C_{1-6}$ alkyl group (e.g., methyl) optionally substituted by 1 to 3 halogen atoms (e.g., a fluorine atom),
(3) a $C_{3-6}$ cycloalkyl group (e.g., cyclopropyl) optionally substituted by 1 to 3 halogen atoms (e.g., a fluorine atom), and
(4) a cyano group; and
$R^6$ is
(1) a $C_{1-6}$ alkyl group (e.g., methyl, ethyl, propyl, isopropyl, butyl) optionally substituted by 1 to 3 substituents selected from
(a) a halogen atom (e.g., a fluorine atom), and
(b) a $C_{3-6}$ cycloalkyl group (e.g., cyclopropyl, cyclobutyl) optionally substituted by 1 to 3 halogen atoms (e.g., a fluorine atom); or
(2) a $C_{3-6}$ cycloalkyl group (e.g., cyclopropyl).
[Compound B-3]
Compound (I) wherein
$R^1$ is
(1) a group represented by the formula: —COR$^2$ wherein R$^2$ is an optionally substituted $C_{1-6}$ alkyl group, an optionally substituted $C_{2-6}$ alkoxy group or an optionally substituted amino group; or
(2) an optionally substituted 5- or 6-membered aromatic ring group
(preferably
(1) a group represented by the formula: —COR$^2$
 wherein
 R$^2$ is
 (a) a $C_{1-6}$ alkyl group (e.g., methyl, ethyl, propyl, butyl, isobutyl, isopentyl) optionally substituted by 1 to 3 substituents selected from
  (i) an amino group,
  (ii) a carboxy group,
  (iii) a $C_{1-6}$ alkoxy-carbonyl group (e.g., methoxycarbonyl, ethoxycarbonyl),
  (iv) a $C_{6-24}$ aryl group (e.g., phenyl),
  (v) a $C_{1-6}$ alkoxy group (e.g., methoxy), and
  (vi) a halogen atom (e.g., a fluorine atom);

(b) a $C_{1-6}$ alkoxy group (e.g., methoxy, tert-butoxy);
(c) an amino group optionally mono- or di-substituted by substituent(s) selected from
 (i) a $C_{2-6}$ alkyl group (e.g., methyl, ethyl, propyl, isopropyl) optionally substituted by 1 to 3 $C_{6-24}$ aryl groups (e.g., phenyl),
 (ii) a $C_{6-24}$ aryl group (e.g., phenyl),
 (iii) a $C_{3-20}$ cycloalkyl group (e.g., cyclopentyl, cyclohexyl),
 (iv) a $C_{2-6}$ alkylsulfonyl group (e.g., methylsulfonyl), and
 (v) an aromatic heterocyclic group (e.g., pyridyl) optionally substituted by 1 to 3 $C_{1-6}$ alkyl groups (e.g., methyl);
or the like; or
(2) a 5-membered aromatic heterocyclic group (e.g., pyrazolyl, oxazolyl, isoxazolyl, thiazolyl, isothiazolyl, thiadiazolyl, preferably isoxazolyl) or phenyl, each of which is optionally substituted by 1 to 3 substituents selected from (1) a halogen atom and (ii) a $C_{1-6}$ alkyl group);
$R^3$ is a $C_{1-6}$ alkyl group optionally substituted by 1 to 7 halogen atoms, or a $C_{3-6}$ cycloalkyl group;
$R^{4a}$ and $R^{4b}$ are independently a hydrogen atom or a fluorine atom;
X is O, CO or $CH_2$;
ring A is benzene, optionally oxidized pyridine, pyrimidine, pyrazole, isoxazole or oxadiazole, each of which is optionally substituted by 1 to 3 substituents selected from
(1) a halogen atom (e.g., a fluorine atom, a chlorine atom),
(2) a $C_{1-6}$ alkyl group (e.g., methyl) optionally substituted by 1 to 3 halogen atoms,
(3) a $C_{1-6}$ alkoxy group (e.g., methoxy), and
(4) a $C_{7-13}$ aralkyl group (e.g., benzyl);
ring P and ring Q are fused to form

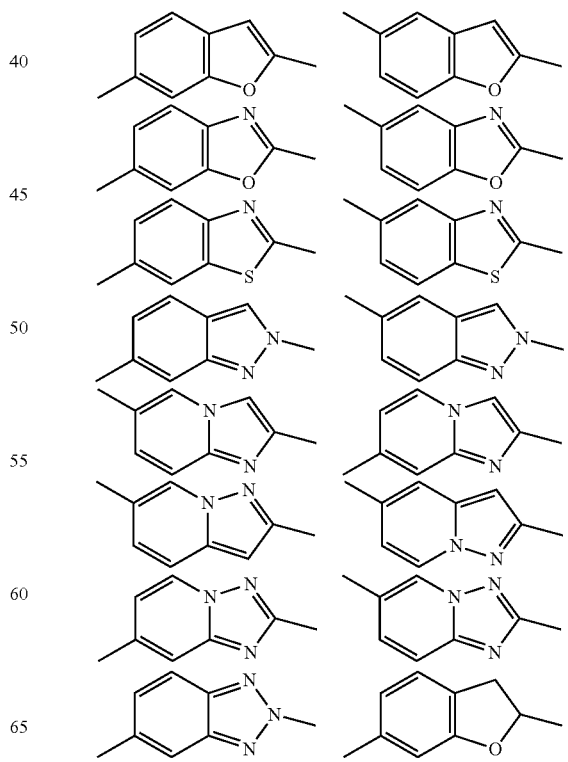

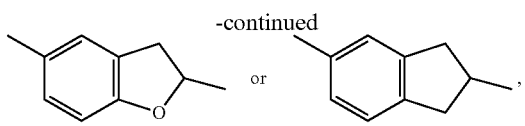

each of which is optionally substituted by 1 to 4 substituents selected from
(1) a halogen atom (e.g., a fluorine atom, a chlorine atom, a bromine atom),
(2) a $C_{1-6}$ alkyl group (e.g., methyl) optionally substituted by 1 to 3 halogen atoms (e.g., a fluorine atom),
(3) a $C_{3-6}$ cycloalkyl group (e.g., cyclopropyl) optionally substituted by 1 to 3 halogen atoms (e.g., a fluorine atom), and
(4) a cyano group; and $R^6$ is
(1) a $C_{1-6}$ alkyl group (e.g., methyl, ethyl, propyl, isopropyl, butyl) optionally substituted by 1 to 3 substituents selected from
(a) a halogen atom (e.g., a fluorine atom), and
(b) a $C_{3-6}$ cycloalkyl group (e.g., cyclopropyl, cyclobutyl) optionally substituted by 1 to 3 halogen atoms (e.g., a fluorine atom); or
(2) a $C_{3-6}$ cycloalkyl group (e.g., cyclopropyl).

[Compound C-3]
Compound (I) wherein
$R^1$ is
(1) a group represented by the formula: —$COR^2$
wherein
$R^2$ is
(a) $C_{1-6}$ alkyl group (e.g., methyl, ethyl, propyl, butyl, isobutyl, isopentyl) optionally substituted by 1 to 3 halogen atoms (e.g., a fluorine atom);
(b) a $C_{1-6}$ alkoxy group (e.g., methoxy, tert-butoxy);
(c) an amino group optionally mono- or di-substituted by $C_{1-6}$ alkyl group(s) (e.g., methyl, ethyl, propyl, isopropyl); or the like;
$R^3$ is a $C_{1-6}$ alkyl group optionally substituted by 1 to 7 halogen atoms;
$R^{4a}$ and $R^{4b}$ are independently a hydrogen atom;
X is O, CO or $CH_2$;
ring A is benzene, optionally oxidized pyridine, pyrimidine, pyrazole or isoxazole, each of which is optionally substituted by 1 to 3 substituents selected from
(1) a halogen atom (e.g., a fluorine atom, a chlorine atom),
(2) a $C_{1-6}$ alkyl group (e.g., methyl) optionally substituted by 1 to 3 halogen atoms,
(3) a $C_{1-6}$ alkoxy group (e.g., methoxy), and
(4) a $C_{7-13}$ aralkyl group (e.g., benzyl);
ring P and ring Q are fused to form

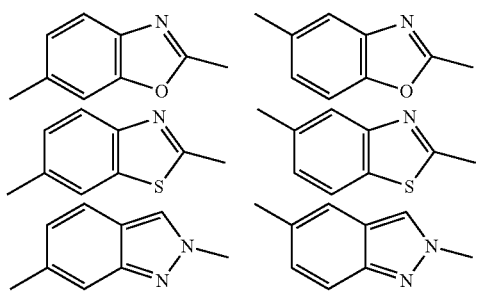

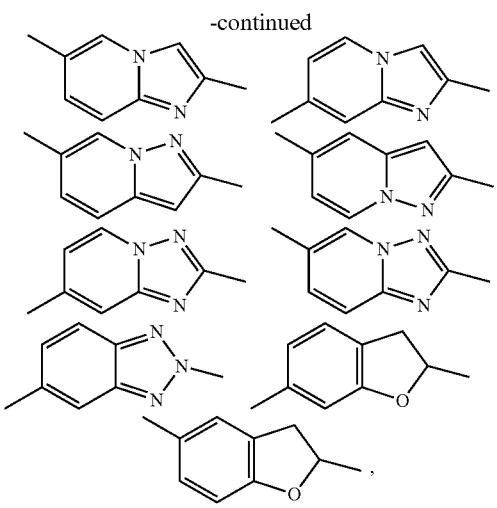

each of which is optionally substituted by 1 to 4 substituents selected from
(1) a halogen atom (e.g., a fluorine atom, a chlorine atom, a bromine atom),
(2) a $C_{1-6}$ alkyl group (e.g., methyl) optionally substituted by 1 to 3 halogen atoms (e.g., a fluorine atom),
(3) a $C_{3-6}$ cycloalkyl group (e.g., cyclopropyl) optionally substituted by 1 to 3 halogen atoms (e.g., a fluorine atom), and
(4) a cyano group; and $R^6$ is a $C_{1-6}$ alkyl group (e.g., methyl, ethyl, propyl, isopropyl, butyl) optionally substituted by 1 to 3 substituents selected from
(a) a halogen atom (e.g., a fluorine atom), and
(b) a $C_{3-6}$ cycloalkyl group (e.g., cyclopropyl, cyclobutyl) optionally substituted by 1 to 3 halogen atoms (e.g., a fluorine atom).

[Compound D-3]
N-[(1S)-2-({6-[6-(cyclopropylmethoxy)-1,3-benzoxazol-2-yl]pyridin-3-yl}oxy)-1-methylethyl]acetamide or a salt thereof.
N-[(1S)-2-({6-[6-(cyclopropylmethoxy)-1,3-benzoxazol-2-yl]-5-fluoropyridin-3-yl}oxy)-1-methylethyl]acetamide or a salt thereof.
N-[(1S)-2-{[6-(6-ethoxy-1,3-benzoxazol-2-yl)pyridin-3-yl]oxy}-1-methylethyl]acetamide or a salt thereof.

A salt of the compound represented by the formula (I) is preferably a pharmacologically acceptable salt. Examples of such salt include salts with inorganic base, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt and the like; aluminum salt; ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

A prodrug of compound (I) means a compound which is converted to compound (I) with a reaction due to an enzyme, an gastric acid, etc. under the physiological condition in the living body, that is, a compound which is converted to compound (I) by oxidation, reduction, hydrolysis, etc. due to an enzyme; a compound which is converted to compound (I) by hydrolysis etc. due to gastric acid, etc.

Examples of the prodrug of compound (I) include a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation); a compound obtained by subjecting a carboxy group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methyl amidation etc.) and the like. These compounds can be produced from compound (I) according to a method known per se.

A prodrug for compound (I) may also be one which is converted to compound (I) under a physiological condition, such as those described in IYAKUHIN no KAIHATSU, Development of Pharmaceuticals, Vol. 7, Design of Molecules, p. 163-198, Published by HIROKAWA SHOTEN, 1990.

In the present specification, a prodrug may be in the form of a salt. Examples of the salt include those exemplified as the salt of the compound represented by the aforementioned formula (I).

Compound (I) may be labeled with an isotope (e.g., $^3$H, $^{13}$C, $^{14}$C, $^{18}$F, $^{35}$S, $^{125}$I) and the like.

Compound (I) may be a hydrate or a non-hydrate, and a solvate or a non-solvate.

Compound (I) also encompasses a deuterium conversion form wherein $^1$H is converted to $^2$H(D).

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization known per se.

Compound (I) or a prodrug thereof (hereinafter sometimes to be abbreviated simply as the compound of the present invention) has low toxicity, and can be used as an agent for the prophylaxis or treatment of various diseases mentioned below in a mammal (e.g., human, mouse, rat, rabbit, dog, cat, bovine, horse, swine, monkey) directly or in the form of a pharmaceutical composition by admixing with a pharmacologically acceptable carrier and the like.

Here, examples of the pharmacologically acceptable carrier include various organic or inorganic carrier substances conventionally used as preparation materials, which are added as excipient, lubricant, binder or disintegrant for solid preparations; as solvent, solubilizing agent, suspending agent, isotonicity agent, buffer or soothing agent for liquid preparation, and the like. Where necessary, preparation additives such as preservative, antioxidant, colorant, sweetener and the like can also be used.

Preferable examples of the excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include pregelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, sodium croscarmellose, sodium carboxymethylstarch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include paraoxybenzoates, chlorobutanol, benzyl alcohol, phenethyl alcohol, dehydroacetic acid and sorbic acid.

Preferable examples of the antioxidant include sulfite, ascorbate and the like.

Preferable examples of the colorant include aqueous food tar colors (e.g., food colors such as Food Red No. 2 and No. 3, Food Yellow No. 4 and No. 5, Food Blue No. 1 and No. 2, etc.), water insoluble lake dye (e.g., aluminum salt of the above-mentioned aqueous food tar color) and natural dye (e.g., β-carotene, chlorophyll, ferric oxide red).

Preferable examples of the sweetening agent include sodium saccharin, dipotassium glycyrrhizinate, aspartame and stevia.

The medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

A pharmaceutical composition can be produced by a method conventionally used in the technical field of pharmaceutical preparation, for example, the method described in the Japanese Pharmacopoeia and the like.

While the content of the compound of the present invention in the pharmaceutical composition varies depending on the dosage form, dose of the compound of the present invention, and the like, it is, for example, about 0.1 to 100 wt %.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention shows low toxicity (e.g., acute toxicity, chronic toxicity, genetic toxicity, reproductive toxicity, pneumotoxicity, carcinogenicity and the like) and a few side effects. Therefore, it can be used as an agent for the prophylaxis or treatment or a diagnostic of various diseases in a mammal (e.g., human, bovine, horse, dog, cat, monkey, mouse, rat).

The compound of the present invention has a superior ACC (acetyl-CoA carboxylase) inhibitory action. Examples of ACC include liver, adipose tissue, pancreas-specific isozyme (ACC1); and muscle specific isozyme (ACC2).

The compound of the present invention has ACC2 selectivity. Particularly, the compounds of Examples of the present invention have high ACC2 selectivity.

The compound of the present invention is superior in the metabolism stability and has advantages such as long half-life of compound, difficult in vivo metabolism and the like.

Moreover, the compound of the present invention is superior in the in vivo kinetics (e.g., oral absorbability, bioavailability).

The compound of the present invention can be used as an agent for the prophylaxis or treatment of obesity, diabetes (e.g., type 1 diabetes, type 2 diabetes, gestational diabetes, obese diabetes), hyperlipidemia (e.g., hypertriglyceridemia, hypercholesterolemia, high LDL-cholesterolemia, hypo-HDL-emia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (pathology having three or more selected from hypertriglyceridemia (TG), low HDL cholesterol (HDL-C), hypertension, abdomen obesity and impaired glucose tolerance), sarcopenia, cancer and the like.

For diagnostic criteria of diabetes, Japan Diabetes Society reported diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 hr level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 hr level (glucose concentration of intravenous plasma) of less than 140 mg/dl" (normal type) is called a "borderline type".

In addition, ADA (American Diabetes Association) in 1997 and WHO in 1998 reported new diagnostic criteria of diabetes.

According to these reports, diabetes is a condition showing a fasting blood glucose level (glucose concentration of intravenous plasma) of not less than 126 mg/dl and a 75 g oral glucose tolerance test 2 hr level (glucose concentration of intravenous plasma) of not less than 200 mg/dl.

According to the above-mentioned reports, impaired glucose tolerance is a condition showing fasting blood sugar level (glucose concentration of intravenous plasma) of less than 126 mg/dl and a 75 g oral glucose tolerance test 2 hr level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 hr level (glucose concentration of intravenous plasma) of less than 140 mg/dl is called IFG (Impaired Fasting Glycemia).

The compound of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned diagnostic criteria. Moreover, the compound of the present invention can prevent progress of borderline type, impaired glucose tolerance, IFG (Impaired Fasting Glucose) or IFG (Impaired Fasting Glycemia) into diabetes.

Since the compound of the present invention has an activity of inhibiting body weight gain, it can be used as a body weight gain inhibitor to mammals. Target mammals may be any mammals of which body weight gain is to be avoided. The mammals may have a risk of body weight gain genetically or may be suffering from lifestyle-related diseases such as diabetes, hypertension and/or hyperlipidemia and the like. The body weight gain may be caused by excessive feeding or diet without nutrient balance, or may be derived from concomitant drug (e.g., agents for enhancing insulin sensitivity having PPARγ-agonistic activity such as troglitazone, rosiglitazone, englitazone, ciglitazone, pioglitazone and the like). In addition, body weight gain may be preliminary to obesity, or may be body weight gain of obesity patients. Here, obesity is defined that BMI (body mass index; body weight (kg)/[height (m)]$^2$) is not less than 25 for Japanese (criterion by Japan Society for the Study of Obesity), or not less than 30 for westerner (criterion by WHO).

The compound (I) is also useful as an agent for the prophylaxis or treatment of metabolic syndrome. Because patients with metabolic syndrome have an extreme high incidence of cardiovascular diseases as compared to patients with single lifestyle-related disease, the prophylaxis or treatment of metabolic syndrome is quite important to prevent cardiovascular diseases.

Criteria for diagnosis of metabolic syndrome are announced by WHO in 1999, and by NCEP in 2001. According to the criterion of WHO, patients with at least two of abdominal obesity, dyslipidemia (high TG or low HDL) and hypertension in addition to hyperinsulinemia or impaired glucose tolerance are diagnosed as metabolic syndrome (World Health Organization: Definition, Diagnosis and Classification of Diabetes Mellitus and Its Complications. Part Diagnosis and Classification of Diabetes Mellitus, World Health Organization, Geneva, 1999). According to the criterion of Adult Treatment Panel III of National Cholesterol Education Program, that is an indicator for managing ischemic heart diseases in America, patients with at least three of abdominal obesity, high triglycerides, low HDL cholesterol, hypertension and impaired glucose tolerance are diagnosed as metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can also be used, for example, as an agent for the prophylaxis or treatment of osteoporosis, cachexia (e.g., carcinomatous cachexia, tuberculous cachexia, diabetic cachexia, hemopathic cachexia, endocrinopathic cachexia, infectious cachexia or cachexia induced by acquired immunodeficiency syndrome), fatty liver, polycystic ovary syndrome, renal disease (e.g., diabetic nephropathy, glomerulonephritis, glomerulosclerosis, nephrosis syndrome, hypertensive nephrosclerosis, terminal renal disorder), muscular dystrophy, myocardial infarction, angina pectoris, cerebrovascular disorder (e.g., cerebral infarction, cerebral apoplexy), Alzheimer's disease, Parkinson's disease, anxiety, dementia, insulin resistance syndrome, syndrome X, hyperinsulinemia, sensory abnormality in hyperinsulinemia, irritable bowel syndrome, acute or chronic diarrhea, inflammatory disease (e.g., rheumatoid arthritis, spondylitis deformans, osteoarthritis, lumbago, gout, postoperative or posttraumatic inflammation, swelling, neuralgia, pharyngolaryngitis, cystitis, hepatitis (including nonalcoholic steatohepatitis), pneumonia, pancreatitis, enteritis, inflammatory bowel disease (including inflammatory colitis), ulcerative colitis, stomach mucosainjury (including stomach mucosainjury caused by aspirin)), small intestine mucosainjury, malabsorption, testis dysfunction, visceral obesity syndrome or sarcopenia.

In addition, the compound of the present invention can also be used as an agent for the prophylaxis or treatment of various carcinomas (particularly breast cancer (e.g., invasive ductal carcinoma, ductal carcinoma in situ, inflammatory breast cancer and the like), prostate cancer (e.g., hormone-dependent prostate cancer, non-hormone dependent prostate cancer and the like), pancreatic cancer (e.g., pancreatic duct cancer and the like), gastric cancer (e.g., papillary adenocarcinoma, mucinous adenocarcinoma, adenosquamous carcinoma and the like), lung cancer (e.g., non-small cell lung cancer, small cell lung cancer, malignant mesothelioma and the like), colorectal cancer (e.g., gastrointestinal stromal tumor and the like), rectal cancer (e.g., gastrointestinal stromal tumor and the like), colorectal cancer (e.g., familial colorectal cancer, hereditary nonpolyposis colorectal cancer, gastrointestinal stromal tumor and the like), small intestinal cancer (e.g., non-Hodgkin lymphoma, gastrointestinal stromal tumor and the like), esophagus cancer, duodenal cancer, cancer of the tongue, pharyngeal cancer (e.g., nasopharyngeal cancer, mesopharyngeal cancer, hypopharyngeal cancer and the like), salivary gland cancer, brain tumor (e.g., pineal astrocytoma, pilocytic astrocytoma, diffuse astrocytoma, anaplastic astrocytoma and the like), schwannoma, liver cancer (e.g., primary liver cancer, Extrahepatic Bile Duct Cancer and the like), kidney cancer (e.g., renal cell carcinoma, transitional carcinoma of kidney pelvis and urinary duct, and the like), biliary tract cancer, endometrial carcinoma, cervical cancer, ovarian cancer (e.g., ovarian epithelial carcinoma, extragonadal germ cell tumor ovarian germ cell tumor ovarian low malignant potential tumor and the like), urinary bladder cancer, urinary tract cancer, skin cancer (e.g., intraocular (ocular) melanoma, Merkel cell carcinoma and the like), Hemangioma, malignant lymphoma, malignant melanoma, thyroid cancer (e.g., medullary thyroid carcinoma and the like), parathyroid cancer, nasal cavity cancer, paranasal sinus cancer, bone tumor (e.g., osteosarcoma, Ewing's tumor uterus sarcoma, soft tissue sarcoma and the like), vascular fibroma, retinoblastoma, penile cancer, testis tumor solid cancer in childhood (e.g., Wilms' tumor childhood kidney tumor and the like), Kaposi's sarcoma, Kaposi's sarcoma derived from AIDS, maxillary tumor fibrous histiocytoma, leiomyosarcoma, rhabdomyosarcoma, leukemia (e.g., acute myeloid leukemia, acute lymphoblastic leukemia and the like) etc.).

The compound of the present invention can also be used for secondary prevention or suppression of progression of the above-mentioned various diseases (e.g., cardiovascular events such as myocardial infarction and the like).

While the dose of the compound of the present invention varies depending on the subject of administration, administration route, target disease, symptom and the like, for example, for oral administration to an adult obese patient it is generally about 0.01 to 100 mg/kg body weight, preferably 0.05 to 30 mg/kg body weight, further preferably 0.5 to 10 mg/kg body weight for one dose, which is desirably administered once to 3 times a day.

With the aim of enhancing the action of the compound of the present invention or decreasing the dose of the compound and the like, the compound can be used in combination with medicaments such as therapeutic agents for diabetes, therapeutic agents for diabetic complications, therapeutic agents for hyperlipidemia, antihypertensive agents, antiobesity agents, diuretics, antithrombotic agents and the like (hereinafter to be abbreviated as concomitant drug). The time of administration of the compound of the present invention and that of the concomitant drug are not limited, and these concomitant drugs may be low-molecular-weight compounds or high-molecular-weight protein, polypeptide, antibody, vaccine and the like. They may be administered simultaneously or in a staggered manner to the administration subject. In addition, the compound of the present invention and the concomitant drug may be administered as two kinds of preparations containing respective active ingredients or a single preparation containing both active ingredients.

The dose of the concomitant drug can be appropriately determined based on the dose employed clinically. In addition, the mixing ratio of the compound of the present invention and the concomitant drug can be appropriately determined according to the administration subject, administration route, target disease, condition, combination, and the like. For example, when the administration subject is a human, the concomitant drug may be used in an amount of 0.01 to 100 parts by weight per 1 part by weight of the compound of the present invention.

Examples of the therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO 2007/013694, WO 2007/018314, WO 2008/093639 or WO 2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors (e.g., Alogliptin, Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidynyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compound described in WO 2004/041266, WO 2004/106276, WO 2005/063729, WO 2005/063725, WO 2005/087710, WO 2005/095338, WO 2007/013689 or WO 2008/001931), GPR119 agonists (e.g., MBX-2982, PSN821, GSK1292263A, APD597), GLP-1 receptor agonists [e.g., GLP-1, GLP-1MR preparation, Liraglutide, Exenatide, AVE-0010, BIM-51077, Aib(8,35)hGLP-1(7,37)NH$_2$, CJC-1131, Albiglutide], amylin agonists (e.g., pramlintide), phosphotyrosine phosphatase inhibitors (e.g., sodium vanadate), gluconeogenesis inhibitors (e.g., glycogen phosphorylase inhibitors glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498), adiponectin or an agonist thereof, IKK inhibitors (e.g., AS-2868), leptin resistance improving drugs, somatostatin receptor agonists, glucokinase activators (e.g., N-(5-(2-methoxyethoxy)-2-{(5-[(1-oxidethiomorpholino)methyl]-4,5-dihydro-1,3-thiazol-2-yl}-1H-indol-7-yl)-N-methylpyridine-2-sulfonamide, AZD1656, AZD6370, AZD6714, TPP355, PSN010, MK-0599, ARRY-403/AMG-151, PF-04937319, compound described in WO 2006/112549, WO 2007/028135, WO 2008/047821, WO 2008/050821, WO 2008/136428 or WO2008/156757), GIP (Glucose-dependent insulinotropic peptide) and the like.

Examples of the therapeutic agents for diabetic complications include aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF, neurotrophic factors and increasing drugs thereof (e.g., 4-(4-chlorophenyl)-2-(2-methyl-1-imidazolyl)-5-[3-(2-methylphenoxy)propyl]oxazole) described in WO 01/14372, a compound described in WO 2004/039365), nerve regeneration promoters (e.g., Y-128), PKC inhibitors (e.g., ruboxistaurin mesylate), AGE inhibitors (e.g., ALT946, pyratoxanthine, N-phenacylthiazolium bromide (ALT766), ALT-711, EXO-226, Pyridorin, pyridoxamine), GABA receptor agonists (e.g., gabapentin, Pregabalin), serotonin noradrenaline re-uptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1(ASK-1) inhibitors and the like.

Examples of the therapeutic agent for hyperlipidemia include statin compounds (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., a compound described in WO 97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterols (e.g., soysterol), γ-oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like.

Examples of the antihypertensive agent include angiotensin converting enzyme inhibitors (e.g., captopril, enalapril, delapril etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, efonidipine, nicardipine, amlodipine, cilnidipine and the like), β blockers (e.g., metoprolol, atenolol, propranolol, carvedilol, pindolol), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor GABA modulators (e.g., topiramate), MCH receptor antagonists (e.g., SB-568849; SNAP-7941; compound described in WO 01/82925 or WO 01/87834), neuropeptide Y antagonists (e.g., velneperit), cannabinoid receptor antagonists (e.g., rimonabant, taranabant), ghrelin antagonists, ghrelin receptor antagonists, ghrelinacylation enzyme inhibitors, opioid receptor antagonists (e.g., GSK-1521498), orexin receptor antagonists, melanocortin 4 receptor agonists (e.g., Palatin, AP-1030), 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, remogliflozin), NFK inhibitors (e.g., HE-3286), PPAR agonists (e.g., GFT-505, DRF-11605), phosphotyrosine phosphatase inhibitors (e.g., sodium vanadate, Trodusquemin), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine and pig; human GLP-1 preparations genetically synthesized using *Escherichia coli* or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obinepitide, TM-30339, TM-30335), oxyntomodulin preparations: FGF21 preparations (e.g., animal FGF21 preparations extracted from the pancreas of bovine and pig; human FGF21 preparations genetically synthesized using *Escherichia coli* or yeast; fragments or derivatives of FGF21)), anorexigenic agents (e.g., P-57) and the like.

Examples of the diuretics include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide agents (e.g., chlortalidone, mefruside, indapamide), azosemide, isosorbide, ethacrynic acid, piretanide, bumetanide, furosemide and the like.

Examples of the antithrombotic agent include heparins (e.g., heparin sodium, heparin calcium, enoxaparin sodium, dalteparin sodium), warfarins (e.g., warfarin potassium), anti-thrombin drugs (e.g., argatroban, dabigatran), thrombolytic agents (e.g., urokinase, tisokinase, alteplase, nateplase, monteplase, pamiteplase), platelet aggregation inhibitors (e.g., ticlopidine hydrochloride, clopidogrel, E5555, SHC530348, cilostazol, ethyl icosapentate, beraprost sodium, sarpogrelate hydrochloride, prasugrel, E5555, SHC530348), FXa inhibitors (e.g., rivaroxaban, apixaban, edoxaban, YM150, compound described in WO 02/06234, WO 2004/048363, WO 2005/030740, WO 2005/058823 or WO 2005/113504) and the like.

The administration time of the aforementioned concomitant drug is not limited, and the compound of the present invention and the concomitant drug may be administered to an administration subject simultaneously, or may be administered at different times. The dosage of the concomitant drug may be determined according to the dosage clinically used, and can be appropriately selected depehding on the administration subject, administration route, diseases, combination thereof and the like.

The administration mode of the concomitant drug is not particularly limited, and the compound of the present invention and the concomitant drug only need to be combined on administration. Examples of such administration mode include the following:
(1) administration of a single preparation obtained by simultaneously processing the compound of the present invention and the concomitant drug,
(2) simultaneous administration of two kinds of preparations of the compound of the present invention and the concomitant drug, which have been separately produced, by the same administration route,
(3) administration of two kinds of preparations of the compound of the present invention and the concomitant drug, which have been separately produced, by the same administration route in a staggered manner,
(4) simultaneous administration of two kinds of preparations of the compound of the present invention and the concomitant drug, which have been separately produced, by different administration routes,
(5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug can be appropriately selected depending on the administration subject, administration route, diseases and the like.

The production method of the compound of the present invention is explained in the following.

In the following Reaction Schemes, starting compounds may be each in the form of a salt as long as it inhibits the reaction. Examples of the salt include those exemplified as the above-mentioned salt of the compound represented by formula (I).

When a specific production method is not described, the starting compound may be easily commercially available, or can also be produced according to a method known per se, or a method analogous thereto.

In each reaction of the following Reaction Schemes, the product can be used for the next reaction as the reaction mixture or as a crude product, or can also be isolated according to a conventional method from the reaction mixture, and can also be easily purified according to a conventional separation means (e.g., recrystallization, distillation, chromatography).

When alkylation reaction, hydrolysis, amination reaction, esterification reaction, amidation reaction, esterification reaction, etherification reaction, oxidation reaction, reduction reaction and the like are to be performed in the following Reaction Schemes, these reactions are performed according to a method known per se. Examples of such method include the methods described in ORGANIC FUNCTIONAL GROUP PREPARATIONS, 2nd ed., ACADEMIC PRESS, INC., 1989; Comprehensive Organic Transformations, VCH Publishers Inc., 1989 and the like, and the like.

The following are explanations of the solvents in generic terms, which are used for the following reactions.

Examples of the "nitrile solvents" include acetonitrile, propionitrile and the like.

Examples of the "amide solvents" include N,N-dimethylformamide (DMF), N,N-dimethylacetamide, N-methylpyrrolidone and the like.

Examples of the "halogenated hydrocarbon solvents" include dichloromethane, chloroform, 1,2-dichloroethane, carbon tetrachloride and the like.

Examples of the "ether solvents" include diethyl ether, diisopropyl ether, tert-butyl methyl ether, tetrahydrofuran (THF), 1,4-dioxane, 1,2-dimethoxyethane and the like.

Examples of the "aromatic solvents" include benzene, toluene, xylene, chlorobenzene, (trifluoromethyl)benzene, pyridine and the like.

Examples of the "aliphatic hydrocarbon solvents" include hexane, pentane, cyclohexane and the like.

Examples of the "sulfoxide solvents" include dimethyl sulfoxide (DMSO) and the like.

Examples of the "alcohol solvents" include methanol, ethanol, propanol, 2-propanol, butanol, isobutanol, tert-butanol and the like.

Examples of the "ester solvents" include methyl acetate, ethyl acetate, n-butyl acetate, tert-butyl acetate and the like.

Examples of the "ketone solvents" include acetone, methyl ethyl ketone and the like.

Examples of the "organic acid solvents" include formic acid, acetic acid, propionic acid, trifluoroacetic acid, methanesulfonic acid and the like.

The following are explanations of the bases in generic terms, which are used for the following reactions.

Examples of the "inorganic bases" include sodium hydroxide, potassium hydroxide, lithium hydroxide, barium hydroxide and the like.

Examples of the "basic salt" include sodium carbonate, potassium carbonate, cesium carbonate, sodium hydrogen carbonate, potassium hydrogen carbonate, tripotassium phosphate and the like.

Examples of the "aromatic amines" include pyridine, imidazole, 2,6-lutidine and the like.

Examples of the "tertiary amines" include triethylamine, diisopropylethylamine, N-methylmorpholine, DBU (1,8-diazabicyclo[5.4.0]undec-7-ene), DBN (1,5-diazabicyclo[4.3.0]non-5-ene) and the like.

Examples of the "hydrides of an alkali metal or alkaline earth metal" include lithium hydride, sodium hydride, potassium hydride, calcium hydride and the like.

Examples of the "metal amides" include lithium amide, sodium amide, lithium diisopropylamide, lithium dicyclohexylamide, lithium hexamethyldisilazide, sodium hexamethyldisilazide, potassium hexamethyldisilazide and the like.

Examples of the "alkyl metals" include n-butyllithium, sec-butyllithium, tert-butyllithium, methylmagnesium bromide and the like.

Examples of the "aryl metals" include phenyllithium, phenylmagnesium bromide and the like.

Examples of the "metal alkoxides" include sodium methoxide, sodium ethoxide, potassium tert-butoxide, sodium tert-butoxide and the like.

In the following production methods, when the starting compound has an amino group, a carboxyl group, a hydroxy group, a carbonyl group or a sulfanyl group as a substituent, a protecting group generally used in peptide chemistry and the like may be introduced into these groups. By removing the protecting group as necessary after the reaction, the object compound can be obtained.

Examples of the amino-protecting group include a formyl group, a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-14}$ aralkyloxy-carbonyl group (e.g., benzyloxycarbonyl), a 9-fluorenylmethoxycarbonyl group, a trityl group, a phthaloyl group, a N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl), a substituted $C_{7-10}$ aralkyl group (e.g., 2,4-dimethoxybenzyl) and the like. These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-10}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group or a nitro group.

Examples of the protected carbonyl group include a cyclic acetal (e.g., 1,3-dioxane), a non-cyclic acetal (e.g., a di-$C_{1-6}$ alkylacetal) and the like.

Examples of the sulfanyl-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl), a 9-fluorenylmethoxycarbonyl group, a 2-tetrahydropyranyl group, a $C_{1-6}$ alkylamino-carbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

The removal method of the protecting group can be carried out according to a method known per se, for example, the method described in Protective Groups in Organic Synthesis, John Wiley and Sons (1980) or the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like can be employed.

Reaction Scheme 1

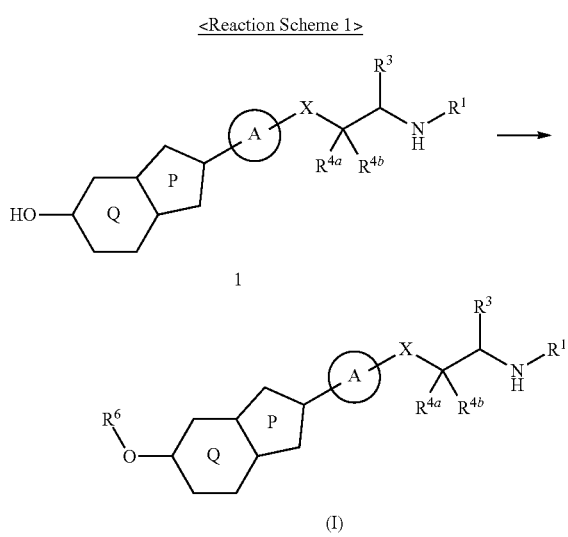

wherein each symbol is as defined above.

Compound (I) can be produced, for example, by subjecting compound (I) to an alkylation reaction.

Examples of the alkylation reaction include the following "method using a base and an alkyl halide or sulfonate corresponding to $R^6$", "method employing the Mitsunobu reaction" and the like.

The "method using a base and an alkyl halide or sulfonate corresponding to $R^6$" can be performed according to a method known per se, for example, the method described in Journal of the Chemical Society, 1530-1534 pages, 1937 or the like, or a method analogous thereto.

This reaction is performed by reacting compound (I) with an alkyl halide or sulfonate corresponding to $R^6$ in the presence of a base, in an inert solvent.

Examples of the above-mentioned "alkyl halide corresponding to $R^6$" include optionally substituted $C_{1-6}$ alkyl halides and optionally substituted $C_{3-6}$ cycloalkyl halides. The amount of the "alkyl halide corresponding to $R^6$" to be used is generally 1 to 10 equivalents, preferably 1 to 5 equivalents, relative to compound (I).

Examples of the above-mentioned "sulfonate corresponding to $R^6$" include optionally substituted $C_{1-6}$ alkyl esters of sulfonic acid, and optionally substituted $C_{3-6}$ cycloalkyl esters of sulfonic acid. Examples of the "sulfonic acid" include methanesulfonic acid, p-toluenesulfonic acid, trifluoromethanesulfonic acid and the like. The amount of the "sulfonate corresponding to $R^6$" to be used is generally 1 to 10 equivalents, preferably 1 to 5 equivalents, relative to compound (1).

Examples of the above-mentioned "base" include "inorganic bases", "basic salts", "aromatic amines", "tertiary amines", "hydrides of an alkali metal or alkaline earth metal", "alkyl metals", "aryl metals", "metal alkoxides" and the like. The amount of the "base" to be used is generally 1 to 10 equivalents, preferably 1 to 5 equivalents, relative to compound (1).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, THF, DMF and the like are preferable.

The reaction temperature is generally $-100°$ C. to $150°$ C., preferably $0°$ C. to $100°$ C.

The reaction time is generally 5 min to 48 hr, preferably 30 min to 24 hr.

The "method employing the Mitsunobu reaction" can be performed according to a method known per se, for example, the method described in Tetrahedron Letters, 769-770 pages, 1980 or the like, or a method analogous thereto.

This reaction is performed by reacting compound (I) with the compound $R^6OH$ in the presence of a hydroxy group-activator, in an inert solvent.

The amount of the above-mentioned "compound $R^6OH$" to be used is generally 1 to 10 equivalents, preferably 1 to 5 equivalents, relative to compound (1).

Examples of the above-mentioned "hydroxy group-activator" include cyanomethylenetri-n-butylphosphorane, a combination of diisopropyl azodicarboxylate and triphenylphosphine, and the like. The amount of the "hydroxy group-activator" to be used is generally 1 to 10 equivalents, preferably 1 to 5 equivalents, relative to compound (1).

Examples of the above-mentioned "inert solvent" include aromatic solvents, aliphatic hydrocarbon solvents, ether solvents, ester solvents, amide solvents and the like. These solvents may be used in a mixture of two or more kinds thereof in an appropriate ratio.

The reaction temperature is generally $-70°$ C. to $150°$ C., preferably $-20°$ C. to $100°$ C.

The reaction time is generally 0.1 hr to 100 hr, preferably 0.1 hr to 48 hr.

Compound (I) wherein X is an oxidized sulfur atom, which is a sulfone derivative or sulfoxide derivative, can be produced by subjecting compound (I) wherein X is sulfur atom to an oxidation reaction.

This reaction can be performed according to the method described in Jikken Kagaku Kouza, 4th Edition, vol. 20 (The Chemical Society of Japan ed.), 276-278 pages, 503 or a method analogous thereto, or the like.

Reaction Scheme 2

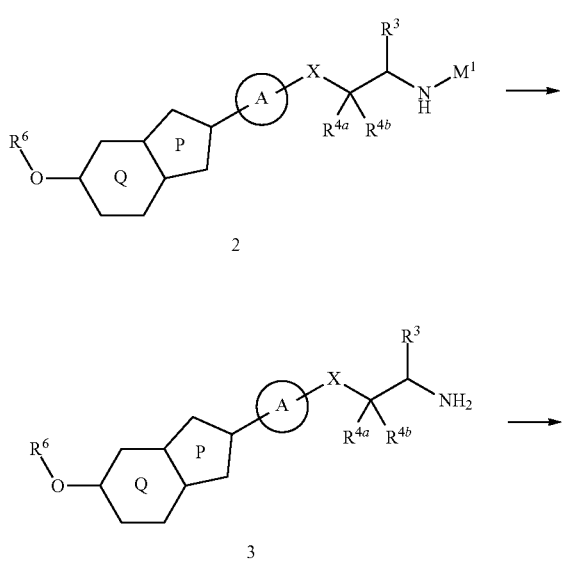

-continued

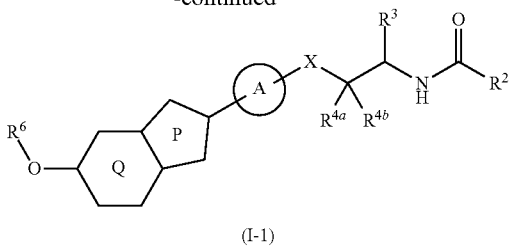

(I-1)

wherein $M^1$ is an amino-protecting group, and the other symbols are as defined above.

Compound (3) can be produced, for example, by subjecting compound (2) to a deprotection reaction.

The deprotection reaction can be performed according to a method known per se, for example, the method described in Protective Groups in Organic Synthesis, John Wiley and Sons (1980) or the like.

Compound (I-1) can be produced, for example, by subjecting compound (3) to an acylation reaction.

The above-mentioned "acylation reaction" encompasses, for example, reactions for production of amide derivatives, carbamate derivatives and urea derivative, and the like.

The production of the "amide derivative" is performed according to the following "method using a carboxylic acid corresponding to $R^2CO$ and a dehydrating condensing agent" or "method using a reactive derivative of a carboxylic acid corresponding to $R^2CO$".

i) The Method Using a Dehydrating Condensing Agent

The method is performed by reacting compound (3) with a carboxylic acid corresponding to $R^2CO$ in the presence of a dehydrating condensing agent, in an inert solvent. Where necessary, the reaction can be performed in the presence of 1-hydroxybenzotriazole (HOBt) in a catalytic amount to 5 equivalents relative to the carboxylic acid corresponding to $R^2CO$, a base in a catalytic amount to 5 equivalents relative to the carboxylic acid corresponding to $R^2CO$, and the like.

The amount of the above-mentioned "carboxylic acid corresponding to $R^2CO$" to be used is generally 0.5 to 5 equivalents, preferably 0.8 to 1.5 equivalents, relative to compound (3).

Examples of the above-mentioned "dehydrating condensing agent" include dicyclohexylcarbodiimide (DCC), 1-ethyl-3-(3-dimethylaminopropyl)carbodiimide hydrochloride (WSC) and the like. Among them, WSC is preferable. The amount of the "dehydrating condensing agent" to be used is generally 1 to 10 equivalents, preferably 1 to 5 equivalents, relative to compound (3).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, amide solvents are preferable.

Examples of the above-mentioned "base" include "aromatic amines", "tertiary amines" and the like.

The reaction temperature is generally −70° C. to 150° C., preferably −20° C. to 100° C.

The reaction time is generally 0.1 hr to 100 hr, preferably 1 hr to 48 hr.

ii) The Method Using a Reactive Derivative of a Carboxylic Acid Corresponding to $R^2CO$ The method is performed by reacting compound (3) with 0.5 to 5 equivalents (preferably 0.8 to 3 equivalents) of a reactive derivative of a carboxylic acid corresponding to $R^2CO$ in an inert solvent. Where necessary, the reaction can be performed in the presence of a base in 1 to 10 equivalents, preferably 1 to 3 equivalents, relative to the carboxylic acid corresponding to $R^2CO$.

Examples of the above-mentioned "reactive derivative of the carboxylic acid corresponding to $R^2CO$" include acid halides (e.g., acid chlorides, acid bromides), mixed acid anhydrides (e.g., acid anhydrides with a $C_{1-6}$ alkyl-carboxylic acid, a $C_{6-10}$ aryl-carboxylic acid, a $C_{1-6}$ alkylcarbonate etc.), activate esters (e.g., esters with a phenol optionally having substituent(s), HOBt, N-hydroxysuccinimide etc.), activate amides (e.g., amides with imidazole, triazole etc.) and the like.

Examples of the above-mentioned "phenol optionally having substituent(s)" include phenols such as phenol, pentachlorophenol, pentafluorophenol, p-nitrophenol and the like.

The above-mentioned "reactive derivative of the carboxylic acid corresponding to $R^2CO$" is preferably an acid anhydride.

Examples of the above-mentioned "inert solvent" include ether solvents, halogenated hydrocarbon solvents, aromatic solvents, aliphatic hydrocarbon solvents, nitrile solvents, amide solvents, sulfoxide solvents and the like. These solvents may be used in a mixture of two or more kinds thereof in an appropriate ratio. Among them, pyridine, acetonitrile, THF, dichloromethane, chloroform and the like are preferable.

Examples of the above-mentioned "base" include "aromatic amines", "tertiary amines" and the like.

The reaction temperature is generally −20° C. to 100° C., preferably −20° C. to 50° C.

The reaction time is generally 5 min to 40 hr, preferably 30 min to 18 hr.

The production of the above-mentioned "carbamate derivative" is performed by reacting compound (3) with 0.5 to 5 equivalents (preferably 0.8 to 3 equivalents) of a dicarbonate or chloroformate corresponding to $R^2CO$ in an inert solvent. Where necessary, the reaction can be performed in the presence of a base in a catalytic amount to 5 equivalents relative to the dicarbonate or chloroformate corresponding to $R^2CO$.

Examples of the above-mentioned "inert solvent" include ether solvents, halogenated hydrocarbon solvents, aromatic solvents, aliphatic hydrocarbon solvents, nitrile solvents, amide solvents and the like. These solvents may be used in a mixture of two or more kinds thereof in an appropriate ratio. Among them, pyridine, acetonitrile, THF, DMF, dichloromethane, chloroform and the like are preferable.

Examples of the above-mentioned "base" include "aromatic amines", "tertiary amines" and the like.

The reaction temperature is generally −20° C. to 100° C., preferably −20° C. to 50° C.

The reaction time is generally 5 min to 40 hr, preferably 30 min to 18 hr.

The production of the above-mentioned "urea derivative" is performed by reacting compound (3) with 0.5 to 5 equivalents (preferably 0.8 to 3 equivalents) of an isocyanate or carbamoyl chloride corresponding to $R^2CO$ in an inert solvent. Where necessary, the reaction can be performed in the presence of a base in a catalytic amount to 5 equivalents relative to the isocyanate or carbamoyl chloride corresponding to $R^2CO$.

Examples of the above-mentioned "inert solvent" include ether solvents, halogenated hydrocarbon solvents, aromatic solvents, aliphatic hydrocarbon solvents, nitrile solvents, amide solvents and the like. These solvents may be used in a mixture of two or more kinds thereof in an appropriate ratio.

Among them, pyridine, acetonitrile, THF, DMF, dichloromethane, chloroform and the like are preferable.

Examples of the above-mentioned "base" include "aromatic amines", "tertiary amines" and the like.

The reaction temperature is generally −20° C. to 100° C., preferably −20° C. to 50° C.

The reaction time is generally 5 min to 40 hr, preferably 30 min to 18 hr.

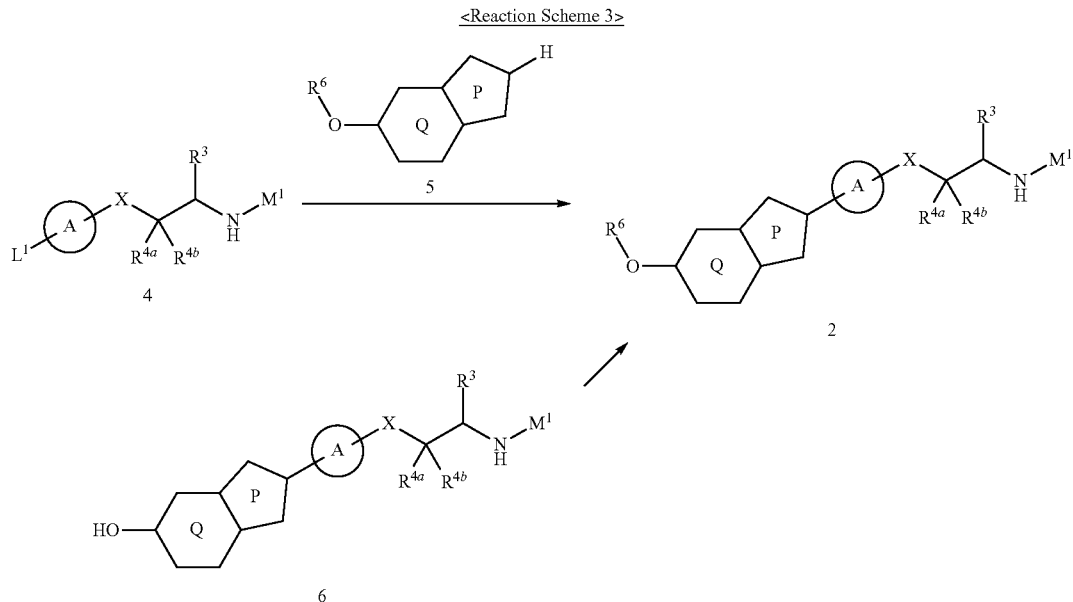

wherein $L^1$ is a halogen atom, and the other symbols are as defined above.

Compound (2) can be produced, for example, by subjecting compound (4) to a coupling reaction with compound (5).

The above-mentioned "coupling reaction" is performed by reacting compound (4) with compound (5) in the presence of a metal catalyst, a ligand and a base, in an inert solvent. This reaction is preferably performed under an inert gas atmosphere.

The amount of compound (4) to be used is generally 0.5 to 5 equivalents, preferably 0.8 to 1.5 equivalents, relative to compound (5).

Examples of the above-mentioned "metal catalyst" include palladium(II) acetate, copper(I) iodide and the like. The amount of the "metal catalyst" to be used is generally 0.001 to 100 equivalents, preferably 0.01 to 10 equivalents, relative to compound (5).

Examples of the above-mentioned "ligand" include butyldi-(1-adamantyl)phosphine, (1R,2R)—N,N'-dimethylcyclohexane-1,2-diamine and the like. The amount of the "ligand" to be used is generally 0.001 to 100 equivalents, preferably 0.01 to 10 equivalents, relative to compound (5).

Examples of the above-mentioned "base" include "basic salts" and the like. Among them, tripotassium phosphate, cesium carbonate and the like are preferable. The amount of the "base" to be used is generally 1 to 10 equivalents, preferably 1 to 5 equivalents, relative to compound (5).

Examples of the above-mentioned "inert solvent" include amide solvents, aromatic solvents, halogenated hydrocarbon solvents and the like.

Examples of the above-mentioned "inert gas" include argon gas, nitrogen gas and the like.

The reaction temperature is generally −20° C. to 200° C., preferably 0° C. to 150° C.

The reaction time is generally 5 min to 40 hr, preferably 30 min to 24 hr.

Compound (2) can also be produced, for example, by subjecting compound (6) to an alkylation reaction.

This reaction is performed in the same manner as in the production method of compound (I) in Reaction Scheme 1.

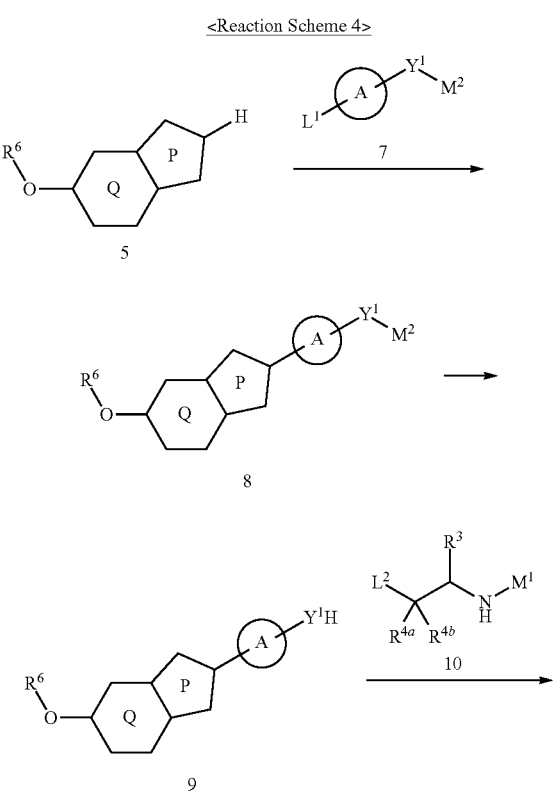

-continued

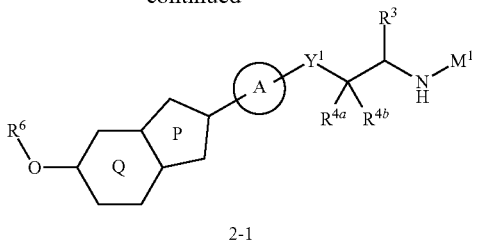

2-1 wherein $L^2$ is a hydroxyl group, a sulfonyloxy group or a halogen atom, $M^2$ is a hydroxyl-protecting group, an amino-protecting group or a sulfanyl-protecting group, $Y^1$ is an oxygen atom, a nitrogen atom substituted by $R^{5c}$ or a sulfur atom, and the other symbols are as defined above.

Compound (8) can be produced, for example, by subjecting compound (5) to a coupling reaction with compound (7).

This reaction is performed in the same manner as in the production method of compound (2) from compound (4) and compound (5) in Reaction Scheme 3.

Compound (9) can be produced, for example, by subjecting compound (8) to a deprotection reaction.

The deprotection reaction can be performed according to a method known per se, for example, the method described in Protective Groups in Organic Synthesis, John Wiley and Sons (1980) or the like.

Compound (2-1) can be produced, for example, by subjecting compound (9) to a coupling reaction with compound (10).

Examples of the above-mentioned "coupling reaction" include a "method employing the Mitsunobu reaction" and the like in the case that $L^2$ of compound (10) is a hydroxyl group, a "method using a base" and the like in the case that $L^2$ of compound (10) is a sulfonyloxy group or a halogen atom.

The "method employing the Mitsunobu reaction" can be performed according to a method known per se, for example, the method described in Tetrahedron Letters, 769-770 pages, 1980 or the like, or a method analogous thereto.

This reaction is performed by reacting compound (9) with compound (10) wherein $L^2$ is a hydroxyl group in the presence of a hydroxy group-activator, in an inert solvent.

The amount of compound (10) wherein $L^2$ is a hydroxyl group to be used is generally 1 to 10 equivalents, preferably 1 to 5 equivalents, relative to compound (9).

Examples of the above-mentioned "hydroxy group-activator" include cyanomethylenetri-n-butylphosphorane, a combination of diisopropyl azodicarboxylate and triphenylphosphine, and the like. The amount of the "hydroxy group-activator" to be used is generally 1 to 10 equivalents, preferably 1 to 5 equivalents, relative to compound (9).

Examples of the above-mentioned "inert solvent" include aromatic solvents, aliphatic hydrocarbon solvents, ether solvents, ester solvents, amide solvents and the like. These solvents may be used in a mixture of two or more kinds thereof in an appropriate ratio.

The reaction temperature is generally −70° C. to 150° C., preferably −20° C. to 100° C.

The reaction time is generally 0.1 hr to 100 hr, preferably 0.1 hr to 48 hr.

The "method using a base" can be performed according to a method known per se, for example, the method described in Journal of the Chemical Society, 1530-1534 pages, 1937 or the like, or a method analogous thereto.

This reaction is performed by reacting compound (9) with compound (10) wherein $L^2$ is a sulfonyloxy group or a halogen atom in the presence of a base, in an inert solvent.

Examples of the above-mentioned "base" include "inorganic bases", "basic salts", "aromatic amines", "tertiary amines", "hydrides of an alkali metal or alkaline earth metal", "alkyl metals", "aryl metals", "metal alkoxides" and the like. The amount of the "base" to be used is generally 1 to 10 equivalents, preferably 1 to 5 equivalents, relative to compound (9).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, THF, DMF and the like are preferable.

The reaction temperature is generally −100° C. to 150° C., preferably 0° C. to 100° C.

The reaction time is generally 5 min to 48 hr, preferably 30 min to 24 hr.

<Reaction Scheme 5>

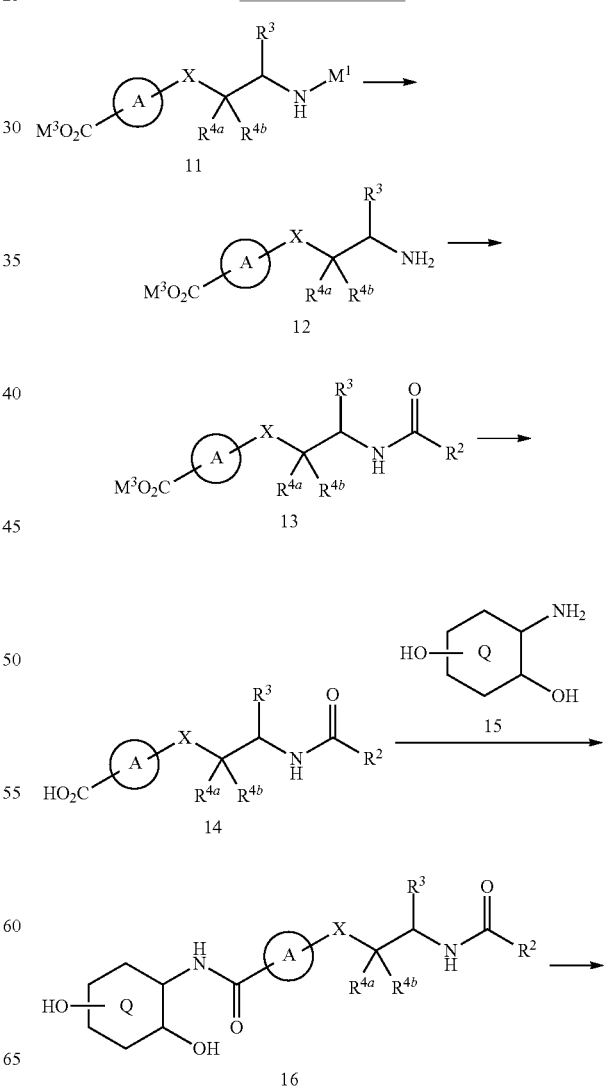

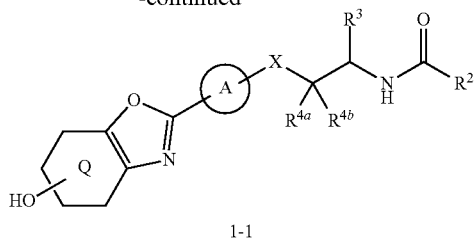

1-1 wherein M³ is a carboxy-protecting group, and the other symbols are as defined above.

Compound (12) can be produced, for example, by subjecting compound (11) to a deprotection reaction.

The deprotection reaction can be performed according to a method known per se, for example, the method described in Protective Groups in Organic Synthesis, John Wiley and Sons (1980) or the like.

Compound (13) can be produced, for example, by subjecting compound (12) to an acylation reaction.

This reaction is performed in the same manner as in the production method of compound (I-1) in Reaction Scheme 2.

Compound (14) can be produced, for example, by subjecting compound (13) to hydrolysis.

This reaction is performed by reacting compound (13) with a base in an inert solvent.

Examples of the above-mentioned "base" include "inorganic bases" and the like. The amount of the "base" to be used is generally 1 to 10 equivalents, preferably 1 to 5 equivalents, relative to compound (13).

Examples of the above-mentioned "inert solvent" include alcohol solvents, ether solvents, amide solvents, halogenated hydrocarbon solvents and the like. These solvents are preferably used in a mixture with water in an appropriate ratio. Among them, alcohol solvents containing water are preferable.

The reaction temperature is generally −78° C. to 150° C., preferably −20° C. to 100° C.

The reaction time is generally 5 min to 100 hr, preferably 30 min to 24 hr.

The production method of compound (14) by the removal of the carboxy-protecting group of compound (13) can also be performed according to a method known per se, for example, the method described in Protective Groups in Organic Synthesis, John Wiley and Sons (1980) or the like.

Compound (16) can be produced, for example, by subjecting compound (14) to an amidation reaction with compound (15).

The above-mentioned "amidation reaction" is performed by reacting compound (14) with compound (15) in the presence of a dehydrating condensing agent, in an inert solvent. Where necessary, the reaction can be performed in the presence of 1-hydroxybenzotriazole (HOBt) in a catalytic amount to 5 equivalents relative to compound (14), a base in a catalytic amount to 5 equivalents relative to compound (14), and the like.

The amount of compound (15) to be used is generally 0.5 to 5 equivalents, preferably 0.8 to 1.5 equivalents, relative to compound (14).

Examples of the above-mentioned "dehydrating condensing agent" include dicyclohexylcarbodiimide (DCC), 1-ethyl-3-(3-dimethylaminopropyl)carbodiimide hydrochloride (WSC), N-[(dimethylamino)(3H-[1,2,3]triazolo[4,5-b]pyridin-3-yloxy)methylidene]-N-methylmethanaminium hexafluorophosphate (HATU) and the like. Among them, HATU is preferable. The amount of the "dehydrating condensing agent" to be used is generally 1 to 10 equivalents, preferably 1 to 5 equivalents, relative to compound (14).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, amide solvents are preferable.

Examples of the above-mentioned "base" include "aromatic amines", "tertiary amines" and the like.

The reaction temperature is generally −70° C. to 150° C., preferably −20° C. to 100° C.

The reaction time is generally 0.1 hr to 100 hr, preferably 1 hr to 48 hr.

Compound (I-1) can be produced, for example, by subjecting compound (16) to a cyclization reaction.

The above-mentioned "cyclization reaction" is performed by reacting compound (16) in the presence of an activator, in an inert solvent.

Examples of the above-mentioned "activator" include p-toluenesulfonic acid, a combination of diethyl azodicarboxylate and triphenylphosphine, a combination of hexachloroethane, triphenylphosphine and a base, and the like. The amount of the "activator" to be used is generally 0.001 to equivalents, preferably 0.01 to 8 equivalents, relative to compound (16).

Examples of the above-mentioned "inert solvent" include aromatic solvents, aliphatic hydrocarbon solvents, ether solvents, ester solvents, amide solvents, nitrile solvents, halogenated hydrocarbon solvents and the like. These solvents may be used in a mixture of two or more kinds thereof in an appropriate ratio.

Examples of the above-mentioned "base" include "aromatic amines", "tertiary amines" and the like.

The reaction temperature is generally −70° C. to 200° C., preferably −20° C. to 150° C.

The reaction time is generally 0.1 hr to 100 hr, preferably 0.1 hr to 40 hr.

<Reaction Scheme 6>

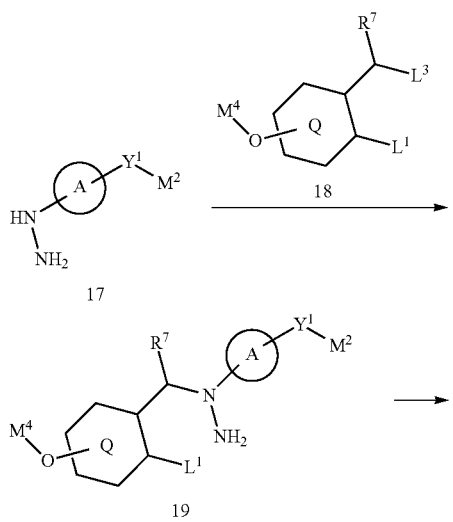

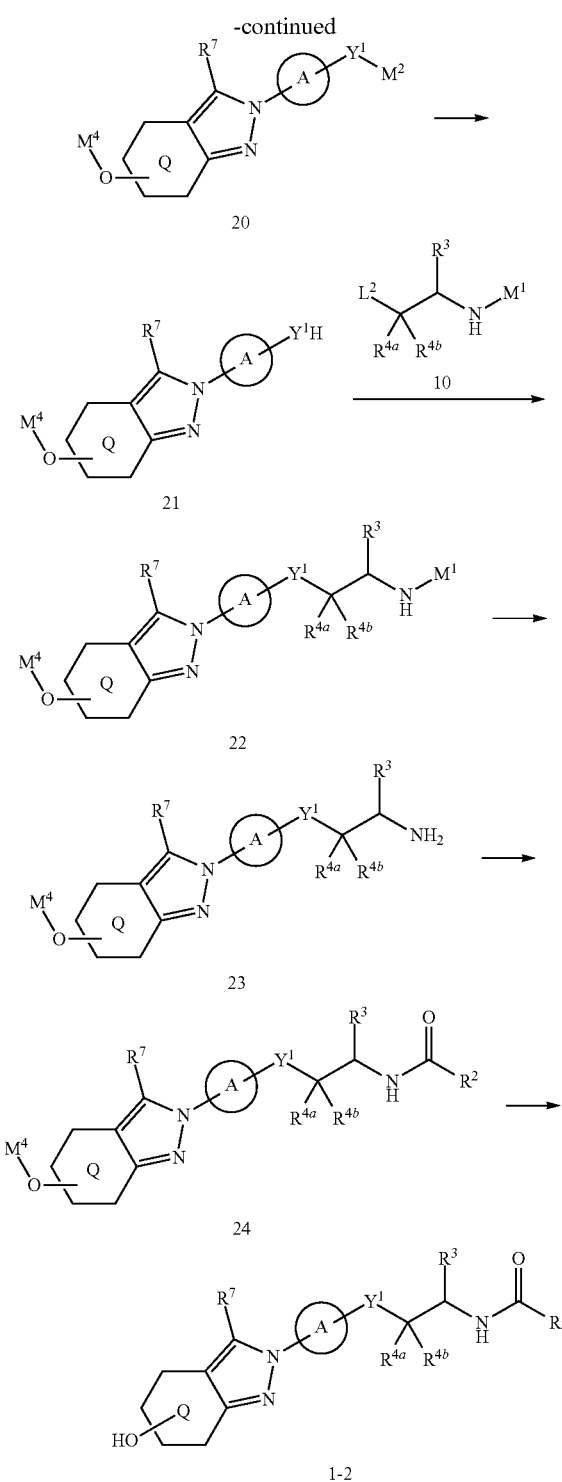

wherein $L^3$ is a halogen atom or a sulfonyloxy group, $M^4$ is a hydroxyl-protecting group, $R^7$ is a substituent, and the other symbols are as defined above.

Compound (19) can be produced, for example, by subjecting compound (17) to a coupling reaction with compound (18).

The above-mentioned "coupling reaction" is performed by reacting compound (17) with a base in an inert solvent to convert the hydrogen atom to a metal atom, and then reacting the resulting compound with compound (18).

The amount of compound (18) to be used is generally 0.5 to 5 equivalents, preferably 0.8 to 1.5 equivalents, relative to compound (17).

Examples of the above-mentioned "base" include "alkyl metals", "metal amides", "inorganic bases", "basic salts", "aryl metals", "metal alkoxides" and the like. The amount of the "base" to be used is generally 1 to 10 equivalents relative to compound (17).

Examples of the above-mentioned "inert solvent" include aliphatic hydrocarbon solvents, aromatic solvents, ether solvents and the like. These solvents may be used in a mixture of two or more kinds thereof in an appropriate ratio.

The reaction temperature is generally −100° C. to 200° C., preferably −100° C. to 100° C.

The reaction time is generally 1 min to 48 hr, preferably 5 min to 24 hr.

Compound (20) can be produced, for example, by subjecting compound (19) to a cyclization reaction.

The above-mentioned "cyclization reaction" is performed by reacting compound (19) in the presence of a metal catalyst, a ligand and a base, in an inert solvent. This reaction is preferably performed under an inert gas atmosphere.

Examples of the above-mentioned "metal catalyst" include palladium(II) acetate and the like. The amount of the "metal catalyst" to be used is generally 0.001 to 100 equivalents, preferably 0.01 to 10 equivalents, relative to compound (19).

Examples of the above-mentioned "ligand" include 1,1'-bis(diphenylphosphino)ferrocene and the like. The amount of the "ligand" to be used is generally 0.001 to 100 equivalents, preferably 0.01 to 10 equivalents, relative to compound (19).

Examples of the above-mentioned "base" include "metal alkoxides" and the like. Among them, sodium tert-butoxide and the like are preferable. The amount of the "base" to be used is generally 1 to 10 equivalents, preferably 1 to 5 equivalents, relative to compound (19).

Examples of the above-mentioned "inert solvent" include aromatic solvents, halogenated hydrocarbon solvents and the like. Among them, aromatic solvents are preferable.

Examples of the above-mentioned "inert gas" include argon gas, nitrogen gas and the like.

The reaction temperature is generally −20° C. to 200° C., preferably 0° C. to 150° C.

The reaction time is generally 5 min to 40 hr, preferably 30 min to 24 hr.

Compound (21) can be produced, for example, by subjecting compound (20) to a deprotection reaction.

The deprotection reaction can be performed according to a method known per se, for example, the method described in Protective Groups in Organic Synthesis, John Wiley and Sons (1980) or the like.

Compound (22) can be produced, for example, by subjecting compound (21) to a coupling reaction with compound (10).

This reaction is performed in the same manner as in the production method of compound (2-1) in Reaction Scheme 4.

Compound (23) can be produced, for example, by subjecting compound (22) to a deprotection reaction.

The deprotection reaction can be performed according to a method known per se, for example, the method described in Protective Groups in Organic Synthesis, John Wiley and Sons (1980) or the like.

Compound (24) can be produced, for example, by subjecting compound (23) to an acylation reaction.

This reaction is performed in the same manner as in the production method of compound (I-1) in Reaction Scheme 2.

Compound (1-2) can be produced, for example, by subjecting compound (24) to a deprotection reaction.

The deprotection reaction can be performed according to a method known per se, for example, the method described in Protective Groups in Organic Synthesis, John Wiley and Sons (1980) or the like.

Compound (11-1) can also be produced, for example, by subjecting compound (4-1) to a carbon monoxide-insertion reaction.

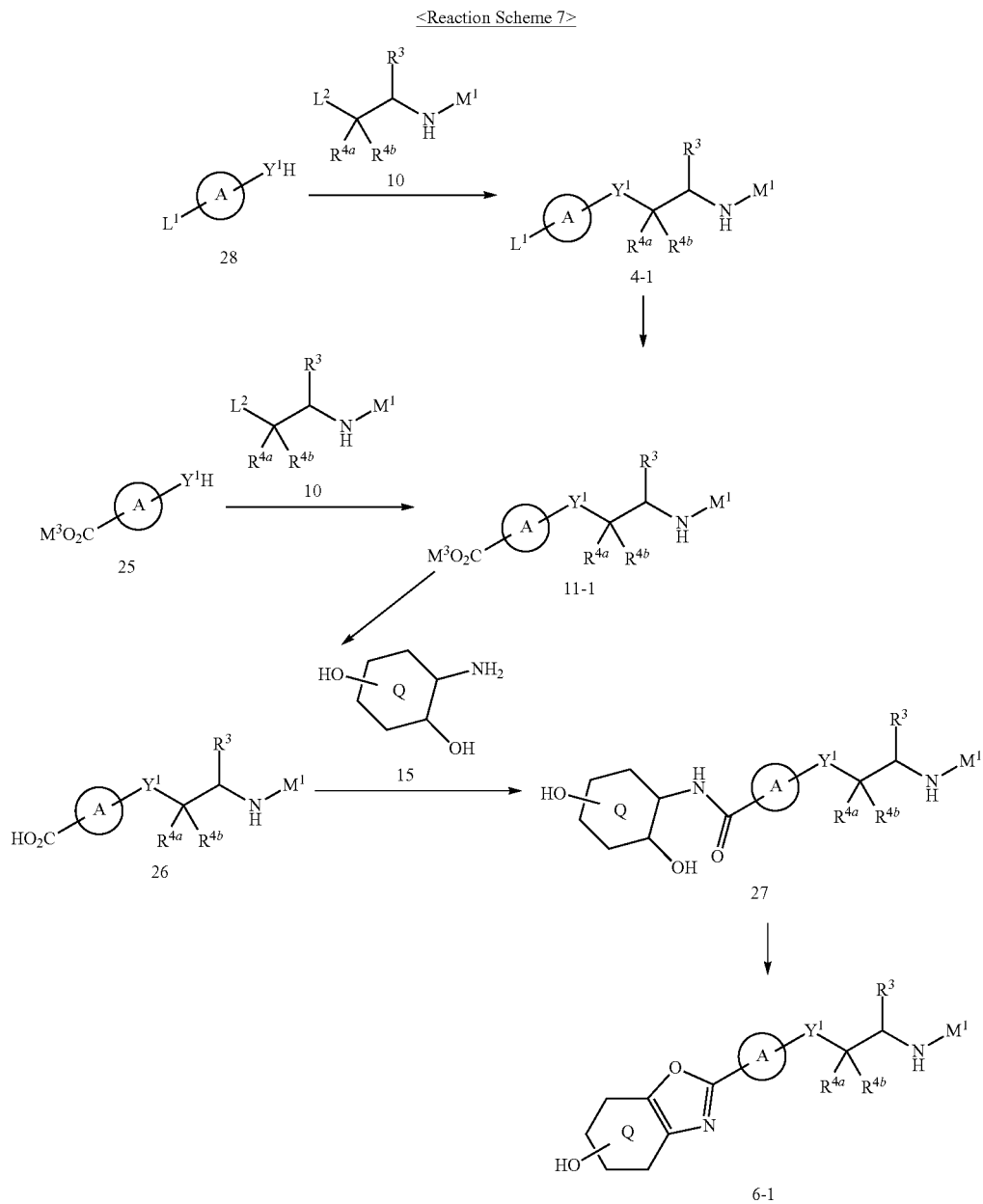

<Reaction Scheme 7> wherein each symbol is as defined above.

Compound (4-1) can be produced, for example, by subjecting compound (28) to a coupling reaction with compound (10).

This reaction is performed in the same manner as in the production method of compound (2-1) in Reaction Scheme 4.

Compound (11-1) can be produced, for example, by subjecting compound (25) to a coupling reaction with compound (10).

This reaction is performed in the same manner as in the production method of compound (2-1) in Reaction Scheme 4.

The above-mentioned "carbon monoxide-insertion reaction" is performed by reacting compound (4-1) with a hydroxide corresponding to $M^3$ in the presence of a metal catalyst and a carbon monoxide source, in an inert solvent. Where necessary, a ligand and base may be used.

Examples of the above-mentioned "hydroxide corresponding to $M^3$" include optionally substituted alkyl alcohols and optionally substituted cycloalkyl alcohols. The amount of the "hydroxide corresponding to $M^3$" to be used is generally 1 equivalent relative to compound (4-1) to a solvent amount.

Examples of the above-mentioned "metal catalyst" include 1,1'-bis(diphenylphosphino)ferrocene-palladium(II) dichloride dichloromethane complex and the like. The amount of the "metal catalyst" to be used is generally 0.001 to 100 equivalents, preferably 0.01 to 10 equivalents, relative to compound (4-1).

Examples of the above-mentioned "ligand" include 1,1'-bis(diphenylphosphino)ferrocene and the like. The amount of the "ligand" to be used is generally 0.001 to 100 equivalents, preferably 0.01 to 10 equivalents, relative to compound (4-1).

Examples of the above-mentioned "carbon monoxide source" include carbon monoxide gas and the like.

Examples of the above-mentioned "base" include "aromatic amines", "tertiary amines" and the like. The amount of the "base" to be used is generally 1 to 10 equivalents, preferably 1 to 5 equivalents, relative to compound (4-1).

Examples of the above-mentioned "inert solvent" include alcohol solvents, amide solvents, aromatic solvents, halogenated hydrocarbon solvents, ether solvents and the like. Among them, alcohol solvents corresponding to $M^3$ are preferable. These solvents may be used in a mixture of two or more kinds thereof in an appropriate ratio.

The reaction temperature is generally −20° C. to 200° C., preferably 0° C. to 150° C.

The reaction time is generally 5 min to 40 hr, preferably 30 min to 24 hr.

Compound (26) can be produced, for example, by subjecting compound (11-1) to hydrolysis.

This reaction is performed in the same manner as in the production method of compound (14) in Reaction Scheme 5.

Compound (27) can be produced, for example, by subjecting compound (26) to an amidation reaction with compound (15).

This reaction is performed in the same manner as in the production method of compound (16) in Reaction Scheme 5.

Compound (6-1) can be produced, for example, by subjecting compound (27) to a cyclization reaction.

This reaction is performed in the same manner as in the production method of compound (1-1) in Reaction Scheme 5.

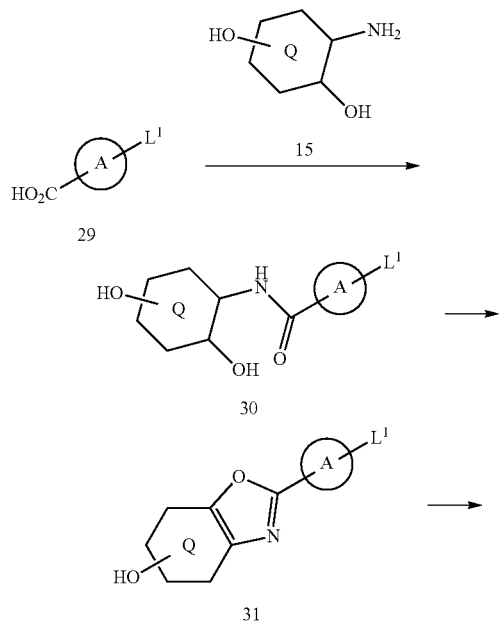

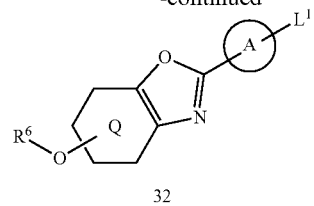

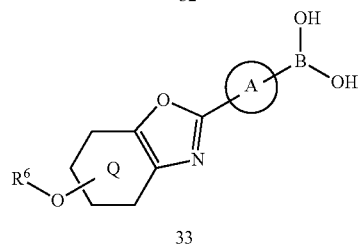

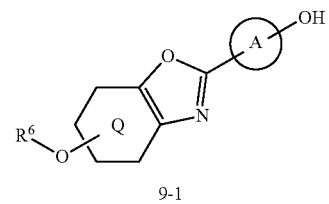

wherein each symbol is as defined above.

Compound (30) can be produced, for example, by subjecting compound (29) to an amidation reaction with compound (15).

This reaction is performed in the same manner as in the production method of compound (16) in Reaction Scheme 5.

Compound (31) can be produced, for example, by subjecting compound (30) to a cyclization reaction.

This reaction is performed in the same manner as in the production method of compound (1-1) in Reaction Scheme 5.

Compound (32) can be produced, for example, by subjecting compound (31) to an alkylation reaction.

This reaction is performed in the same manner as in the production method of compound (I) in Reaction Scheme 1.

Compound (33) can be produced, for example, by subjecting compound (32) to a boration reaction.

The above-mentioned "boration reaction" is performed by reacting compound (32) with an alkyl metal in an inert solvent to convert the halogen atom to a metal atom, and then reacting the resulting compound with an organic boron compound.

Examples of the above-mentioned "alkyl metal" include alkyllithiums, alkylmagnesium halides and the like. The amount of the "alkyl metal" to be used is generally 1 to 10 equivalents relative to compound (32).

Examples of the above-mentioned "organic boron compound" include trialkoxyborane and the like. The amount of the "organic boron compound" to be used is generally 1 to 10 equivalents relative to compound (32).

Examples of the above-mentioned "inert solvent" include aliphatic hydrocarbon solvents, aromatic solvents, ether solvents and the like. These solvents may be used in a mixture of two or more kinds thereof in an appropriate ratio.

The reaction temperature is generally −100° C. to 200° C., preferably −100° C. to 100° C.

The reaction time is generally 1 min to 48 hr, preferably 5 min to 24 hr.

Compound (9-1) can be produced, for example, by subjecting compound (33) to an oxidation reaction.

The above-mentioned "oxidation reaction" is performed by reacting compound (33) with an oxidant in an inert solvent. Where necessary, a base may be used.

Examples of the above-mentioned "oxidant" include oxygen, hydrogen peroxide, organic peroxides (e.g., m-chloroperbenzoic acid), inorganic peroxides (e.g., sodium perborate) and the like. The amount of the "oxidant" to be used is generally 1 to 10 equivalents relative to compound (33).

Examples of the above-mentioned "base" include "inorganic bases" and the like. The amount of the "base" to be used is generally 1 to 100 equivalents, preferably 1 to 50 equivalents, relative to compound (33).

Examples of the above-mentioned "inert solvent" include water, aliphatic hydrocarbon solvents, aromatic solvents, ether solvents and the like. These solvents may be used in a mixture of two or more kinds thereof in an appropriate ratio.

The reaction temperature is generally −100° C. to 200° C., preferably −100° C. to 100° C.

The reaction time is generally 1 min to 48 hr, preferably 5 min to 24 hr.

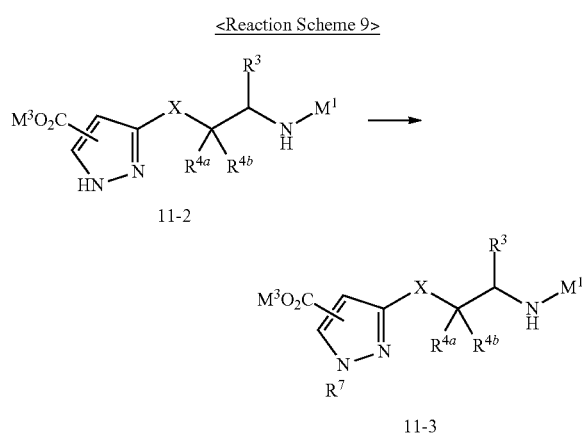

wherein each symbol is as defined above.

Compound (11-3) can be produced, for example, by subjecting compound (11-2) to a substitution reaction.

This reaction is performed by reacting compound (11-2) with a halide corresponding to $R^7$ in the presence of a base, in an inert solvent.

Examples of the above-mentioned "halide corresponding to $R^7$" include optionally substituted alkyl halides, optionally substituted cycloalkyl halides, optionally substituted cycloalkylalkyl halides and optionally substituted aralkyl halides. The amount of the "halide corresponding to $R^7$" to be used is generally 1 to 10 equivalents, preferably 1 to 5 equivalents, relative to compound (11-2).

Examples of the above-mentioned "base" include "inorganic bases", "basic salts", "aromatic amines", "tertiary amines", "hydrides of an alkali metal or alkaline earth metal", "alkyl metals", "aryl metals", "metal alkoxides" and the like. The amount of the "base" to be used is generally 1 to 10 equivalents, preferably 1 to 5 equivalents, relative to compound (11-2).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, THF, DMF and the like are preferable.

The reaction temperature is generally −100° C. to 150° C., preferably 0° C. to 100° C.

The reaction time is generally 5 min to 48 hr, preferably 30 min to 24 hr.

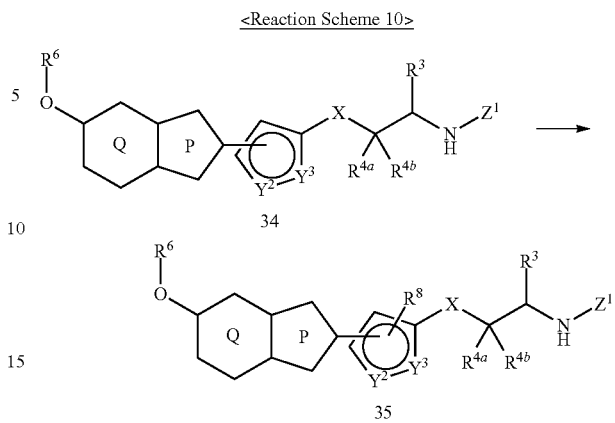

wherein $R^9$ is a substituent, $Y^2$ is a nitrogen atom when $Y^3$ is an oxygen atom, $Y^2$ is an oxygen atom or a nitrogen atom when $Y^3$ is a nitrogen atom, the nitrogen is optionally substituted by $R^7$, $Z^1$ is $M^1$ or $R^1$, and the other symbols are as defined above.

Compound (35) can be produced, for example, by subjecting compound (34) to a substitution reaction.

The above-mentioned "substitution reaction" is performed by reacting compound (34) with an alkyl metal in an inert solvent to convert the hydrogen atom to a metal atom, and then reacting the resulting compound with, for example, a halogenating agent or halide.

Examples of the above-mentioned "alkyl metal" include alkyllithiums, alkylmagnesium halides and the like. The amount of the "alkyl metal" to be used is generally 1 to 10 equivalents relative to compound (34).

Examples of the above-mentioned "halogenating agent" include N-fluoro-N-(phenylsulfonyl)benzenesulfonamide, bromine, iodine and the like. The amount of the "halogenating agent" to be used is generally 2 to 10 equivalents relative to compound (34).

Examples of the above-mentioned "halide" include optionally substituted alkyl halides, optionally substituted cycloalkyl halides, optionally substituted cycloalkylalkyl halides and optionally substituted aralkyl halides. The amount of the "halide" to be used is generally 1 to 10 equivalents, preferably 1 to 5 equivalents, relative to compound (34).

Examples of the above-mentioned "inert solvent" include aliphatic hydrocarbon solvents, aromatic solvents, ether solvents and the like. These solvents may be used in a mixture of two or more kinds thereof in an appropriate ratio.

The reaction temperature is generally −100° C. to 200° C., preferably −100° C. to 100° C.

The reaction time is generally 1 min to 48 hr, preferably 5 min to 24 hr.

The above-mentioned "substitution reaction" is also performed by reacting compound (34) with a halogenating agent in an inert solvent.

Examples of the above-mentioned "halogenating agent" include 1-(chloromethyl)-4-fluoro-1,4-diazoniabicyclo[2.2.2]octane ditetrafluoroborate, bromine, iodine and the like. The amount of the "halogenating agent" to be used is generally 2 to 20 equivalents relative to compound (34)

Examples of the above-mentioned "inert solvent" include nitrile solvents, aliphatic hydrocarbon solvents, aromatic solvents, ether solvents and the like. These solvents may be used in a mixture of two or more kinds thereof in an appropriate ratio.

The reaction temperature is generally −100° C. to 200° C., preferably −100° C. to 100° C.

The reaction time is generally 1 min to 48 hr, preferably 5 min to 24 hr.

<Reaction Scheme 11>

(I-2)

(I-3)

wherein $M^5$ is a protecting group such as an aralkyl group, a tetrahydropyranyl group and the like, and the other symbols are as defined above.

Compound (I-3) can be produced, for example, by subjecting compound (I-2) to a deprotection reaction.

The above-mentioned "deprotection reaction" is performed by reacting compound (I-2) in the presence of a metal catalyst and a hydrogen source, in an inert solvent. Where necessary, the reaction can be performed in the presence of an organic acid in a catalytic amount to a solvent amount, or hydrogen chloride in 1 to 50 equivalents relative to compound (I-2).

Examples of the above-mentioned "metal catalyst" include palladium-carbon, palladium black, palladium chloride, palladium hydroxide, rhodium-carbon, platinum oxide, platinum black, platinum-palladium, Raney-nickel, Raney-cobalt and the like. The amount of the "metal catalyst" to be used is generally 0.001 to 1000 equivalents, preferably 0.01 to 100 equivalents, relative to compound (I-2).

Examples of the above-mentioned "hydrogen source" include hydrogen gas and the like.

Examples of the above-mentioned "organic acid" include acetic acid and the like.

Examples of the above-mentioned "inert solvent" include alcohol solvents, nitrile solvents, aromatic solvents, aliphatic hydrocarbon solvents, ether solvents, amide solvents, halogenated hydrocarbon solvents and the like. These solvents may be used in a mixture of two or more kinds thereof in an appropriate ratio.

The reaction temperature is generally −70° C. to 150° C., preferably −20° C. to 100° C.

The reaction time is generally 0.1 hr to 100 hr, preferably 0.1 hr to 40 hr.

The above-mentioned "deprotection reaction" is also performed by reacting compound (I-2) in the presence of an acid, in an inert solvent.

Examples of the above-mentioned "acid" include hydrochloric acid, p-toluenesulfonic acid, trifluoroacetic acid and the like. The amount of the "acid" to be used is a catalytic amount to a solvent amount.

Examples of the above-mentioned "inert solvent" include alcohol solvents, ether solvents, halogenated hydrocarbon solvents, ester solvents and the like. These solvents may be used in a mixture with water in an appropriate ratio.

The reaction temperature is generally −70° C. to 150° C., preferably −20° C. to 100° C.

The reaction time is generally 0.1 hr to 100 hr, preferably 0.1 hr to 40 hr.

<Reaction Scheme 12>

36

5 wherein each symbol is as defined above.

Compound (5) can be produced, for example, by subjecting compound (36) to an alkylation reaction.

This reaction is performed in the same manner as in the production method of compound (I) in Reaction Scheme 1.

<Reaction Scheme 13>

37

38

28-1 wherein $L^{1a}$ is a halogen atom, and the other symbols are as defined above.

Compound (38) can be produced, for example, by subjecting compound (37) to a boronation reaction.

This reaction is performed in the same manner as in the production method of compound (33) in Reaction Scheme 8.

Compound (28-1) can be produced, for example, by subjecting compound (38) to an oxidation reaction.

This reaction is performed in the same manner as in the production method of compound (9-1) in Reaction Scheme 8.

<Reaction Scheme 14>

39

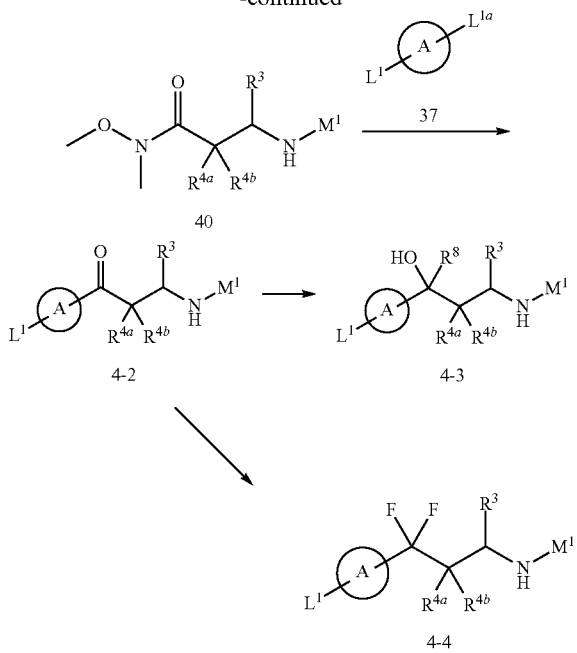

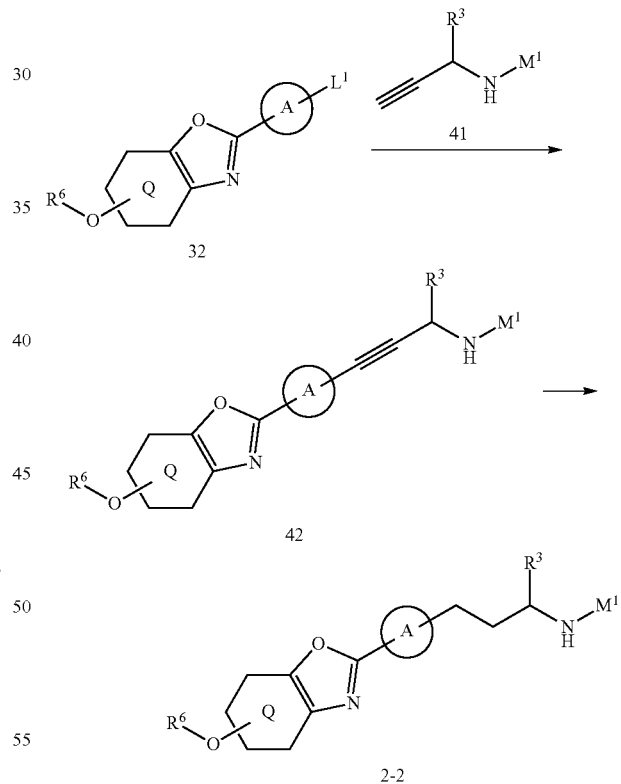

wherein each symbol is as defined above.

Compound (40) can be produced, for example, by subjecting compound (39) to an amidation reaction with N,O-dimethylhydroxylamine.

The above-mentioned "amidation reaction" is performed in the same manner as in the production method of "amide derivative" which is described as one of the production methods of compound (I-1) in Reaction Scheme 2.

Compound (4-2) can be produced, for example, by subjecting compound (40) to a coupling reaction with compound (37).

This reaction is performed by reacting compound (37) with an alkyl metal in an inert solvent to convert the halogen atom to a metal atom, and then reacting the resulting compound with compound (40).

Examples of the above-mentioned "alkyl metal" include alkyllithiums, alkylmagnesium halides and the like. The amount of the "alkyl metal" to be used is generally 1 to 10 equivalents relative to compound (37).

Examples of the above-mentioned "inert solvent" include aliphatic hydrocarbon solvents, aromatic solvents, ether solvents and the like. These solvents may be used in a mixture of two or more kinds thereof in an appropriate ratio.

The reaction temperature is generally −100° C. to 200° C., preferably −100° C. to 100° C.

The reaction time is generally 1 min to 48 hr, preferably 5 min to 24 hr.

Compound (4-3) can be produced, for example, by reacting compound (4-2) with an organic metal reagent corresponding to $R^8$ in an inert solvent.

Examples of the above-mentioned "organic metal reagent corresponding to $R^8$" include organic Grignard reagents (e.g., methylmagnesium bromide, methylmagnesium chloride), organic lithium reagents (e.g., methyllithium) and the like. The amount of the "organic metal reagent corresponding to $R^8$" to be used is generally 1 to 20 equivalents, preferably 1 to 5 equivalents, relative to compound (4-2).

Examples of the above-mentioned "inert solvent" include aromatic solvents, aliphatic hydrocarbon solvents, ether solvents, amide solvents, halogenated hydrocarbon solvents and the like. These solvents may be used in a mixture of two or more kinds thereof in an appropriate ratio. Among them, THF and the like are preferable.

The reaction temperature is generally −78° C. to 150° C., preferably −20° C. to 100° C.

The reaction time is generally 5 min to 48 hr, preferably 30 min to 24 hr.

Compound (4-4) can be produced, for example, by subjecting compound (4-2) to a fluorination reaction.

This reaction is performed by reacting compound (4-2) with a fluorinating agent in an inert solvent.

Examples of the above-mentioned "fluorinating agent" include (diethylamino)sulfur trifluoride and the like. The amount of the "fluorinating agent" to be used is generally 2 to 10 equivalents relative to compound (4-2).

Examples of the above-mentioned "inert solvent" include aliphatic hydrocarbon solvents, aromatic solvents, ether solvents, nitrile solvents, halogenated hydrocarbon solvents and the like. These solvents may be used in a mixture of two or more kinds thereof in an appropriate ratio.

The reaction temperature is generally −100° C. to 200° C., preferably −100° C. to 100° C.

The reaction time is generally 1 min to 48 hr, preferably 5 min to 24 hr.

<Reaction Scheme 15> wherein each symbol is as defined above.

Compound (42) can be produced, for example, by subjecting compound (32) to the Sonogashira coupling reaction with compound (41).

The above-mentioned "Sonogashira coupling reaction" is performed by reacting compound (32) with compound (41) in the presence of a metal catalyst and a base, in an inert solvent. This reaction is preferably performed under an inert gas atmosphere.

The amount of compound (41) to be used is generally 0.5 to 5 equivalents, preferably 0.8 to 2 equivalents, relative to compound (32).

Examples of the above-mentioned "metal catalyst" include a combination of bis(triphenylphosphine)palladium(II) dichloride and copper(I) iodide, and the like. The amount of the "metal catalyst" to be used is generally 0.001 to 100 equivalents, preferably 0.01 to 10 equivalents, relative to compound (32).

Examples of the above-mentioned "base" include "aromatic amines", "tertiary amines" and the like. The amount of the "base" to be used is generally 1 to 10 equivalents, preferably 1 to 5 equivalents, relative to compound (32).

Examples of the above-mentioned "inert solvent" include amide solvents, aromatic solvents, halogenated hydrocarbon solvents and the like.

Examples of the above-mentioned "inert gas" include argon gas, nitrogen gas and the like.

The reaction temperature is generally −20° C. to 200° C., preferably 0° C. to 150° C.

The reaction time is generally 5 min to 40 hr, preferably 30 min to 24 hr.

Compound (2-2) can be produced, for example, by subjecting compound (42) to a reduction reaction.

This reaction is performed by reacting compound (42) in the presence of a metal catalyst and a hydrogen source, in an inert solvent. Where necessary, the reaction can be performed in the presence of an organic acid in a catalytic amount to a solvent amount, or hydrogen chloride in 1 to 50 equivalents relative to compound (42).

Examples of the above-mentioned "metal catalyst" include palladium-carbon, palladium black, palladium chloride, palladium hydroxide, rhodium-carbon, platinum oxide, platinum black, platinum-palladium, Raney-nickel, Raney-cobalt and the like. The amount of the "metal catalyst" to be used is generally 0.001 to 1000 equivalents, preferably 0.01 to 100 equivalents, relative to compound (42).

Examples of the above-mentioned "hydrogen source" include hydrogen gas and the like.

Examples of the above-mentioned "organic acid" include acetic acid and the like.

Examples of the above-mentioned "inert solvent" include alcohol solvents, nitrile solvents, aromatic solvents, aliphatic hydrocarbon solvents, ether solvents, amide solvents, halogenated hydrocarbon solvents and the like. These solvents may be used in a mixture of two or more kinds thereof in an appropriate ratio.

The reaction temperature is generally −70° C. to 150° C., preferably −20° C. to 100° C.

The reaction time is generally 0.1 hr to 100 hr, preferably 0.1 hr to 40 hr.

<Reaction Scheme 16>

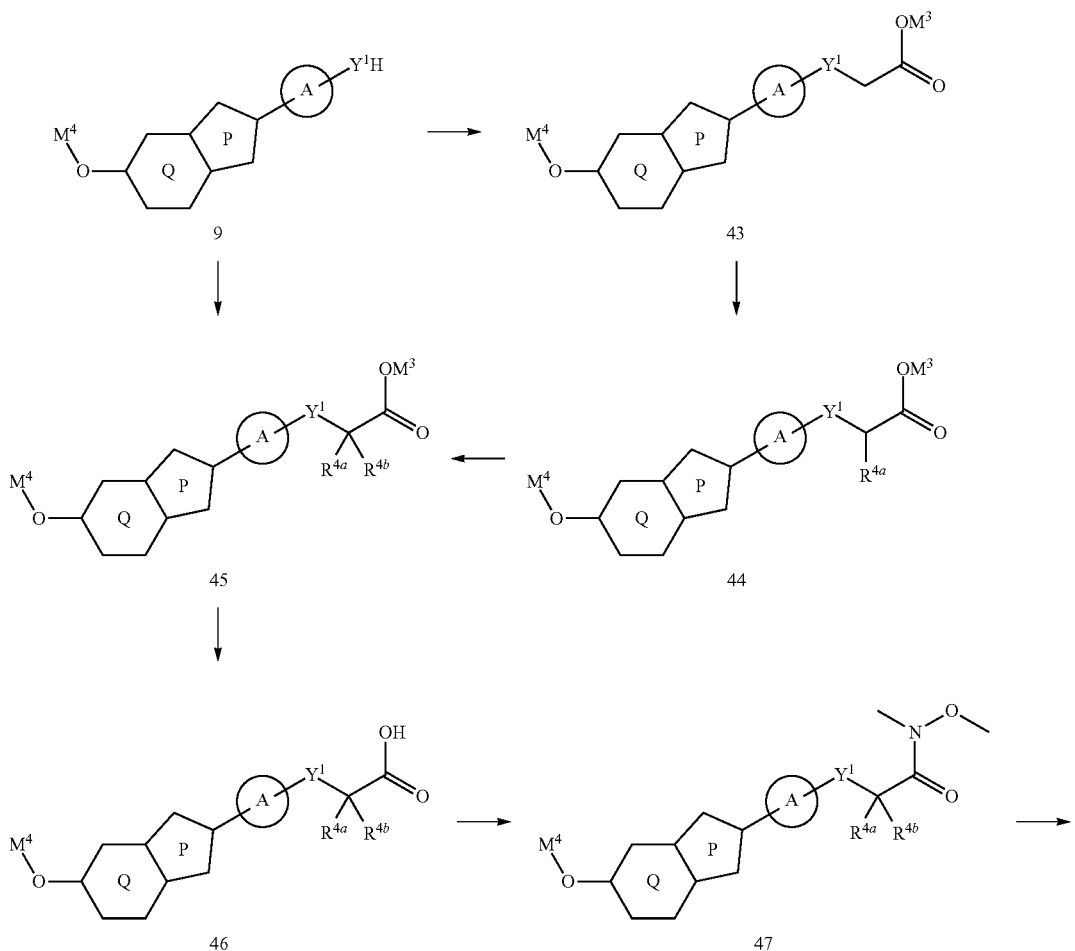

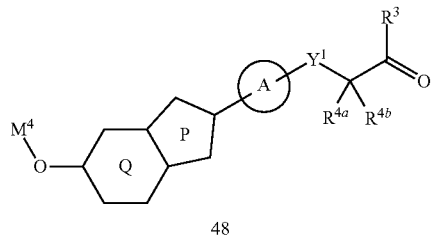
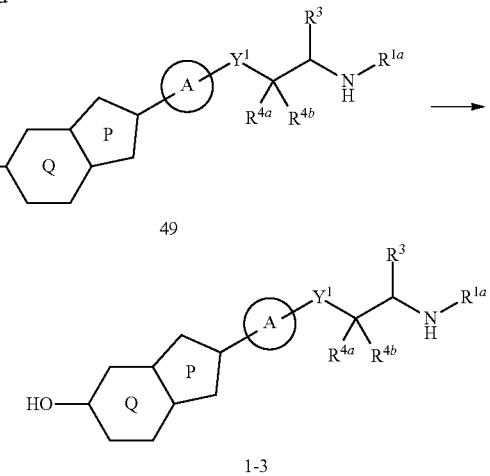

wherein $R^{1a}$ is an optionally substituted 5- or 6-membered aromatic ring, and the other symbols are as defined above.

Compound (43) can be produced, for example, by subjecting compound (9) to an alkylation reaction with a haloacetate, or by reacting compound (9) with a diazoacetate.

The above-mentioned "alkylation reaction with a haloacetate" is performed by reacting compound (9) with a haloacetate in the presence of a base, in an inert solvent. Where necessary, the reaction can be performed in the presence of a phase-transfer catalyst.

Examples of the above-mentioned "haloacetate" include ethyl bromoacetate, tert-butyl bromoacetate and the like. The amount of the "haloacetate" to be used is generally 1 to 10 equivalents, preferably 1 to 5 equivalents, relative to compound (9).

Examples of the above-mentioned "base" include "inorganic bases", "basic salts", "aromatic amines", "tertiary amines", "hydrides of an alkali metal or alkaline earth metal", "metal alkoxides" and the like. The amount of the "base" to be used is generally 1 to 10 equivalents, preferably 1 to 5 equivalents, relative to compound (9).

Examples of the above-mentioned "inert solvent" include aromatic solvents, amide solvents, halogenated hydrocarbon solvents, ether solvents and the like. These solvent may be used in a mixture with water in an appropriate ratio, or in a mixture of two or more kinds thereof in an appropriate ratio. Among them, THF, DMF and the like are preferable.

Examples of the above-mentioned "phase-transfer catalyst" include quaternary ammonium salts (e.g., tetrabutylammonium bromide, benzyltrioctylammonium chloride, tetrabutylammonium hydrogensulfate) and the like. The amount of the "phase-transfer catalyst" to be used is generally 0.001 to 10 equivalents, preferably 0.01 to 1 equivalents, relative to compound (9).

The reaction temperature is generally −100° C. to 150° C., preferably 0° C. to 100° C.

The reaction time is generally 5 min to 100 hr, preferably 30 min to 48 hr.

The above-mentioned "reaction with a diazoacetate" is performed by reacting compound (9) with a diazoacetate in the presence of a metal catalyst, in an inert solvent.

Examples of the above-mentioned "diazoacetate" include diazoethyl acetate and the like. The amount of the "diazoacetate" to be used is generally 1 to 10 equivalents, preferably 1 to 5 equivalents, relative to compound (9).

Examples of the above-mentioned "metal catalyst" include rhodium acetate dimer and the like. The amount of the "metal catalyst" to be used is generally 0.001 to 10 equivalents, preferably 0.01 to 1 equivalents, relative to compound (9).

Examples of the above-mentioned "inert solvent" include aromatic solvents, aliphatic hydrocarbon solvents, nitrile solvents, amide solvents, halogenated hydrocarbon solvents, ether solvents and the like. These solvents may be used in a mixture of two or more kinds thereof in an appropriate ratio. Among them, toluene, dichloromethane and the like are preferable.

The reaction temperature is generally −100° C. to 150° C., preferably 0° C. to 100° C.

The reaction time is generally 5 min to 48 hr, preferably 5 min to 24 hr.

Compound (44) can be produced, for example, by subjecting compound (43) to a substitution reaction.

This reaction is performed by reacting compound (43) with a base in an inert solvent to convert the hydrogen atom to a metal atom, and then reacting the resulting compound with, for example, a halogenating agent or halide.

Examples of the above-mentioned "base" include "hydrides of an alkali metal or alkaline earth metal", "metal amides", "metal alkoxides" and the like. The amount of the "base" to be used is generally 1 to 10 equivalents relative to compound (43).

Examples of the above-mentioned "halogenating agent" include N-fluoro-N-(phenylsulfonyl)benzenesulfonamide and the like. The amount of the "halogenating agent" to be used is generally 2 to 10 equivalents relative to compound (43).

Examples of the above-mentioned "halide" include optionally substituted alkyl halides, optionally substituted cycloalkyl halides, optionally substituted cycloalkylalkyl halides, optionally substituted aralkyl halides and the like. The amount of the "halide" to be used is generally 1 to 10 equivalents, preferably 1 to 5 equivalents, relative to compound (43).

Examples of the above-mentioned "inert solvent" include aliphatic hydrocarbon solvents, aromatic solvents, ether solvents, amide solvents, alcohol solvents and the like. These solvents may be used in a mixture of two or more kinds thereof in an appropriate ratio.

The reaction temperature is generally −100° C. to 200° C., preferably −100° C. to 100° C.

The reaction time is generally 1 min to 48 hr, preferably 5 min to 24 hr.

Compound (45) can be produced, for example, by subjecting compound (44) to a substitution reaction.

This reaction is performed in the same manner as in the production method of compound (44) in Reaction Scheme 16.

Compound (45) can also be produced, for example, by subjecting compound (9) to an alkylation reaction.

This reaction can be produced, for example, by subjecting compound (9) to an alkylation reaction with an optionally substituted haloacetate.

The above-mentioned "alkylation reaction" is performed by reacting compound (9) with an optionally substituted haloacetate in the presence of a base, in an inert solvent. Where necessary, the reaction can be performed in the presence of a phase-transfer catalyst.

Examples of the above-mentioned "optionally substituted haloacetate" include ethyl bromoacetate, tert-butyl bromoacetate and the like. The amount of the "optionally substituted haloacetate" to be used is generally 1 to 10 equivalents, preferably 1 to 5 equivalents, relative to compound (9).

Examples of the above-mentioned "base" include "inorganic bases", "basic salts", "aromatic amines", "tertiary amines", "hydrides of an alkali metal or alkaline earth metal", "metal alkoxides" and the like. The amount of the "base" to be used is generally 1 to 10 equivalents, preferably 1 to 5 equivalents, relative to compound (9).

Examples of the above-mentioned "inert solvent" include aromatic solvents, amide solvents, halogenated hydrocarbon solvents, ether solvents and the like. These solvent may be used in a mixture with water in an appropriate ratio, or in a mixture of two or more kinds thereof in an appropriate ratio. Among them, THF, DMF and the like are preferable.

Examples of the above-mentioned "phase-transfer catalyst" include quaternary ammonium salts (e.g., tetrabutylammonium bromide, benzyltrioctylammonium chloride, tetrabutylammonium hydrogensulfate) and the like. The amount of the "phase-transfer catalyst" to be used is generally 0.001 to 10 equivalents, preferably 0.01 to 1 equivalents, relative to compound (9).

The reaction temperature is generally −100° C. to 150° C., preferably 0° C. to 100° C.

The reaction time is generally 5 min to 100 hr, preferably 30 min to 48 hr.

Compound (46) can be produced, for example, by subjecting compound (45) to hydrolysis.

This reaction is performed in the same manner as in the production method of compound (14) in Reaction Scheme 5.

Compound (47) can be produced, for example, by subjecting compound (46) to an amidation reaction with N,O-dimethylhydroxylamine.

The above-mentioned "amidation reaction" is performed in the same manner as in the production method of compound (40) in Reaction Scheme 14.

Compound (48) can be produced, for example, by reacting compound (47) with an organic metal reagent in an inert solvent.

This reaction is performed in the same manner as in the production method of compound (4-2) in Reaction Scheme 14.

Compound (49) can be produced, for example, by subjecting compound (48) to a reductive amination reaction.

The reductive amination reaction can be performed according to a method known per se, for example, the method described in Tetrahedron Letters, 8345-8349 pages, 2001 or the like, or a method analogous thereto.

This reaction is performed by reacting compound (48) with the compound $R^{1a}NH_2$ in the presence of a reducing agent, in an inert solvent. Where necessary, the reaction can be performed in the presence of an organic acid in 1 equivalent relative to compound (48) to a solvent amount.

The amount of the above-mentioned "compound $R^{1a}NH_2$" to be used is generally 1 to 5 equivalents, preferably 1 to 4 equivalents, relative to compound (48).

Examples of the above-mentioned "reducing agent" include metal hydrogen compounds (e.g., diisobutylaluminum hydride), metal hydride complex compounds (e.g., sodium bis(2-methoxyethoxy)aluminum hydride, sodium borohydride, sodium cyanoborohydride, sodium triacetoxyborohydride, lithium aluminum hydride, sodium aluminum hydride), decaborane and the like. The amount of the "reducing agent" to be used is generally 0.1 to 20 equivalents, preferably 1 to 5 equivalents, relative to compound (48).

Examples of the above-mentioned "inert solvent" include alcohol solvents, amide solvents, halogenated hydrocarbon solvents, ester solvents, ether solvents and the like. These solvents may be used in a mixture of two or more kinds thereof in an appropriate ratio. Among them, methanol, THF, dichloroethane, dichloromethane and the like are preferable.

Examples of the above-mentioned "organic acid" include acetic acid and the like.

The reaction temperature is generally −78° C. to 100° C., preferably −20° C. to 50° C.

The reaction time is generally 5 min to 48 hr, preferably 30 min to 24 hr.

Compound (1-3) can be produced, for example, by subjecting compound (49) to a deprotection reaction.

The deprotection reaction can be performed according to a method known per se, for example, the method described in Protective Groups in Organic Synthesis, John Wiley and Sons (1980) or the like.

<Reaction Scheme 17>

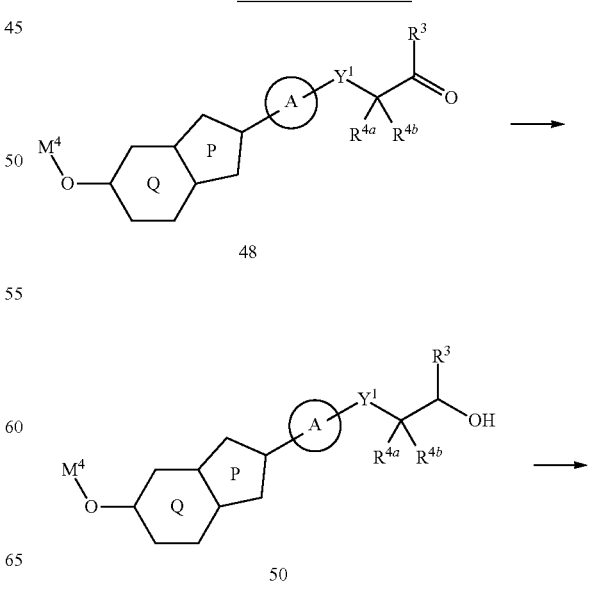

-continued

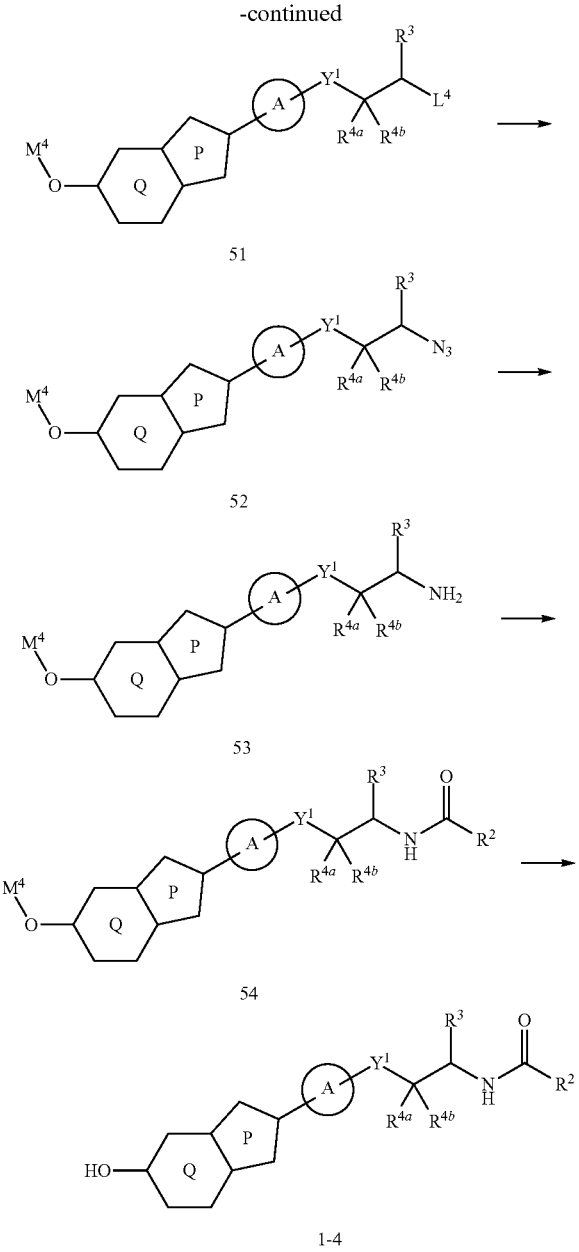

51

52

53

54

1-4 wherein L⁴ is a sulfonyloxy group, and the other symbols are as defined above.

Compound (50) can be produced, for example, by subjecting compound (48) to a reduction reaction.

This reaction is performed by reacting compound (48) with a reducing agent in an inert solvent.

Examples of the above-mentioned "reducing agent" include metal hydrogen compounds (e.g., diisobutylaluminum hydride), metal hydride complex compounds (e.g., sodium borohydride, sodium cyanoborohydride, lithium aluminum hydride, sodium aluminum hydride, sodium bis(2-methoxyethoxy)aluminum hydride) and the like. The amount of the "reducing agent" to be used is generally 0.1 to 20 equivalents, preferably 1 to 5 equivalents, relative to compound (48).

Examples of the above-mentioned "inert solvent" include alcohol solvents, aromatic solvents, aliphatic hydrocarbon solvents, ether solvents, amide solvents, halogenated hydrocarbon solvents and the like. These solvents may be used in a mixture of two or more kinds thereof in an appropriate ratio. Among them, THF, ethanol, methanol and the like are preferable.

The reaction temperature is generally −78° C. to 150° C., preferably −20° C. to 100° C.

The reaction time is generally 5 min to 48 hr, preferably 30 min to 24 hr.

Compound (51) can be produced, for example, by subjecting the hydroxyl group of compound (50) to a sulfonylation reaction.

This reaction is performed by reacting compound (50) with a sulfonylating agent in the presence of a base, in an inert solvent.

Examples of the above-mentioned "sulfonylating agent" include methanesulfonyl chloride, p-toluenesulfonyl chloride and the like. The amount of the "sulfonylating agent" to be used is generally 1 to 10 equivalents, preferably 1 to 1.5 equivalents, relative to compound (50).

Examples of the above-mentioned "base" include "aromatic amines", "tertiary amines" and the like are preferable. The amount of the "base" to be used is generally 1 to 20 equivalents, preferably 1 to 10 equivalents, relative to compound (50).

Examples of the above-mentioned "inert solvent" include aromatic solvents, aliphatic hydrocarbon solvents, ether solvents, ester solvents, amide solvents and the like. These solvents may be used in a mixture of two or more kinds thereof in an appropriate ratio.

The reaction temperature is generally −70° C. to 150° C., preferably −20° C. to 100° C.

The reaction time is generally 0.1 hr to 100 hr, preferably 0.1 hr to 48 hr.

Compound (52) can be produced, for example, by subjecting compound (51) to an azidation reaction.

This reaction is performed by reacting compound (51) with an azidating agent in an inert solvent.

Examples of the above-mentioned "azidating agent" include sodium azide, lithium azide, trimethylsilyl azide and the like. The amount of the "azidating agent" to be used is generally 1 to 20 equivalents, preferably 1 to 10 equivalents, relative to compound (51).

Examples of the above-mentioned "inert solvent" include ether solvents, amide solvents, sulfoxide solvents and the like. These solvents may be used in a mixture of two or more kinds thereof in an appropriate ratio.

The reaction temperature is generally −70° C. to 200° C., preferably 0° C. to 150° C.

The reaction time is generally 0.1 hr to 100 hr, preferably 0.1 hr to 48 hr.

Compound (53) can be produced, for example, by subjecting compound (52) to a reduction reaction.

This reaction is performed by reacting compound (52) in the presence of a metal catalyst and a hydrogen source, in an inert solvent.

Examples of the above-mentioned "metal catalyst" include palladium-carbon, palladium black, palladium chloride, palladium hydroxide, platinum oxide, platinum black, Raney-nickel, Raney-cobalt and the like. The amount of the "metal catalyst" to be used is generally 0.001 to 100 equivalents, preferably 0.01 to 10 equivalents, relative to compound (52).

Examples of the above-mentioned "hydrogen source" include hydrogen gas, formic acid, formic acid amine salt, phosphinates, hydrazine and the like.

Examples of the above-mentioned "inert solvent" include alcohol solvents, ester solvents, ether solvents, amide solvents, halogenated hydrocarbon solvents and the like. These solvents may be used in a mixture with water in an appropriate ratio. Among them, alcohol solvent is preferable.

The reaction temperature is generally −70° C. to 150° C., preferably −20° C. to 100° C.

The reaction time is generally 0.1 to 100 hr, preferably 0.1 to 48 hr.

This reaction can also be performed by reacting compound (52) with triphenylphosphine and water in an inert solvent.

Examples of the above-mentioned "inert solvent" include aromatic solvents, aliphatic hydrocarbon solvents, ether solvents, amide solvents, sulfoxide solvents, halogenated hydrocarbon solvents and the like. These solvents may be used in a mixture with water in an appropriate ratio. Among them, ether solvents are preferable.

The reaction temperature is generally −70° C. to 150° C., preferably −20° C. to 100° C.

The reaction time is generally 0.1 to 100 hr, preferably 0.1 to 40 hr.

Compound (54) can be produced, for example, by subjecting compound (53) to an acylation reaction.

This reaction is performed in the same manner as in the production method of compound (I-1) in Reaction Scheme 2.

Compound (1-4) can be produced, for example, by subjecting compound (54) to a deprotection reaction.

The deprotection reaction can be performed according to a method known per se, for example, the method described in Protective Groups in Organic Synthesis, John Wiley and Sons (1980) or the like.

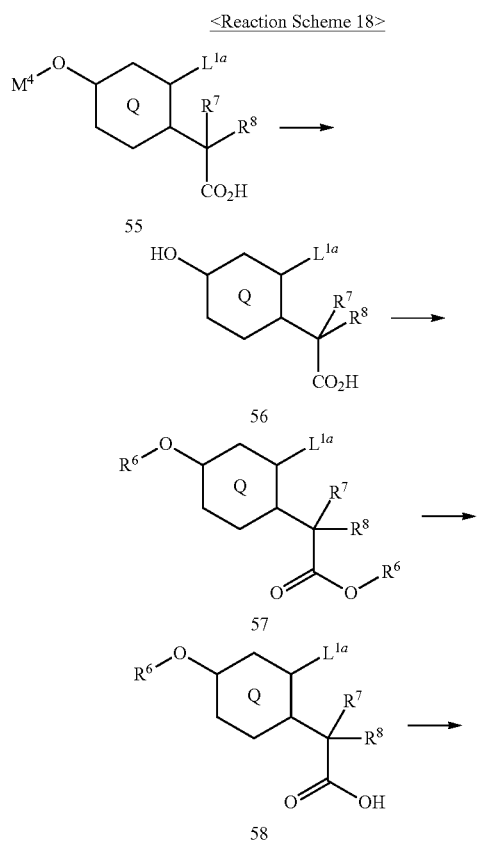

<Reaction Scheme 18>

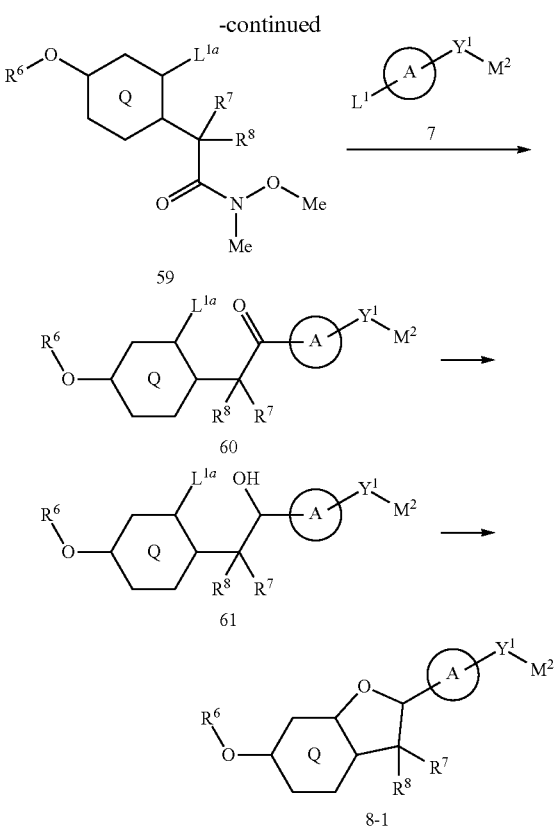

wherein each symbol is as defined above.

Compound (56) can be produced, for example, by subjecting compound (55) to a deprotection reaction.

The deprotection reaction can be performed according to a method known per se, for example, the method described in Protective Groups in Organic Synthesis, John Wiley and Sons (1980) or the like.

Compound (57) can be produced, for example, by subjecting compound (56) to an alkylation reaction.

Examples of the alkylation reaction include the following "method using a base and an alkyl halide or sulfonate corresponding to $R^6$" and the like.

The "method using a base and an alkyl halide or sulfonate corresponding to $R^6$" can be performed according to a method known per se, for example, the method described in Journal of the Chemical Society, 1530-1534 pages, 1937 or the like, or a method analogous thereto.

This reaction is performed by reacting compound (56) with an alkyl halide or sulfonate corresponding to $R^6$ in the presence of a base, in an inert solvent.

Examples of the above-mentioned "alkyl halide corresponding to $R^6$" include optionally substituted $C_{1-6}$ alkyl halides and optionally substituted $C_{3-6}$ cycloalkyl halides. The amount of the "alkyl halide corresponding to $R^6$" to be used is generally 2 to 10 equivalents, preferably 2 to 5 equivalents, relative to compound (56).

Examples of the above-mentioned "sulfonate corresponding to $R^6$" include optionally substituted $C_{1-6}$ alkyl esters of sulfonic acid, and optionally substituted $C_{3-6}$ cycloalkyl esters of sulfonic acid. Examples of the "sulfonic acid" include methylsulfonic acid, p-methylphenylsulfonic acid, trifluoromethylsulfonic acid and the like. The amount of the "sulfonate corresponding to $R^6$" to be used is generally 2 to 10 equivalents, preferably 2 to 5 equivalents, relative to compound (56).

Examples of the above-mentioned "base" include "inorganic bases", "basic salts", "aromatic amines", "hydrides of an alkali metal or alkaline earth metal", "alkyl metals", "aryl metals", "metal alkoxides" and the like. The amount of the "base" to be used is generally 2 to 10 equivalents, preferably 2 to 5 equivalents, relative to compound (56).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, THF, DMF and the like are preferable.

The reaction temperature is generally −100° C. to 150° C., preferably 0° C. to 100° C.

The reaction time is generally 5 min to 48 hr, preferably 30 min to 24 hr.

Compound (58) can be produced, for example, by subjecting compound (57) to hydrolysis.

This reaction is performed by reacting compound (57) with a base in an inert solvent.

Examples of the above-mentioned "base" include "inorganic bases" and the like. The amount of the "base" to be used is generally 1 to 10 equivalents, preferably 1 to 1.5 equivalents, relative to compound (57).

Examples of the above-mentioned "inert solvent" include alcohol solvents, ether solvents, amide solvents, halogenated hydrocarbon solvents and the like. These solvents are preferably used in a mixture with water in an appropriate ratio. Among them, alcohol solvents containing water are preferable.

The reaction temperature is generally −78° C. to 150° C., preferably −20° C. to 100° C.

The reaction time is generally 5 min to 100 hr, preferably 30 min to 24 hr.

Compound (59) can be produced, for example, by subjecting compound (58) to an amidation reaction with N,O-dimethylhydroxylamine.

The above-mentioned "amidation reaction" is performed in the same manner as in the production method of compound (40) in Reaction Scheme 14.

Compound (60) can be produced, for example, by reacting compound (7) with an alkyl metal in an inert solvent to convert the halogen atom of compound (7) to a metal atom, and then reacting the resulting compound with compound (59).

Examples of the above-mentioned "alkyl metal" include alkyllithiums, alkylmagnesium halides and the like. The amount of the "alkyl metal" to be used is generally 1 to 10 equivalents relative to compound (7).

Examples of the above-mentioned "inert solvent" include aliphatic hydrocarbon solvents, aromatic solvents, ether solvents and the like. These solvents may be used in a mixture of two or more kinds thereof in an appropriate ratio.

The reaction temperature is generally −100° C. to 200° C., preferably −100° C. to 100° C.

The reaction time is generally 1 min to 48 hr, preferably 5 min to 24 hr.

Compound (61) can be produced, for example, by subjecting compound (60) to a reduction reaction.

This reaction is performed by reacting compound (60) with a reducing agent in an inert solvent.

Examples of the above-mentioned "reducing agent" include metal hydrogen compounds (e.g., diisobutylaluminum hydride), metal hydride complex compounds (e.g., sodium borohydride, sodium cyanoborohydride, lithium aluminum hydride, sodium aluminum hydride, sodium bis(2-methoxyethoxy)aluminum hydride) and the like. The amount of the "reducing agent" to be used is generally 0.1 to 20 equivalents, preferably 1 to 5 equivalents, relative to compound (60).

Examples of the above-mentioned "inert solvent" include alcohol solvents, aromatic solvents, aliphatic hydrocarbon solvents, ether solvents, amide solvents, halogenated hydrocarbon solvents and the like. These solvents may be used in a mixture of two or more kinds thereof in an appropriate ratio. Among them, THF, ethanol, methanol and the like are preferable.

The reaction temperature is generally −78° C. to 150° C., preferably −20° C. to 100° C.

The reaction time is generally 5 min to 48 hr, preferably 30 min to 24 hr.

Compound (8-1) can be produced, for example, by subjecting compound (61) to a cyclization reaction.

This reaction is performed by reacting compound (61) in the presence of a base and a metal catalyst in an inert solvent.

Examples of the above-mentioned "base" include "inorganic bases", "basic salts", "aromatic amines", "tertiary amines", "hydrides of an alkali metal or alkaline earth metal", "alkyl metals", "aryl metals" and the like. The amount of the "base" to be used is generally 1 to 10 equivalents, preferably 1 to 5 equivalents, relative to compound (61).

Examples of the above-mentioned "metal catalyst" include copper halides such as copper(I) chloride, copper(I) bromide, copper(II) chloride and the like and the like. The amount of the "metal catalyst" to be used is generally 0.001 to 100 equivalents, preferably 0.01 to 10 equivalents, relative to compound (61).

Examples of the above-mentioned "inert solvent" include aromatic solvents, aliphatic hydrocarbon solvents, ether solvents, amide solvents, halogenated hydrocarbon solvents and the like. These solvents may be used in a mixture of two or more kinds thereof in an appropriate ratio. Among them, THF, toluene and the like are preferable.

The reaction temperature is generally −78° C. to 200° C., preferably −20° C. to 150° C.

The reaction time is generally 5 min to 48 hr, preferably 30 min to 24 hr.

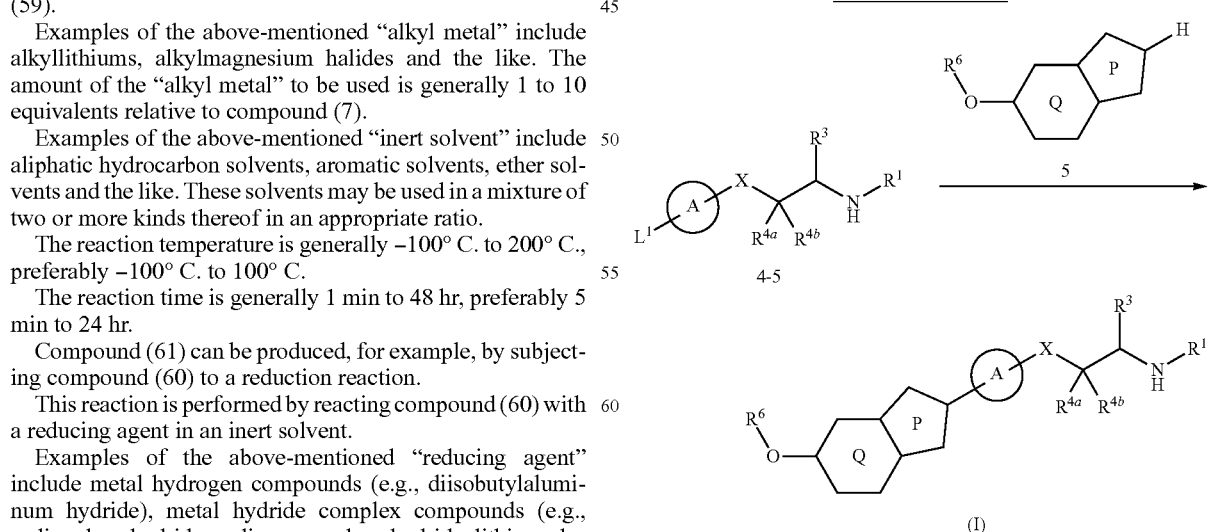

<Reaction Scheme 19> wherein each symbol is as defined above.

Compound (I) can be produced, for example, by subjecting compound (4-5) to a coupling reaction with compound (5).

This reaction is performed in the same manner as in the production method of compound (2) from compound (4) and compound (5) in Reaction Scheme 3.

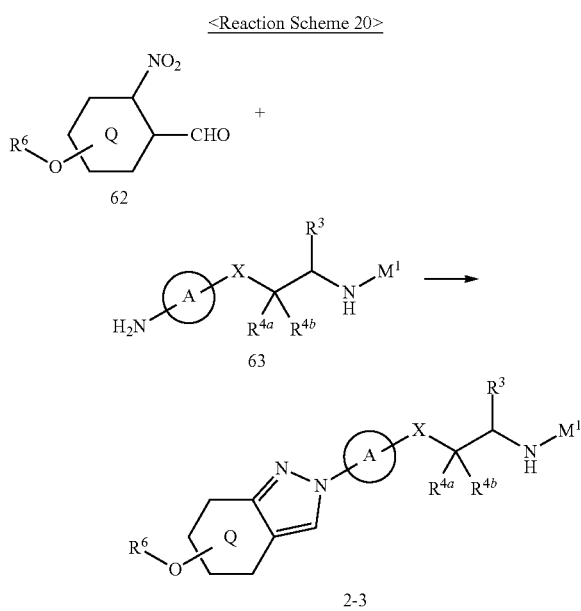

<Reaction Scheme 20> wherein each symbol is as defined above.

Compound (2-3) can be produced, for example, by subjecting compound (62) to a dehydration-condensation reaction with compound (63), and then subjecting the resulting compound to a cyclization reaction.

The above-mentioned "dehydration-condensation reaction" is performed by reacting compound (62) with compound (63) in the presence of a dehydrating agent, in an inert solvent.

The amount of compound (63) to be used is generally 0.01 to 5 equivalents relative to compound (62).

Examples of the above-mentioned "dehydrating agent" include magnesium sulfate and the like. The amount of the "dehydrating agent" to be used is generally 1 to 1000 equivalents relative to compound (62).

Examples of the above-mentioned "inert solvent" include alcohol solvents, aromatic solvents, aliphatic hydrocarbon solvents, ether solvents, amide solvents, halogenated hydrocarbon solvents and the like. These solvents may be used in a mixture of two or more kinds thereof in an appropriate ratio. Among them, alcohol solvent is preferable.

The reaction temperature is generally −78° C. to 200° C., preferably 50° C. to 150° C.

The reaction time is generally 5 min to 48 hr, preferably 30 min to 24 hr.

The above-mentioned "cyclization reaction" is performed by reacting the compound obtained in the above-mentioned dehydration-condensation reaction of compound (62) with compound (63) in the presence of an activator.

Examples of the above-mentioned "activator" include trimethylphosphite, triethylphosphite and the like. The amount of the "activator" to be used is generally 5 equivalents to an excess amount relative to compound (62).

The reaction temperature is generally −78° C. to 200° C., preferably 50° C. to 150° C.

The reaction time is generally 5 min to 48 hr, preferably 30 min to 24 hr.

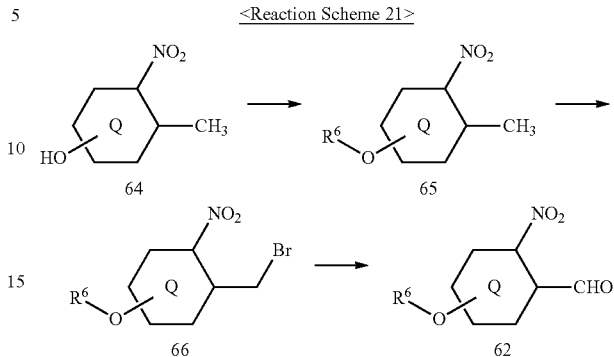

<Reaction Scheme 21> wherein each symbol is as defined above.

Compound (65) can be produced, for example, by subjecting compound (64) to an alkylation reaction.

This reaction is performed in the same manner as in the production method of compound (I) in Reaction Scheme 1.

Compound (66) can be produced, for example, by subjecting compound (65) to a bromination reaction.

The above-mentioned "bromination reaction" is performed by reacting compound (65) in the presence of a brominating agent and a radical initiator, in an inert solvent.

Examples of the above-mentioned "brominating agent" include bromine, N-bromosucciniinide and the like. The amount of the "brominating agent" to be used is generally 1 to 10 equivalents relative to compound (65).

Examples of the above-mentioned "radical initiator" include 2,2'-azobis(2-methylpropionitrile) and the like. The amount of the "radical initiator" to be used is generally 0.01 to 10 equivalents relative to compound (65).

Examples of the above-mentioned "inert solvent" include nitrile solvents, aromatic solvents, aliphatic hydrocarbon solvents, ether solvents, amide solvents, halogenated hydrocarbon solvents and the like. Among them, nitrile solvents, aromatic solvents and halogenated hydrocarbon solvents are preferable.

The reaction temperature is generally −78° C. to 200° C., preferably 50° C. to 150° C.

The reaction time is generally 5 min to 48 hr, preferably 30 min to 24 hr.

Compound (62) can be produced, for example, by subjecting compound (66) to an oxidation reaction.

The above-mentioned "oxidation reaction" is performed by reacting compound (66) in the presence of an oxidant and a dehydrating agent, in an inert solvent. This reaction is preferably performed under an inert gas atmosphere.

Examples of the above-mentioned "oxidant" include 4-methylmorpholine N-oxide and the like. The amount of the "oxidant" to be used is generally 1 to 100 equivalents, preferably 1 to 10 equivalents, relative to compound (66).

Examples of the above-mentioned "dehydrating agent" include molecular sieves 4A and the like. The amount of the "dehydrating agent" to be used is generally 0.1- to 100-fold amount, preferably 0.5- to 10-fold amount, relative to the weight of compound (66).

Examples of the above-mentioned "inert solvent" include nitrile solvents, aromatic solvents, aliphatic hydrocarbon solvents, ether solvents, amide solvents, halogenated hydrocarbon solvents and the like. Among them, nitrile solvents and halogenated hydrocarbon solvents are preferable.

Examples of the above-mentioned "inert gas" include argon gas, nitrogen gas and the like.

The reaction temperature is generally −78° C. to 150° C., preferably −20° C. to 100° C.

The reaction time is generally 5 min to 48 hr, preferably 30 min to 24 hr.

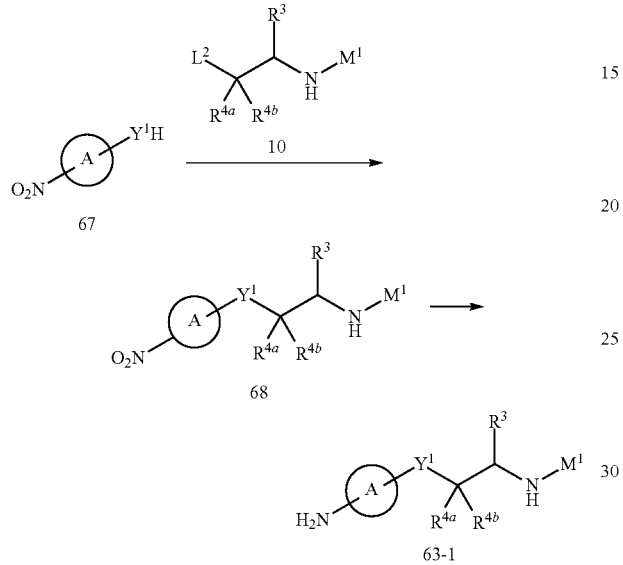

wherein each symbol is as defined above.

Compound (68) can be produced, for example, by subjecting compound (67) to a coupling reaction with compound (10).

This reaction is performed in the same manner as in the production method of compound (2-1) in Reaction Scheme 4.

Compound (63-1) can be produced, for example, by subjecting compound (68) to a hydrogenation reaction.

The above-mentioned "hydrogenation reaction" is performed by reacting compound (68) in the presence of a metal catalyst and a hydrogen source, in an inert solvent. Where necessary, the reaction can be performed in the presence of an organic acid in a catalytic amount to an excess amount relative to compound (68), or hydrogen chloride in 1 to 50 equivalents relative to compound (68).

Examples of the above-mentioned "metal catalyst" include palladium-carbon, palladium black, palladium chloride, palladium hydroxide, rhodium-carbon, platinum oxide, platinum black, platinum-palladium, Raney-nickel, Raney-cobalt and the like. The amount of the "metal catalyst" to be used is generally 0.001 to 1000 equivalents, preferably 0.01 to 100 equivalents, relative to compound (68).

Examples of the above-mentioned "hydrogen source" include hydrogen gas and the like.

Examples of the above-mentioned "organic acid" include acetic acid and the like.

Examples of the above-mentioned "inert solvent" include alcohol solvents, nitrile solvents, aromatic solvents, aliphatic hydrocarbon solvents, ether solvents, amide solvents, halogenated hydrocarbon solvents and the like. These solvents may be used in a mixture of two or more kinds thereof in an appropriate ratio.

The reaction temperature is generally −70° C. to 150° C., preferably −20° C. to 100° C.

The reaction time is generally 0.1 hr to 100 hr, preferably 0.1 hr to 40 hr.

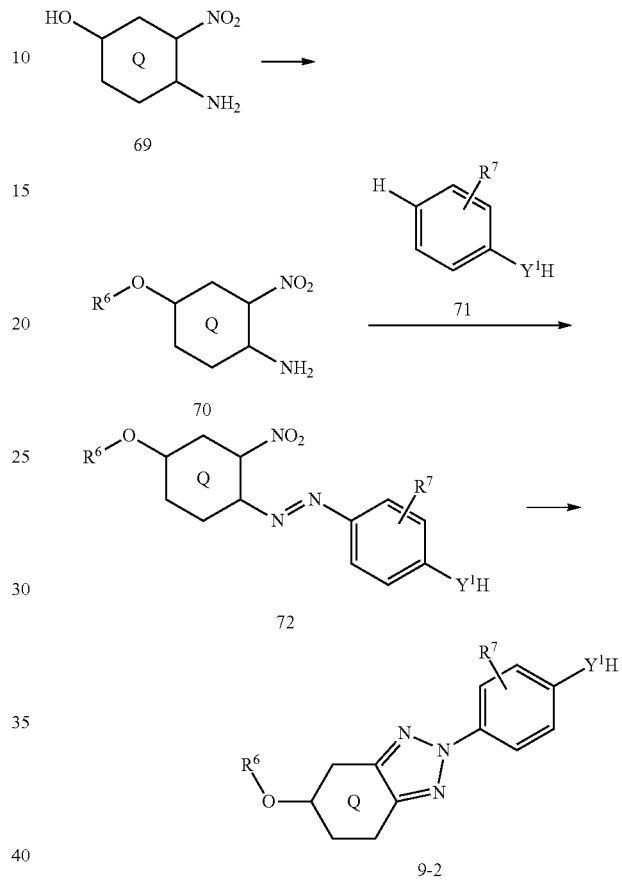

wherein each symbol is as defined above.

Compound (70) can be produced, for example, by subjecting compound (69) to an alkylation reaction.

This reaction is performed in the same manner as in the production method of compound (I) in Reaction Scheme 1.

Compound (72) can be produced, for example, by subjecting compound (70) to a diazocoupling reaction with compound (71).

The above-mentioned "diazocoupling reaction" is performed by reacting compound (70) with a diazotizating agent under an acidic condition, and then reacting the resulting diazonium salt with compound (71) under a basic condition.

The production reaction of the above-mentioned "diazonium salt" is performed by reacting compound (70) with a diazotizating agent in an acidic aqueous solution such as hydrochloric acid, sulfuric acid and the like.

Examples of the above-mentioned "diazotizating agent" include sodium nitrite and the like. The amount of the "diazotizating agent" to be used is generally 1 to 100 equivalents, preferably 1 to 10 equivalents, relative to compound (70).

The reaction temperature is generally −70° C. to 150° C., preferably −20° C. to 30° C.

The reaction time is generally 0.1 hr to 100 hr, preferably 0.1 hr to 40 hr.

The reaction of the above-mentioned "diazonium salt" with compound (71) is performed by reacting the "diazonium salt" with compound (71) in an basic aqueous solution such as an aqueous sodium hydroxide solution and the like.

The amount of compound (71) to be used is generally 0.5 to 10 equivalents, preferably 0.8 to 5 equivalents, relative to compound (70).

The reaction temperature is generally −70° C. to 150° C., preferably −20° C. to 50° C.

The reaction time is generally 0.1 hr to 100 hr, preferably 0.1 hr to 40 hr.

Compound (9-2) can be produced, for example, by subjecting compound (72) to a cyclization reaction.

The above-mentioned "cyclization reaction" is performed by reacting compound (72) in the presence of an activator, in an inert solvent.

Examples of the above-mentioned "activator" include trimethylphosphite, triethylphosphite and the like. The amount of the "activator" to be used is 1 to 100 equivalents (an excess amount) relative to compound (72).

The reaction temperature is generally −78° C. to 200° C., preferably 50° C. to 150° C.

The reaction time is generally 5 min to 48 hr, preferably 30 min to 24 hr.

The above-mentioned "fluorination reaction" is performed by reacting compound (74) in the presence of a fluorinating agent, in an inert solvent.

Examples of the above-mentioned "fluorinating agent" include diethylaminosulfur trifluoride, bis(2-methoxyethyl)aminosulfur trifluoride and the like. The amount of the "fluorinating agent" to be used is generally 3 to 100 equivalents, preferably 3 to 10 equivalents, relative to compound (74).

Examples of the above-mentioned "inert solvent" include nitrile solvents, aromatic solvents, aliphatic hydrocarbon solvents, ether solvents, halogenated hydrocarbon solvents and the like. Among them, aromatic solvents and halogenated hydrocarbon solvents are preferable.

The reaction temperature is generally −70° C. to 150° C., preferably −20° C. to 100° C.

The reaction time is generally 0.1 hr to 100 hr, preferably 0.1 hr to 40 hr.

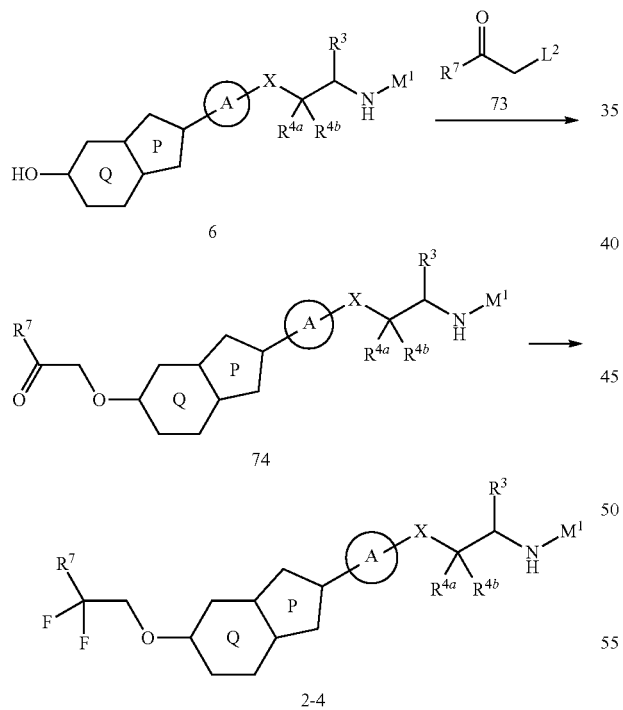

<Reaction Scheme 24>

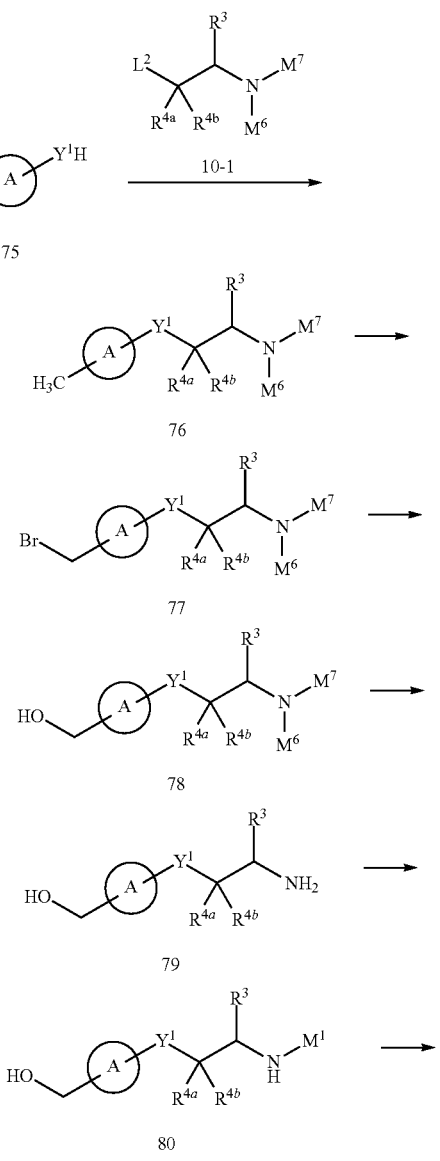

<Reaction Scheme 25> wherein each symbol is as defined above.

Compound (74) can be produced, for example, by subjecting compound (6) to a coupling reaction with compound (73).

This reaction is performed in the same manner as in the production method of compound (2-1) in Reaction Scheme 4.

Compound (2-4) can be produced, for example, by subjecting compound (74) to a fluorination reaction.

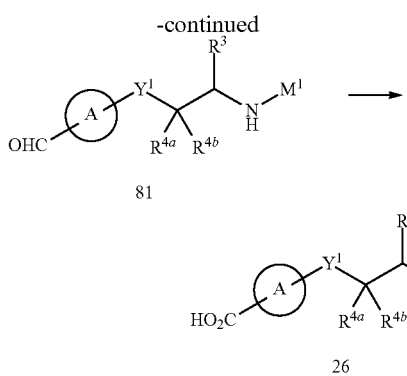

wherein $M^6$ and $M^7$ are each a nitrogen atom-protecting group, or $M^6$ is a hydrogen atom and $M^7$ is a nitrogen atom-protecting group, and the other symbols are as defined above.

Compound (76) can be produced, for example, by subjecting compound (75) to a coupling reaction with compound (10-1).

This reaction is performed in the same manner as in the production method of compound (2-1) in Reaction Scheme 4.

Compound (77) can be produced, for example, by subjecting compound (76) to a bromination reaction.

This reaction is performed in the same manner as in the production method of compound (66) in Reaction Scheme 21.

Compound (78) can be produced, for example, by subjecting compound (77) to a substitution reaction.

The above-mentioned "substitution reaction" is performed by reacting compound (77) in a mixed solvent of water and an inert solvent.

Examples of the above-mentioned "inert solvent" include amide solvents and the like. Among them, N-methylpyrrolidone is preferable.

The reaction temperature is generally −70° C. to 150° C., preferably −20° C. to 120° C.

The reaction time is generally 0.1 hr to 100 hr, preferably 0.1 hr to 40 hr.

Compound (79) can be produced, for example, by subjecting compound (78) to a deprotection reaction.

The deprotection reaction can be performed according to a method known per se, for example, the method described in Protective Groups in Organic Synthesis, John Wiley and Sons (1980) or the like.

Compound (80) can be produced, for example, by subjecting compound (79) to a protection reaction.

The protection reaction can be performed according to a method known per se, for example, the method described in Protective Groups in Organic Synthesis, John Wiley and Sons (1980) or the like.

Compound (81) can be produced, for example, by subjecting compound (80) to an oxidation reaction.

The above-mentioned "oxidation reaction" is performed by reacting compound (80) with an oxidant in an inert solvent.

Examples of the above-mentioned "oxidant" include manganese dioxide, tetrapropylammonium perruthenate, chromium trioxide, Dess-Martin reagent and the like. The amount of the "oxidant" to be used is generally 1 to 5 equivalents, preferably 1 to 2 equivalents, relative to compound (80).

Examples of the above-mentioned "inert solvent" include alcohol solvents, nitrile solvents, amide solvents, halogenated hydrocarbon solvents, ether solvents, aromatic solvents and the like. These solvents may be used in a mixture of two or more kinds thereof in an appropriate ratio. Among them, nitrile solvents, halogenated hydrocarbon solvents and the like are preferable.

The reaction temperature is generally −100° C. to 50° C., preferably −78° C. to 30° C.

The reaction time is generally 5 min to 48 hr, preferably 30 min to 24 hr.

The above-mentioned "oxidation reaction" can also be performed according to a method known per se, for example, the method described in Journal of the Medicinal Chemistry, 5282-5290 pages, 2006 or the like, or a method analogous thereto.

Compound (26) can be produced, for example, by subjecting compound (81) to an oxidation reaction.

The above-mentioned "oxidation reaction" is performed by reacting compound (81) with an oxidant in an inert solvent.

Examples of the above-mentioned "oxidant" include sodium dihydrogen phosphate, chromium trioxide and the like. Where necessary, an additive such as 2-methylbut-2-ene and the like may be added. The amount of the "oxidant" to be used is generally 1 to 5 equivalents, preferably 1 to 2 equivalents, relative to compound (81).

Examples of the above-mentioned "inert solvent" include alcohol solvents, ketone solvents and the like. These solvents are preferably used in a mixture with water in an appropriate ratio.

The reaction temperature is generally −100° C. to 100° C., preferably −78° C. to 50° C.

The reaction time is generally 5 min to 48 hr, preferably 30 min to 24 hr.

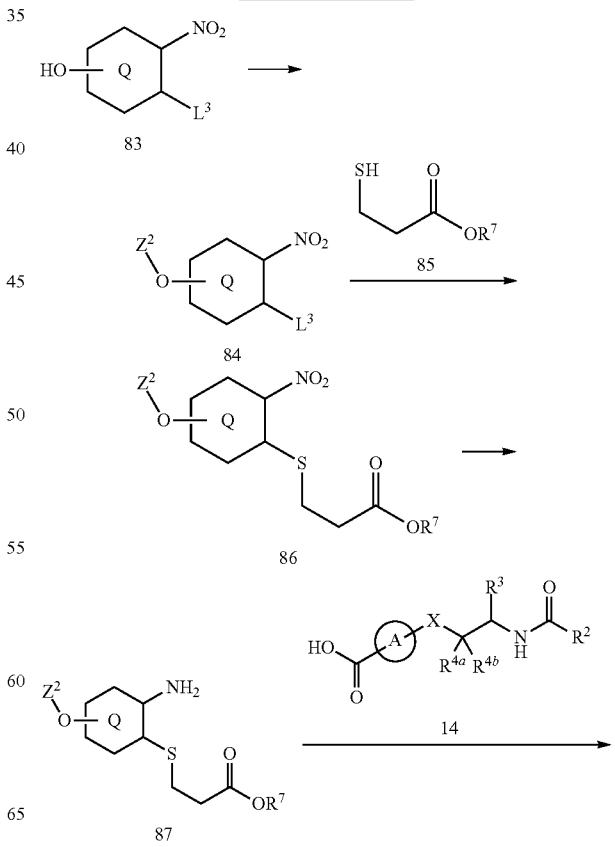

-continued

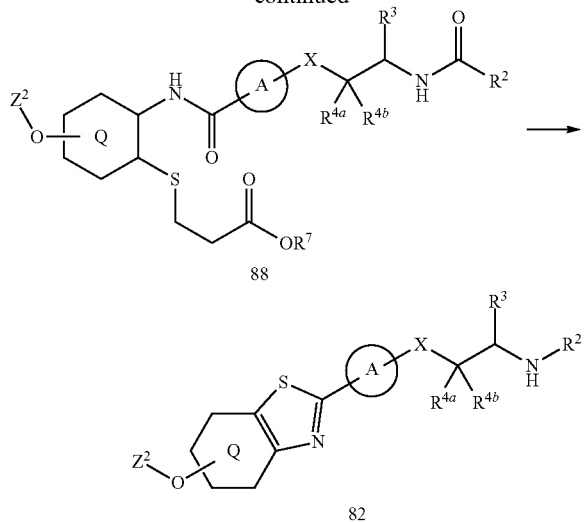

wherein $Z^2$ is $R^6$ or a hydroxyl-protecting group, and the other symbols are as defined above.

Compound (84) can be produced, for example, by subjecting compound (83) to an alkylation reaction.

This reaction is performed in the same manner as in the production method of compound (I) in Reaction Scheme 1.

Compound (84) can also be produced, for example, by subjecting compound (83) to a protection reaction.

The protection reaction can be performed according to a method known per se, for example, the method described in Protective Groups in Organic Synthesis, John Wiley and Sons (1980) or the like.

Compound (86) can be produced, for example, by subjecting compound (84) to a substitution reaction with compound (85).

This reaction is performed in the same manner as in the "method using a base", from among the production methods of compound (2-1) in Reaction Scheme 4.

Compound (87) can be produced, for example, by subjecting compound (86) to a hydrogenation reaction.

The above-mentioned "hydrogenation reaction" is performed by reacting compound (86) in the presence of a metal and a hydrogen source, in an inert solvent. Where necessary, the reaction can be performed in the presence of an organic acid in a catalytic amount to a solvent amount, or hydrogen chloride in 1 to 50 equivalents relative to compound (86).

Examples of the above-mentioned "metal" include palladium-carbon, palladium black, palladium chloride, palladium hydroxide, rhodium-carbon, platinum oxide, platinum black, platinum-palladium, Raney-nickel, Raney-cobalt and the like. The amount of the "metal" to be used is generally 0.001 to 1000 equivalents, preferably 0.01 to 100 equivalents, relative to compound (86).

Examples of the above-mentioned "hydrogen source" include hydrogen gas, ammonium formate and the like.

Examples of the above-mentioned "organic acid" include acetic acid and the like.

Examples of the above-mentioned "inert solvent" include alcohol solvents, aromatic solvents, aliphatic hydrocarbon solvents, ether solvents, amide solvents, halogenated hydrocarbon solvents and the like. These solvents may be used in a mixture of two or more kinds thereof in an appropriate ratio.

The reaction temperature is generally –70° C. to 150° C., preferably –20° C. to 100° C.

The reaction time is generally 0.1 hr to 100 hr, preferably 0.1 hr to 40 hr.

The above-mentioned "hydrogenation reaction" is also performed by reacting compound (86) in the presence of a metal and a hydrochloric acid source, in an inert solvent.

Examples of the above-mentioned "metal" include iron, zinc, tin and the like. The amount of the "metal" to be used is generally 0.1 to 1000 equivalents, preferably 1 to 100 equivalents, relative to compound (86).

Examples of the above-mentioned "hydrochloric acid source" include hydrochloric acid, hydrogen chloride gas, ammonium chloride and the like. The amount of the "hydrochloric acid source" to be used is generally 1 equivalent to an excess amount relative to compound (86).

Examples of the above-mentioned "inert solvent" include alcohol solvents, aromatic solvents, aliphatic hydrocarbon solvents, ether solvents, amide solvents, halogenated hydrocarbon solvents and the like. These solvents may be used in a mixture with water in an appropriate ratio.

The reaction temperature is generally –70° C. to 150° C., preferably –20° C. to 100° C.

The reaction time is generally 0.1 hr to 100 hr, preferably 0.1 hr to 40 hr.

Compound (88) can be produced, for example, by subjecting compound (87) to an amidation reaction with compound (14).

This reaction is performed in the same manner as in the production method of compound (16) in Reaction Scheme 5.

Compound (82) can be produced, for example, by subjecting compound (88) to a cyclization reaction.

The above-mentioned "cyclization reaction" can be produced by reacting compound (88) with a base in an inert solvent, and then reacting the resulting compound with an acid.

Examples of the above-mentioned "base" include "metal alkoxides" and the like. The amount of the "base" to be used is generally 2 to 100 equivalents, preferably 2 to 10 equivalents, relative to compound (88).

Examples of the above-mentioned "acid" include "organic acids" and the like. The amount of the "acid" to be used is generally 3 to 1000 equivalents, preferably 3 to 100 equivalents, relative to compound (88).

Examples of the above-mentioned "inert solvent" include alcohol solvents, halogenated hydrocarbon solvents, ether solvents and the like.

The reaction temperature is generally –100° C. to 150° C., preferably 0° C. to 100° C.

The reaction time is generally 5 min to 48 hr, preferably 30 min to 24 hr.

<Reaction Scheme 27>

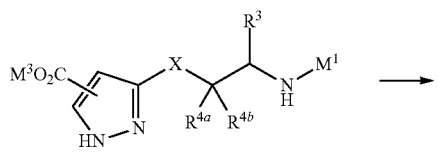

11-2

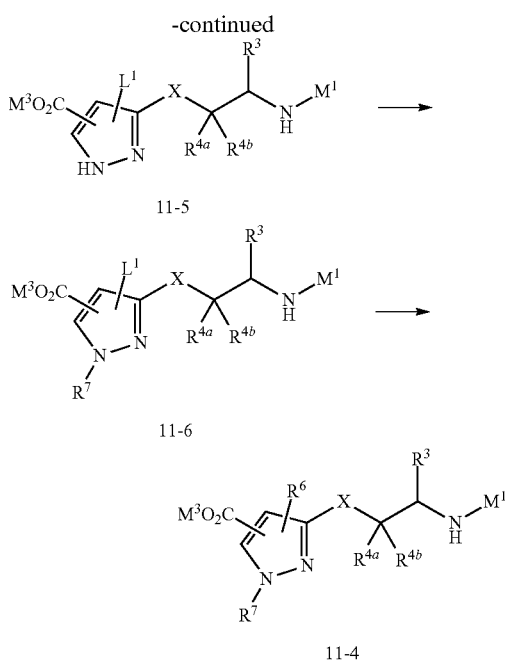

wherein each symbol is as defined above.

Compound (11-5) can be produced, for example, by subjecting compound (11-2) to a substitution reaction.

The above-mentioned "substitution reaction" is performed by reacting compound (11-2) with a halogenating agent in an inert solvent.

Examples of the above-mentioned "halogenating agent" include 1-(chloromethyl)-4-fluoro-1,4-diazoniabicyclo[2.2.2]octane ditetrafluoroborate, N-bromosuccinimide, N-iodosuccinimide and the like. The amount of the "halogenating agent" to be used is generally 2 to 20 equivalents relative to compound (11-2).

Examples of the above-mentioned "inert solvent" include nitrile solvents, aliphatic hydrocarbon solvents, aromatic solvents, ether solvents and the like. These solvents may be used in a mixture of two or more kinds thereof in an appropriate ratio.

The reaction temperature is generally −100° C. to 200° C., preferably −100° C. to 100° C.

The reaction time is generally 1 min to 48 hr, preferably 5 min to 24 hr.

Compound (11-6) can be produced, for example, by subjecting compound (11-5) to a substitution reaction.

This reaction is performed in the same manner as in the production method of compound (11-3) in Reaction Scheme 9.

Compound (11-4) can be produced, for example, by subjecting compound (11-6) to a coupling reaction.

The above-mentioned "coupling reaction" is performed, for example, by reacting compound (11-6) and a boron compound corresponding to $R^8$ in the presence of a metal catalyst, a ligand and a base, in an inert solvent. This reaction is preferably performed under an inert gas atmosphere.

Examples of the above-mentioned "boron compound corresponding to $R^8$" include trimethylboroxin, phenylboronic acid and the like. The amount of the "boron compound corresponding to $R^8$" to be used is generally 0.5 to 5 equivalents, preferably 1 to 3 equivalents, relative to compound (11-6).

Examples of the above-mentioned "metal catalyst" include palladium(II) acetate, [1,1'-bis(diphenylphosphino)ferrocene]palladium(II) dichloride and the like. The amount of the "metal catalyst" to be used is generally 0.001 to 100 equivalents, preferably 0.01 to 10 equivalents, relative to compound (11-6).

Examples of the above-mentioned "ligand" include triphenylphosphine, 1,1'-bis(diphenylphosphino)ferrocene and the like. The amount of the "ligand" to be used is generally 0.0001 to 100 equivalents, preferably 0.001 to 10 equivalents, relative to compound (11-6).

Examples of the above-mentioned "base" include "basic salts" and the like. The amount of the "base" to be used is generally 1 to 10 equivalents, preferably 1 to 5 equivalents, relative to compound (11-6).

Examples of the above-mentioned "inert solvent" include amide solvents, aromatic solvents, halogenated hydrocarbon solvents, ether solvents and the like.

Examples of the above-mentioned "inert gas" include argon gas, nitrogen gas and the like.

The reaction temperature is generally −20° C. to 200° C., preferably 0° C. to 150° C.

The reaction time is generally 5 min to 40 hr, preferably 30 min to 24 hr.

<Reaction Scheme 28>

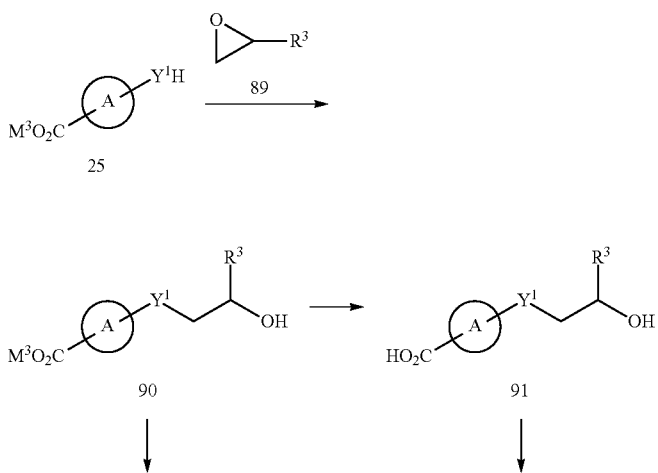

-continued

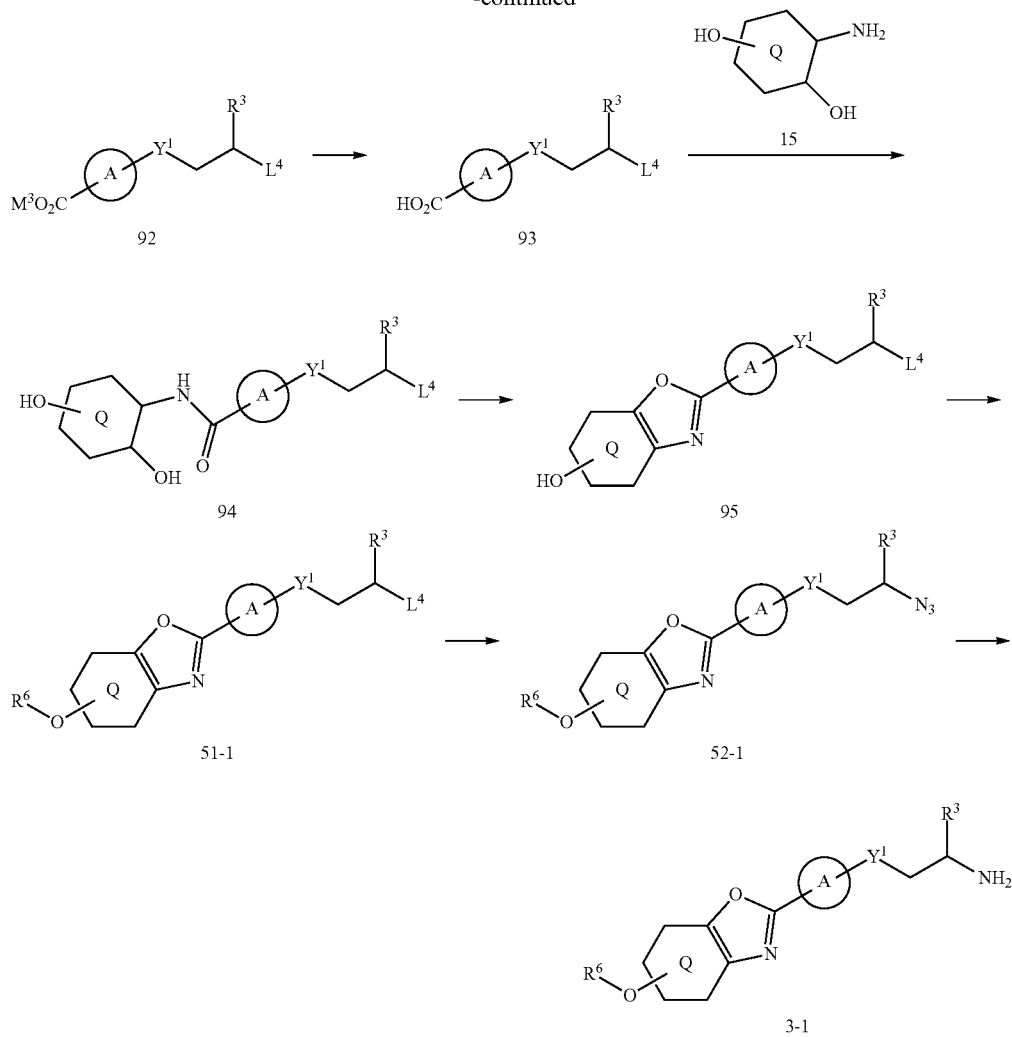

wherein each symbol is as defined above.

Compound (90) can be produced, for example, by subjecting compound (25) to a substitution reaction with compound (89).

This reaction is performed in the same manner as in the production method of compound (I) in Reaction Scheme 1.

Compound (91) can be produced, for example, by subjecting compound (90) to hydrolysis.

This reaction is performed in the same manner as in the production method of compound (14) in Reaction Scheme 5.

Compound (92) can be produced, for example, by subjecting compound (90) to a sulfonylation reaction.

This reaction is performed in the same manner as in the production method of compound (51) in Reaction Scheme 17.

Compound (93) can be produced, for example, by subjecting compound (91) to a sulfonylation reaction.

This reaction is performed in the same manner as in the production method of compound (51) in Reaction Scheme 17.

Compound (93) can also be produced, for example, by subjecting compound (92) to hydrolysis.

This reaction is performed in the same manner as in the production method of compound (14) in Reaction Scheme 5.

Compound (94) can be produced, for example, by subjecting compound (93) to an amidation reaction with compound (15).

This reaction is performed in the same manner as in the production method of compound (16) in Reaction Scheme 5.

Compound (95) can be produced, for example, by subjecting compound (94) to a cyclization reaction.

This reaction is performed in the same manner as in the production method of compound (1-1) in Reaction Scheme 5.

Compound (51-1) can be produced, for example, by subjecting compound (95) to an alkylation reaction.

This reaction is performed in the same manner as in the production method of compound (I) in Reaction Scheme 1.

Compound (52-1) can be produced, for example, by subjecting compound (51-1) to an azidation reaction.

This reaction is performed in the same manner as in the production method of compound (52) in Reaction Scheme 17.

Compound (3-1) can be produced, for example, by subjecting compound (52-1) to a reduction reaction.

This reaction is performed in the same manner as in the production method of compound (53) in Reaction Scheme 17.

111

<Reaction Scheme 29>

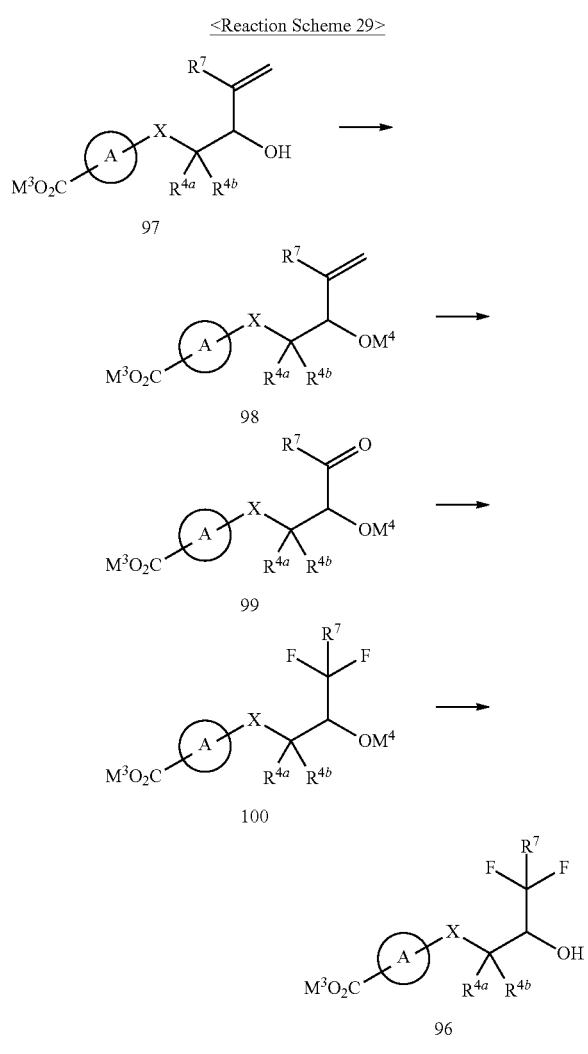

wherein each symbol is as defined above.

Compound (98) can be produced, for example, by subjecting compound (97) to a protection reaction.

The protection reaction can be performed according to a method known per se, for example, the method described in Protective Groups in Organic Synthesis, John Wiley and Sons (1980) or the like.

Compound (99) can be produced, for example, by subjecting compound (98) to an oxidative cleavage or ozone oxidation.

This reaction is performed by reacting compound (98) with an oxidant in an inert solvent. Where necessary, a re-oxidant may be used.

Examples of the above-mentioned "oxidant" include osmium tetraoxide, potassium permanganate, ozone and the like. The amount of the "oxidant" to be used is generally 0.001 to 10 equivalents, preferably 0.01 to 3 equivalents, relative to compound (98).

Examples of the above-mentioned "re-oxidant" include sodium periodate and the like. The amount of the "re-oxidant" to be used is generally 1 to 10 equivalents, preferably 1 to 3 equivalents, relative to the "oxidant".

Examples of the above-mentioned "inert solvent" include ketone solvents, nitrile solvents, amide solvents, halogenated hydrocarbon solvents, ether solvents, aromatic solvents and the like. These solvent may be used in a mixture with water in an appropriate ratio, or in a mixture of two or more kinds thereof in an appropriate ratio.

The reaction temperature is generally −100° C. to 200° C., preferably 0° C. to 150° C.

The reaction time is generally 5 min to 48 hr, preferably 30 min to 24 hr.

Compound (100) can be produced, for example, by subjecting compound (99) to a fluorination reaction.

This reaction is performed by reacting compound (99) with a fluorinating agent in an inert solvent.

Examples of the above-mentioned "fluorinating agent" include (diethylamino)sulfur trifluoride and the like. The amount of the "fluorinating agent" to be used is generally 1 to 10 equivalents, preferably 1 to 3 equivalents, relative to compound (99).

Examples of the above-mentioned "inert solvent" include nitrile solvents, amide solvents, halogenated hydrocarbon solvents, ether solvents, aromatic solvents and the like. These solvents may be used in a mixture of two or more kinds thereof in an appropriate ratio. Among them, toluene, dichloromethane and the like are preferable.

The reaction temperature is generally −100° C. to 200° C., preferably 0° C. to 150° C.

The reaction time is generally 5 min to 48 hr, preferably 30 min to 24 hr.

Compound (96) can be produced, for example, by subjecting compound (100) to a deprotection reaction.

The deprotection reaction can be performed according to a method known per se, for example, the method described in Protective Groups in Organic Synthesis, John Wiley and Sons (1980) or the like.

<Reaction Scheme 30>

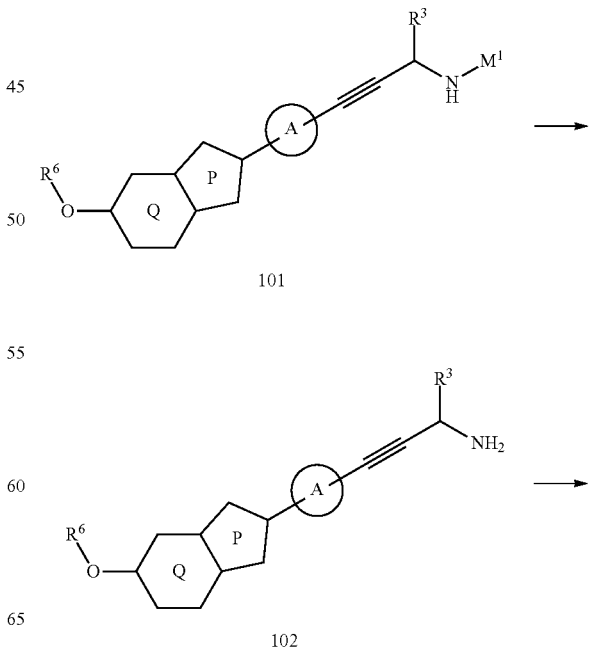

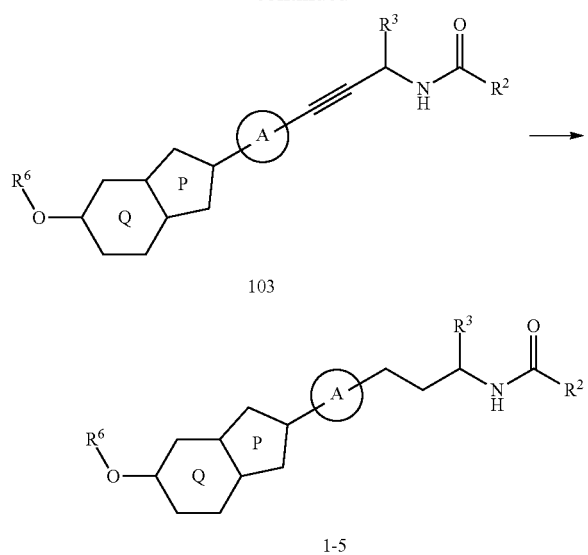

103

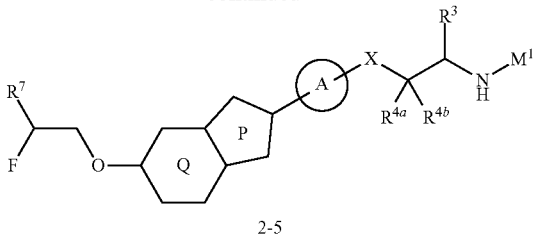

2-5 wherein each symbol is as defined above.

Compound (104) can be produced, for example, by subjecting compound (74) to a reduction reaction.

This reaction is performed in the same manner as in the production method of compound (50) in Reaction Scheme 17.

Compound (2-5) can be produced, for example, by subjecting compound (104) to a fluorination reaction.

This reaction is performed in the same manner as in the production method of compound (2-4) in Reaction Scheme 24.

1-5 wherein each symbol is as defined above.

Compound (102) can be produced, for example, by subjecting compound (101) to a deprotection reaction.

The deprotection reaction can be performed according to a method known per se, for example, the method described in Protective Groups in Organic Synthesis, John Wiley and Sons (1980) or the like.

Compound (103) can be produced, for example, by subjecting compound (102) to an acylation reaction.

This reaction is performed in the same manner as in the production method of compound (I-1) in Reaction Scheme 2.

Compound (1-5) can be produced, for example, by subjecting compound (103) to a reduction reaction.

This reaction is performed in the same manner as in the production method of compound (2-2) in Reaction Scheme 15.

<Reaction Scheme 32>

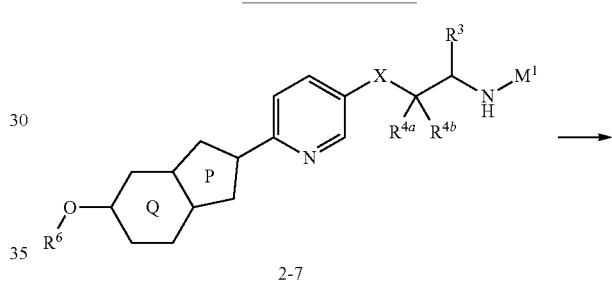

2-7

2-8

<Reaction Scheme 31>

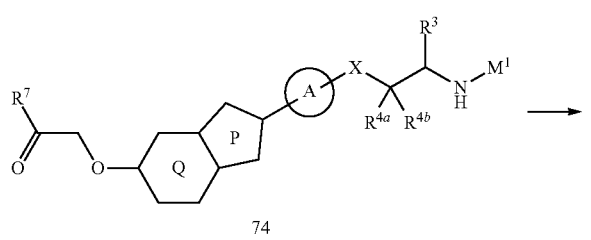

74

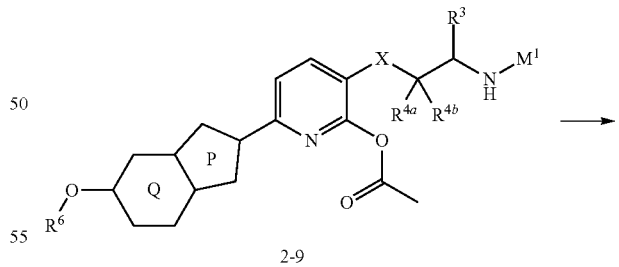

2-9

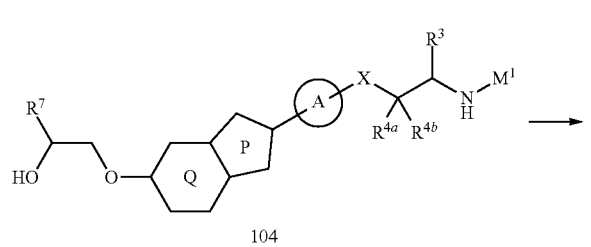

104

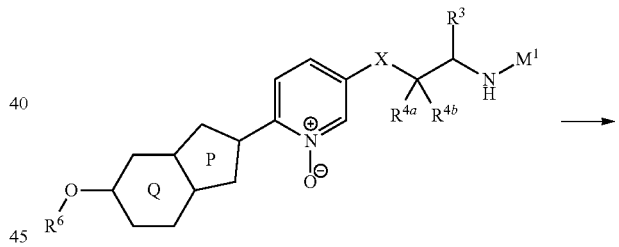

2-10

-continued

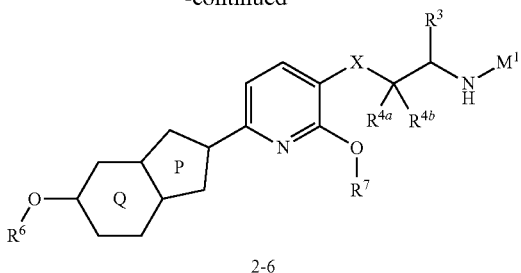

2-6 wherein each symbol is as defined above.

Compound (2-8) can be produced, for example, by subjecting compound (2-7) to an oxidation reaction.

The above-mentioned "oxidation reaction" can be produced by reacting compound (2-7) in the presence of an oxidant, in an inert solvent. Where necessary, the reaction can be performed in the presence of an organic acid in a catalytic amount to an excess amount.

Examples of the above-mentioned "oxidant" include m-chloroperbenzoic acid, hydrogen peroxide and the like. The amount of the "oxidant" to be used is generally 1 to 10 equivalents, preferably 1 to 5 equivalents, relative to compound (2-7).

Examples of the above-mentioned "organic acid" include acetic acid and the like.

Examples of the above-mentioned "inert solvent" include nitrile solvents, halogenated hydrocarbon solvents, aromatic solvents and the like. Among them, toluene, dichloromethane and the like are preferable.

The reaction temperature is generally −100° C. to 200° C., preferably 0° C. to 150° C.

The reaction time is generally 5 min to 48 hr, preferably 30 min to 24 hr.

Compound (2-9) can be produced, for example, by subjecting compound (2-8) to a rearrangement reaction.

The above-mentioned "rearrangement reaction" can be produced, for example, by reacting compound (2-8) with acetic anhydride in an inert solvent. The amount of the acetic anhydride to be used is generally 1 equivalent to an excess amount, relative to compound (2-8).

Examples of the above-mentioned "inert solvent" include nitrile solvents, halogenated hydrocarbon solvents, aromatic solvents and the like.

The reaction temperature is generally −100° C. to 200° C., preferably 0° C. to 150° C.

The reaction time is generally 5 min to 48 hr, preferably 30 min to 24 hr.

Compound (2-10) can be produced, for example, by subjecting compound (2-9) to hydrolysis.

This reaction is performed in the same manner as in the production method of compound (14) in Reaction Scheme 5.

Compound (2-6) can be produced, for example, by subjecting compound (2-10) to an alkylation reaction.

This reaction is performed in the same manner as in the production method of compound (I) in Reaction. Scheme 1.

<Reaction Scheme 33>

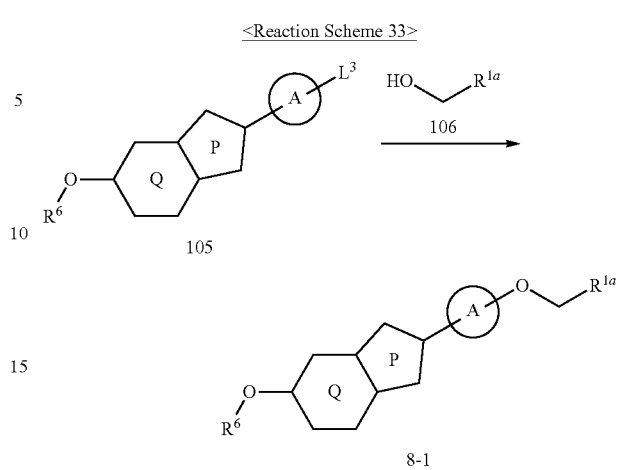

wherein each symbol is as defined above.

Compound (8-1) can be produced, for example, by subjecting compound (105) to a coupling reaction with compound (106).

The above-mentioned "coupling reaction" is performed by reacting compound (105) with compound (106) in the presence of a metal catalyst, a ligand and a base, in an inert solvent. This reaction is preferably performed under an inert gas atmosphere.

The amount of compound (106) to be used is generally 0.5 to 100 equivalents, preferably 0.8 to 20 equivalents, relative to compound (105).

Examples of the above-mentioned "metal catalyst" include tris(dibenzylideneacetone)dipalladium(0), palladium(II) acetate, copper(I) iodide and the like. The amount of the "metal catalyst" to be used is generally 0.001 to 100 equivalents, preferably 0.01 to 10 equivalents, relative to compound (105).

Examples of the above-mentioned "ligand" include (1R, 2R)—N,N'-dimethylcyclohexane-1,2-diamine, 1,10-phenanthroline, triphenylphosphine, 1,1'-bis(diphenylphosphino)ferrocene and the like. The amount of the "ligand" to be used is generally 0.001 to 100 equivalents, preferably 0.01 to 10 equivalents, relative to compound (105).

Examples of the above-mentioned "base" include "basic salts" and the like. Among them, tripotassium phosphate, cesium carbonate and the like are preferable. The amount of the "base" to be used is generally 1 to 10 equivalents, preferably 1 to 5 equivalents, relative to compound (105).

Examples of the above-mentioned "inert solvent" include amide solvents, aromatic solvents, halogenated hydrocarbon solvents and the like.

Examples of the above-mentioned "inert gas" include argon gas, nitrogen gas and the like.

The reaction temperature is generally −20° C. to 200° C., preferably 0° C. to 150° C.

The reaction time is generally 5 min to 40 hr, preferably 30 min to 24 hr.

<Reaction Scheme 34>

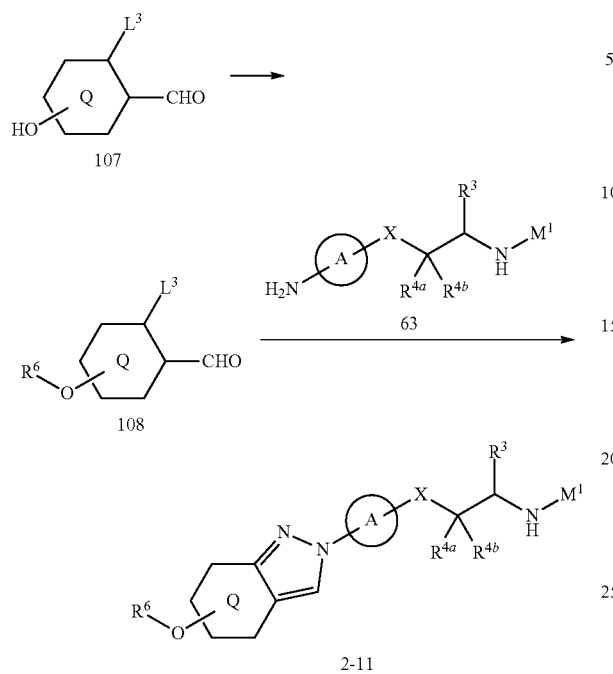

2-11 wherein each symbol is as defined above.

Compound (108) can be produced, for example, by subjecting compound (107) to an alkylation reaction.

This reaction is performed in the same manner as in the production method of compound (I) in Reaction Scheme 1.

Compound (2-11) can be produced, for example, by subjecting compound (108) to a dehydration-condensation reaction with compound (63), and then subjecting the resulting compound to a condensation pyrazole ring-formation reaction.

The above-mentioned "dehydration-condensation reaction" is performed by reacting compound (108) with compound (63) in an inert solvent. Where necessary, a dehydrating agent may be used. The amount of compound (63) to be used is generally 1 to 5 equivalents relative to compound (108).

Examples of the above-mentioned "dehydrating agent" include magnesium sulfate and the like. The amount of the "dehydrating agent" to be used is generally 1 to 1000 equivalents relative to compound (108).

Examples of the above-mentioned "inert solvent" include alcohol solvents, aromatic solvents, aliphatic hydrocarbon solvents, ether solvents, amide solvents, halogenated hydrocarbon solvents and the like. These solvents may be used in a mixture of two or more kinds thereof in an appropriate ratio.

The reaction temperature is generally –78° C. to 200° C., preferably 50° C. to 150° C.

The reaction time is generally 5 min to 48 hr, preferably 30 min to 24 hr.

The above-mentioned "condensation pyrazole ring-formation reaction" is performed by reacting subjecting the above-mentioned compound (108) to dehydration-condensation reaction with compound (63), and then reacting the resulting compound with an azidating agent in an inert solvent.

Examples of the above-mentioned "azidating agent" include sodium azide and the like. The amount of the "azidating agent" to be used is generally 1 equivalent to an excess amount relative to compound (108).

The reaction temperature is generally –78° C. to 200° C., preferably 50° C. to 150° C.

The reaction time is generally 5 min to 48 hr, preferably 30 min to 24 hr.

<Reaction Scheme 35>

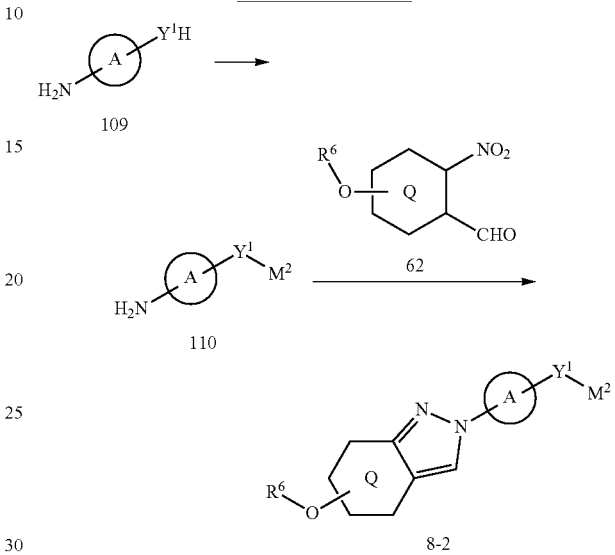

8-2 wherein each symbol is as defined above.

Compound (110) can be produced, for example, by subjecting compound (109) to a protection reaction.

The protection reaction can be performed according to a method known per se, for example, the method described in Protective Groups in Organic Synthesis, John Wiley and Sons (1980) or the like.

Compound (8-2) can be produced, for example, by subjecting compound (110) to a dehydration-condensation reaction with compound (62), and then subjecting the resulting compound to a cyclization reaction.

This reaction is performed in the same manner as in the production method of compound (2-3) in Reaction Scheme 20.

<Reaction Scheme 36>

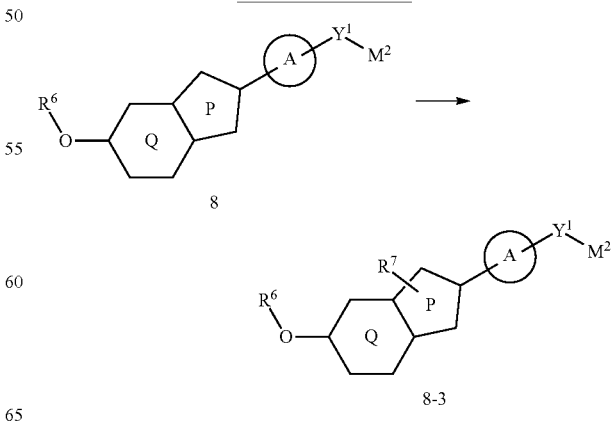

8-3 wherein each symbol is as defined above.

Compound (8-3) can be produced, for example, by subjecting compound (8) to a substitution reaction.

The above-mentioned "substitution reaction" is performed by reacting compound (8) with an alkyl metal, a metal amide or the like in an inert solvent to convert the hydrogen atom to a metal atom, and then reacting the resulting compound with, for to example, a halogenating agent or a halide corresponding to $R^7$.

Examples of the above-mentioned "alkyl metal" include alkyllithiums, alkylmagnesium halides and the like. The amount of the "alkyl metal" to be used is generally 1 to 10 equivalents relative to compound (8).

Examples of the above-mentioned "metal amides" include lithiumdiisopropylamide, lithiumhexamethyl disilazide and the like. The amount of the "metal amides" to be used is generally 1 to 10 equivalents relative to compound (8).

Examples of the above-mentioned "halogenating agent" include N-fluoro-N-(phenylsulfonyl)benzenesulfonamide, N-chlorosuccinimide, N-bromosuccinimide, N-iodosuccinimide, bromine, iodine and the like. The amount of the "halogenating agent" to be used is generally 2 to 10 equivalents relative to compound (8).

Examples of the above-mentioned "halide corresponding to $R^7$" include optionally substituted alkyl halides, optionally substituted cycloalkyl halides, optionally substituted cycloalkylalkyl halides and optionally substituted aralkyl halides. The amount of the "halide corresponding to $R^7$" to be used is generally 1 to 10 equivalents, preferably 1 to 5 equivalents, relative to compound (8).

Examples of the above-mentioned "inert solvent" include aliphatic hydrocarbon solvents, aromatic solvents, ether solvents and the like. These solvents may be used in a mixture of two or more kinds thereof in an appropriate ratio.

The reaction temperature is generally −100° C. to 200° C., preferably −100° C. to 100° C.

The reaction time is generally 1 min to 48 hr, preferably 5 min to 24 hr.

The above-mentioned "substitution reaction" is also performed by reacting compound (8) with a halogenating agent in an inert solvent. Where necessary, a radical initiator may be used.

Examples of the above-mentioned "halogenating agent" include 1-(chloromethyl)-4-fluoro-1,4-diazoniabicyclo[2.2.2]octane ditetrafluoroborate, N-chlorosuccinimide, N-bromosuccinimide, N-iodosuccinimide, bromine, iodine and the like. The amount of the "halogenating agent" to be used is generally 2 to 20 equivalents relative to compound (8).

Examples of the above-mentioned "radical initiator" include 2,2'-azobis(2-methylpropionitrile) and the like. The amount of the "radical initiator" to be used is generally 0.01 to 10 equivalents relative to compound (8).

Examples of the above-mentioned "inert solvent" include nitrile solvents, aliphatic hydrocarbon solvents, aromatic solvents, ether solvents and the like. These solvents may be used in a mixture of two or more kinds thereof in an appropriate ratio.

The reaction temperature is generally −100° C. to 200° C., preferably −100° C. to 100° C.

The reaction time is generally 1 min to 48 hr, preferably 5 min to 24 hr.

<Reaction Scheme 37>

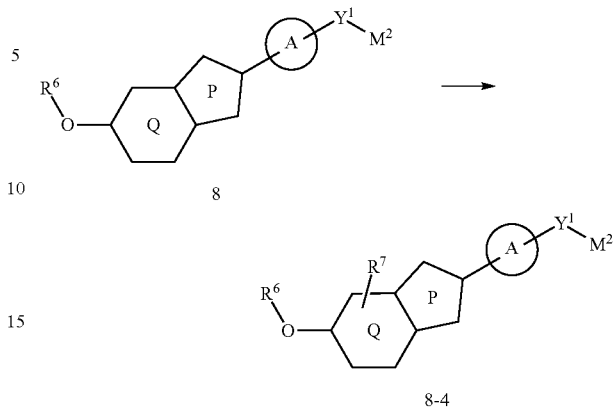

wherein each symbol is as defined above.

Compound (8-4) can be produced, for example, by subjecting compound (B) to a substitution reaction.

This reaction is performed in the same manner as in the production method of compound (8-3) in Reaction Scheme 36.

<Reaction Scheme 38>

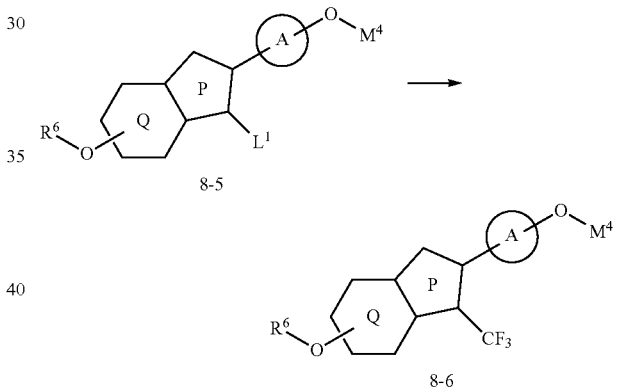

wherein each symbol is as defined above.

Compound (8-6) can be produced, for example, by subjecting compound (8-5) to a trifluoromethylation reaction.

The above-mentioned "trifluoromethylation reaction" is performed by reacting compound (8-5) with a trifluoromethylating agent in the presence of a metal catalyst, in an inert solvent. This reaction is preferably performed under an inert gas atmosphere.

Examples of the above-mentioned "trifluoromethylating agent" include methyl difluoro(fluorosulfonyl)acetate and the like. The amount of the "trifluoromethylating agent" to be used is generally 0.5 to 100 equivalents, preferably 1 to 20 equivalents, relative to compound (8-5).

Examples of the above-mentioned "metal catalyst" include copper(I) iodide and the like. The amount of the "metal catalyst" to be used is generally 0.001 to 100 equivalents, preferably 0.01 to 10 equivalents, relative to compound (8-5).

Examples of the above-mentioned "inert solvent" include amide solvents, aromatic solvents, halogenated hydrocarbon solvents and the like.

Examples of the above-mentioned "inert gas" include argon gas, nitrogen gas and the like.

The reaction temperature is generally −20° C. to 200° C., preferably 0° C. to 150° C.

The reaction time is generally 5 min to 40 hr, preferably 30 min to 24 hr.

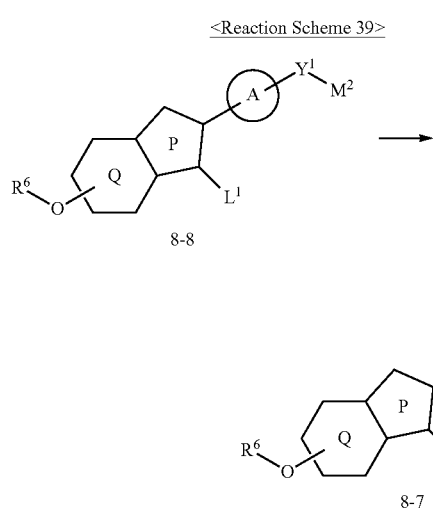

8-8

8-7 wherein each symbol is as defined above.

Compound (8-7) can be produced, for example, by subjecting compound (8-8) to a cyanation reaction.

The above-mentioned "cyanation reaction" is performed by reacting compound (8-8) with a cyanating agent in the presence of a metal catalyst and a ligand, in an inert solvent. Where necessary, zinc may be used in a catalytic amount to an excess amount as an additive. This reaction is preferably performed under an inert gas atmosphere.

Examples of the above-mentioned "cyanating agent" include zinc cyanide and the like. The amount of the "cyanating agent" to be used is generally 0.5 to 100 equivalents, preferably 1 to 20 equivalents, relative to compound (8-8).

Examples of the above-mentioned "metal catalyst" include tris(dibenzylideneacetone)dipalladium(0) and the like. The amount of the "metal catalyst" to be used is generally 0.001 to 100 equivalents, preferably 0.01 to 10 equivalents, relative to compound (8-8).

Examples of the above-mentioned "ligand" include triphenylphosphine, 1,1'-bis(diphenylphosphino)ferrocene and the like. The amount of the "ligand" to be used is generally 0.0001 to 100 equivalents, preferably 0.001 to 10 equivalents, relative to compound (8-8).

Examples of the above-mentioned "inert solvent" include amide solvents, aromatic solvents, halogenated hydrocarbon solvents and the like.

Examples of the above-mentioned "inert gas" include argon gas, nitrogen gas and the like.

The reaction temperature is generally −20° C. to 200° C., preferably 0° C. to 150° C.

The reaction time is generally 5 min to 40 hr, preferably 30 min to 24 hr.

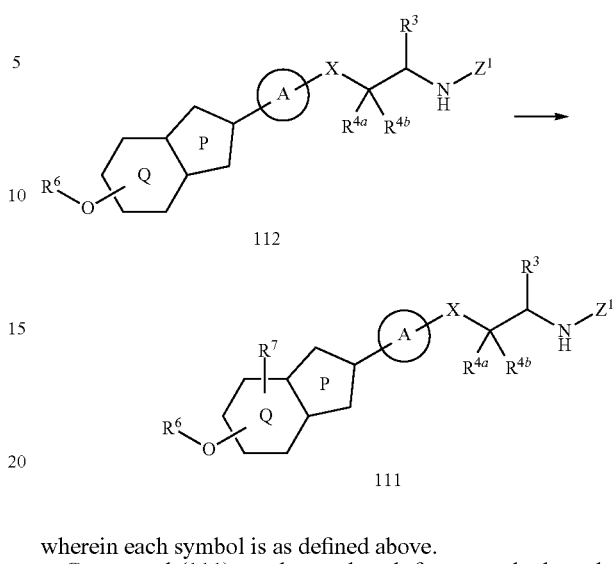

112

111 wherein each symbol is as defined above.

Compound (111) can be produced, for example, by subjecting compound (112) to a substitution reaction.

This reaction is performed in the same manner as in the production method of compound (8-3) in Reaction Scheme 36.

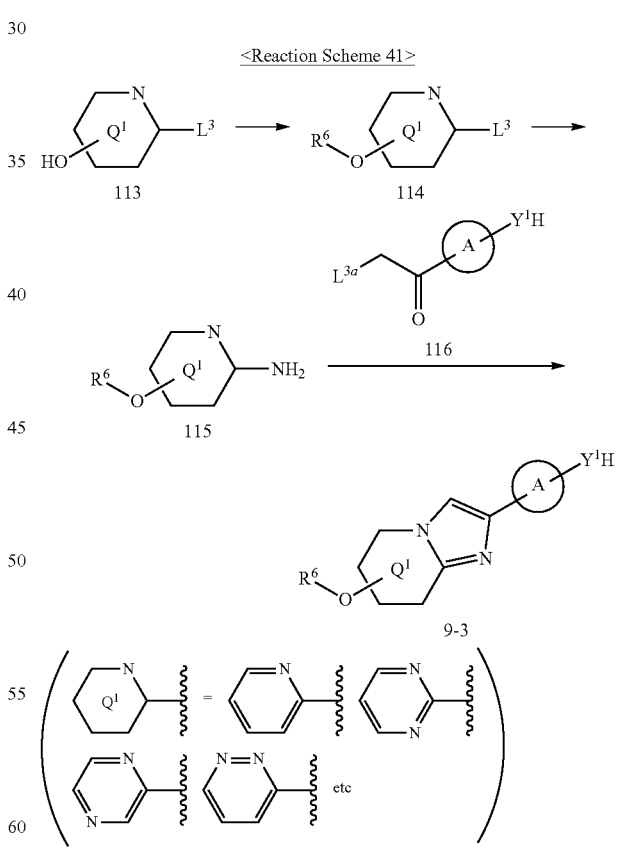

wherein $Q^1$ is a 6-membered ring heterocycle such as the above-mentioned ring shown in the reaction scheme, and the like, and the other symbols are as defined above.

Compound (114) can be produced, for example, by subjecting compound (113) to an alkylation reaction.

This reaction is performed in the same manner as in the production method of compound (I) in Reaction Scheme 1.

Compound (115) can be produced, for example, by subjecting compound (114) to an amination reaction.

The above-mentioned "amination reaction" is performed by reacting compound (114) with an aminating agent in the presence of a metal catalyst, a ligand and a base, in an inert solvent. This reaction is preferably performed under an inert gas atmosphere.

Examples of the above-mentioned "aminating agent" include 1,1-diphenylmethanimine, ammonia and the like. The amount of the "aminating agent" to be used is generally 0.5 to 100 equivalents, preferably 1 to 10 equivalents, relative to compound (114).

Examples of the above-mentioned "metal catalyst" include tris(dibenzylideneacetone)dipalladium(0), palladium(II) acetate, copper(I) iodide and the like. The amount of the "metal catalyst" to be used is generally 0.001 to 100 equivalents, preferably 0.01 to 10 equivalents, relative to compound (114).

Examples of the above-mentioned "ligand" include 2,2'-bis(diphenylphosphino)-1,1'-binaphthyl, butyldi-(1-adamantyl)phosphine, (1R,2R)—N,N'-dimethylcyclohexane-1,2-diamine, 1,10-phenanthroline, triphenylphosphine, 1,1'-bis(diphenylphosphino)ferrocene and the like. The amount of the "ligand" to be used is generally 0.001 to 100 equivalents, preferably 0.01 to 10 equivalents, relative to compound (114).

Examples of the above-mentioned "base" include "basic salts", "metal alkoxides" and the like. The amount of the "base" to be used is generally 1 to 10 equivalents, preferably 1 to 5 equivalents, relative to compound (114).

Examples of the above-mentioned "inert solvent" include amide solvents, aromatic solvents, halogenated hydrocarbon solvents and the like.

Examples of the above-mentioned "inert gas" include argon gas, nitrogen gas and the like.

The reaction temperature is generally −20° C. to 200° C., preferably 0° C. to 150° C.

The reaction time is generally 5 min to 40 hr, preferably 30 min to 24 hr.

Compound (9-3) can be produced, for example, by subjecting compound (115) to a condensation imidazole ring-formation reaction with compound (116).

The above-mentioned "condensation imidazole ring-formation reaction" is performed by reacting compound (115) with compound (116) in an inert solvent.

The amount of compound (116) to be used is generally 0.5 to 100 equivalents, preferably 0.8 to 5 equivalents, relative to compound (115).

Examples of the above-mentioned "inert solvent" include alcohol solvents, aromatic solvents, halogenated hydrocarbon solvents and the like.

The reaction temperature is generally −20° C. to 200° C., preferably 0° C. to 150° C.

The reaction time is generally 5 min to 40 hr, preferably 30 min to 24 hr.

<Reaction Scheme 42>

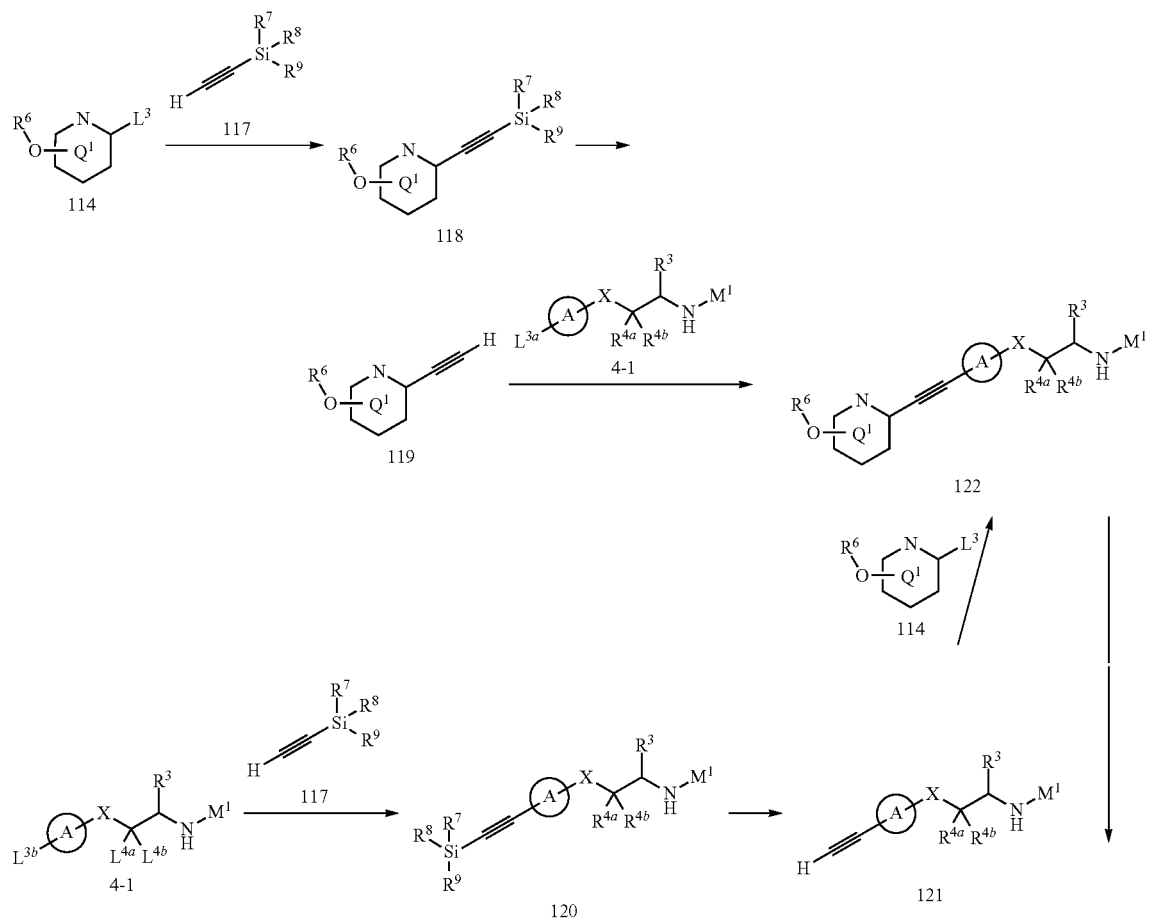

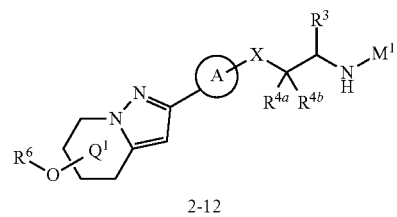

2-12 wherein $L^{3b}$ is a halogen atom, and the other symbols are as defined above.

Compound (118) can be produced, for example, by subjecting compound (114) to the Sonogashira coupling reaction with compound (117).

This reaction is performed in the same manner as in the production method of compound (42) in Reaction Scheme 15.

Compound (119) can be produced, for example, by subjecting compound (118) to a desilylation reaction.

The desilylation reaction can be performed according to a method known per se, for example, the method described in Protective Groups in Organic Synthesis, John Wiley and Sons (1980) or the like.

Compound (120) can be produced, for example, by subjecting compound (4-1) to the Sonogashira coupling reaction with compound (117).

This reaction is performed in the same manner as in the production method of compound (42) in Reaction Scheme 15.

Compound (121) can be produced, for example, by subjecting compound (120) to a desilylation reaction.

The desilylation reaction can be performed according to a method known per se, for example, the method described in Protective Groups in Organic Synthesis, John Wiley and Sons (1980) or the like.

Compound (122) can be produced, for example, by subjecting compound (4-1) to the Sonogashira coupling reaction with compound (119).

This reaction is performed in the same manner as in the production method of compound (42) in Reaction Scheme 15.

Compound (122) can also be produced, for example, by subjecting compound (121) to the Sonogashira coupling reaction with compound (114).

This reaction is performed in the same manner as in the production method of compound (42) in Reaction Scheme 15.

Compound (2-12) can be produced, for example, by subjecting compound (122) to an amination reaction and subsequent cyclization reaction.

The above-mentioned "amination reaction and subsequent cyclization reaction" is performed by reacting compound (122) with an aminating agent in an inert solvent, and then reacting the resulting compound with a base.

Examples of the above-mentioned "aminating agent" include 2-[(aminooxy)sulfonyl]-1,3,5-trimethylbenzene, (aminooxy)(hydroxy)sulfane dioxide and the like. The amount of the "aminating agent" to be used is generally 0.5 to 100 equivalents, preferably 1 to 10 equivalents, relative to compound (122).

Examples of the above-mentioned "base" include "basic salts" and the like. The amount of the "base" to be used is generally 1 to 100 equivalents, preferably 1 to 10 equivalents, relative to compound (122).

Examples of the above-mentioned "inert solvent" include ether solvents, amide solvents, alcohol solvents, aromatic solvents, halogenated hydrocarbon solvents and the like. These solvents may be used in a mixture with water in an appropriate ratio.

The reaction temperature is generally −20° C. to 200° C., preferably 0° C. to 150° C.

The reaction time is generally 5 min to 40 hr, preferably 30 min to 24 hr.

<Reaction Scheme 43>

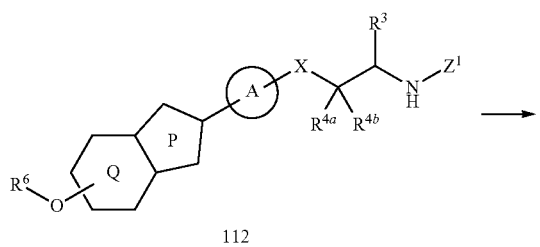

112

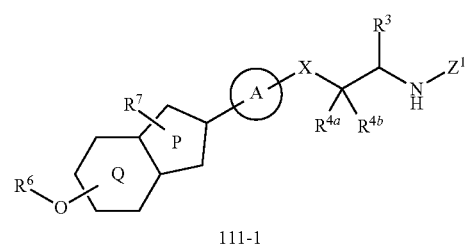

111-1 wherein each symbol is as defined above.

Compound (111-1) can be produced, for example, by subjecting compound (112) to a substitution reaction.

This reaction is performed in the same manner as in the production method of compound (8-3) in Reaction Scheme 36.

<Reaction Scheme 44>

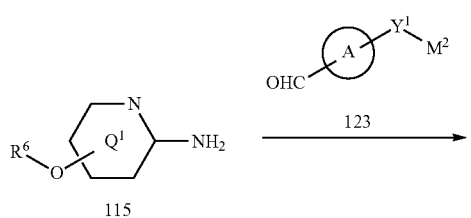

115

-continued

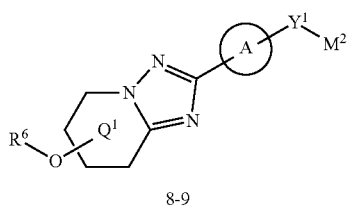

8-9 wherein each symbol is as defined above.

Compound (8-9) can be produced, for example, by subjecting compound (115) to an amination reaction, and then subjecting the resulting compound to dehydration-condensation and cyclization reaction with compound (123).

The above-mentioned "amination reaction" is performed by reacting compound (115) with an aminating agent in an inert solvent.

Examples of the above-mentioned "aminating agent" include 2-[(aminooxy)sulfonyl]-1,3,5-trimethylbenzene, (aminooxy)(hydroxy)sulfane dioxide and the like. The amount of the "aminating agent" to be used is generally 0.5 to 100 equivalents, preferably 1 to 10 equivalents, relative to compound (115).

Examples of the above-mentioned "inert solvent" include ether solvents, amide solvents, alcohol solvents, aromatic solvents, halogenated hydrocarbon solvents and the like. These solvents may be used in a mixture with water in an appropriate ratio.

The reaction temperature is generally −20° C. to 200° C., preferably 0° C. to 150° C.

The reaction time is generally 5 min to 40 hr, preferably 30 min to 24 hr.

The above-mentioned "dehydration-condensation reaction and cyclization reaction" is performed, for example, by reacting the compound obtained in the above-mentioned "amination reaction" with compound (123) in the presence of a base, in an inert solvent.

The amount of compound (123) to be used is generally 0.5 to 100 equivalents, preferably 1 to 10 equivalents, relative to compound (115).

Examples of the above-mentioned "base" include "basic salts" and the like. The amount of the "base" to be used is generally 1 to 100 equivalents, preferably 1 to 10 equivalents, relative to compound (115).

Examples of the above-mentioned "inert solvent" include ether solvents, amide solvents, alcohol solvents, aromatic solvents, halogenated hydrocarbon solvents and the like. These solvents may be used in a mixture with water in an appropriate ratio.

The reaction temperature is generally −20° C. to 200° C., preferably 0° C. to 150° C.

The reaction time is generally 5 min to 40 hr, preferably 30 min to 24 hr.

<Reaction Scheme 45>

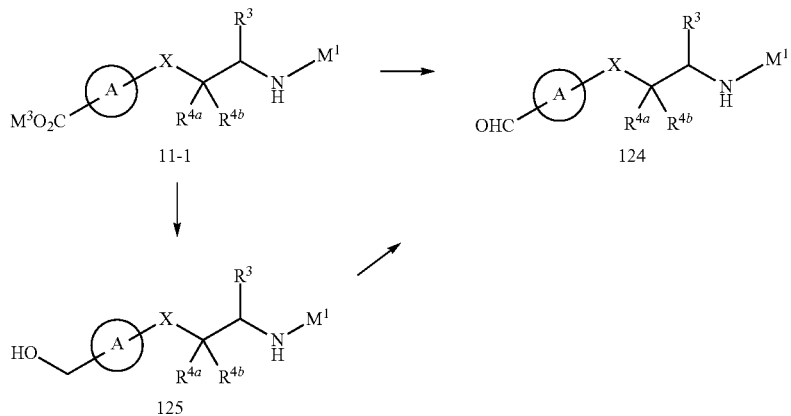

wherein each symbol is as defined above.

Compound (125) can be produced, for example, by subjecting compound (11-1) to a reduction reaction.

This reaction is performed by reacting compound (11-1) in the presence of a reducing agent, in an inert solvent.

Examples of the above-mentioned "reducing agent" include metal hydrogen compounds (e.g., sodium bis(2-methoxyethoxy)aluminum hydride, diisobutylaluminum hydride), metal hydride complex compounds (e.g., sodium borohydride, lithium borohydride, lithium aluminum hydride, sodium aluminum hydride) and the like. The amount of the "reducing agent" to be used is generally 0.1 to 20 equivalents, preferably 1 to 5 equivalents, relative to compound (11-1).

Examples of the above-mentioned "inert solvent" include alcohol solvents, aromatic solvents, aliphatic hydrocarbon is solvents, ether solvents, ester solvents, amide solvents and the like. These solvents may be used in a mixture of two or more kinds thereof in an appropriate ratio.

The reaction temperature is generally −70 to 150° C., preferably −20 to 100° C.

The reaction time is generally 0.1 to 100 hr, preferably 0.1 to 40 hr.

Compound (124) can be produced, for example, by subjecting compound (11-1) to a reduction reaction.

The reduction reaction can be performed according to a method known per se, for example, the method described in Journal of the Medicinal Chemistry, 3434-3442 pages, 2000 or the like, or a method analogous thereto.

This reaction is performed by reacting compound (11-1) with a reducing agent in an inert solvent.

Examples of the above-mentioned "reducing agent" include metal hydrogen compounds (e.g., sodium bis(2-methoxyethoxy)aluminum hydride, diisobutylaluminum hydride), metal hydride complex compounds (e.g., sodium borohydride, sodium cyanoborohydride, lithium aluminum hydride, sodium aluminum hydride) and the like. The amount of the "reducing agent" to be used is generally 0.1 to 20 equivalents, preferably 1 to 5 equivalents, relative to compound (11-1).

Examples of the above-mentioned "inert solvent" include alcohol solvents, aromatic solvents, aliphatic hydrocarbon solvents, ether solvents, ester solvents, amide solvents and the like. These solvents may be used in a mixture of two or more kinds thereof in an appropriate ratio.

The reaction temperature is generally −70 to 150° C., preferably −20 to 100° C.

The reaction time is generally 0.1 to 100 hr, preferably 0.1 to 40 hr.

Compound (124) can also be produced for example, by subjecting compound (125) to an oxidation reaction.

The oxidation reaction can be performed according to a method known per se, for example, the method described in Journal of the Medicinal Chemistry, 5282-5290 pages, 2006 or the like, or a method analogous thereto.

This reaction is performed by reacting compound (125) with an oxidant in an inert solvent.

Examples of the above-mentioned "oxidant" include manganese dioxide, tetrapropylammonium perruthenate, chromium trioxide, Dess-Martin reagent and the like. The amount of the "oxidant" to be used is generally 1 to 5 equivalents, preferably 1 to 1.5 equivalents, relative to compound (125).

Examples of the above-mentioned "inert solvent" include alcohol solvents, nitrile solvents, amide solvents, halogenated hydrocarbon solvents, ether solvents, aromatic solvents and the like. These solvents may be used in a mixture of two or more kinds thereof in an appropriate ratio. Among them, halogenated hydrocarbon solvents and the like are preferable.

The reaction temperature is generally −100° C. to 50° C., preferably −78° C. to 30° C.

The reaction time is generally 5 min to 48 hr, preferably 30 min to 24 hr.

<Reaction Scheme 46>

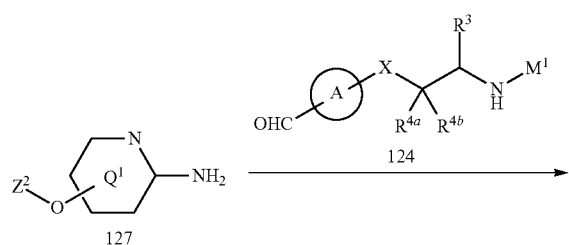

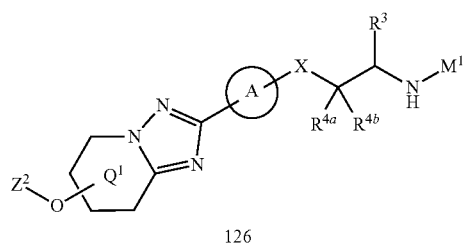

126 wherein each symbol is as defined above.

Compound (126) can be produced, for example, by subjecting compound (127) to an amination reaction, and then subjecting the resulting compound to a dehydration-condensation reaction and cyclization reaction with compound (124).

This reaction is performed in the same manner as in the production method of compound (8-9) in Reaction Scheme 45.

<Reaction Scheme 47>

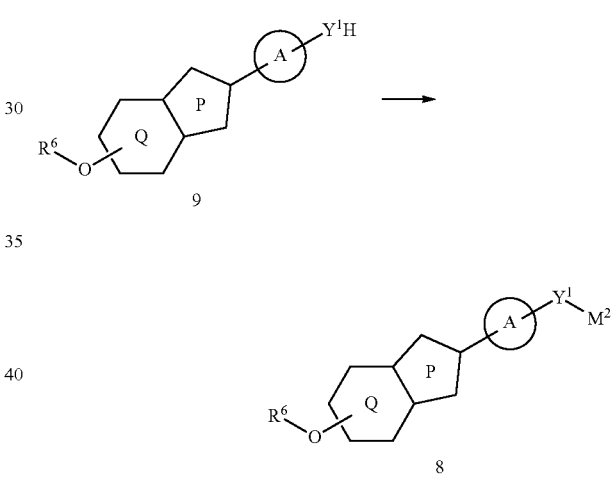

wherein each symbol is as defined above.

Compound (8) can be produced, for example, by subjecting compound (9) to a protection reaction.

The protection reaction can be performed according to a method known per se, for example, the method described in Protective Groups in Organic Synthesis, John Wiley and Sons (1980) or the like.

<Reaction Scheme 48>

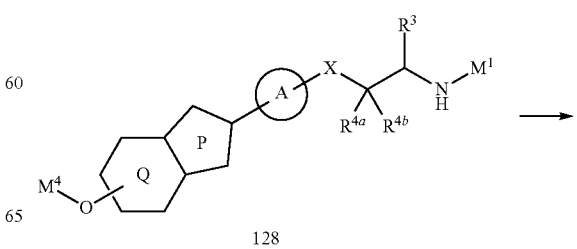

-continued

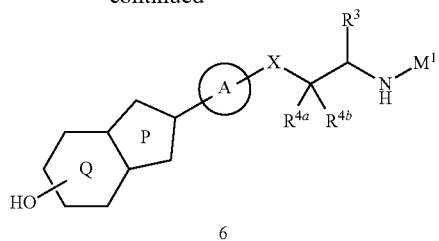

6 wherein each symbol is as defined above.

Compound (6) can be produced, for example, by subjecting compound (128) to a deprotection reaction.

The deprotection reaction can be performed according to a method known per se, for example, the method described in Protective Groups in Organic Synthesis, John Wiley and Sons (1980) or the like.

<Reaction Scheme 49>

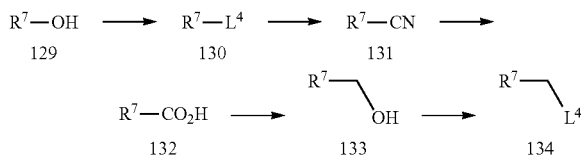

wherein each symbol is as defined above.

Compound (130) can be produced, for example, by subjecting compound (129) to a sulfonylation reaction.

This reaction is performed in the same manner as in the production method of compound (51) in Reaction Scheme 17.

Compound (131) can be produced, for example, by subjecting compound (130) to a cyanation reaction.

The above-mentioned "cyanation reaction" is performed, for example, by reacting compound (130) with a cyanating agent in an inert solvent. Where necessary, a base may be used in a catalytic amount to an excess amount.

Examples of the above-mentioned "cyanating agent" include sodium cyanide, potassium cyanide and the like. The amount of the "cyanating agent" to be used is generally 1 to 5 equivalents, preferably 1 to 3 equivalents, relative to compound (130).

Examples, of the above-mentioned "base" include "basic amines", "aromatic amines", "tertiary amines" and the like.

Examples of the above-mentioned "inert solvent" include nitrile solvents, amide solvents, halogenated hydrocarbon solvents, ether solvents, aromatic solvents and the like.

The reaction temperature is generally −100° C. to 150° C., preferably −78° C. to 120° C.

The reaction time is generally 5 min to 48 hr, preferably 30 min to 24 hr.

Compound (132) can be produced, for example, by subjecting compound (131) to hydrolysis.

This reaction is performed by reacting compound (131) with a base in an inert solvent.

Examples of the above-mentioned "base" include "inorganic bases" and the like. The amount of the "base" to be used is generally 1 to 10 equivalents, preferably 1 to 5 equivalents, relative to compound (131).

Examples of the above-mentioned "inert solvent" include alcohol solvents, ether solvents, amide solvents, halogenated hydrocarbon solvents and the like. These solvents are preferably used in a mixture with water in an appropriate ratio. Among them, alcohol solvents containing water are preferable.

The reaction temperature is generally −78° C. to 150° C., preferably −20° C. to 100° C.

The reaction time is generally 5 min to 100 hr, preferably 30 min to 24 hr.

This reaction is also performed by reacting compound (131) with an acid in an inert solvent.

Examples of the above-mentioned "acid" include hydrochloric acid, sulfuric acid and the like. The amount of the "acid" to be used is generally 1 equivalent to an excess amount, preferably 1 to 10 equivalents, relative to compound (131).

Examples of the above-mentioned "inert solvent" include alcohol solvents, ether solvents, amide solvents, halogenated hydrocarbon solvents and the like. These solvents are preferably used in a mixture with water in an appropriate ratio. Among them, alcohol solvents containing water are preferable.

The reaction temperature is generally −78° C. to 150° C., preferably −20° C. to 100° C.

The reaction time is generally 5 min to 100 hr, preferably 30 min to 24 hr.

Compound (133) can be produced, for example, by subjecting compound (132) to a reduction reaction.

This reaction is performed in the same manner as in the production method of compound (125) in Reaction Scheme 45.

Compound (134) can be produced, for example, by subjecting compound (133) to a sulfonylation reaction.

This reaction is performed in the same manner as in the production method of compound (51) in Reaction Scheme 17.

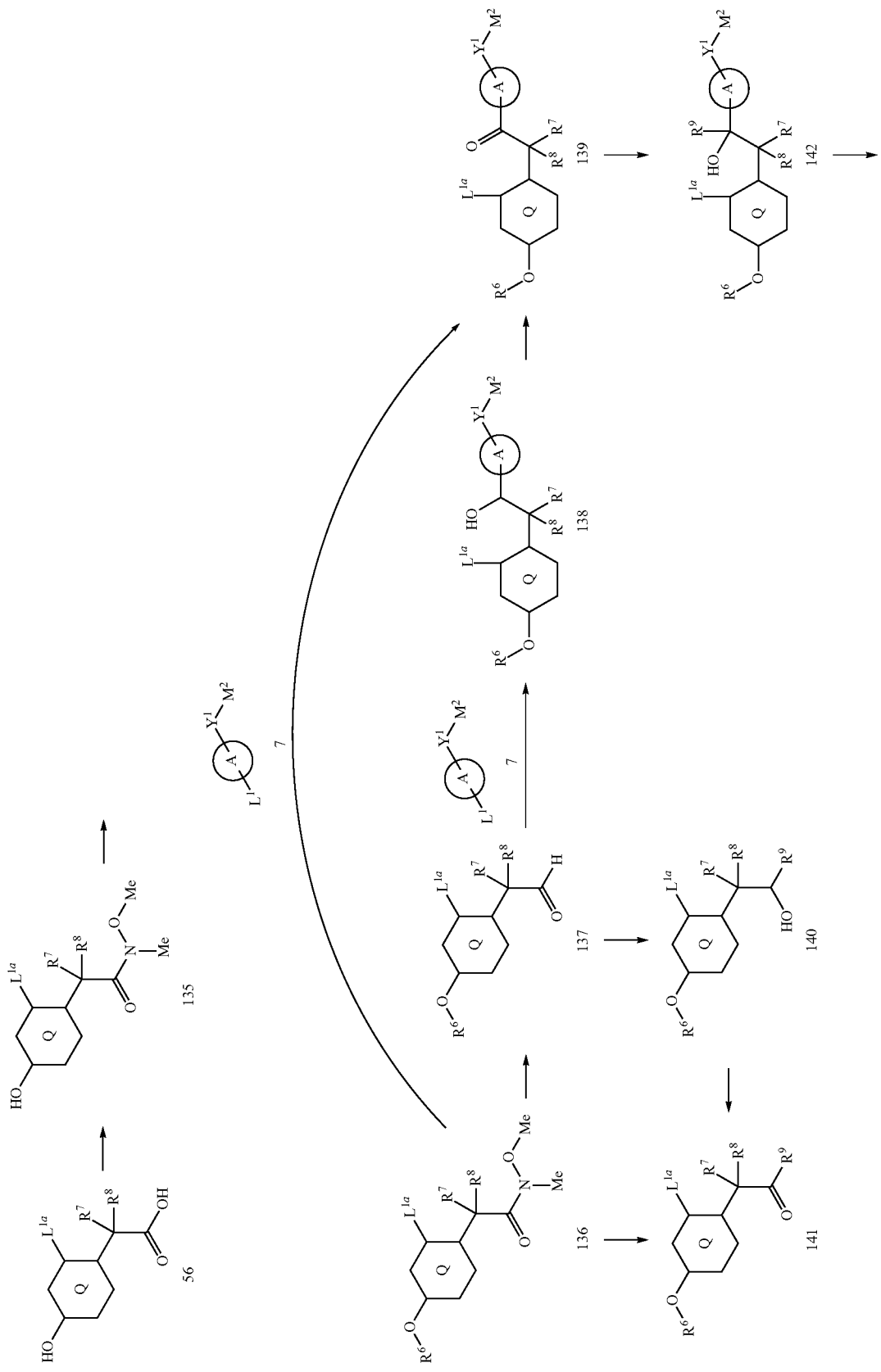
<Reaction Scheme 50>

-continued
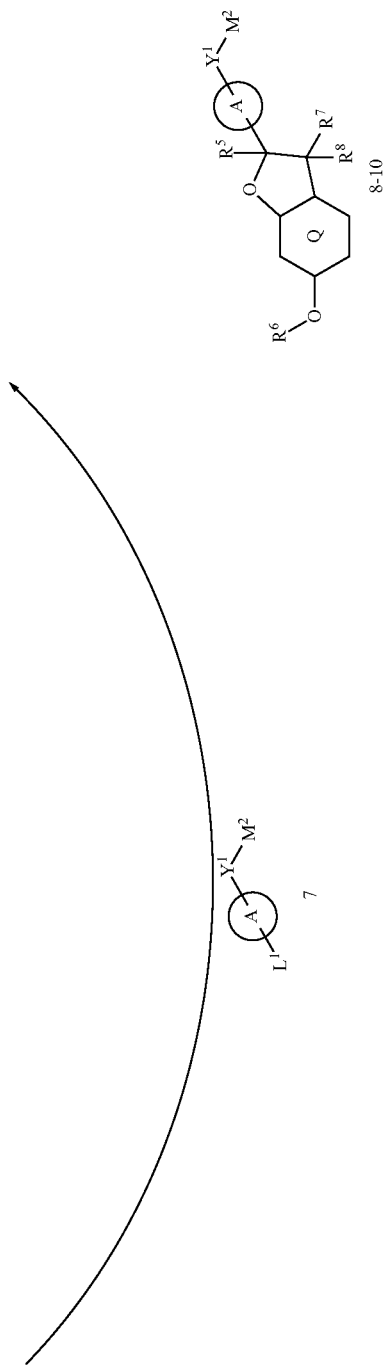

wherein R⁹ is a substituent, and the other symbols are as defined above.

Compound (135) can be produced, for example, by subjecting compound (56) to an amidation reaction with N,O-dimethylhydroxylamine.

The above-mentioned "amidation reaction" is performed in the same manner as in the production method of compound (40) in Reaction Scheme 14.

Compound (136) can be produced, for example, by subjecting compound (135) to an alkylation reaction.

This reaction is performed in the same manner as in the production method of compound (I) in Reaction Scheme 1.

Compound (137) can be produced, for example, by subjecting compound (136) to a reduction reaction.

The above-mentioned "reduction reaction" is performed by reacting compound (136) with a reducing agent in an inert solvent.

Examples of the above-mentioned "reducing agent" include metal hydrogen compounds (e.g., sodium bis(2-methoxyethoxy)aluminum hydride, diisobutylaluminum hydride), metal hydride complex compounds (e.g., sodium borohydride, sodium cyanoborohydride, lithium aluminum hydride, sodium aluminum hydride) and the like. The amount of the "reducing agent" to be used is generally 0.1 to 20 equivalents, preferably 1 to 5 equivalents, relative to compound (136).

Examples of the above-mentioned "inert solvent" include alcohol solvents, aromatic solvents, aliphatic hydrocarbon solvents, ether solvents, ester solvents, amide solvents and the like. These solvents may be used in a mixture of two or more kinds thereof in an appropriate ratio.

The reaction temperature is generally −70 to 150° C., preferably −20 to 100° C.

The reaction time is generally 0.1 to 100 hr, preferably 0.1 to 40 hr.

Compound (138) can be produced, for example, by reacting compound (7) with an alkyl metal in an inert solvent to convert the halogen atom of compound (7) to a metal atom, and then reacting the resulting compound with compound (137).

This reaction is performed in the same manner as in the production method of compound (60) in Reaction Scheme 18.

Compound (139) can be produced, for example, by subjecting compound (138) to an oxidation reaction.

The oxidation reaction can be performed according to a method known per se, for example, the method described in Journal of the Medicinal Chemistry, 5282-5290 pages, 2006 or the like, or a method analogous thereto.

This reaction is performed by reacting compound (138) with an oxidant in an inert solvent.

Examples of the above-mentioned "oxidant" include manganese dioxide, tetrapropylammonium perruthenate, chromium trioxide, Dess-Martin reagent and the like. The amount of the "oxidant" to be used is generally 1 to 5 equivalents, preferably 1 to 1.5 equivalents, relative to compound (138).

Examples of the above-mentioned "inert solvent" include alcohol solvents, nitrile solvents, amide solvents, halogenated hydrocarbon solvents, ether solvents, aromatic solvents and the like. These solvents may be used in a mixture of two or more kinds thereof in an appropriate ratio. Among them, halogenated hydrocarbon solvents and the like are preferable.

The reaction temperature is generally −100° C. to 50° C., preferably −78° C. to 30° C.

The reaction time is generally 5 min to 48 hr, preferably 30 min to 24 hr.

Compound (139) can also be produced, for example, by reacting compound (7) with an alkyl metal in an inert solvent to convert the halogen atom of compound (7) to a metal atom, and then reacting the resulting compound with compound (136).

This reaction is performed in the same manner as in the production method of compound (60) in Reaction Scheme 18.

Compound (140) can be produced, for example, by reacting compound (137) with an organic metal reagent corresponding to $R^9$ in an inert solvent.

Examples of the above-mentioned "organic metal reagent corresponding to $R^9$" include organic Grignard reagents (e.g., methylmagnesium bromide, methylmagnesium chloride), organic lithium reagents (e.g., methyllithium) and the like. The amount of the "organic metal reagent corresponding to $R^9$" to be used is generally 1 to 20 equivalents, preferably 1 to 5 equivalents, relative to compound (137).

Examples of the above-mentioned "inert solvent" include aromatic solvents, aliphatic hydrocarbon solvents, ether solvents, amide solvents, halogenated hydrocarbon solvents and the like. These solvents may be used in a mixture of two or more kinds thereof in an appropriate ratio. Among them, THF and the like are preferable.

The reaction temperature is generally −78° C. to 150° C., preferably −20° C. to 100° C.

The reaction time is generally 5 min to 48 hr, preferably 30 min to 24 hr.

Compound (140) can also be produced, for example, by subjecting compound (137) to a perfluoroalkylation reaction.

This reaction is performed by reacting compound (137) with a perfluoroalkylating agent in the presence of a fluoride, in an inert solvent. Where necessary, a desilylation reaction may be performed after completion of the reaction.

Examples of the above-mentioned "perfluoroalkylating agent" include trimethyl(perfluoroalkyl)silane (e.g., trimethyl(trifluoromethyl)silane) and the like. The amount of the "perfluoroalkylating agent" to be used is generally 1 to 20 equivalents, preferably 1 to 5 equivalents, relative to compound (137).

Examples of the above-mentioned "fluoride" include tetraalkylammonium fluorides (e.g., tetrabutylammonium fluoride), metal fluorides (e.g., potassium fluoride) and the like. The amount of the "fluoride" to be used is generally so catalytic amount to 20 equivalents, preferably 0.1 to 5 equivalents, relative to compound (137).

Examples of the above-mentioned "inert solvent" include aromatic solvents, aliphatic hydrocarbon solvents, ether solvents, amide solvents, halogenated hydrocarbon solvents and the like. These solvents may be used in a mixture of two or more kinds thereof in an appropriate ratio. Among them, THF and the like are preferable.

The reaction temperature is generally −78° C. to 150° C., preferably −20° C. to 100° C.

The reaction time is generally 5 min to 48 hr, preferably 30 min to 24 hr.

The above-mentioned "desilylation reaction" can be performed according to a method known per se, for example, the method described in Protective Groups in Organic Synthesis, John Wiley and Sons (1980) or the like.

Compound (141) can be produced, for example, by reacting compound (136) with an organic metal reagent corresponding to $R^9$ in an inert solvent.

This reaction is performed in the same manner as in the production method of compound (4-3) in Reaction Scheme 14.

Compound (141) can also be produced, for example, by subjecting compound (140) to an oxidation reaction.

This reaction is performed in the same manner as in the "oxidation reaction", from among the production methods of compound (139) in Reaction Scheme 50.

Compound (142) can be produced, for example, by reacting compound (7) with alkyl metal an in an inert solvent to convert the halogen atom of compound (7) to a metal atom, and then reacting the resulting compound with compound (141).

This reaction is performed in the same manner as in the production method of compound (60) in Reaction Scheme 18.

Compound (142) can also be produced, for example, by reacting compound (139) with an organic metal reagent corresponding to $R^9$ in an inert solvent.

This reaction is performed in the same manner as in the method using "organic metal reagent", from among the production methods of compound (140) in Reaction Scheme 50.

Compound (142) can also be produced, for example, by subjecting compound (139) to a perfluoroalkylation reaction.

This reaction is performed in the same manner as in the method using "perfluoroalkylating agent", from among the production methods of compound (140) in Reaction Scheme 50.

Compound (8-10) can be produced, for example, by subjecting compound (142) to a cyclization reaction.

This reaction is performed in the same manner as in the production method of compound (8-1) in Reaction Scheme 18.

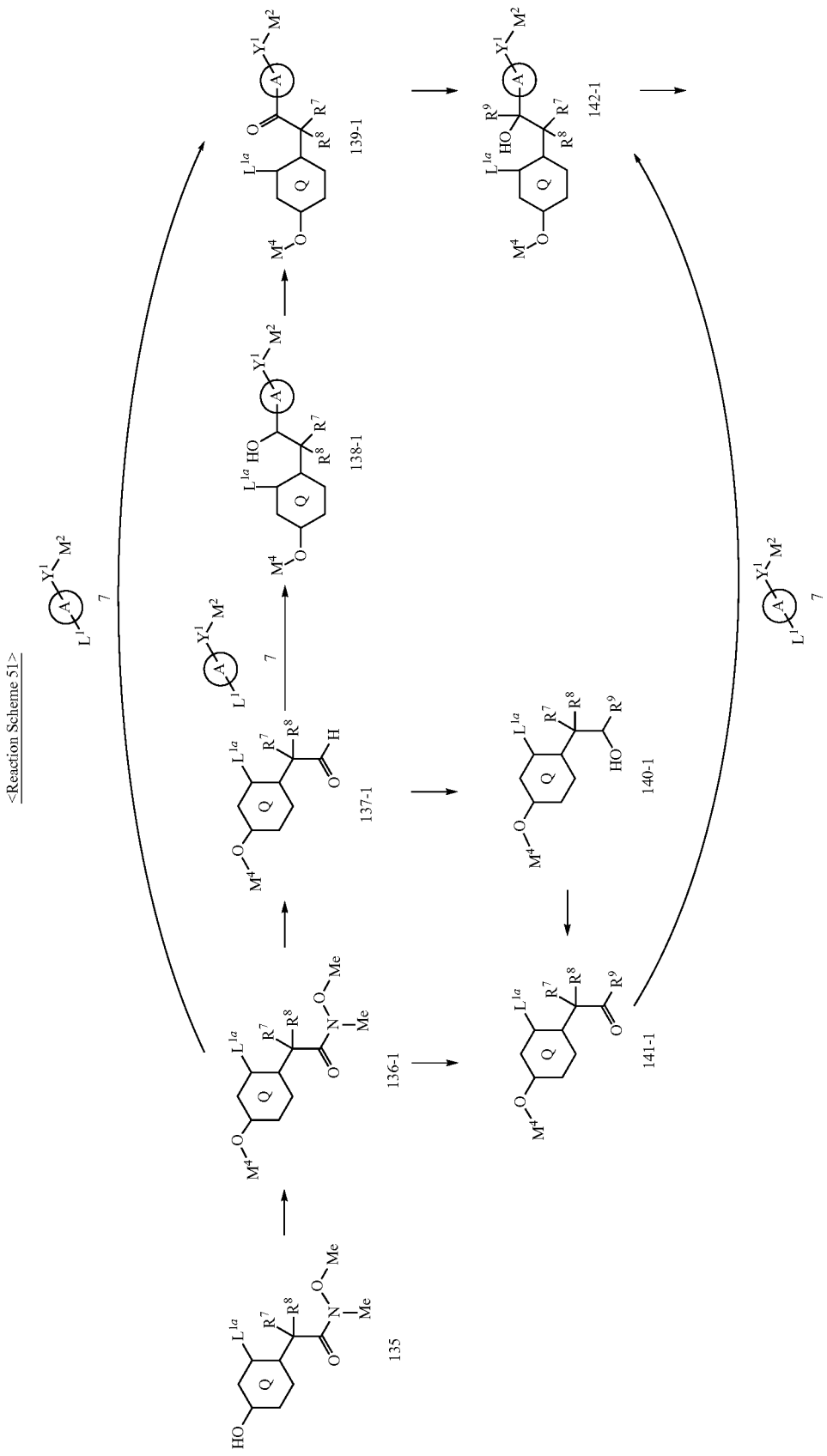
<Reaction Scheme 51>

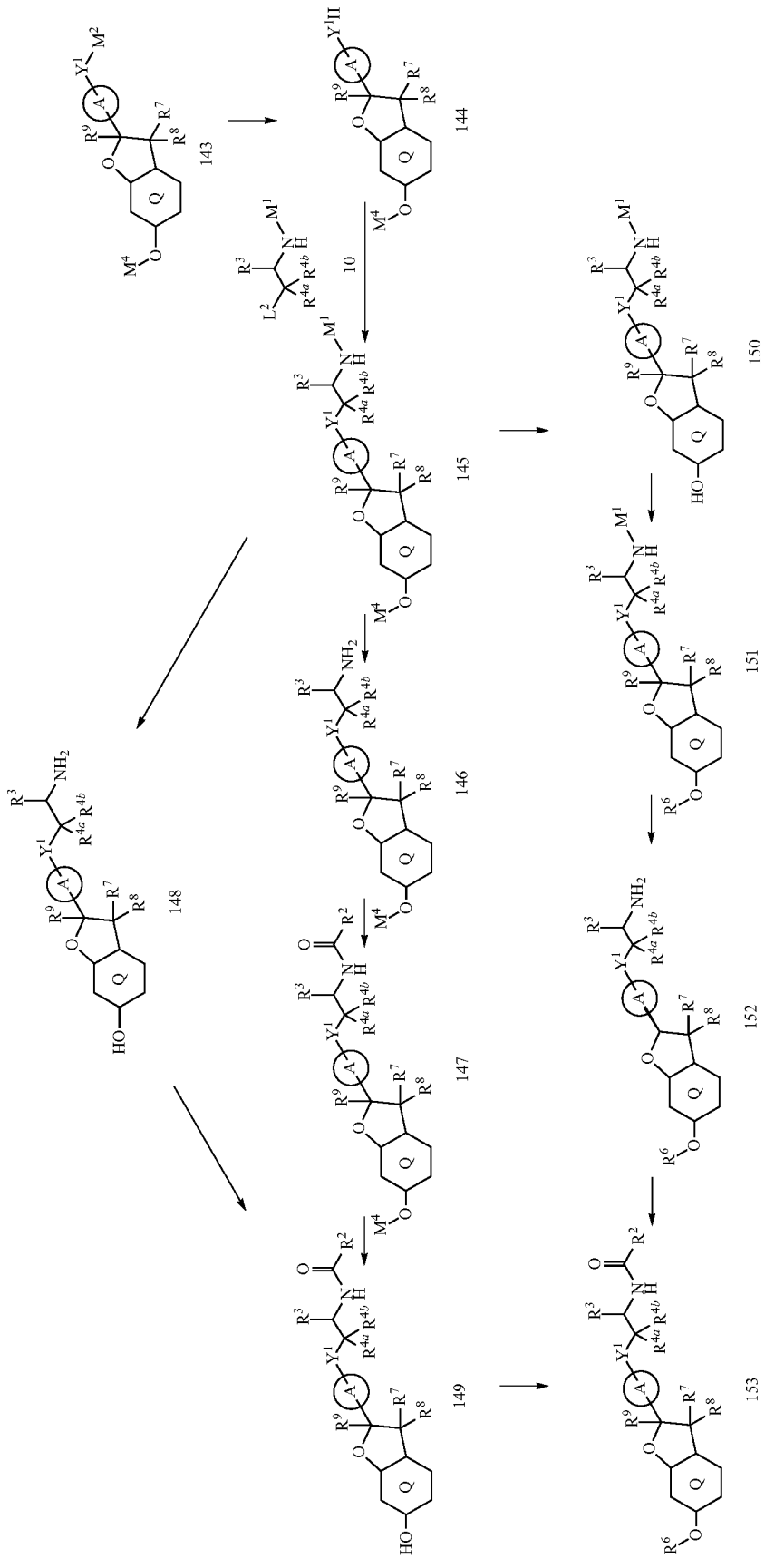

wherein each symbol is as defined above.

Compound (136-1) can be produced, for example, by subjecting compound (135) to a protection reaction.

The protection reaction can be performed according to a method known per se, for example, the method described in Protective Groups in Organic Synthesis, John Wiley and Sons (1980) or the like.

Compound (137-1) can be produced, for example, by subjecting compound (136-1) to a reduction reaction.

This reaction is performed in the same manner as in the production method of compound (137) in Reaction Scheme 50.

Compound (138-1) can be produced, for example, by reacting compound (7) with an alkyl metal in an inert solvent to convert the halogen atom of compound (7) to a metal atom, and then reacting the resulting compound with compound (137-1).

This reaction is performed in the same manner as in the production method of compound (60) in Reaction Scheme 18.

Compound (139-1) can be produced, for example, by subjecting compound (138-1) to an oxidation reaction.

This reaction is performed in the same manner as in the method using "oxidation reaction", from among the production methods of compound (139) in Reaction Scheme 50.

Compound (139-1) can also be produced, for example, by reacting compound (7) with an alkyl metal in an inert solvent to convert the halogen atom of compound (7) to a metal atom, and then reacting the resulting compound with compound (136-1).

This reaction is performed in the same manner as in the production method of compound (60) in Reaction Scheme 18.

Compound (140-1) can be produced, for example, by reacting compound (137-1) with an organic metal reagent corresponding to $R^9$ in an inert solvent.

This reaction is performed in the same manner as in the method using "organic metal reagent", from among the production methods of compound (140) in Reaction Scheme 50.

Compound (140-1) can also be produced, for example, by subjecting compound (137-1) to a perfluoroalkylation reaction.

This reaction is performed in the same manner as in the method using "perfluoroalkylating agent", from among the production methods of compound (140) in Reaction Scheme 50.

Compound (141-1) can be produced, for example, by reacting compound (136-1) with an organic metal reagent corresponding to $R^9$ in an inert solvent.

This reaction is performed in the same manner as in the production method of compound (4-3) in Reaction Scheme 14.

Compound (141-1) can also be produced, for example, by subjecting compound (140-1) to an oxidation reaction.

This reaction is performed in the same manner as in the "oxidation reaction", from among the production methods of compound (139) in Reaction Scheme 50.

Compound (142-1) can be produced, for example, by reacting compound (7) with an alkyl metal in an inert solvent to convert the halogen atom of compound (7) to a metal atom, and then reacting the resulting compound with compound (141-1).

This reaction is performed in the same manner as in the production method of compound (60) in Reaction Scheme 18.

Compound (142-1) can also be produced, for example, by reacting compound (139-1) with an organic metal reagent corresponding to $R^9$ in an inert solvent.

This reaction is performed in the same manner as in the method using "organic metal reagent", from among the production methods of compound (140) in Reaction Scheme 50.

Compound (142-1) can also be produced, for example, by subjecting compound (139-1) to a perfluoroalkylation reaction.

This reaction is performed in the same manner as in the method using "perfluoroalkylating agent", from among the production methods of compound (140) in Reaction Scheme 50.

Compound (143) can be produced, for example, by subjecting compound (142) to a cyclization reaction.

This reaction is performed in the same manner as in the production method of compound (8-1) in Reaction Scheme 18.

Compound (144) can be produced, for example, by subjecting compound (143) to a deprotection reaction.

The deprotection reaction can be performed according to a method known per se, for example, the method described in Protective Groups in Organic Synthesis, John Wiley and Sons (1980) or the like.

Compound (145) can be produced, for example, by subjecting compound (10) to a substitution reaction with compound (144).

This reaction is performed in the same manner as in the production method of compound (2-1) in Reaction Scheme 4.

Compound (146) can be produced, for example, by subjecting compound (145) to a deprotection reaction.

The deprotection reaction can be performed according to a method known per se, for example, the method described in Protective Groups in Organic Synthesis, John Wiley and Sons (1980) or the like.

Compound (147) can be produced, for example, by subjecting compound (146) to an acylation reaction.

This reaction is performed in the same manner as in the production method of compound (I-1) in Reaction Scheme 2.

Compound (148) can be produced, for example, by subjecting compound (145) to a deprotection reaction.

The deprotection reaction can be performed according to a method known per se, for example, the method described in Protective Groups in Organic Synthesis, John Wiley and Sons (1980) or the like.

Compound (149) can be produced, for example, by subjecting compound (148) to an acylation reaction.

This reaction is performed in the same manner as in the production method of compound (I-1) in Reaction Scheme 2.

Compound (149) can also be produced, for example, by subjecting compound (147) to a deprotection reaction.

The deprotection reaction can be performed according to a method known per se, for example, the method described in Protective Groups in Organic Synthesis, John Wiley and Sons (1980) or the like.

Compound (150) can be produced, for example, by subjecting compound (145) to a deprotection reaction.

The deprotection reaction can be performed according to a method known per se, for example, the method described in Protective Groups in Organic Synthesis, John Wiley and Sons (1980) or the like.

Compound (151) can be produced, for example, by subjecting compound (150) to an alkylation reaction.

This reaction is performed in the same manner as in the production method of compound (I) in Reaction Scheme 1.

Compound (152) can be produced, for example, by subjecting compound (151) to a deprotection reaction.

The deprotection reaction can be performed according to a method known per se, for example, the method described in Protective Groups in Organic Synthesis, John Wiley and Sons (1980) or the like.

Compound (153) can be produced, for example, by subjecting compound (152) to an acylation reaction.

This reaction is performed in the same manner as in the production method of compound (I-1) in Reaction Scheme 2.

Compound (153) can also be produced, for example, by subjecting compound (149) to an alkylation reaction.

This reaction is performed in the same manner as in the production method of compound (I) in Reaction Scheme 1.

<Reaction Scheme 52> wherein each symbol is as defined above.

Compound (154) can be produced, for example, by subjecting compound (59) to a reduction reaction.

This reaction is performed in the same manner as in the production method of compound (137) in Reaction Scheme 50.

Compound (61) can be produced, for example, by reacting compound (7) with an alkyl metal in an inert solvent to convert the halogen atom of compound (7) to a metal atom, and then reacting the resulting compound with compound (154).

This reaction is performed in the same manner as in the production method of compound (60) in Reaction Scheme 18.

In compound (I) thus obtained, a functional group in a molecule can also be converted to a desired functional group by a combination of chemical reactions known per se. Examples of the chemical reaction include oxidation reaction, reduction reaction, alkylation reaction, acylation reaction, creation reaction, hydrolysis reaction, amination reaction, esterification reaction, aryl coupling reaction, deprotection reaction and the like.

Compound (I) obtained by the above-mentioned production methods can be isolated and purified according to a known means, for example, solvent extraction, liquid conversion, phase transfer, crystallization, recrystallization, chromatography and the like.

When compound (I) contains an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced according to a method known per se.

Compound (I) may be a crystal.

Crystals of compound (I) (hereinafter sometimes to be abbreviated as the crystals of the present invention) can be produced according to crystallization methods known per se.

In the present specification, the melting point means that measured using, for example, a micromelting point apparatus (Yanako, MP-500D or Buchi, B-545), a DSC (differential scanning calorimetry) device (SEIKO, EXSTAR6000) or the like.

In general, the melting points vary depending on the measurement apparatuses, the measurement conditions and the like. The crystal in the present specification may show different values from the melting point described in the present specification, as long as they are within each of a general error range.

The crystal of the present invention is superior in physicochemical properties (e.g., melting point, solubility, stability) and biological properties (e.g., pharmacokinetics (absorption, distribution, metabolism, excretion), efficacy expression), and thus it is extremely useful as a medicament.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

In the following Examples, the following abbreviations are used.

mp: melting point
THF: tetrahydrofuran
DMF: N,N-dimethylformamide
WSC: 1-ethyl-3-(3-dimethylaminopropyl)carbodiimide hydrochloride
HOBt: 1-hydroxybenzotriazole monohydrate
HATU: N-[(dimethylamino)(3H-[1,2,3]triazolo[4,5-b]pyridin-3-yloxy)methylidene]-N-methylmethanaminium hexafluorophosphate
$^1$H NMR (proton nuclear magnetic resonance spectrum) was measured by Fourier-transform type NMR. For the analysis, ACD/SpecManager (trade name) and the like were used. Peaks with very mild protons such as hydroxyl group, amino group and the like are not described.

Other abbreviations used in the specification mean the following.

s: singlet
d: doublet
t: triplet q: quartet
m: multiplet
br: broad
J: coupling constant
Hz: hertz
CDCl$_3$: deuterated chloroform
DMSO-d$_6$: d$_6$-dimethyl sulfoxide
$^1$H-NMR: proton nuclear magnetic resonance
TFA: trifluoroacetic acid MS (mass spectrum) was measured by LC/MS (liquid chromatography mass spectrometer). As the ionization method, ESI (ElectroSpray Ionization) method, or APCI (Atmospheric Pressure Chemical Ionization) method was used. The data indicates those found. Generally, a molecular ion peak is observed. In the case of a compound having a tert-butoxycarbonyl group (-Boc), a peak after elimination of a tert-butoxycarbonyl group or tert-butyl group may be observed as a fragment ion. In the case of a compound having a hydroxyl group (—OH), a peak after elimination of H$_2$O may be observed as a fragment ion. In the case of a salt, a molecular ion peak or fragment ion peak of free form is generally observed.

The unit of reagent concentration (c) in optical rotation ($[\alpha]_D$) is g/100 mL.

The elemental analysis value (Anal.) shows Calculated (Calcd) and Found.

Example 1

N-[(1S)-2-({6-[6-(cyclopropylmethoxy)-1,3-benzoxazol-2-yl]pyridin-3-yl}oxy)-1-methylethyl]acetamide A) 6-(cyclopropylmethoxy)-1,3-benzoxazole A mixture of 1,3-benzoxazol-6-ol (2.31 g), (bromomethyl)cyclopropane (3.46 g), potassium carbonate (3.54 g) and DMF (25 mL) was stirred at 60° C. for 3 hr. Water was added to the reaction mixture, and the mixture was extracted with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound (2.88 g).

$^1$H NMR (300 MHz, DMSO-d$_6$) δ 0.23-0.41 (2H, m), 0.51-0.66 (2H, m) 1.18-1.37 (1H, m), 3.88 (2H, d, J=7.2 Hz), 6.99 (1H, dd, J=8.7, 2.3 Hz), 7.35 (1H, d, J=2.3 Hz), 7.65 (1H, d, J=8.7 Hz), 8.58 (1H, s).

B) tert-butyl {(1S)-2-[(6-bromopyridin-3-yl)oxy]-1-methylethyl}carbamate

To a solution of 6-bromopyridin-3-ol (4.90 g), tert-butyl [(1S)-2-hydroxy-1-methylethyl]carbamate (4.93 g) and triphenylphosphine (11.06 g) in THF (100 mL) was added dropwise a toluene solution (1.9 M, 22 mL) of diisopropyl azodicarboxylate, and the mixture was stirred at room temperature for 3 hr. To the reaction mixture was added ethyl acetate, and the mixture was washed with water and saturated aqueous sodium hydrogen carbonate solution, dried over anhydrous magnesium sulfate, and the solvent was evaporated under reduced pressure. The residue was purified by silica gel column chromatography (hexane/ethyl acetate) to give the title compound (5.35 g).

$^1$H NMR (300 MHz, DMSO-d$_6$) δ 1.11 (3H, d, J=6.4 Hz), 1.37 (9H, s), 3.73-4.00 (2H, m), 4.69-5.01 (1H, m), 6.90 (1H, d, J=7.6 Hz), 7.39 (1H, dd, J=8.7, 3.0 Hz), 7.53 (1H, d, J=8.7 Hz), 8.11 (1H, d, J=3.0 Hz).

C) tert-butyl [(1S)-2-({6-[6-(cyclopropylmethoxy)-1,3-benzoxazol-2-yl]pyridin-3-yl}oxy)-1-methylethyl]carbamate A mixture of 6-(cyclopropylmethoxy)-1,3-benzoxazole (500 mg), tert-butyl {(1S)-2-[(6-bromopyridin-3-yl)oxy]-1-methylethyl}carbamate (1.31 g), palladium(II) acetate (29 mg), butyldi(1-adamantyl)phosphine (93 mg), tripotassium phosphate (1.12 g) and N-methylpyrrolidone (12 mL) was stirred under an argon atmosphere at 125° C. for 15 hr. The reaction mixture was allowed to cool to room temperature, and filtered through celite. The filtrate was diluted with ethyl acetate and water, and the organic layer was separated. The combined organic layer was washed with saturated brine, and dried over anhydrous magnesium sulfate, and the solvent was evaporated under reduced pressure. The residue was purified by silica gel column chromatography (hexane/ethyl acetate) to give the title compound (400 mg).

$^1$H NMR (300 MHz, DMSO-d$_6$) δ 0.31-0.40 (2H, m), 0.53-0.67 (2H, m), 1.15 (3H, d, J=6.4 Hz), 1.21-1.32 (1H, m), 1.38 (9H, s), 3.81-3.96 (3H, m), 3.96-4.13 (2H, m), 6.96 (1H, d, J=7.6 Hz), 7.02 (1H, dd, J=8.7, 2.3 Hz), 7.39 (1H, d, J=2.3 Hz), 7.61 (1H, dd, J=9.0, 2.7 Hz), 7.68 (1H, d, J=8.7 Hz), 8.20 (1H, d, J=9.0 Hz), 8.45 (1H, d, J=2.7 Hz).

MS (ESI+): [M+H]$^+$ 440.5.

D) N-[(1S)-2-({6-[6-(cyclopropylmethoxy)-1,3-benzoxazol-2-yl]pyridin-3-yl}oxy)-1-methylethyl]acetamide To a solution of tert-butyl [(1S)-2-({6-[6-(cyclopropylmethoxy)-1,3-benzoxazol-2-yl]pyridin-3-yl}oxy)-1-methylethyl]carbamate (350 mg) in ethyl acetate (20 mL) was added 4M hydrogen chloride/ethyl acetate (10 mL), and the mixture was stirred at room temperature for 2 hr. The solvent was evaporated under reduced pressure, and the residue was dissolved in pyridine (15 mL). Acetic anhydride (163 mg) was added thereto, and the mixture was stirred at room temperature for 15 hr. The reaction mixture was concentrated under reduced pressure, and the residue was purified by silica gel column chromatography (ethyl acetate/methanol), and recrystallized (hexane/ethyl acetate) to give the title compound (201 mg).

$^1$H NMR (300 MHz, DMSO-d$_6$) δ 0.29-0.43 (2H, m), 0.53-0.67 (2H, m), 1.18 (3H, d, J=6.4 Hz), 1.21-1.38 (1H, m), 1.83 (3H, s), 3.91 (2H, d, J=6.8 Hz), 3.98-4.06 (1H, m), 4.06-4.21 (2H, m), 7.02 (1H, dd, J=8.8, 2.3 Hz), 7.39 (1H, d, J=2.3 Hz), 7.63 (1H, dd, J=8.8, 2.7 Hz), 7.68 (1H, d, J=8.8 Hz), 7.99 (1H, d, J=7.5 Hz), 8.21 (1H, d, J=8.8 Hz), 8.47 (1H, d, J=2.7 to Hz).

mp 179-180° C.

Anal. Calcd for C$_{21}$H$_{23}$N$_3$O$_4$: C, 66.13; H, 6.08; N, 11.02. Found: C, 66.09; H, 6.18; N, 11.02.

Example 2

N-[(1S)-2-({5-[5-(cyclopropylmethoxy)-1,3-benzoxazol-2-yl]isoxazol-3-yl}oxy)-1-methylethyl]acetamide A) methyl 3-({(2S)-2-[(tert-butoxycarbonyl)amino]propyl}oxy)isoxazole-5-carboxylate To a solution of methyl 3-hydroxyisoxazole-5-carboxylate (20 g), tert-butyl [(1S)-2-hydroxy-1-methylethyl]carbamate (25 g) and triphenylphosphine (55.1 g) in THF (800 mL) was added dropwise a toluene solution (1.9 M, 110 mL) of diisopropyl azodicarboxylate, and the mixture was refluxed for 5 hr. The reaction mixture was allowed to cool to room temperature, and ethyl acetate was added thereto. The mixture was washed with water and saturated aqueous sodium hydrogen carbonate solution, dried over anhydrous magnesium sulfate, and the solvent was evaporated under reduced pressure. The residue was purified by silica gel column chromatography (hexane/ethyl acetate) to give the title compound (25 g).

$^1$H NMR (300 MHz, DMSO-$d_6$) δ 1.09 (3H, d, J=6.8 Hz), 1.37 (9H, s), 3.77-3.93 (4H, m), 4.11 (2H, d, J=6.4 Hz), 6.94 (1H, d, J=8.0 Hz), 7.08 (1H, s).

B) 3-({(2S)-2-[(tert-butoxycarbonyl)amino]propyl}oxy)isoxazole-5-carboxylic acid 2M Aqueous sodium hydroxide solution (20 mL) was added to a solution of methyl 3-({(2S)-2-[(tert-butoxycarbonyl)amino]propyl}oxy)isoxazole-5-carboxylate (4.0 g) in THF/methanol (20 mL/20 mL), and the mixture was stirred at room temperature for 15 hr. The solvent was evaporated under reduced pressure, and the residue was neutralized with 6M hydrochloric acid and extracted with ethyl acetate. The combined organic layer was washed with saturated brine, and dried over anhydrous magnesium sulfate, and the solvent was evaporated under reduced pressure to give the title compound (3.5 g).

MS (ESI+): [M+H]$^+$ 287.2.

C) tert-butyl [(1S)-2-({5-[(2,5-dihydroxyphenyl)carbamoyl]isoxazol-3-yl}oxy)-1-methylethyl]carbamate To a solution of 3-({(2S)-2-[(tert-butoxycarbonyl)amino]propyl}oxy)isoxazole-5-carboxylic acid (1.5 g), 2-aminobenzene-1,4-diol hydrochloride (0.847 g) and HATU (1.99 g) in DMF (20 mL) was added N,N-diisopropylethylamine (1.80 mL), and the mixture was stirred at room temperature for 5 hr. The solvent was evaporated under reduced pressure, 0.1M hydrochloric acid was added thereto, and the mixture was extracted with ethyl acetate. The combined organic layer was washed with saturated brine, and dried over anhydrous magnesium sulfate, and the solvent was evaporated under reduced pressure. The residue was purified by silica gel chromatography (hexane/ethyl acetate) to give the title compound (1.11 g).

$^1$H NMR (300 MHz, DMSO-$d_6$) δ 1.10 (3H, d, J=6.8 Hz), 1.38 (9H, s), 3.81-3.93 (1H, m), 4.11 (2H, d, J=6.0 Hz), 6.46 (1H, dd, J=8.7, 2.6 Hz), 6.73 (1H, d, J=8.7 Hz), 6.88-7.08 (2H, m), 7.27 (1H, d, J=2.6 Hz), 8.90 (1H, s), 9.27 (1H, brs), 9.45 (1H, brs).

D) tert-butyl [(1S)-2-{[5-(5-hydroxy-1,3-benzoxazol-2-yl)isoxazol-3-yl]oxy}-1-methylethyl]carbamate Triethylamine (2.83 mL) was added to a solution of triphenylphosphine (2.0 g) and hexachloroethane (1.5 g) in acetonitrile (25 mL), and the mixture was stirred at room temperature for 20 min. To the reaction mixture was further added a solution of tert-butyl [(1S)-2-({5-[(2,5-dihydroxyphenyl)carbamoyl]isoxazol-3-yl}oxy)-1-methylethyl]carbamate (1.0 g) in acetonitrile (5 mL), and the mixture was stirred at room temperature overnight. Water was added to the reaction mixture, and the mixture was extracted with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound (503 mg).

$^1$H NMR (300 MHz, DMSO-$d_6$) δ (3H, d, J=6.8 Hz), 1.38 (9H, s), 3.76-3.99 (1H, m), 4.16 (2H, d, J=6.0 Hz), 6.96 (1H, d, J=2.3 Hz), 6.99 (1H, d, J=2.6 Hz), 7.16 (1H, d, J=2.3 Hz), 7.21 (1H, s), 7.66 (1H, d, J=9.1 Hz), 9.76 (1H, s).

E) tert-butyl [(1S)-2-({5-[5-(cyclopropylmethoxy)-1,3-benzoxazol-2-yl]isoxazol-3-yl}oxy)-1-methylethyl]carbamate (Bromomethyl)cyclopropane (0.388 mL) was added to a mixture of tert-butyl [(1S)-2-{[5-(5-hydroxy-1,3-benzoxazol-2-yl)isoxazol-3-yl]oxy}-1-methylethyl]carbamate (500 mg), potassium carbonate (552 mg) and DMF (13 mL), and the mixture was stirred at 60° C. for 5 hr. The solvent was evaporated under reduced pressure, water was added thereto, and the mixture was extracted with ethyl acetate. The combined organic layer was washed with saturated brine, and dried over anhydrous magnesium sulfate, and the solvent was evaporated under reduced pressure. The residue was washed with hexane-ethyl acetate to give the title compound (510 mg).

$^1$H NMR (300 MHz, DMSO-$d_6$) δ 0.30-0.39 (2H, m), 0.54-0.65 (2H, m), 1.12 (3H, d, J=6.8 Hz), 1.21-1.30 (1H, m), 1.38 (9H, s), 3.84-3.97 (3H, m), 4.17 (2H, d, J=6.1 Hz), 6.97 (1H, d, J=8.0 Hz), 7.14 (1H, dd, J=8.9, 2.5 Hz), 7.23 (1H, s), 7.40 (1H, d, J=2.3 Hz), 7.76 (1H, d, J=9.1 Hz).

F) N-[1S)-2-({5-[5-(cyclopropylmethoxy)-1,3-benzoxazol-2-yl]isoxazol-3-yl}oxy)-1-methylethyl]acetamide To a solution of tert-butyl [(1S)-2-({5-[5-(cyclopropylmethoxy)-1,3-benzoxazol-2-yl]isoxazol-3-yl}oxy)-1-methylethyl]carbamate (510 mg) in ethyl acetate (11 mL) was added 4M hydrogen chloride/ethyl acetate (12 mL), and the mixture was stirred at room temperature for 5 hr. The solvent was evaporated under reduced pressure, and the residue was dissolved in pyridine (1.5 ml). Acetic anhydride (1.5 mL) was added thereto, and the mixture was stirred at room temperature overnight. The reaction mixture was concentrated under reduced pressure, and the residue was purified by silica gel column chromatography (hexane/ethyl acetate/methanol), and recrystallized (hexane/ethyl acetate) to give the title compound (182 mg).

$^1$H NMR (300 MHz, DMSO-$d_6$) δ 0.29-0.42 (2H, m), 0.54-0.66 (2H, m), 1.15 (3H, d, J=6.4 Hz), 1.20-1.31 (1H, m), 1.82 (3H, s), 3.90 (2H, d, J=7.2 Hz), 4.08-4.31 (3H, m), 7.14 (1H, dd, J 9.1, 2.3 Hz), 7.25 (1H, s), 7.40 (1H, d, J=2.3 Hz), 7.76 (1H, d, J=8.7 Hz), 8.00 (1H, d, J=6.4 Hz).

mp 156-157° C.

Anal. Calcd for $C_{19}H_{22}N_3O_5$: C, 61.28; H, 5.95; N, 11.28. Found: C, 61.49; H, 5.76; N, 11.14.

Example 3

N-[(1S)-2-{4-[6-(cyclopropylmethoxy)-1,3-benzoxazol-2-yl]phenoxy}-1-methylethyl]acetamide

A) methyl 4-{[(2S)-2-(acetylamino)propyl]oxy}benzoate

To a solution of methyl 4-hydroxybenzoate (4.77 g), tert-butyl [(1S)-2-hydroxy-1-methylethyl]carbamate (5.00 g) and triphenylphosphine (11.2 g) in THF (70 mL) was added dropwise a toluene solution (2.2 M, 20 mL) of diethyl azodicarboxylate, and the mixture was stirred at room temperature for 1 hr. The reaction mixture was concentrated under reduced pressure, and the residue was purified by silica gel column chromatography (ethyl acetate). Using the obtained residue, and in the same manner as in Example 1, step D, the title compound (3.80 g) was obtained.

$^1$H NMR (300 MHz, CDCl$_3$) δ 1.32 (3H, d, J=6.8 Hz), 2.00 (3H, s), 3.89 (3H, s), 3.95-4.09 (2H, m), 4.32-4.49 (1H, m), 5.68 (1H, d, J=7.6 Hz), 6.93 (2H, d, J=9.1 Hz), 7.99 (2H, d, J=9.1 Hz).

B) 4-{([(2S)-2-(acetylamino)propyl]oxy}benzoic acid

1M Aqueous sodium hydroxide solution (23 mL) was added to a solution (7 mL) of methyl 4-{[(2S)-2-(acetylamino)propyl]oxy}benzoate (3.80 g) in methanol, and the mixture was stirred at 60° C. for 40 min. The reaction mixture was neutralized with 6M hydrochloric acid, and extracted with ethyl acetate. The combined organic layer was washed with saturated brine, and dried over anhydrous magnesium sulfate, and the solvent was evaporated under reduced pressure. The residue was washed with diisopropyl ether, and the precipitated solid was collected by filtration to give the title compound (3.33 g).

$^1$H NMR (300 MHz, DMSO-d$_6$) δ 1.15 (3H, d, J=6.8 Hz), 1.81 (3H, s), 3.78-4.20 (3H, m), 7.02 (2H, d, J=9.1 Hz), 7.87 (2H, d, J=9.1 Hz), 7.95 (1H, d, J=7.6 Hz), 12.63 (1H, brs).

C) 4-{[(2S)-2-(acetylamino)propyl]oxy}-N-(2,4-dihydroxyphenyl)benzamide

Using 4-{[(2S)-2-(acetylamino)propyl]oxy}benzoic acid and 4-aminobenzene-1,3-diol hydrochloride, and in the same manner as in Example 2, step C, the title compound was obtained.

$^1$H NMR (300 MHz, DMSO-d$_6$) δ 1.16 (3H, d, J=6.8 Hz), 1.82 (3H, s), 3.82-3.93 (1H, m), 3.96-4.05 (1H, m), 4.06-4.20 (1H, m), 6.23 (1H, dd, J=8.3, 2.7 Hz), 6.35 (1H, d, J=2.7 Hz), 7.05 (2H, d, J=9.1 Hz), 7.24 (1H, d, J=8.3 Hz), 7.82-8.02 (3H, m), 9.36 (1H, s).

D) N-{(1S)-2-[4-(6-hydroxy-1,3-benzoxazol-2-yl)phenoxy]-1-methylethyl}acetamide To a solution of 4-{[(2S)-2-(acetylamino)propyl]oxy}-N-(2,4-dihydroxyphenyl)benzamide (628 mg) and triphenylphosphine (716 mg) in THF (6.0 mL) was added dropwise a toluene solution (2.2 M, 1.24 mL) of diethyl azodicarboxylate, and the mixture was stirred under a nitrogen atmosphere at room temperature overnight. The reaction mixture was concentrated under reduced pressure, and the residue was purified by silica gel column chromatography (NH, ethyl acetate/methanol) to give the title compound (326 mg).

$^1$H NMR (300 MHz, DMSO-d$_6$) δ 1.17 (3H, d, J=6.8 Hz), 1.82 (3H, s), 3.84-4.22 (3H, m), 6.82 (1H, dd, J=8.3, 2.3 Hz), 7.06 (1H, d, J=2.3 Hz), 7.14 (2H, d, J=8.7 Hz), 7.52 (1H, d, J=8.3 Hz), 7.96 (1H, d, J=7.6 Hz), 8.04 (2H, d, J=9.1 Hz), 9.79 (1H, s).

E) N-[(1S)-2-{4-[6-(cyclopropylmethoxy)-1,3-benzoxazol-2-yl]phenoxy}-1-methylethyl]acetamide Using N-{(1S)-2-[4-(6-hydroxy-1,3-benzoxazol-2-yl)phenoxy]-1-methylethyl}acetamide, and in the same manner as in Example 1, step A, the title compound was obtained.

Example 4

N-[(1S)-2-({6-[6-(cyclopropylmethoxy)-1,3-benzoxazol-2-yl]-5-methylpyridin-3-yl}oxy)-1-methylethyl]acetamide

A) tert-butyl {(1S)-2-[(6-bromo-5-methylpyridin-3-yl)oxy]-1-methylethyl}carbamate Under an argon atmosphere, to a solution of 2,5-dibromo-3-methylpyridine (12.4 g) in THF (100 mL) was added dropwise a hexane solution (1.6 M, 30.9 mL) of n-butyllithium at −78° C., and the obtained mixture was stirred at −78° C. for 30 min. To the reaction mixture was added trimethoxyborane (5.52 mL), and the obtained mixture was stirred at −78° C. for 30 min, then at 0° C. for 1 hr. To the reaction mixture were added 8M aqueous sodium hydroxide solution (6.18 mL) and aqueous 30% hydrogen peroxide (100 mL), and the obtained mixture was stirred at 0° C. for 30 min, then at room temperature for 30 min. The reaction mixture was acidified with 1M hydrochloric acid, and extracted with ethyl acetate. The combined organic layer was washed with saturated aqueous sodium thiosulfate solution and then saturated brine, and dried over anhydrous magnesium sulfate, and the solvent was evaporated under reduced pressure. The residue was purified by silica gel column chromatography (hexane/ethyl acetate), and the obtained residue was mixed with tert-butyl [(1S)-2-hydroxy-1-methylethyl]carbamate (4.43 g), triphenylphosphine (6.63 g) and THF (40 mL). A toluene solution (1.9 M, 13.3 mL) of diisopropyl azodicarboxylate was added dropwise thereto, and the obtained mixture was stirred at room temperature for 1 hr, then at 70° C. overnight. Water was added to the reaction mixture, and the mixture was extracted with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) and HPLC (C18, mobile phase: water/acetonitrile (containing 5 mM ammonium acetate)) to give the title compound (0.739 g).

$^1$H NMR (300 MHz, DMSO-d$_6$) δ 1.11 (3H, d, J=6.8 Hz), 1.37 (9H, s), 2.30 (3H, s), 3.72-4.00 (3H, m), 6.91 (1H, d, J=7.2 Hz), 7.36-7.52 (1H, m), 7.94 (1H, d, J=3.0 Hz).

B) tert-butyl [(1S)-2-({6-[6-(cyclopropylmethoxy)-1,3-benzoxazol-2-yl]-5-methylpyridin-3-yl}oxy)-1-methylethyl]carbamate Using tert-butyl {(1S)-2-[(6-bromo-5-methylpyridin-3-yl)oxy]-1-methylethyl}carbamate, and in the same manner as in Example 1, step C, the title compound was obtained.

MS (ESI+): [M+H]$^+$ 454.5.

C) N-[(1S)-2-({6-[6-(cyclopropylmethoxy)-1,3-benzoxazol-2-yl]-methylpyridin-3-yl}oxy)-1-methylethyl]acetamide Using tert-butyl [(1S)-2-({6-[6-(cyclopropylmethoxy)-1,3-benzoxazol-2-yl]-5-methylpyridin-3-yl}oxy)-1-methylethyl]carbamate, and in the same manner as in Example 1, step D, the title compound was obtained.

Example 5

N-[(1S)-2-({5-chloro-6-[6-(cyclopropylmethoxy)-1,3-benzoxazol-2-yl]pyridin-3-yl}oxy)-1-methylethyl]acetamide

A) 5-bromo-3-chloro-N-(2,4-dihydroxyphenyl)pyridine-2-carboxamide

Using 5-bromo-3-chloropyridine-2-carboxylic acid and 4-aminobenzene-1,3-diol hydrochloride, and in the same manner as in Example 2, step C, the title compound was obtained.

$^1$H NMR (300 MHz, DMSO-$d_6$) δ 6.24 (1H, dd, J=8.7, 2.6 Hz), 6.40 (1H, d, J=2.6 Hz), 7.83 (1H, d, J=8.7 Hz), 8.49 (1H, d, J=1.9 Hz), 8.78 (1H, d, J=1.9 Hz), 9.21 (1H, s), 9.82 (1H, s), 9.90 (1H, s).

B) 2-(5-bromo-3-chloropyridin-2-yl)-6-(cyclopropylmethoxy)-1,3-benzoxazole

Using 5-bromo-3-chloro-N-(2,4-dihydroxyphenyl)pyridine-2-carboxamide, and in the same manner as in Example 2, steps D-E, the title compound was obtained.

$^1$H NMR (300 MHz, DMSO-$d_6$) δ 0.25-0.43 (2H, m), 0.54-0.70 (2H, m), 1.16-1.39 (1H, m), 3.93 (2H, d, J=6.8 Hz), 7.07 (1H, dd, J=8.8, 2.3 Hz), 7.44 (1H, d, J=2.3 Hz), 7.79 (1H, d, J=8.8 Hz), 8.62 (1H, d, J=2.1 Hz), 8.90 (1H, d, J=2.1 Hz).

C) N-[(1S)-2-({5-chloro-6-[6-(cyclopropylmethoxy)-1,3-benzoxazol-2-yl]pyridin-3-yl}oxy)-1-methylethyl]acetamide Under an argon atmosphere, to a solution of 2-(5-bromo-3-chloropyridin-2-yl)-6-(cyclopropylmethoxy)-1,3-benzoxazole (300 mg) and trimethoxyborane (0.177 mL) in THF (5 mL) was added dropwise a hexane solution (1.6 M, 1.23 mL) of n-butyllithium at 0° C., and the obtained mixture was stirred at 0° C. for 1 hr. To the reaction mixture was added 1M hydrochloric acid, and the mixture was extracted with ethyl acetate. The combined organic layer was washed with saturated brine, and dried over anhydrous magnesium sulfate, and the solvent was evaporated under reduced pressure. The residue was mixed with 30% aqueous hydrogen peroxide (1 mL) and THF (5 mL), and the obtained mixture was stirred at 70° C. for 2 hr. To the reaction mixture were added water and saturated aqueous sodium thiosulfate solution, and the mixture was extracted with ethyl acetate. The combined organic layer was washed with saturated brine, and dried over anhydrous magnesium sulfate, and the solvent was evaporated under reduced pressure. The obtained residue was mixed with tert-butyl [(1S)-2-hydroxy-1-methylethyl]carbamate (138 mg), triphenylphosphine (207 mg) and THF (5 mL). A toluene solution (1.9 M, 0.416 mL) of diisopropyl azodicarboxylate was added dropwise thereto, and the mixture was stirred at room temperature for 1 hr, then at 70° C. for 1 hr. Water was added to the reaction mixture, and the mixture was extracted with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate), and mixed with ethyl acetate (2 mL) and 4M hydrogen chloride/ethyl acetate (2 mL). The obtained mixture was stirred at room temperature for 3 hr. The solvent was evaporated under reduced pressure, and the residue was mixed with pyridine (2 mL) and acetic anhydride (2 mL), and the obtained mixture was stirred at room temperature for 2 hr. The reaction mixture was concentrated under reduced pressure, and the residue was purified by silica gel column chromatography (hexane/ethyl acetate/methanol) to give the title compound (22.2 mg).

Example 6

N-[(1S)-2-({6-[6-(cyclopropylmethoxy)-1,3-benzoxazol-2-yl]-5-fluoropyridin-3-yl}oxy)-1-methylethyl]acetamide

A) 6-chloro-5-fluoropyridin-3-ol

Under an argon atmosphere, to a mixture of 5-bromo-2-chloro-3-fluoropyridine (4.45 g) and toluene (50 mL) was added dropwise a hexane solution (1.6 M, 15.8 mL) of n-butyllithium at –78° C., and the obtained mixture was stirred at –78° C. for 5 min. To the reaction mixture was added trimethoxyborane (2.84 mL), and the obtained mixture was stirred at –78° C. for 15 min, and then at room temperature overnight. The reaction mixture was cooled to 0° C., 8M aqueous sodium hydroxide solution (3.17 mL) and 30% aqueous hydrogen peroxide (20 mL) were added thereto, and the obtained mixture was stirred at room temperature for 2 hr. The reaction mixture was cooled to 0° C., and saturated aqueous sodium thiosulfate solution was added thereto. The mixture was neutralized with 1M hydrochloric acid, and extracted with ethyl acetate. The combined organic layer was washed with water and saturated brine, and dried over anhydrous magnesium sulfate, and the solvent was evaporated under reduced pressure. The residue was purified by silica gel column chromatography (hexane/ethyl acetate) to give the title compound (2.20 g).

$^1$H NMR (300 MHz, DMSO-$d_6$) δ 7.32 (1H, dd, J=10.2, 2.3 Hz), 7.85 (1H, d, J=2.3 Hz), 10.77 (1H, s).

B) tert-butyl {(1S)-2-[(6-chloro-5-fluoropyridin-3-yl)oxy]-1-methylethyl}carbamate To a mixture of 6-chloro-5-fluoropyridin-3-ol (2.43 g), tert-butyl [(1S)-2-hydroxy-1-methylethyl]carbamate (3.46 g), triphenylphosphine (6.48 g) and THF (25 mL) was added dropwise a toluene solution (1.9 M, 13.0 mL) of diisopropyl azodicarboxylate at room temperature, and the obtained mixture was stirred at room temperature for 3 days. The reaction mixture was concentrated under reduced pressure, and the residue was purified by silica gel column chromatography (hexane/ethyl acetate) to give the title compound (2.88 g).

$^1$H NMR (300 MHz, DMSO-$d_6$) δ 1.11 (3H, d, J=6.8 Hz), 1.37 (9H, s), 3.69-4.19 (3H, m), 6.92 (1H, d, J=7.5 Hz), 7.72 (1H, dd, J=10.5, 2.5 Hz), 8.04 (1H, d, J=2.5 Hz).

C) ethyl 5-({(2S)-2-[(tert-butoxycarbonyl)amino]propyl}oxy)-3-fluoropyridine-2-carboxylate Under a carbon monoxide atmosphere, a mixture of tert-butyl {(1S)-2-[(6-chloro-5-fluoropyridin-3-yl)oxy]-1-methylethyl}carbamate (500 mg), [1,1'-bis(diphenylphosphino)ferrocene]dichloropalladium(II) dichloromethane adduct (135 mg), triethylamine (0.229 mL), ethanol (5 mL) and DMF (5 mL) was stirred at 80° C. overnight. Water was added to the reaction mixture, and the mixture was extracted with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound (402 mg).

MS (ESI+): [M+H]$^+$ 343.3.

D) 5-({(2S)-2-[(tert-butoxycarbonyl)amino]propyl}oxy)-3-fluoropyridine-2-carboxylic acid A mixture of ethyl 5-({(2S)-2-[(tert-butoxycarbonyl)amino]propyl}oxy)-3-fluoropyridine-2-carboxylate (402 mg), THF (4 mL), ethanol (4 mL) and 1M aqueous lithium hydroxide solution (4 mL) was stirred at 0° C. for 3 hr. The reaction mixture was neutralized with 1M hydrochloric acid at 0° C., and extracted with ethyl acetate. The combined organic layer was washed with saturated brine, and dried over anhydrous magnesium sulfate, and the solvent was evaporated under reduced pressure to give the title compound (357 mg).

MS (ESI+): [M+H]$^+$ 315.2.

E) tert-butyl [(1S)-2-({6-[(2,4-dihydroxyphenyl)carbamoyl]-5-fluoropyridin-3-yl}oxy)-1-methylethyl]carbamate A mixture of 5-({(2S)-2-[(tert-butoxycarbonyl)amino]propyl}oxy)-3-fluoropyridine-2-carboxylic acid (357 mg), 4-aminobenzene-1,3-diol hydrochloride (184 mg), HATU (432 mg), N,N-diisopropylethylamine (0.391 mL) and DMF (5 mL) was stirred at room temperature overnight. Water was added to the reaction mixture, and the mixture was extracted with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound (321 mg).

MS (ESI+): [M+H]$^+$ 422.3.

F) tert-butyl [(1S)-2-({6-[6-(cyclopropylmethoxy)-1,3-benzoxazol-2-yl]-5-fluoropyridin-3-yl}oxy)-1-methylethyl]carbamate Triethylamine (0.849 mL) was added to a solution of triphenylphosphine (599 mg) and hexachloroethane (451 mg) in acetonitrile (5 mL) at room temperature, and the obtained mixture was stirred at room temperature for 10 min. To the reaction mixture was further added a mixture of tert-butyl [(1S)-2-({6-[(2,4-dihydroxyphenyl)carbamoyl]-5-fluoropyridin-3-yl}oxy)-1-methylethyl]carbamate (321 mg) and acetonitrile (5 mL), and the mixture was stirred at room temperature for 2 hr. Water was added to the reaction mixture, and the mixture was extracted with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate), and the obtained residue (305 mg) was mixed with (bromomethyl)cyclopropane (204 mg), potassium carbonate (209 mg) and DMF (5 mL) at room temperature. The obtained mixture was stirred at room temperature overnight. Water was added to the reaction mixture, and the mixture was extracted with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound (101 mg).

MS (ESI+): [M+H]$^+$ 458.2.

G) N-[(1S)-2-({6-[6-(cyclopropylmethoxy)-1,3-benzoxazol-2-yl]-5-fluoropyridin-3-yl}oxy)-1-methylethyl]acetamide A mixture of tert-butyl [(1S)-2-({6-[6-(cyclopropylmethoxy)-1,3-benzoxazol-2-yl]-5-fluoropyridin-3-yl}oxy)-1-methylethyl]carbamate (101 mg), 4M hydrogen chloride/ethyl acetate (1 mL) and ethyl acetate (1 mL) was stirred at room temperature for 2 hr. The solvent was evaporated under reduced pressure, and the residue was mixed with acetic anhydride (1 mL) and pyridine (1 mL), and the obtained mixture was stirred at room temperature for 1 hr. To the reaction mixture was added 1M hydrochloric acid, and the mixture was extracted with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate/methanol), and recrystallized (hexane/ethyl acetate) to give the title compound (53.1 mg).

$^1$H NMR (300 MHz, DMSO-d$_6$) δ 0.29-0.43 (2H, m), 0.53-0.68 (2H, m), 1.11-1.38 (4H, m), 1.83 (3H, s), 3.91 (2H, d, J=7.2 Hz), 3.98-4.24 (3H, m), 7.03 (1H, dd, J=8.9, 2.4 Hz), 7.41 (1H, d, J=2.4 Hz), 7.66-7.81 (2H, m), 8.02 (1H, d, J=7.2 Hz), 8.29-8.44 (1H, m).

mp 158-159° C.

Anal. Calcd for C$_{21}$H$_{22}$N$_3$O$_4$F: C, 63.15; H, 5.55; N, 10.52. Found: C, 63.13; H, 5.65; N, 10.31.

Example 7

N-[(1S)-2-({5-[6-(cyclopropylmethoxy)-1,3-benzoxazol-2-yl]isoxazol-3-yl}oxy)-1-methylethyl]acetamide Using 3-({(2S)-2-[(tert-butoxycarbonyl)amino]propyl}oxy)isoxazole-5-carboxylic acid and 4-aminobenzene-1,3-diol hydrochloride, and in the same manner as in Example 2, steps C-F, the title compound was obtained.

Example 8

N-[(1S)-2-({5-[6-(cyclopropylmethoxy)-1,3-benzoxazol-2-yl]-1H-pyrazol-3-yl}oxy)-1-methylethyl]acetamide A) methyl 3-({(2S)-2-[(tert-butoxycarbonyl)amino]propyl}oxy)-1H-pyrazole-5-carboxylate Using methyl 3-hydroxy-1H-pyrazole-5-carboxylate, and in the same manner as in Example 2, step A, the title compound was obtained.

MS (ESI+): [M+H]$^+$ 300.4.

B) methyl 1-benzyl-3-({(2S)-2-[(tert-butoxycarbonyl)amino]propyl}oxy)-1H-pyrazole-5-carboxylate Using methyl 3-({(2S)-2-[(tert-butoxycarbonyl)amino]propyl}oxy)-1H-pyrazole-5-carboxylate and (bromomethyl)benzene, and in the same manner as in Example 1, step A (reaction temperature was room temperature), the title compound was obtained.

MS (ESI+): [M+H]$^+$ 390.4.

C) 1-benzyl-3-({(2S)-2-[(tert-butoxycarbonyl) amino]propyl}oxy)-1H-pyrazole-5-carboxylic acid Using methyl 1-benzyl-3-({(2S)-2-[(tert-butoxycarbonyl) amino]propyl}oxy)-1H-pyrazole-5-carboxylate, and in the same manner as in Example 2, step B, the title compound was obtained.
MS (ESI+): [M+H]+ 376.4.

D) tert-butyl [(1S)-2-({1-benzyl-5-[(2,4-dihydroxyphenyl)carbamoyl]-1H-pyrazol-3-yl}oxy)-1-methylethyl]carbamate Using 1-benzyl-3-({(2S)-2-[(tert-butoxycarbonyl)amino] propyl}oxy)-1H-pyrazole-5-carboxylic acid, and in the same manner as in Example 5, step A, the title compound was obtained.
MS (ESI+): [M+H]+ 483.4.

E) tert-butyl [(1S)-2-{[1-benzyl-5-(6-hydroxy-1,3-benzoxazol-2-yl)-1H-pyrazol-3-yl]oxy}-1-methylethyl]carbamate Using tert-butyl [(1S)-2-({1-benzyl-5-[(2,4-dihydroxyphenyl)carbamoyl]-1H-pyrazol-3-yl}oxy)-1-methylethyl] carbamate, and in the same manner as in Example 2, step D, the title compound was obtained.
MS (ESI+): [M+H]+ 465.4.

F) tert-butyl [(1S)-2-({1-benzyl-5-[6-(cyclopropylmethoxy)-1,3-benzoxazol-2-yl]-1H-pyrazol-3-yl}oxy)-1-methylethyl]carbamate Using tert-butyl [(1S)-2-{[1-benzyl-5-(6-hydroxy-1,3-benzoxazol-2-yl)-1H-pyrazol-3-yl]oxy}-1-methylethyl]carbamate, and in the same manner as in Example 2, step E, the title compound was obtained.
MS (ESI+): [M+H]+ 519.4.

G) N-[(1S)-2-({1-benzyl-5-[6-(cyclopropylmethoxy)-1,3-benzoxazol-2-yl]-1H-pyrazol-3-yl}oxy)-1-methylethyl]acetamide Using tert-butyl [(1S)-2-({1-benzyl-5-[6-(cyclopropylmethoxy)-1,3-benzoxazol-2-yl]-1H-pyrazol-3-yl}oxy)-1-methylethyl]carbamate, and in the same manner as in Example 1, step D, the title compound was obtained.
MS (ESI+): [M+H]+ 461.5.

H) N-[(1S)-2-({5-[6-(cyclopropylmethoxy)-1,3-benzoxazol-2-yl]-1H-pyrazol-3-yl}oxy)-1-methylethyl]acetamide Under a hydrogen atmosphere, a mixture of N-[(1S)-2-({1-benzyl-5-[6-(cyclopropylmethoxy)-1,3-benzoxazol-2-yl]-1H-pyrazol-3-yl}oxy)-1-methylethyl]acetamide (120 mg), 20% palladium hydroxide/carbon (containing water (50%), 60 mg), ethanol (5 mL) and THF (3 mL) was stirred at 50° C. for 4 hr. The catalyst was removed by filtration, and the obtained filtrate was concentrated under reduced pressure. The residue was purified by silica gel column chromatography (hexane/ethyl acetate) to give the title compound (23.4 mg).

Example 9

N-[(1S)-2-({5-[6-(cyclopropylmethoxy)-1,3-benzoxazol-2-yl]-4-fluoro-1H-pyrazol-3-yl}oxy)-1-methylethyl]acetamide Under a hydrogen atmosphere, a mixture of N-[(1S)-2-({1-benzyl-5-[6-(cyclopropylmethoxy)-1,3-benzoxazol-2-yl]-1H-pyrazol-3-yl}oxy)-1-methylethyl]acetamide (200 mg), 20% palladium hydroxide/carbon (containing water (50%), 200 mg), ethanol (7 mL) and THF (4 mL) was stirred at 50° C. for 4 hr. The catalyst was removed by filtration, and the obtained filtrate was concentrated under reduced pressure. The residue was mixed with acetonitrile (10 mL), THF (10 mL) and 1-(chloromethyl)-4-fluoro-1,4-diazoniabicyclo [2.2.2]octane ditetrafluoroborate (369 mg), and the obtained mixture was stirred at 70° C. for 3 hr. To the reaction mixture was further added 1-(chloromethyl)-4-fluoro-1,4-diazoniabicyclo[2.2.2]octane ditetrafluoroborate (369 mg), and the obtained mixture was stirred at 70° C. for 2 hr. To the reaction mixture was further added 1-(chloromethyl)-4-fluoro-1,4-diazoniabicyclo[2.2.2]octane ditetrafluoroborate (369 mg), and the obtained mixture was stirred at 70° C. for 2 hr. Water was added to the reaction mixture, and the mixture was extracted with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) and HPLC (Ascentis RP-Amide, mobile phase: water/acetonitrile (containing 5 mM ammonium acetate)) to give the title compound (6.2 mg).

Example 10

N-[(1S)-2-({5-[6-(cyclopropylmethoxy)-1,3-benzoxazol-2-yl]-1-methyl-1H-pyrazol-3-yl}oxy)-1-methylethyl]acetamide A) methyl 3-({(2S)-2-[(tert-butoxycarbonyl)amino] propyl}oxy)-1-methyl-1H-pyrazole-5-carboxylate Using methyl 3-({(2S)-2-[(tert-butoxycarbonyl)amino] propyl}oxy)-1H-pyrazole-5-carboxylate and iodomethane, and in the same manner as in Example 8, step B, the title compound was obtained.
MS (ESI+): [M+H]+ 314.5.

B) 3-({(2S)-2-[(tert-butoxycarbonyl)amino] propyl}oxy)-1-methyl-1H-pyrazole-5-carboxylic acid Using methyl 3-({(2S)-2-[(tert-butoxycarbonyl)amino] propyl}oxy)-1-methyl-1H-pyrazole-5-carboxylate, and in the same manner as in Example 2, step B, the title compound was obtained.
MS (ESI+): [M+H]+ 300.4.

C) tert-butyl [(1S)-2-({5-[(2,4-dihydroxyphenyl) carbamoyl]-1-methyl-1H-pyrazol-3-yl}oxy)-1-methylethyl]carbamate Using 3-({(2S)-2-[(tert-butoxycarbonyl)amino] propyl}oxy)-1-methyl-1H-pyrazole-5-carboxylic acid, and in the same manner as in Example 5, step A, the title compound was obtained.
MS (ESI+): [M+H]+ 407.3.

D) tert-butyl [(1S)-2-{([5-(6-hydroxy-1,3-benzoxazol-2-yl)-1-methyl-1H-pyrazol-3-yl]oxy}-1-methylethyl]carbamate Using tert-butyl [(1S)-2-({5-[(2,4-dihydroxyphenyl)carbamoyl]-1-methyl-1H-pyrazol-3-yl}oxy)-1-methylethyl]carbamate, and in the same manner as in Example 2, step D, the title compound was obtained.
MS (ESI+): [M+H]$^+$ 389.3.

E) tert-butyl [(1S)-2-({5-[6-(cyclopropylmethoxy)-1,3-benzoxazol-2-yl]-1-methyl-1H-pyrazol-3-yl}oxy)-1-methylethyl]carbamate Using tert-butyl [(1S)-2-{[5-(6-hydroxy-1,3-benzoxazol-2-yl)-1-methyl-1H-pyrazol-3-yl]oxy}-1-methylethyl]carbamate, and in the same manner as in Example 2, step E, the title compound was obtained.
MS (ESI+): [M+H]$^+$ 443.5.

F) N-[(1S)-2-({5-[6-(cyclopropylmethoxy)-1,3-benzoxazol-2-yl]-1-methyl-1H-pyrazol-3-yl}oxy)-1-methylethyl]acetamide Using tert-butyl [(1S)-2-({5-[6-(cyclopropylmethoxy)-1,3-benzoxazol-2-yl]-1-methyl-1H-pyrazol-3-yl}oxy)-1-methylethyl]carbamate, and in the same manner as in Example 1, step D, the title compound was obtained.

Example 11

N-[(1S)-2-({5-[6-(cyclopropylmethoxy)-1,3-benzoxazol-2-yl]-4-fluoro-1-methyl-1H-pyrazol-3-yl}oxy)-1-methylethyl]acetamide A mixture of N-[(1S)-2-({5-[6-(cyclopropylmethoxy)-1,3-benzoxazol-2-yl]-1-methyl-1H-pyrazol-3-yl}oxy)-1-methylethyl]acetamide (193 mg), 1-(chloromethyl)-4-fluoro-1,4-diazoniabicyclo[2.2.2]octane ditetrafluoroborate (427 mg) and acetonitrile (10 mL) was stirred at 60° C. for 7 hr. Water was added to the reaction mixture, and the mixture was extracted with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound (11.2 mg).

Example 12

N-[(1S)-2-{4-[5-(cyclopropylmethoxy)-2H-indazol-2-yl]phenoxy}-1-methylethyl]acetamide

A) 1-[4-(benzyloxy)phenyl]-1-(2-bromo-5-methoxybenzyl)hydrazine

To a solution of [4-(benzyloxy)phenyl]hydrazine hydrochloride (2.0 g) in THF (25 mL) was added dropwise a THF solution (1.9 M, 8.4 ml) of sodium hexamethyldisilazide under ice-cooling, and the mixture was stirred at room temperature for 1 hr. To the reaction mixture was added 1-bromo-2-(bromomethyl)-4-methoxybenzene (2.23 g) under ice-cooling, and the mixture was stirred at room temperature for 1 hr. Water was added to the reaction mixture, and the solvent was evaporated under reduced pressure. To the residue was added water, and the mixture was extracted with ethyl acetate. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound (1.56 g).
$^1$H NMR (300 MHz, CDCl$_3$) δ 3.63 (2H, s), 3.73 (3H, s), 4.52 (2H, s), 5.02 (2H, s), 6.71 (1H, dd, J=8.7, 3.0 Hz), 6.85-6.97 (3H, m), 6.97-7.07 (2H, m), 7.27-7.54 (6H, m).

B) 2-[4-(benzyloxy)phenyl]-5-methoxy-2H-indazole

A mixture of 1-[4-(benzyloxy)phenyl]-1-(2-bromo-5-methoxybenzyl)hydrazine (1.50 g), palladium(II) acetate (41 mg), 1,1'-bis(diphenylphosphino)ferrocene (151 mg), sodium tert-butoxide (436 mg) and toluene (18 mL) was stirred under an argon atmosphere at 90° C. overnight. The solvent was evaporated under reduced pressure, and the obtained mixture was diluted with ethyl acetate and water, and the organic layer was separated. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound (163 mg).
$^1$H NMR (300 MHz, DMSO-d$_6$) δ 3.80 (3H, s), 5.19 (2H, s), 6.97 (1H, dd, J=9.1, 2.3 Hz), 7.01 (1H, d, J=1.5 Hz), 7.13-7.26 (2H, m), 7.28-7.55 (5H, m), 7.61 (1H, d, J=9.4 Hz), 7.83-8.03 (2H, m), 8.79 (1H, d, J=1.1 Hz).

C) 4-(5-methoxy-2H-indazol-2-yl)phenol

Under a hydrogen atmosphere, a mixture of 2-[4-(benzyloxy)phenyl]-5-methoxy-2H-indazole (160 mg), 10% palladium/carbon (containing water (50%), 52 mg), methanol (10 mL) and THF (5 mL) was stirred at room temperature for 1 hr. The catalyst was removed by filtration, and the obtained filtrate was concentrated under reduced pressure to give the title compound (121 mg).
$^1$H NMR (300 MHz, DMSO-d$_6$) δ 3.79 (3H, s), 6.86-6.93 (2H, m), 6.95 (1H, dd, J=9.3, 2.5 Hz), 7.01 (1H, d, J=1.9 Hz), 7.59 (1H, d, J=9.4 Hz), 7.75-7.85 (2H, m), 8.71 (1H, d, J=1.1 Hz), 9.88 (1H, brs).

D) tert-butyl {(1S)-2-[4-(5-methoxy-2H-indazol-2-yl)phenoxy]-1-methylethyl}carbamate Using 4-(5-methoxy-2H-indazol-2-yl)phenol, and in the same manner as in Example 1, step B, the title compound was obtained.
$^1$H NMR (300 MHz, DMSO-d$_6$) δ 1.32 (3H, d, J=6.8 Hz), 1.46 (9H, s), 3.86 (3H, s), 3.99 (2H, d, J=3.8 Hz), 4.02-4.16 (1H, m), 6.90 (1H, d, J=2.3 Hz), 6.97-7.07 (3H, m), 7.67 (1H, d, 8.7 Hz), 7.77 (2H, d, J=9.1 Hz), 8.18 (1H, s),

E) N-{(1S)-2-[4-(5-methoxy-2H-indazol-2-yl)phenoxy]-1-methylethyl}acetamide

Using tert-butyl {(1S)-2-[4-(5-methoxy-2H-indazol-2-yl)phenoxy]-1-methylethyl}carbamate, and in the same manner as in Example 1, step D, the title compound was obtained.
$^1$H NMR (300 MHz, DMSO-d$_6$) δ 1.17 (3H, d, J=6.4 Hz), 1.83 (3H, s), 3.80 (3H, s), 3.83-3.93 (1H, m), 3.94-4.05 (1H, m), 4.05-4.21 (1H, m), 6.91-7.05 (2H, m), 7.07-7.19 (2H, m), 7.60 (1H, d, J=9.1 Hz), 7.89-8.02 (3H, m), 8.80 (1H, d, J=0.8 Hz).

F) N-{(1S)-2-[4-(5-hydroxy-2H-indazol-2-yl)phenoxy]-1-methylethyl}acetamide

To a solution of N-{(1S)-2-[4-(5-methoxy-2H-indazol-2-yl)phenoxy]-1-methylethyl}acetamide (70 mg) in dichloromethane (3 mL) was added dropwise a dichloromethane solution (1.0 M, 0.83 mL) of tribromoborane under ice-cooling, and the mixture was stirred at room temperature for 3 hr. To the reaction mixture was added saturated aqueous sodium hydrogen carbonate solution under ice-cooling, and the mixture was extracted with ethyl acetate. The separated organic layer was washed with saturated brine, and dried over anhydrous magnesium sulfate, and the solvent was evaporated under reduced pressure. The residue was purified by silica gel column chromatography (hexane/ethyl acetate) to give the title compound (48 mg).
$^1$H NMR (300 MHz, CDCl$_3$) δ 1.17 (3H, d, J=6.8 Hz), 1.83 (3H, s), 3.82-3.92 (1H, m), 3.95-4.05 (1H, m), 4.05-4.22 (1H, m), 6.81-6.96 (2H, m), 7.07-7.19 (2H, m), 7.54 (1H, d, J=9.1 Hz), 7.86-7.99 (3H, m), 8.68 (1H, d, J=0.8 Hz), 9.25 (1H, s).

G) N-[(1S)-2-{4-[5-(cyclopropylmethoxy)-2H-indazol-2-yl]phenoxy}-1-methylethyl]acetamide Using N-{(1S)-2-[4-(5-hydroxy-2H-indazol-2-yl)phenoxy]-1-methylethyl}acetamide, and in the same manner as in Example 2, step E, the title compound was obtained.

Example 13

N-[(1S)-2-{4-[6-(cyclopropylmethoxy)-2H-indazol-2-yl]phenoxy}-1-methylethyl]acetamide A) 6-(cyclopropylmethoxy)-1H-indazole Using 6-hydroxy-1H-indazole, and in the same manner as in Example 1, step A, the title compound was obtained.
$^1$H NMR (300 MHz, CDCl$_3$) δ 0.33-0.44 (2H, m), 0.58-0.74 (2H, m), 1.19-1.42 (1H, m), 3.85 (2H, d, J=7.2 Hz), 6.74-6.93 (2H, m), 7.60 (1H, dd, J=8.7, 0.8 Hz), 7.96 (1H, d, J=0.8 Hz), 9.92 (1H, brs).

B) 2-[4-(benzyloxy)phenyl]-6-(cyclopropylmethoxy)-2H-indazole

A mixture of 6-(cyclopropylmethoxy)-1H-indazole (376 mg), 1-(benzyloxy)-4-bromobenzene (632 mg), copper(I) iodide (38.1 mg), (1RS,2RS)—N,N'-dimethylcyclohexane-1,2-diamine (114 mg), tripotassium phosphate (892 mg) and toluene (2 mL) was stirred under an argon atmosphere at 110° C. overnight. The reaction mixture was diluted with ethyl acetate and water, and filtered through celite. The organic layer separated from the obtained filtrate was washed with saturated brine, and dried over anhydrous magnesium sulfate, and the solvent was evaporated under reduced pressure. The residue was purified by silica gel column chromatography (hexane/ethyl acetate) to give a mixture (741 mg) of the title compound and 1-[4-(benzyloxy)phenyl]-6-(cyclopropylmethoxy)-1H-indazole.
MS (ESI+): [M+H]$^+$ 371.2.

C) 4-[6-(cyclopropylmethoxy)-2H-indazol-2-yl]phenol

Using a mixture of 2-[4-(benzyloxy)phenyl]-6-(cyclopropylmethoxy)-2H-indazole and 1-[4-(benzyloxy)phenyl]-6-(cyclopropylmethoxy)-1H-indazole, and in the same manner as in Example 12, step C, a mixture of the title compound and 4-[6-(cyclopropylmethoxy)-1H-indazol-1-yl]phenol was obtained.
MS (ESI+): [M+H]$^+$ 281.2.

D) tert-butyl [(1S)-2-{4-[6-(cyclopropylmethoxy)-2H-indazol-2-yl]phenoxy}-1-methylethyl]carbamate Using a mixture of 4-[6-(cyclopropylmethoxy)-2H-indazol-2-yl]phenol and 4-[6-(cyclopropylmethoxy)-1H-indazol-1-yl]phenol, and in the same manner as in Example 1, step B, the title compound was obtained.
MS (ESI+): [M+H]$^+$ 438.4.

E) N-[(1S)-2-{4-[6-(cyclopropylmethoxy)-2H-indazol-2-yl]phenoxy}-1-methylethyl]acetamide Using tert-butyl [(1S)-2-{4-[6-(cyclopropylmethoxy)-2H-indazol-2-yl]phenoxy}-1-methylethyl]carbamate (100 mg), and in the same manner as in Example 1, step D, the title compound was obtained (50.1 mg).

Example 14

N-[(1S)-2-({6-[6-(cyclopropylmethoxy)-2H-indazol-2-yl]pyridin-3-yl}oxy)-1-methylethyl]acetamide A) 2-[5-(benzyloxy)pyridin-2-yl]-6-(cyclopropylmethoxy)-2H-indazole Using 6-(cyclopropylmethoxy)-1H-indazole and 5-(benzyloxy)-2-chloropyridine, and in the same manner as in Example 13, step B, the title compound was obtained.
$^1$H NMR (300 MHz, DMSO-d$_6$) δ 0.29-0.44 (2H, m), 0.53-0.67 (2H, m), 1.22-1.30 (1H, m), 3.88 (2H, d, J=6.8 Hz), 5.27 (2H, s), 6.78 (1H, dd, J=9.1, 2.3 Hz), 6.94 (1H, d, J=1.9 Hz), 7.30-7.47 (3H, m), 7.47-7.54 (2H, m), 7.65 (1H, d, J=9.1 Hz), 7.74 (1H, dd, J=9.1, 3.0 Hz), 8.07 (1H, d, J=8.7 Hz), 8.32 (1H, d, J=2.7 Hz), 8.99 (1H, d, J=0.8 Hz).

B) 6-[6-(cyclopropylmethoxy)-2H-indazol-2-yl]pyridin-3-ol

Using 2-[5-(benzyloxy)pyridin-2-yl]-6-(cyclopropylmethoxy)-2H-indazole, and in the same manner as in Example 12, step C, the title compound was obtained.
$^1$H NMR (300 MHz, DMSO-d$_6$) δ 0.26-0.44 (2H, m), 0.51-0.68 (2H, m), 1.21-1.29 (1H, m), 3.87 (2H, d, J=7.2 Hz), 6.77 (1H, dd, J=9.1, 2.3 Hz), 6.91-6.98 (1H, m), 7.41 (1H, dd, J=8.9, 2.8 Hz), 7.64 (1H, d, J=9.1 Hz), 7.97 (1H, d, J=8.7 Hz), 8.05 (1H, d, J=3.0 Hz), 8.94 (1H, d, J=0.8 Hz), 10.41 (1H, brs).

C) tert-butyl [(1S)-2-({6-[6-(cyclopropylmethoxy)-2H-indazol-2-yl]pyridin-3-yl}oxy)-1-methylethyl]carbamate Using 6-[6-(cyclopropylmethoxy)-2H-indazol-2-yl]pyridin-3-ol, and in the same manner as in Example 1, step B, the title compound was obtained.
MS (ESI+): [M+H]$^+$ 439.1.

D) N-[(1S)-2-({6-[6-(cyclopropylmethoxy)-2H-indazol-2-yl]pyridin-3-yl}oxy)-1-methylethyl]acetamide Using tert-butyl [(1S)-2-({6-[6-(cyclopropylmethoxy)-2H-indazol-2-yl]pyridin-3-yl}oxy)-1-methylethyl]carbamate, and in the same manner as in Example 1, step D, the title compound was obtained.

Example 15

1-[(1S)-2-({6-[6-(cyclopropylmethoxy)-1,3-benzoxazol-2-yl]pyridin-3-yl}oxy)-1-methylethyl]urea A mixture of tert-butyl [(1S)-2-({6-[6-(cyclopropylmethoxy)-1,3-benzoxazol-2-yl]pyridin-3-yl}oxy)-1-methylethyl]carbamate (84.7 mg), ethyl acetate (2 mL) and 4M hydrogen chloride/ethyl acetate (2 mL) was stirred at room temperature for 3 hr. The solvent was evaporated under reduced pressure, and the residue was mixed with triethylamine (1 mL), THF (5 mL) and trichloroacetyl isocyanate (0.034 mL) at 0° C., and the obtained mixture was stirred at 0° C. for 30 min. To the reaction mixture was added 8M ammonia/methanol (5 mL), and the obtained mixture was stirred at room temperature for 2 hr. The reaction mixture was concentrated under reduced pressure, and the residue was purified by silica gel column chromatography (hexane/ethyl acetate/methanol) to give the title compound (6.3 mg).

Example 16

1-[(1S)-2-({6-[6-(cyclopropylmethoxy)-1,3-benzoxazol-2-yl]pyridin-3-yl}oxy)-1-methylethyl]-3-methylurea A mixture of tert-butyl [(1S)-2-({6-[6-(cyclopropylmethoxy)-1,3-benzoxazol-2-yl]pyridin-3-yl}oxy)-1-methylethyl]carbamate (86.8 mg), ethyl acetate (2 mL) and 4M hydrogen chloride/ethyl acetate (2 mL) was stirred at room temperature for 3 hr. The solvent was evaporated under reduced pressure, and the residue was mixed with triethylamine (0.5 mL), THF (2 mL) and methyl isocyanate (0.014 mL) at 0° C., and the obtained mixture was stirred at room temperature for 2 hr. Water was added to the reaction mixture, and the mixture was extracted with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate/methanol) to give the title compound (20 mg).

Example 17 methyl [(1S)-2-({6-[6-(cyclopropylmethoxy)-1,3-benzoxazol-2-yl]pyridin-3-yl}oxy)-1-methylethyl]carbamate A mixture of tert-butyl [(1S)-2-({6-[6-(cyclopropylmethoxy)-1,3-benzoxazol-2-yl]pyridin-3-yl}oxy)-1-methylethyl]carbamate (84.6 mg), ethyl acetate (2 mL) and 4M hydrogen chloride/ethyl acetate (2 mL) was stirred at room temperature for 3 hr. The solvent was evaporated under reduced pressure, and the residue was mixed with triethylamine (0.5 mL), THF (2 mL) and methyl chloroformate (0.044 ml) at 0° C., and the obtained mixture was stirred at room temperature for 2 hr. Water was added to the reaction mixture, and the mixture was extracted with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound (17.5 mg).

Example 18

1-[(1S)-2-({6-[6-(cyclopropylmethoxy)-1,3-benzoxazol-2-yl]-5-fluoropyridin-3-yl}oxy)-1-methylethyl]urea Using tert-butyl [(1S)-2-({6-[6-(cyclopropylmethoxy)-1,3-benzoxazol-2-yl]-5-fluoropyridin-3-yl}oxy)-1-methylethyl]carbamate, and in the same manner as in Example 15, step A (using pyridine instead of triethylamine), the title compound was obtained.

Example 19

1-[(1S)-2-({6-[6-(cyclopropylmethoxy)-1,3-benzoxazol-2-yl]-5-fluoropyridin-3-yl}oxy)-1-methylethyl]-3-methylurea Using tert-butyl [(1S)-2-({6-[6-(cyclopropylmethoxy)-1,3-benzoxazol-2-yl]-5-fluoropyridin-3-yl}oxy)-1-methylethyl]carbamate, and in the same manner as in Example 16, step A (using pyridine instead of triethylamine), the title compound was obtained.

Example 20

1-[(1S)-2-({5-[5-(cyclopropylmethoxy)-1,3-benzoxazol-2-yl]isoxazol-3-yl}oxy)-1-methylethyl]-3-methylurea Using tert-butyl [(1S)-2-({5-[5-(cyclopropylmethoxy)-1,3-benzoxazol-2-yl]isoxazol-3-yl}oxy)-1-methylethyl]carbamate, and in the same manner as in Example 16, step A, the title compound was obtained.

Example 21 methyl [(1S)-2-({5-[5-(cyclopropylmethoxy)-1,3-benzoxazol-2-yl]isoxazol-3-yl}oxy)-1-methylethyl]carbamate Using tert-butyl [(1S)-2-({5-[5-(cyclopropylmethoxy)-1,3-benzoxazol-2-yl]isoxazol-3-yl}oxy)-1-methylethyl]carbamate, and in the same manner as in Example 17, step A, the title compound was obtained.

Example 22

1-[(1S)-2-({5-[5-(cyclopropylmethoxy)-1,3-benzoxazol-2-yl]isoxazol-3-yl}oxy)-1-methylethyl]urea A mixture of tert-butyl [(1S)-2-({5-[5-(cyclopropylmethoxy)-1,3-benzoxazol-2-yl]isoxazol-3-yl}oxy)-1-methylethyl]carbamate (430 mg), ethyl acetate (8 mL), methanol (1 mL) and 4M hydrogen chloride/ethyl acetate (5 mL) was stirred at room temperature overnight. The precipitated solid was collected by filtration, and washed with hexane. The obtained solid was suspended in THF (10 mL), triethylamine (4 mL) and (trimethyl)silyl isocyanate (0.271 mL) were added thereto at room temperature, and the mixture was stirred at room temperature for 4 hr. The precipitated solid was collected by filtration, and washed with diethyl ether to give the title compound (43.9 mg).

Example 23

N-[(1S)-2-({5-[5-(cyclopropylmethoxy)-1,3-benzoxazol-2-yl]-4-methylisoxazol-3-yl}oxy)-1-methylethyl]acetamide A) tert-butyl [(1S)-2-({5-[5-(cyclopropylmethoxy)-1,3-benzoxazol-2-yl]-4-methylisoxazol-3-yl}oxy)-1-methylethyl]carbamate Under an argon atmosphere, to a solution of tert-butyl [(1S)-2-({5-[5-(cyclopropylmethoxy)-1,3-benzoxazol-2-yl]isoxazol-3-yl}oxy)-1-methylethyl]carbamate (644 mg) in THF (15 mL) was added dropwise a hexane solution (1.6 M, 2.156 mL) of n-butyllithium at −78° C., and the mixture was stirred at −78° C. for 20 min. To the reaction mixture was added iodomethane (0.140 mL), and the mixture was stirred at −78° C. for 15 min, and then at 0° C. for 1 hr. The reaction mixture was neutralized with 1M hydrochloric acid, and extracted with ethyl acetate. The combined organic layer was washed with water and saturated brine, and dried over anhydrous magnesium sulfate, and the solvent was evaporated under reduced pressure. The residue was purified by silica gel column chromatography (hexane/ethyl acetate) to give the title compound (46.0 mg).

$^1$H NMR (300 MHz, DMSO-$d_6$) δ 0.30-0.39 (2H, m), 0.54-0.63 (2H, m), 1.12 (3H, d, J=6.4 Hz), 1.22-1.29 (1H, m), 1.38 (9H, s), 2.26 (3H, s), 3.86-4.02 (3H, m), 4.09-4.26 (2H, m), 6.90-7.00 (1H, m), 7.12 (1H, dd, J=9.1, 2.3 Hz), 7.41 (1H, d, J=2.3 Hz), 7.76 (1H, d, J=9.1 Hz).

B) N-[(1S)-2-({5-[5-(cyclopropylmethoxy)-1,3-benzoxazol-2-yl]-4-methylisoxazol-3-yl}oxy)-1-methylethyl]acetamide Using tert-butyl [(1S)-2-({5-[5-(cyclopropylmethoxy)-1,3-benzoxazol-2-yl]-4-methylisoxazol-3-yl}oxy)-1-methylethyl]carbamate, and in the same manner as in Example 1, step D, the title compound was obtained.

Example 24

N-[(1S)-2-({6-[6-(cyclopropylmethoxy)-2,3-dihydro-1-benzofuran-2-yl]pyridin-3-yl}oxy)-1-methylethyl]acetamide A) (2-bromo-4-hydroxyphenyl)acetic acid A dichloromethane solution (1.0 M, 150 mL) of tribromoborane was added dropwise to a solution of (2-bromo-4-methoxyphenyl)acetic acid (15.0 g) in dichloromethane (160 mL) at room temperature, and the reaction mixture was refluxed for 3 hr, allowed to cool to room temperature, and poured into ice water. The mixture was extracted with ethyl acetate, and the organic layer was separated. The organic layer was dried over anhydrous magnesium sulfate, and the solvent was evaporated under reduced pressure. The obtained yellow solid was collected by filtration and washed with hexane-diethyl ether to give the title compound (10.3 g).

$^1$H NMR (300 MHz, DMSO-$d_6$) δ 3.58 (2H, s), 6.73 (1H, dd, J=8.3, 2.3 Hz), 6.98 (1H, d, J=2.3 Hz), 7.17 (1H, d, J=8.3 Hz), 9.76 (1H, s), 12.31 (1H, brs).

B) cyclopropylmethyl [2-bromo-4-(cyclopropylmethoxy)phenyl]acetate

A solution of (bromomethyl)cyclopropane (10.52 g), (2-bromo-4-hydroxyphenyl)acetic acid (6.0 g) and potassium carbonate (7.18 g) in DMF (200 mL) was stirred at 80° C. for 8 hr. The reaction mixture was allowed to cool to room temperature, and the solvent was evaporated under reduced pressure. The residue was diluted with diethyl ether and water, and the organic layer was separated. The organic layer was washed with saturated brine, and dried over anhydrous magnesium sulfate, and the solvent was evaporated under reduced pressure. The residue was purified by silica gel column chromatography (hexane/ethyl acetate) to give the title compound (7.89 g).

$^1$H NMR (300 MHz, DMSO-$d_5$) δ 0.20-0.28 (2H, m), 0.28-0.35 (2H, m), 0.43-0.52 (2H, m), 0.52-0.63 (2H, m), 0.97-1.14 (1H, m), 1.14-1.29 (1H, m), 3.73 (2H, s), 3.82 (2H, d, J=6.8 Hz), 3.89 (2H, d, J=7.2 Hz), 6.92 (1H, dd, J=8.5, 2.7 Hz), 7.16 (1H, d, J=2.7 Hz), 7.29 (1H, d, J=8.5 Hz).

C) [2-bromo-4-(cyclopropylmethoxy)phenyl]acetic acid

1M Aqueous sodium hydroxide solution (30 mL) was added to a solution of cyclopropylmethyl [2-bromo-4-(cyclopropylmethoxy)phenyl]acetate (6 g) in methanol (50 mL) at room temperature, and the mixture was stirred at 50° C. for 2 hr. The reaction mixture was allowed to cool to room temperature, water was added thereto, and the mixture was washed with diisopropyl ether. The aqueous layer was acidified with 1M hydrochloric acid, and extracted with ethyl acetate. The combined organic layer was washed with saturated brine, and dried over anhydrous magnesium sulfate, and the solvent was evaporated under reduced pressure to give the title compound (4.48 g).

$^1$H NMR (300 MHz, DMSO-$d_6$) δ 0.16-0.44 (2H, m), 0.44-0.69 (2H, m), 0.99-1.33 (1H, m), 3.62 (2H, s), 3.82 (2H, d, J=7.2 Hz), 6.91 (1H, dd, J=8.3, 2.4 Hz), 7.14 (1H, d, J=2.4 Hz), 7.27 (1H, d, J=8.3 Hz), 12.37 (1H, brs).

D) 2-[2-bromo-4-(cyclopropylmethoxy)phenyl]-N-methoxy-N-methylacetamide

WSC (4.89 g) was added to a solution of N,O-dimethylhydroxyamine hydrochloride (2.49 g), [2-bromo-4-(cyclopropylmethoxy)phenyl]acetic acid (4.85 g), HOBt (3.91 g) and triethylamine (3.56 mL) in acetonitrile (100 mL), and the mixture was stirred at room temperature for 15 hr. The reaction mixture was concentrated under reduced pressure, and the residue was diluted with ethyl acetate. The mixture was washed with 1M hydrochloric acid, water, saturated sodium hydrogen carbonate and saturated brine. The organic layer was dried over anhydrous magnesium sulfate, passed through an NH silica gel pad, and the solvent was evaporated under reduced pressure to give the title compound (4.78 g). MS (ESI+): [M+H]$^+$ 328.0.

E) 2-[2-bromo-4-(cyclopropylmethoxy)phenyl]-1-(5-{[tris(1-methylethyl)silyl]oxy}pyridin-2-yl)ethanone A hexane solution (1.6 M, 11.43 mL) of n-butyllithium was added dropwise to a solution of 2-bromo-5-{([tris(1-methylethyl)silyl]oxy}pyridine (4.03 g) in diethyl ether (60 mL) at −78° C. The reaction mixture was stirred at −78° C. for 15 min and allowed to warm to 0° C. over 1 hr. The reaction mixture was cooled to −78° C., and a solution of 2-[2-bromo-4-(cyclopropylmethoxy)phenyl]-N-methoxy-N-methylacetamide (4.0 g) in diethyl ether (30 mL) was added dropwise thereto. The reaction mixture was allowed to warm to room temperature, and stirred at room temperature for 15 hr. The reaction mixture was poured into an ice-cooled saturated aqueous ammonium chloride solution, and the mixture was extracted with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound (1.50 g).

$^1$H NMR (300 MHz, DMSO-$d_6$) δ 0.26-0.37 (2H, m), 0.49-0.64 (2H, m), 1.09 (18H, d, J=7.2 Hz), 1.14-1.28 (4H, m), 3.81 (2H, dd, J=4.7, 2.1 Hz), 4.58 (2H, s), 6.86-6.96 (1H, m), 7.11-7.33 (2H, m), 7.48 (1H, dd, J=8.7, 2.6 Hz), 7.95 (1H, d, J=8.7 Hz), 8.37 (1H, d, J=2.6 Hz).

F) 2-[2-bromo-4-(cyclopropylmethoxy)phenyl]-1-(5-{[tris(1-methylethyl)silyl]oxy}pyridin-2-yl)ethanol Sodium borohydride (0.109 g) was added to a solution of 2-[2-bromo-4-(cyclopropylmethoxy)phenyl]-1-(5-{[tris(1-methylethyl)silyl]oxy}pyridin-2-yl)ethanone (1.50 g) in ethanol (10 mL) at room temperature. The reaction mixture was stirred at room temperature for 1 hr, and the solvent was evaporated under reduced pressure. The residue was diluted with ethyl acetate and water, and the organic layer was separated. The organic layer was washed with saturated brine, and dried over anhydrous magnesium sulfate, and the solvent was evaporated under reduced pressure. The residue was purified by silica gel column chromatography (hexane/ethyl acetate) to give the title compound (1.210 g).

$^1$H NMR (300 MHz, DMSO-$d_6$) δ 0.25-0.35 (2H, m), 0.49-0.61 (2H, m), 1.06 (18H, d, J=7.2 Hz), 1.13-1.22 (4H, m), 2.89 (1H, dd, J=13.6, 7.9 Hz), 3.11 (1H, dd, J=13.6, 5.7 Hz), 3.75-3.81 (2H, m), 4.65-4.85 (1H, m), 5.38 (1H, d, J=5.3 Hz), 6.87 (1H, dd, J=8.3, 2.6 Hz), 6.98-7.14 (2H, m), 7.15-7.39 (1H, m), 8.09 (2H, d, J=2.3 Hz).

G) 6-[6-(cyclopropylmethoxy)-2,3-dihydro-1-benzofuran-2-yl]pyridin-3-ol

Sodium hydride (27.7 mg) was added to a suspension of 2-[2-bromo-4-(cyclopropylmethoxy)phenyl]-1-(5-{[tris(1-methylethyl)silyl]oxy}pyridin-2-yl)ethanol (600 mg) and copper(I) chloride (5.71 mg) in toluene (10 mL) at room temperature. The reaction mixture was stirred at 120° C. for 3 hr, and allowed to cool to room temperature. Water was added to the mixture, and the mixture was extracted with ethyl acetate. The combined organic layer was washed with saturated brine, and dried over anhydrous magnesium sulfate, and the solvent was evaporated under reduced pressure. The residue was dissolved in THF (10 mL), and a THF solution (1.0 M, 5.76 mL) of tetrabutylammonium fluoride was added thereto. The reaction mixture was stirred at room temperature for 30 min, and the solvent was evaporated under reduced pressure. The residue was purified by silica gel column chromatography (hexane/ethyl acetate) to give the title compound (180 mg).

MS (ESI+): [M+H]$^+$ 284.1.

H) tert-butyl [(1S)-2-({6-[6-(cyclopropylmethoxy)-2,3-dihydro-1-benzofuran-2-yl]pyridin-3-yl}oxy)-1-methylethyl]carbamate A toluene solution (1.9 M, 0.474 mL) of diisopropyl azodicarboxylate was added dropwise to a solution of tert-butyl [(1S)-2-hydroxy-1-methylethyl]carbamate (158 mg), triphenylphosphine (236 mg) and 6-[6-(cyclopropylmethoxy)-2,3-dihydro-1-benzofuran-2-yl]pyridin-3-ol (170 mg) in THF (30 mL) at room temperature. The reaction mixture was stirred at room temperature for 16 hr, and the solvent was evaporated under reduced pressure. The residue was purified by silica gel column chromatography (hexane/ethyl acetate) to give the title compound (80 mg).

MS (ESI+): [M+H]$^+$ 441.2.

I) N-[(1S)-2-({6-[6-(cyclopropylmethoxy)-2,3-dihydro-1-benzofuran-2-yl]pyridin-3-yl}oxy)-1-methylethyl]acetamide 4M Hydrogen chloride/ethyl acetate (10 mL) was added dropwise to a solution of tert-butyl [(1S)-2-({6-[6-(cyclopropylmethoxy)-2,3-dihydro-1-benzofuran-2-yl]pyridin-3-yl}oxy)-1-methylethyl]carbamate (80 mg) in ethyl acetate (5 mL) at room temperature, and the reaction mixture was stirred at room temperature for 6 hr. The solvent was evaporated under reduced pressure, and the residue was dissolved in pyridine (10 mL), and acetic anhydride (0.026 mL) was added thereto at room temperature. The reaction mixture was stirred at room temperature for 2 hr, and the solvent was evaporated under reduced pressure. The residue was diluted with water, and the mixture was extracted with ethyl acetate. The combined organic layer was washed with saturated sodium hydrogen carbonate and saturated brine, and dried over anhydrous magnesium sulfate, and the solvent was evaporated under reduced pressure. The residue was purified by silica gel column chromatography (ethyl acetate/methanol) to give the title compound (49.3 mg).

Example 25

N-{(1S)-2-[4-(6-ethoxy-2H-indazol-2-yl)-3-fluorophenoxy]-1-methylethyl}acetamide monohydrate A) 4-ethoxy-1-methyl-2-nitrobenzene 4-Methyl-3-nitrophenol (10.0 g) was mixed with iodoethane (10.5 mL), potassium carbonate (13.5 g) and DMF (130 mL), and the obtained mixture was stirred at 60° C. overnight. Water was added to the reaction mixture, and the mixture was extracted twice with diethyl ether. The combined organic layer was washed with saturated brine, and dried over anhydrous magnesium sulfate, and the solvent was evaporated under reduced pressure to give the title compound as a yellow oil (11.8 g).

$^1$H NMR (300 MHz, CDCl$_3$) δ 1.43 (3H, t, J=7.0 Hz), 2.52 (3H, s), 4.06 (2H, q, J=6.8 Hz), 7.04 (1H, dd, J=8.5, 2.8 Hz), 7.21 (1H, d, J=8.7 Hz), 7.49 (1H, d, J=3.0 Hz).

B) 1-(bromomethyl)-4-ethoxy-2-nitrobenzene

A mixture of 4-ethoxy-1-methyl-2-nitrobenzene (11.8 g), N-bromosuccinimide (17.4 g), 2,2'-azobisisobutyronitrile (1.07 g) and ethyl acetate (300 mL) was stirred under an argon atmosphere at 90° C. overnight. The solvent was evaporated under reduced pressure, and the residue was diluted with diethyl ether, and the mixture was washed three times with water. The separated organic layer was washed with saturated brine, and dried over anhydrous magnesium sulfate, and the solvent was evaporated under reduced pressure. The residue was purified by silica gel column chromatography (hexane/ethyl acetate) to give the title compound as a yellow oil (11.3 g).

¹H NMR (300 MHz, CDCl₃) δ 1.45 (3H, t, J=7.2 Hz), 4.10 (2H, q, J=6.8 Hz), 4.80 (2H, s), 7.11 (1H, dd, J=8.5, 2.8 Hz), 7.44 (1H, d, J=8.3 Hz), 7.54 (1H, d, J=2.6 Hz).

C) 4-ethoxy-2-nitrobenzaldehyde

A mixture of 1-(bromomethyl)-4-ethoxy-2-nitrobenzene (11.3 g), 4-methylmorpholine N-oxide (10.1 g), molecular sieves 4A (11 g) and acetonitrile (220 ml) was stirred under an argon atmosphere at room temperature for 1 hr. The reaction mixture was filtered through celite, and the solvent of the filtrate was evaporated under reduced pressure. The residue was diluted with ethyl acetate, and the mixture was washed twice with water. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as a yellow solid (5.65 g).

¹H NMR (300 MHz, CDCl₃) δ 1.49 (3H, t, J=7.0 Hz), 4.19 (2H, q, J=6.8 Hz), 7.21 (1H, dd, J=8.5, 2.1 Hz), 7.50 (1H, d, J=2.3 Hz), 7.97 (1H, d, J=8.7 Hz), 10.29 (1H, s).

D) tert-butyl [(1S)-2-(3-fluoro-4-nitrophenoxy)-1-methylethyl]carbamate

To a mixture of 3-fluoro-4-nitrophenol (2.02 g), tert-butyl [(1S)-2-hydroxy-1-methylethyl]carbamate (5.62 g), triphenylphosphine (8.41 g) and THF (60 mL) was added dropwise a toluene solution (1.9 M, 16.9 mL) of diisopropyl azodicarboxylate at room temperature, and the mixture was stirred at room temperature overnight. The reaction mixture was concentrated under reduced pressure, and the residue was purified by silica gel column chromatography (hexane/ethyl acetate) to give the title compound as a pale-yellow solid (4.03 g).

¹H NMR (300 MHz, CDCl₃) δ 1.30 (3H, d, J=6.8 Hz), 1.45 (9H, s), 3.94-4.14 (3H, m), 4.62 (1H, brs), 6.68-6.87 (2H, m), 8.02-8.17 (1H, m).

E) tert-butyl [(1S)-2-(4-amino-3-fluorophenoxy)-1-methylethyl]carbamate

Under a hydrogen atmosphere, a mixture of tert-butyl [(1S)-2-(3-fluoro-4-nitrophenoxy)-1-methylethyl]carbamate (10.2 g), 10% palladium/carbon (containing water (50%), 500 mg) and ethanol (150 mL) was stirred at room temperature for 1 hr. The catalyst was removed by filtration, and the obtained filtrate was concentrated under reduced pressure to give the title compound as a brown solid (8.64 g).

¹H NMR (300 MHz, CDCl₃) δ 1.26 (3H, d, J=6.8 Hz), 1.45 (9H, s), 3.44 (2H, brs), 3.79-3.89 (2H, m), 4.00 (1H, brs), 4.74 (1H, brs), 6.50-6.58 (1H, m), 6.62 (1H, dd, J=12.5, 2.7 Hz), 6.71 (1H, dd, J=9.8, 8.7 Hz).

MS (ESI+): [M+H]⁺ 185.2.

F) tert-butyl {(1S)-2-[4-(6-ethoxy-2H-indazol-2-yl)-3-fluorophenoxy]-1-methylethyl}carbamate A mixture of 4-ethoxy-2-nitrobenzaldehyde (5.20 g), tert-butyl [(1S)-2-(4-amino-3-fluorophenoxy)-1-methylethyl]carbamate (7.58 g), magnesium sulfate (3.21 g) and ethanol (60 mL) was stirred under reflux overnight. The reaction mixture was concentrated under reduced pressure, triethyl phosphite (13.7 ml) was added to the residue, and the mixture was stirred at 130° C. for 3 hr. The reaction mixture was purified by silica gel column chromatography (hexane/ethyl acetate) to give the title compound as a yellow solid (6.53 g).

¹H NMR (300 MHz, CDCl₃) δ 1.31 (3H, d, J=6.8 Hz), 1.44-1.51 (12H, m), 3.98 (2H, d, J=3.8 Hz), 4.03-4.17 (3H, m), 4.71 (1H, brs), 6.76-6.88 (3H, m), 6.98 (1H, s), 7.56 (1H, d, J=9.1 Hz), 7.86-7.95 (1H, m), 8.28 (1H, d, J=2.3 Hz).

MS (ESI+): [M+H]⁺ 430.3.

G) N-{(1S)-2-[4-(6-ethoxy-2H-indazol-2-yl)-3-fluorophenoxy]-1-methylethyl}acetamide monohydrate A mixture of tert-butyl {(1S)-2-[4-(6-ethoxy-2H-indazol-2-yl)-3-fluorophenoxy]-1-methylethyl}carbamate (6.53 g), 4M hydrogen chloride/ethyl acetate (20 mL) and ethyl acetate (40 mL) was stirred at room temperature for 1 hr. The reaction mixture was concentrated under reduced pressure, and the obtained residue was mixed with acetic anhydride (20 mL) and pyridine (50 mL). The obtained mixture was stirred at room temperature for 1 hr. The reaction mixture was concentrated under reduced pressure, and the residue was diluted with THF and ethyl acetate, and the mixture was washed three times with 1M hydrochloric acid. The separated aqueous layer was extracted again with ethyl acetate. The combined organic layer was washed with saturated aqueous sodium hydrogen carbonate and saturated brine, and dried over anhydrous magnesium sulfate, and the solvent was evaporated under reduced pressure. The residue was dissolved in ethanol, and the solution was filtered through silica gel. The filtrate was concentrated, and the residue was recrystallized (ethanol/ethyl acetate) to give the title compound as colorless crystals (2.36 g).

¹H NMR (300 MHz, DMSO-d₆) δ 1.17 (3H, d, J=6.8 Hz), 1.38 (3H, t, J=7.0 Hz), 1.83 (3H, s), 3.87-3.95 (1H, m), 3.99-4.20 (4H, m), 6.76 (1H, dd, J=9.0, 2.3 Hz), 6.93-7.05 (2H, m), 7.19 (1H, dd, J=13.6, 2.6 Hz), 7.64 (1H, d, J=9.0 Hz), 7.81 (1H, t, J=9.0 Hz), 7.96 (1H, d, J=7.5 Hz), 8.59 (1H, d, J=1.9 Hz).

Anal. Calcd for $C_{20}H_{22}N_3O_3F \cdot H_2O$: C, 61.69; H, 6.21; N, 10.79

Found: C, 61.45; H, 6.31; N, 10.65.

Example 26

N-{(1S)-2-[4-(6-ethoxy-2H-indazol-2-yl)phenoxy]-1-methylethyl}acetamide

A) tert-butyl [(1S)-1-methyl-2-(4-nitrophenoxy)ethyl]carbamate

Using 4-nitrophenol (5.29 g), and in the same manner as in Example 25, step D, the title compound was obtained as a pale-yellow solid (11.23 g).

¹H NMR (300 MHz, CDCl₃) δ 1.31 (3H, d, J=6.8 Hz), 1.45 (9H, s), 3.95-4.16 (3H, m), 4.67 (1H, brs), 6.93-7.03 (2H, m), 8.12-8.29 (2H, m).

B) tert-butyl [(1S)-2-(4-aminophenoxy)-1-methylethyl]carbamate

Using tert-butyl [(1S)-1-methyl-2-(4-nitrophenoxy)ethyl]carbamate (444 mg), and in the same manner as in Example 25, step E, the title compound was obtained as a pale-yellow solid (399 mg).

¹H NMR (300 MHz, CDCl₃) δ 1.27 (3H, d, J=6.8 Hz), 1.45 (9H, s), 3.42 (2H, brs), 3.78-3.90 (2H, m), 4.00 (1H, brs), 4.79 (1H, brs), 6.59-6.67 (2H, m), 6.70-6.79 (2H, m).

MS (ESI+): [M+H-Boc]⁺ 167.3.

C) tert-butyl {(1S)-2-[4-(6-ethoxy-2H-indazol-2-yl)phenoxy]-1-methylethyl}carbamate Using 4-ethoxy-2-nitrobenzaldehyde (293 mg) and tert-butyl [(1S)-2-(4-aminophenoxy)-1-methylethyl]carbamate (399 mg), and in the same manner as in Example 25, step F, the title compound was obtained as a pale-brown solid (459 mg).

$^1$H NMR (300 MHz, CDCl$_3$) δ 1.32 (3H, d, J=6.8 Hz), 1.44-1.51 (12H, m), 3.98 (2H, d, J=4.1 Hz), 4.03-4.18 (3H, m), 4.76 (1H, brs), 6.80 (1H, dd, J=9.0, 2.3 Hz), 6.99-7.06 (3H, m), 7.55 (1H, d, J=9.0 Hz), 7.69-7.81 (2H, m), 8.21 (1H, s).
MS (ESI+): [M+H]$^+$ 412.3.

D) N-{(1S)-2-[4-(6-ethoxy-2H-indazol-2-yl)phenoxy]-1-methylethyl}acetamide

Using tert-butyl {(1S)-2-[4-(6-ethoxy-2H-indazol-2-yl)phenoxy]-1-methylethyl}carbamate (459 mg), and in the same manner as in Example 25, step G, the title compound was obtained as colorless crystals (139 mg).

$^1$H NMR (300 MHz, DMSO-d$_6$) δ 1.17 (3H, d, J=6.8 Hz), 1.38 (3H, t, J=6.8 Hz), 1.83 (3H, s), 3.82-3.92 (1H, m), 3.96-4.18 (4H, m), 6.74 (1H, dd, J=9.1, 2.3 Hz), 6.98 (1H, d, J=1.5 Hz), 7.07-7.17 (2H, m), 7.61 (1H, d, J=9.1 Hz), 7.86-8.01 (3H, m), 8.86 (1H, d, J=0.8 Hz).
Anal. Calcd for C$_{20}$H$_{23}$N$_3$O$_3$: C, 67.97; H, 6.56; N, 11.89. Found: C, 67.96; H, 6.57; N, 12.17.

Example 27

N-[1S)-2-{4-[5-(cyclopropylmethoxy)-2H-benzotriazol-2-yl]phenoxy}-1-methylethyl]acetamide

A) 4-(cyclopropylmethoxy)-2-nitroaniline

Using 4-amino-3-nitrophenol (1.54 g), and in the same manner as in Example 2, step E, the title compound was obtained as a pale-orange solid (1.15 g).

$^1$H NMR (300 MHz, DMSO-d$_6$) δ 0.25-0.39 (2H, m), 0.48-0.64 (2H, m), 1.07-1.28 (1H, m), 3.76 (2H, d, J=7.2 Hz), 6.99 (1H, d, J=9.4 Hz), 7.17 (1H, dd, J=9.1, 3.0 Hz), 7.25 (2H, s), 7.33 (1H, d, J=3.0 Hz).

B) 4-{[4-(cyclopropylmethoxy)-2-nitrophenyl]diazenyl}phenol

To a mixture of 4-(cyclopropylmethoxy)-2-nitroaniline (416 mg) and ethanol (2 mL) was added 6M hydrochloric acid (1.5 mL), and ethanol was evaporated under reduced pressure. To the obtained suspension was added a mixture of sodium nitrite (145 mg) and water (1 mL) under ice-cooling, and the mixture was stirred for 30 min. A mixture of phenol (245 mg) and 8M aqueous sodium hydroxide solution (1.2 mL) was added thereto, and the mixture was stirred for 1 hr. To the reaction mixture was added 1M hydrochloric acid, and the mixture was extracted twice with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as a dark red solid (187 mg).

$^1$H NMR (300 MHz, CDCl$_3$) δ 0.34-0.44 (2H, m), 0.64-0.76 (2H, m), 1.24-1.39 (1H, m), 3.92 (2H, d, J=6.8 Hz), 5.25 (1H, s), 6.87-6.98 (2H, m), 7.15 (1H, dd, J=9.1, 2.7 Hz), 7.30 (1H, d, J=2.7 Hz), 7.76 (1H, d, J=9.1 Hz), 7.80-7.89 (2H, m).
MS (ESI+): [M+H]$^+$ 314.2.

C) 4-[5-(cyclopropylmethoxy)-2H-benzotriazol-2-yl]phenol

A mixture of 4-{[4-(cyclopropylmethoxy)-2-nitrophenyl]diazenyl}phenol and triethyl phosphite (4 mL) was stirred at 140° C. overnight. The reaction mixture was purified by silica gel column chromatography (hexane/ethyl acetate) to give the title compound as a yellow solid (103 mg).

$^1$H NMR (300 MHz, CDCl$_3$) δ 0.35-0.45 (2H, m), 0.62-0.75 (2H, m), 1.27-1.41 (1H, m), 3.89 (2H, d, J=6.8 Hz), 5.14 (1H, brs), 6.90-7.02 (2H, m), 7.07 (1H, d, J=2.3 Hz), 7.13 (1H, dd, J=9.4, 2.3 Hz), 7.77 (1H, d, J=9.1 Hz), 8.09-8.21 (2H, m).

D) tert-butyl [(1S)-2-{4-[5-(cyclopropylmethoxy)-2H-benzotriazol-2-yl]phenoxy}-1-methylethyl]carbamate Using 4-[5-(cyclopropylmethoxy)-2H-benzotriazol-2-yl]phenol (100 mg), and in the same manner as in Example 1, step B, the title compound was obtained as a yellow solid (121 mg).

$^1$H NMR (300 MHz, CDCl$_3$) δ 0.35-0.47 (2H, m), 0.64-0.76 (2H, m), 1.30-1.39 (4H, m), 1.46 (9H, s), 3.89 (2H, d, J=6.8 Hz), 4.00 (2H, d, J=4.2 Hz), 4.04-4.16 (1H, m), 4.76 (1H, brs), 7.00-7.09 (3H, m), 7.13 (1H, dd, J=9.1, 2.3 Hz), 7.78 (1H, J=9.1 Hz), 8.13-8.26 (2H, m).
MS (ESI+): [M+H-Boc]$^+$ 339.2.

E) N-[(1S)-2-{4-[5-(cyclopropylmethoxy)-2H-benzotriazol-2-yl]phenoxy}-1-methylethyl]acetamide Using tert-butyl [(1S)-2-{4-[5-(cyclopropylmethoxy)-2H-benzotriazol-2-yl]phenoxy}-1-methylethyl]carbamate (119 mg), and in the same manner as in Example 25, step G, the title compound was obtained as colorless crystals (60.3 mg).

$^1$H NMR (300 MHz, DMSO-d$_6$) δ 0.31-0.42 (2H, m), 0.56-0.67 (2H, m), 1.18 (3H, d, J=6.8 Hz), 1.22-1.37 (1H, m), 1.83 (3H, s), 3.86-3.97 (3H, m), 3.98-4.06 (1H, m), 4.06-4.20 (1H, m), 7.11-7.23 (3H, m), 7.25 (1H, d, J=1.9 Hz), 7.88 (1H, d, J=9.0 Hz), 7.96 (1H, d, J=7.5 Hz), 8.09-8.21 (2H, m).
Anal. Calcd for C$_{21}$H$_{24}$N$_4$O$_3$: C, 66.30; H, 6.36; N, 14.73. Found: C, 66.21; H, 6.36; N, 14.68.

Example 28

N-[(1S)-2-{[6-(6-ethoxy-1,3-benzoxazol-2-yl)pyridin-3-yl]oxy}-1-methylethyl]acetamide

A) tert-butyl [(1S)-2-{[6-(6-ethoxy-1,3-benzoxazol-2-yl)pyridin-3-yl]oxy}-1-methylethyl]carbamate To a mixture of methyl 5-hydroxypyridine-2-carboxylate (5.30 g), tert-butyl [(1S)-2-hydroxy-1-methylethyl]carbamate (6.67 g), triphenylphosphine (12.71 g) and THF (50 mL) was added dropwise a toluene solution (1.9 M, 25.5 mL) of diisopropyl azodicarboxylate at room temperature, and the mixture was stirred at room temperature overnight. The reaction mixture was concentrated under reduced pressure, and the residue was purified by silica gel column chromatography (hexane/ethyl acetate) to give a mixture (7.52 g) of methyl 5-({(2S)-2-[(tert-butoxycarbonyl)amino]propyl}oxy)pyridine-2-carboxylate and impurity. A mixture of the obtained methyl 5-({(2S)-2-[(tert-butoxycarbonyl)amino]propyl}oxy)pyridine-2-carboxylate (7.52 g, mixture with impurity), THF (70 mL), methanol (70 mL) and 1M sodium hydroxide (70 mL) was stirred at room temperature overnight. The reaction mixture was neutralized with 6M hydrochloric acid at 0° C., and concentrated under reduced pressure, and the residue was extracted with a mixed solvent of ethyl acetate/2-propanol (volume ratio 3/1). The obtained organic layer was dried over anhydrous sodium sulfate, and the solvent was evaporated under reduced pressure to give a mixture (7.17 g) of 5-({(2S)-2-[(tert-butoxycarbonyl)amino]propyl}oxy)pyridine-2-carboxylic acid and impurity. A mixture of the obtained 5-({(2S)-2-[(tert-butoxycarbonyl)amino]propyl}oxy)pyridine-2-carboxylic acid (7.17 g, mixture with impurity), 4-aminobenzene-1,3-diol hydrochloride (3.91 g), HATU (9.20 g), N,N-diisopropylethylamine (8.34 mL) and DMF (70 mL) was stirred at room temperature overnight. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give tert-butyl [(1S)-2-({6-[(2,4-dihydroxyphenyl)carbamoyl]pyridin-3-yl}oxy)-1-methylethyl]carbamate as a mixture with impurity (14.1 g). To a solution of hexachloroethane (13.2 g) and triphenylphosphine (18.3 g) in acetonitrile (100 mL) was added triethylamine (24.4 mL) at room temperature, and the obtained mixture was stirred at room temperature for 10 min. A mixture of tert-butyl [(1S)-2-({6-[(2,4-dihydroxyphenyl)carbamoyl]pyridin-3-yl}oxy)-1-methylethyl]carbamate (14.1 g, mixture with impurity) obtained by the aforementioned method and acetonitrile (100 mL) was added thereto. The obtained mixture was stirred at room temperature overnight. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give tert-butyl [(1S)-2-{([6-(6-hydroxy-1,3-benzoxazol-2-yl)pyridin-3-yl]oxy}-1-methylethyl]carbamate as a mixture with impurity (17.5 g). A mixture of the obtained tert-butyl [(1S)-2-{[6-(6-hydroxy-1,3-benzoxazol-2-yl)pyridin-3-yl]oxy}-1-methylethyl]carbamate (17.5 g, mixture with impurity), iodoethane (3.99 mL), potassium carbonate (6.90 g) and DMF (150 mL) was stirred at 60° C. for 5 hr. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound as a white powder (5.53 g).

$^1$H NMR (300 MHz, DMSO-$d_6$) δ 1.15 (3H, d, J=6.8 Hz), 1.28-1.43 (12H, m), 3.78-4.19 (5H, m), 6.89-7.05 (2H, m), 7.40 (1H, d, J=2.3 Hz), 7.61 (1H, dd, J=8.9, 2.8 Hz), 7.68 (1H, d, J=8.7 Hz), 8.20 (1H, d, J=8.7 Hz), 8.45 (1H, d, J=2.6 Hz).

MS (ESI+): [M+H]$^+$ 414.2.

B) N-[(1S)-2-{[6-(6-ethoxy-1,3-benzoxazol-2-yl)pyridin-3-yl]oxy}-1-methylethyl]acetamide A mixture of tert-butyl [(1S)-2-{[6-(6-ethoxy-1,3-benzoxazol-2-yl)pyridin-3-yl]oxy}-1-methylethyl]carbamate (5.53 g), 4M hydrogen chloride/ethyl acetate (100 mL) and ethyl acetate (100 mL) was stirred at room temperature for 2 hr. The reaction mixture was concentrated under reduced pressure, and the obtained residue was mixed with acetic anhydride (50 mL) and pyridine (50 mL). The obtained mixture was stirred at room temperature overnight. To the reaction mixture was added 1M hydrochloric acid, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate/methanol), and recrystallized (ethanol/hexane) to give the title compound as white crystals (3.48 g).

$^1$H NMR (300 MHz, DMSO-$d_6$) δ 1.18 (3H, d, J=6.4 Hz), 1.37 (3H, t, J=7.0 Hz), 1.82 (3H, s), 3.94-4.23 (5H, m), 7.00 (1H, dd, J=8.7, 2.3 Hz), 7.40 (1H, d, J=2.3 Hz), 7.63 (1H, dd, J=8.7, 3.0 Hz), 7.68 (1H, d, J=8.7 Hz), 7.98 (1H, d, J=7.5 Hz), 8.21 (1H, d, J=8.7 Hz), 8.47 (1H, d, J=2.6 Hz).

Anal. Calcd for $C_{19}H_{21}N_3O_4$: C, 64.21; H, 5.96; N, 11.82. Found: C, 64.04; H, 6.00; N, 11.72.

Example 29

N-{(1S)-2-[(6-{6-[(3,3-difluorocyclobutyl)methoxy]-1,3-benzoxazol-2-yl}pyridin-3-yl)oxy]-1-methylethyl}acetamide

A) tert-butyl {(1S)-2-[(6-{6-[(3,3-difluorocyclobutyl)methoxy]-1,3-benzoxazol-2-yl}pyridin-3-yl)oxy]-1-methylethyl}carbamate Using tert-butyl [(1S)-2-{[6-(6-hydroxy-1,3-benzoxazol-2-yl)pyridin-3-yl]oxy}-1-methylethyl]carbamate and (3,3-difluorocyclobutyl)methyl methanesulfonate, and in the same manner as in Example 2, step E, the title compound was obtained.

MS (ESI+): [M+H]$^+$ 490.1.

B) N-{(1S)-2-[(6-{6-[(3,3-difluorocyclobutyl)methoxy]-1,3-benzoxazol-2-yl}pyridin-3-yl)oxy]-1-methylethyl}acetamide Using tert-butyl {(1S)-2-[(6-{6-[(3,3-difluorocyclobutyl)methoxy]-1,3-benzoxazol-2-yl}pyridin-3-yl)oxy}-1-methylethyl]carbamate, and in the same manner as in Example 1, step D, the title compound was obtained.

Example 30

N-[1S)-2-({6-[6-(2,2-difluoropropoxy)-1,3-benzoxazol-2-yl]pyridin-3-yl}oxy)-1-methylethyl]acetamide

A) tert-butyl [(1S)-1-methyl-2-({6-[6-(2-oxopropoxy)-1,3-benzoxazol-2-yl]pyridin-3-yl}oxy)ethyl]carbamate Using tert-butyl [(1S)-2-{[6-(6-hydroxy-1,3-benzoxazol-2-yl)pyridin-3-yl]oxy}-1-methylethyl]carbamate and 1-bromopropan-2-one, and in the same manner as in Example 2, step E, the title compound was obtained.

MS (ESI+): [M+H]$^+$ 442.3.

B) tert-butyl [(1S)-2-({6-[6-(2,2-difluoropropoxy)-1,3-benzoxazol-2-yl]pyridin-3-yl}oxy)-1-methylethyl]carbamate A mixture of tert-butyl [(1S)-1-methyl-2-({6-[6-(2-oxopropoxy)-1,3-benzoxazol-2-yl]pyridin-3-yl}oxy)ethyl]carbamate (1.30 g), bis(2-methoxyethyl)aminosulfur trifluoride (1.63 mL) and toluene (20 mL) was stirred at room temperature for 1 hr, then at 80° C. for 3 hr. To the reaction mixture was added saturated aqueous sodium hydrogen carbonate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (180 mg).
MS (ESI+): [M+H]+ 464.2.

C) N-[(1S)-2-({6-[6-(2,2-difluoropropoxy)-1,3-benzoxazol-2-yl]pyridin-3-yl}oxy)-1-methylethyl]acetamide Using tert-butyl [(1S)-2-({6-[6-(2,2-difluoropropoxy)-1,3-benzoxazol-2-yl]pyridin-3-yl}oxy)-1-methylethyl]carbamate, and in the same manner as in Example 1, step D, the title compound was obtained.

Example 31

N-[(1S)-2-({6-[5-(cyclopropylmethoxy)-1,3-benzoxazol-2-yl]pyridin-3-yl}oxy)-1-methylethyl]acetamide A) tert-butyl [(1S)-2-({6-[5-(cyclopropylmethoxy)-1,3-benzoxazol-2-yl]pyridin-3-yl}oxy)-1-methylethyl]carbamate Using methyl 5-hydroxypyridine-2-carboxylate, and in the same manner as in Example 2, steps A-E, the title compound was obtained.
MS (ESI+): [M+H]+ 440.5.

B) N-[(1S)-2-({6-[5-(cyclopropylmethoxy)-1,3-benzoxazol-2-yl]pyridin-3-yl}oxy)-1-methylethyl]acetamide Using tert-butyl [(1S)-2-({6-[5-(cyclopropylmethoxy)-1,3-benzoxazol-2-yl]pyridin-3-yl}oxy)-1-methylethyl]carbamate, and in the same manner as in Example 1, step D, the title compound was obtained.

Example 32

N-[(1S)-2-({6-[5-(2-cyclopropylethoxy)-1,3-benzoxazol-2-yl]pyridin-3-yl}oxy)-1-methylethyl]acetamide A) tert-butyl [(1S)-2-({6-[5-(2-cyclopropylethoxy)-1,3-benzoxazol-2-yl]pyridin-3-yl}oxy)-1-methylethyl]carbamate Using tert-butyl [(1S)-2-{([6-(5-hydroxy-1,3-benzoxazol-2-yl)pyridin-3-yl]oxy}-1-methylethyl]carbamate and 2-cyclopropylethyl methanesulfonate, and in the same manner as in Example 2, step E, the title compound was obtained.
MS (ESI+): [M+H]+ 454.1.

B) N-[(1S)-2-({6-[5-(2-cyclopropylethoxy)-1,3-benzoxazol-2-yl]pyridin-3-yl}oxy)-1-methylethyl]acetamide Using tert-butyl [(1S)-2-({6-[5-(2-cyclopropylethoxy)-1,3-benzoxazol-2-yl]pyridin-3-yl}oxy)-1-methylethyl]carbamate, and in the same manner as in Example 1, step D, the title compound was obtained.

Example 33

N-[(1S)-1-methyl-2-({5-[5-(1-methylethoxy)-1,3-benzoxazol-2-yl]isoxazol-3-yl}oxy)ethyl]acetamide A) tert-butyl [(1S)-1-methyl-2-({5-[5-(1-methylethoxy)-1,3-benzoxazol-2-yl]isoxazol-3-yl}oxy)ethyl]carbamate Using tert-butyl [(1S)-2-{[5-(5-hydroxy-1,3-benzoxazol-2-yl)isoxazol-3-yl]oxy}-1-methylethyl]carbamate (200 mg) and 2-iodopropane (0.106 mL), and in the same manner as in Example 2, step E, the title compound was obtained (246 mg).
MS (ESI+): [M+H]+ 418.2.

B) N-[(1S)-1-methyl-2-({5-[5-(1-methylethoxy)-1,3-benzoxazol-2-yl]isoxazol-3-yl}oxy)ethyl]acetamide Using tert-butyl [(1S)-1-methyl-2-({5-[5-(1-methylethoxy)-1,3-benzoxazol-2-yl]isoxazol-3-yl}oxy)ethyl]carbamate (240 mg), and in the same manner as in Example 1, step 0, the title compound was obtained (111 mg).

Example 34

N-[(1S)-2-({5-[5-(cyclopropylmethoxy)-1,3-benzoxazol-2-yl]-4-fluoroisoxazol-3-yl}oxy)-1-methylethyl]acetamide A) 2-{(1S)-2-[(4-fluoro-5-methylisoxazol-3-yl)oxy]-1-methylethyl}-1H-isoindole-1,3(2H)-dione Using 4-fluoro-5-methylisoxazol-3-ol and 2-[(1S)-2-hydroxy-1-methylethyl]-1H-isoindole-1,3(2H)-dione, and in the same manner as in Example 1, step B, the title compound was obtained.
$^1$H NMR (300 MHz, DMSO-d$_6$) δ 1.45 (3H, d, J=6.8 Hz), 2.30 (3H, d, J=2.3 Hz), 4.31-4.84 (3H, m), 7.68-7.99 (4H, m).

B) 2-[(1S)-2-{[4-fluoro-5-(hydroxymethyl)isoxazol-3-yl]oxy}-1-methylethyl]-1H-isoindole-1,3(2H)-dione A mixture of 2-{(1S)-2-[(4-fluoro-5-methylisoxazol-3-yl)oxy]-1-methylethyl}-1H-isoindole-1,3(2H)-dione (383 mg), N-bromosuccinimide (269 mg), 2,2'-azobis(2-methylpropionitrile) (20.7 mg) and (trifluoromethyl)benzene (5 mL) was stirred at 100° C. overnight. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate). The obtained residue was mixed with 1-methylpyrrolidin-2-one (5 mL) and water (10 mL), and the mixture was stirred at 105° C. overnight. The reaction mixture was extracted with ethyl acetate, and the obtained organic layer was washed with saturated brine, and dried over anhydrous magnesium sulfate, and the solvent was evaporated under reduced pressure. The residue was purified by silica gel column chromatography (hexane/ethyl acetate) to give the title compound as a colorless oil (118 mg).
$^1$H NMR (300 MHz, DMSO-d$_6$) δ 1.46 (3H, d, J=6.4 Hz), 4.36-4.81 (5H, m), 5.66 (1H, t, J=6.0 Hz), 7.66-8.00 (4H, m).

C) tert-butyl [(1S)-2-{[4-fluoro-5-(hydroxymethyl)isoxazol-3-yl]oxy}-1-methylethyl]carbamate A mixture of 2-[(1S)-2-{[4-fluoro-5-(hydroxymethyl)isoxazol-3-yl]oxy}-1-methylethyl]-1H-isoindole-1,3(2H)- dione (118 mg), hydrazine monohydrate (92 mg) and THF (2 mL) was stirred at 60° C. for 2 hr. The reaction mixture was concentrated under reduced pressure, and the precipitate was filtered. The filtrate was concentrated under reduced pressure, and the obtained residue was mixed with di-tert-butyl dicarbonate (201 mg) and ethanol (2 ml). The obtained mixture was stirred at 50° C. overnight, and allowed to cool to room temperature, and 1M sodium hydroxide (2 mL) was added thereto. The obtained mixture was stirred at room temperature for 3 hr, neutralized with 1M hydrochloric acid at 0° C., and extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound as a colorless oil (60.8 mg).

$^1$H NMR (300 MHz, DMSO-$d_6$) δ 1.09 (3H, d, J=6.8 Hz), 1.37 (9H, s), 3.78-4.21 (3H, m), 4.49 (2H, dd, J=6.0, 1.7 Hz), 5.69 (1H, t, J=6.0 Hz), 6.93 (1H, d, J=7.9 Hz).

D) tert-butyl {(1S)-2-[(4-fluoro-5-formylisoxazol-3-yl)oxy]-1-methylethyl}carbamate A mixture of tert-butyl [(1S)-2-{[4-fluoro-5-(hydroxymethyl)isoxazol-3-yl]oxy}-1-methylethyl]carbamate (164 mg), Dess-Martin periodinane (288 mg) and acetonitrile (3 mL) was stirred at 0° C. for 1 hr, and then at room temperature for 30 min. To the reaction mixture was further added Dess-Martin periodinane (288 mg), and the mixture was stirred at room temperature for 30 min. To the reaction mixture were added saturated aqueous sodium hydrogen carbonate solution and saturated aqueous sodium thiosulfate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound as a colorless oil (155 mg).

$^1$H NMR (300 MHz, DMSO-$d_6$) δ 1.10 (3H, d, J=6.8 Hz), 1.37 (9H, s), 3.83-3.98 (1H, m), 4.12-4.39 (2H, m), 6.97 (1H, d, J=8.0 Hz), 9.83 (1H, s).

E) 3-({(2S)-2-[(tert-butoxycarbonyl)amino]propyl}oxy)-4-fluoroisoxazole-5-carboxylic acid To a mixture of tert-butyl {(1S)-2-[(4-fluoro-5-formylisoxazol-3-yl)oxy]-1-methylethyl}carbamate (244 mg), sodium dihydrogen phosphate (305 mg), 2-methylbut-2-ene (449 mL), 2-methylpropan-2-ol (5 mL) and water (1 mL) was added sodium chlorite (115 mg) at room temperature, and the obtained mixture was stirred at room temperature overnight. Water was added to the reaction mixture, and the mixture was extracted with a mixed solvent of ethyl acetate/2-propanol (volume ratio 3/1). The obtained organic layer was dried over anhydrous sodium sulfate, and the solvent was evaporated under reduced pressure to give the title compound as a white powder (256 mg).

$^1$H NMR (300 MHz, DMSO-$d_6$) δ 1.08 (3H, d, J=6.8 Hz), 1.37 (9H, s), 3.78-4.23 (3H, m), 6.94 (1H, d, J=7.9 Hz).

F) tert-butyl [(1S)-2-({5-[(2,5-dihydroxyphenyl)carbamoyl]-4-fluoroisoxazol-3-yl}oxy)-1-methylethyl]carbamate Using 3-({(2S)-2-[(tert-butoxycarbonyl)amino]propyl}oxy)-4-fluoroisoxazole-5-carboxylic acid, and in the same manner as in Example 2, step C, the title compound was obtained.

MS (ESI–): [M–H]$^-$ 410.3.

G) N-[(1S)-2-({5-[5-(cyclopropylmethoxy)-1,3-benzoxazol-2-yl]-4-fluoroisoxazol-3-yl}oxy)-1-methylethyl]acetamide Using tert-butyl [(1S)-2-({5-[(2,5-dihydroxyphenyl)carbamoyl]-4-fluoroisoxazol-3-yl}oxy)-1-methylethyl]carbamate, and in the same manner as in Example 2, steps D-E and Example 1, step D, the title compound was obtained.

Example 35

N-[(1S)-2-{4-[6-(cyclopropylmethoxy)-1,3-benzothiazol-2-yl]phenoxy}-1-methylethyl]acetamide A) 2-ethylhexyl 3-{[5-(benzyloxy)-2-nitrophenyl]sulfanyl}propanoate To a mixture of 4-(benzyloxy)-2-fluoro-1-nitrobenzene (2.00 g), potassium carbonate (1.23 g) and DMF (11 mL) was added dropwise 2-ethylhexyl 3-sulfanylpropanoate (2.02 mL), and the mixture was stirred at room temperature overnight. The reaction mixture was diluted with ethyl acetate, and washed with saturated brine. The obtained organic layer was dried over anhydrous magnesium sulfate, and the solvent was evaporated under reduced pressure. The residue was purified by silica gel column chromatography (hexane/ethyl acetate) to give the title compound as a yellow liquid (3.60 g).

$^1$H NMR (300 MHz, DMSO-$d_6$) δ 0.75-0.90 (6H, m), 1.15-1.35 (8H, m), 1.44-1.57 (1H, m), 2.68 (2H, t, J=6.8 Hz), 3.26 (2H, t, J=6.8 Hz), 3.96 (2H, d, J=5.7 Hz), 5.32 (2H, s), 6.93-7.12 (2H, m), 7.31-7.53 (5H, m), 8.18-8.28 (1H, m).

B) 2-ethylhexyl 3-{[2-amino-5-(benzyloxy)phenyl]sulfanyl}propanoate

To a solution of 2-ethylhexyl 3-{[5-(benzyloxy)-2-nitrophenyl]sulfanyl}propanoate (3.60 g) and 6M hydrochloric acid (2.69 mL) in ethanol (46 mL) was added reduced iron (4.51 g), and the mixture was heated under reflux for 3 hr. The insoluble material was removed by filtration, and the solvent of the filtrate was evaporated under reduced pressure. The residue was purified by silica gel column chromatography (hexane/ethyl acetate) to give the title compound as a dark red liquid (2.38 g).

$^1$H NMR (300 MHz, CDCl$_3$) δ 0.80-0.95 (6H, m), 1.18-1.42 (9H, m), 2.54 (2H, t, J=7.2 Hz), 2.99 (2H, t, J=7.2 Hz), 4.00 (2H, dd, J=5.8, 1.7 Hz), 4.04-4.13 (2H, m), 4.98 (2H, s), 6.68 (1H, d, J=8.7 Hz), 6.79-6.86 (1H, m), 7.04 (1H, d, J=3.0 Hz), 7.28-7.47 (5H, m).

C) 2-ethylhexyl 3-{[2-{[(4-{[(2S)-2-(acetylamino)propyl]oxy}phenyl)carbonyl]amino}-5-(benzyloxy)phenyl]sulfanyl}propanoate Using 2-ethylhexyl 3-{[2-amino-5-(benzyloxy)phenyl]sulfanyl}propanoate (1.00 g) and 4-{[(2S)-2-(acetylamino)propyl]oxy}benzoic acid (628 mg), and in the same manner as in Example 2, step C, the title compound (1.02 g) was obtained.

$^1$H NMR (300 MHz, CDCl$_3$) δ 0.80-0.95 (6H, m), 1.21-1.40 (11H, m), 1.48-1.60 (1H, m), 2.01 (3H, s), 2.52 (2H, t, J=7.1 Hz), 3.02 (2H, t, J=7.1 Hz), 3.91-4.13 (4H, m), 4.37-4.49 (1H, m), 5.06 (2H, s), 5.70 (1H, d, J=7.5 Hz), 6.93-7.06

(3H, m), 7.16 (1H, d, J=3.0 Hz), 7.23-7.44 (5H, m), 7.90 (2H, d, J=8.7 Hz), 8.44 (1H, d, J=9.0 Hz), 9.01 (1H, s).

D) N-[(1S)-2-{4-[6-(benzyloxy)-1,3-benzothiazol-2-yl]phenoxy}-1-methylethyl]acetamide To a solution of 2-ethylhexyl 3-{[2-{[(4-{([(2S)-2-(acetylamino)propyl]oxy}phenyl)carbonyl]amino}-5-(benzyloxy)phenyl]sulfanyl}propanoate (1.00 g) in THF (7.0 mL) was added sodium methoxide (28% methanol solution, 2.0 mL), and the mixture was stirred at room temperature for 1 hr under a nitrogen atmosphere. The reaction mixture was cooled to 0° C., trifluoroacetic acid (4.0 mL) was added thereto, and the mixture was stirred at 80° C. for 3 hr. The reaction mixture was diluted with ethyl acetate, and washed with aqueous potassium carbonate solution and saturated brine, and the solvent was evaporated under reduced pressure. The residue was purified by NH silica gel column chromatography (ethyl acetate), and washed with a 1:1 mixture of ethyl acetate/diisopropyl ether to give the title compound (504 mg).
$^1$H NMR (300 MHz, CDCl$_3$) δ 1.34 (3H, d, J=6.9 Hz), 2.01 (3H, s), 4.02 (2H, td, J=8.9, 3.9 Hz), 4.37-4.50 (1H, m), 5.14 (2H, s), 5.70 (1H, d, J=7.8 Hz), 6.99 (2H, d, J=8.7 Hz), 7.14 (1H, dd, J=9.3, 2.6 Hz), 7.29-7.51 (6H, m), 7.91 (1H, d, J=9.0 Hz), 7.97 (2H, d, J=8.7 Hz).

E) N-[(1S)-2-{4-[6-(cyclopropylmethoxy)-1,3-benzothiazol-2-yl]phenoxy}-1-methylethyl]acetamide A mixture of N-[(1S)-2-{4-[6-(benzyloxy)-1,3-benzothiazol-2-yl]phenoxy}-1-methylethyl]acetamide (46 mg), trifluoroacetic acid (1 mL) and thioanisole (0.1 mL) was stirred at 55° C. for 16 hr. The reaction mixture was concentrated under reduced pressure, and the residue was washed with diisopropyl ether to give N-{(1S)-2-[4-(6-hydroxy-1,3-benzothiazol-2-yl)phenoxy]-1-methylethyl}acetamide (38.6 mg) as a powder. Using the obtained powder, and in the same manner as in Example 1, step A, the title compound was obtained.
$^1$H NMR (300 MHz, CDCl$_3$) δ 0.35-0.41 (2H, m), 0.64-0.71 (2H, m), 1.30-1.36 (4H, m), 2.01 (3H, s), 3.87 (2H, d, J=6.9 Hz), 4.02 (2H, td, J=9.0, 3.6 Hz), 4.39-4.45 (1H, m), 5.65-5.75 (1H, m), 6.99 (2H, d, J=9.0 Hz), 7.08 (1H, dd, J=9.0, 2.7 Hz), 7.32 (1H, d, J=2.4 Hz), 7.89 (1H, d, J=9.0 Hz), 7.97 (2H, d, J=9.0 Hz).

Example 36

N-[(1S)-2-({5-[6-(cyclopropylmethoxy)-1,3-benzothiazol-2-yl]isoxazol-3-yl}oxy)-1-methylethyl]acetamide A) 4-(cyclopropylmethoxy)-2-fluoro-1-nitrobenzene Using 3-fluoro-4-nitrophenol, and in the same manner as in Example 1, step A, the title compound was obtained.
$^1$H NMR (300 MHz, DMSO-d$_6$) δ 0.28-0.43 (2H, m), 0.50-0.66 (2H, m), 1.19-1.35 (1H, m), 3.99 (2H, d, J=7.2 Hz), 6.97 (1H, d, J=9.4 Hz), 7.16 (1H, dd, J=13.6, 2.6 Hz), 8.13 (1H, t, J=9.1 Hz).

B) 2-ethylhexyl 3-{[5-(cyclopropylmethoxy)-2-nitrophenyl]sulfanyl}propanoate

Using 4-(cyclopropylmethoxy)-2-fluoro-1-nitrobenzene, and in the same manner as in Example 35, step A, the title compound was obtained.
$^1$H NMR (300 MHz, DMSO-d$_6$) δ 0.32-0.41 (2H, m), 0.55-0.66 (2H, m), 0.81-0.91 (6H, m), 1.20-1.37 (9H, m), 1.47-1.59 (1H, m), 2.73 (2H, t, J=6.8 Hz), 3.29 (2H, t, J=6.8 Hz), 3.97 (2H, d, J=5.7 Hz), 4.01 (2H, d, J=3.0 Hz), 6.89-6.98 (2H, m), 8.22 (1H, d, J=9.8 Hz).

C) 2-ethylhexyl 3-{[2-amino-5-(cyclopropylmethoxy)phenyl]sulfanyl}propanoate

Using 2-ethylhexyl 3-{[5-(cyclopropylmethoxy)-2-nitrophenyl]sulfanyl}propanoate, and in the same manner as in Example 35, step B, the title compound was obtained.
$^1$H NMR (300 MHz, DMSO-d$_6$) δ 0.22-0.32 (2H, m), 0.53 (2H, dd, J=8.3, 1.9 Hz), 0.80-0.91 (6H, m), 1.20-1.38 (9H, m), 1.46-1.60 (1H, m), 2.51-2.56 (2H, m), 2.92 (2H, t, J=7.0 Hz), 3.67 (2H, d, J=6.8 Hz), 3.95 (2H, d, J=5.7 Hz), 4.86 (2H, s), 6.63-6.69 (1H, m), 6.70 (1H, d, J=2.6 Hz), 6.80 (1H, d, J=2.6 Hz).

D) methyl 3-{[(2S)-2-(acetylamino)propyl]oxy}isoxazole-5-carboxylate

Using methyl 3-({(2S)-2-[(tert-butoxycarbonyl)amino]propyl}oxy)isoxazole-5-carboxylate, and in the same manner as in Example 1, step D, the title compound was obtained.
MS (ESI+): [M+H]$^+$ 243.1.

E) 3-{[(2S)-2-(acetylamino)propyl]oxy}isoxazole-5-carboxylic acid

Using methyl 3-{[(2S)-2-(acetylamino)propyl]oxy}isoxazole-5-carboxylate, and in the same manner as in Example 2, step B, the title compound was obtained.
MS (ESI+): [M+H]$^+$ 229.1.

F) 2-ethylhexyl 3-{[2-{[(3-{[(2S)-2-(acetylamino)propyl]oxy}isoxazol-5-yl)carbonyl]amino}-5-(cyclopropylmethoxy)phenyl]sulfanyl}propanoate Using 3-{[(2S)-2-(acetylamino)propyl]oxy}isoxazole-5-carboxylic acid and 2-ethylhexyl 3-{[2-amino-5-(cyclopropylmethoxy)phenyl]sulfanyl}propanoate, and in the same manner as in Example 2, step C, the title compound was obtained.
MS (ESI+): [M+H]$^+$ 590.1.

G) N-[1S)-2-({5-[6-(cyclopropylmethoxy)-1,3-benzothiazol-2-yl]isoxazol-3-yl}oxy)-1-methylethyl]acetamide A mixture of 2-ethylhexyl 3-{[2-{[(3-{[(2S)-2-(acetylamino)propyl]oxy}isoxazol-5-yl)carbonyl]amino}-5-(cyclopropylmethoxy)phenyl]sulfanyl}propanoate (935 mg), sodium ethoxide (20% ethanol solution, 1.08 g) and THF (10 mL) was stirred at room temperature for 30 min. To the reaction mixture was added trifluoroacetic acid (0.611 mL) at 0° C., and the obtained mixture was stirred at 70° C. overnight. To the reaction mixture was added saturated aqueous sodium hydrogen carbonate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate), and recrystallized (ethyl acetate) to give the title compound as white crystals (71.6 mg).

Example 37

N-[(1S)-2-({5-[5-(cyclopropylmethoxy)-1,3-benzothiazol-2-yl]isoxazol-3-yl}oxy)-1-methylethyl]acetamide A) 4-(cyclopropylmethoxy)-1-fluoro-2-nitrobenzene Using 4-fluoro-3-nitrophenol, and in the same manner as in Example 1, step A, the title compound was obtained.
$^1$H NMR (300 MHz, DMSO-d$_6$) δ 0.29-0.41 (2H, m), 0.53-0.63 (2H, m), 1.20-1.30 (1H, m), 3.91 (2H, d, J=6.8 Hz), 7.34-7.43 (1H, m), 7.47-7.56 (1H, m), 7.57-7.63 (1H, m).

B) 2-ethylhexyl 3-{[4-(cyclopropylmethoxy)-2-nitrophenyl]sulfanyl}propanoate

Using 4-(cyclopropylmethoxy)-1-fluoro-2-nitrobenzene, and in the same manner as in Example 35, step A, the title compound was obtained.
$^1$H NMR (300 MHz, DMSO-d$_6$) δ 0.29-0.42 (2H, m), 0.52-0.65 (2H, m), 0.75-0.93 (6H, m), 1.08-1.39 (9H, m), 1.43-1.60 (1H, m), 2.57-2.70 (2H, m), 3.21 (2H, t, J=7.0 Hz), 3.86-4.00 (4H, m), 7.33 (1H, dd, J=8.9, 2.8 Hz), 7.52-7.67 (2H, m).

C) 2-ethylhexyl 3-{[2-amino-4-(cyclopropylmethoxy)phenyl]sulfanyl}propanoate

Using 2-ethylhexyl 3-{[4-(cyclopropylmethoxy)-2-nitrophenyl]sulfanyl}propanoate, and in the same manner as in Example 35, step B, the title compound was obtained.
$^1$H NMR (300 MHz, DMSO-d$_6$) δ 0.23-0.34 (2H, m), 0.48-0.61 (2H, m), 0.76-0.92 (6H, m), 1.21-1.38 (9H, m), 1.45-1.60 (1H, m), 2.41-2.49 (2H, m), 2.73-2.80 (2H, m), 3.71 (2H, d, J=7.2 Hz), 3.93 (2H, d, J=5.7 Hz), 5.37 (2H, s), 6.09 (1H, dd, J=8.7, 2.6 Hz), 6.29 (1H, d, J=2.6 Hz), 7.09 (1H, d, J=8.7 Hz).

D) 2-ethylhexyl 3-{([2-{[(3-{[(2S)-2-(acetylamino)propyl]oxy}isoxazol-5-yl)carbonyl]amino}-4-(cyclopropylmethoxy)phenyl]sulfanyl}propanoate Using 3-{[(2S)-2-(acetylamino)propyl]oxy}isoxazole-5-carboxylic acid and 2-ethylhexyl 3-{[2-amino-4-(cyclopropylmethoxy)phenyl]sulfanyl}propanoate, and in the same manner as in Example 2, step C, the title compound was obtained.
MS (ESI+): [M+H]$^+$ 590.1.

E) N-[(1S)-2-({5-[5-(cyclopropylmethoxy)-1,3-benzothiazol-2-yl]isoxazol-3-yl}oxy)-1-methylethyl]acetamide Using 2-ethylhexyl 3-{2-[[(3-{[(2S)-2-(acetylamino)propyl]oxy}isoxazol-5-yl)carbonyl]amino}-4-(cyclopropylmethoxy)phenyl]sulfanyl}propanoate, and in the same manner as in Example 36, step G, the title compound was obtained.

Example 38

N-[(1S)-2-({5-[6-(cyclopropylmethoxy)-1,3-benzoxazol-2-yl]-4-methyl-1H-pyrazol-3-yl}oxy)-1-methylethyl]acetamide A) methyl 4-bromo-3-({(2S)-2-[(tert-butoxycarbonyl)amino]propyl}oxy)-1H-pyrazole-5-carboxylate A mixture of methyl 3-({(2S)-2-[(tert-butoxycarbonyl)amino]propyl}oxy)-1H-pyrazole-5-carboxylate (2.00 g), N-bromosuccinimide (1.43 g) and acetonitrile (50 mL) was stirred at room temperature overnight. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound as a white powder (2.20 g).
$^1$H NMR (300 MHz, DMSO-d$_6$) δ 1.08 (3H, d, J=6.8 Hz), 1.37 (9H, s), 3.68-4.20 (6H, m), 6.84 (1H, d, J=8.3 Hz), 13.53 (1H, s).

B) methyl 1-benzyl-4-bromo-3-({(2S)-2-[(tert-butoxycarbonyl)amino]propyl}oxy)-1H-pyrazole-5-carboxylate Using methyl 4-bromo-3-({(2S)-2-[(tert-butoxycarbonyl)amino]propyl}oxy)-1H-pyrazole-5-carboxylate and benzyl bromide, and in the same manner as in Example 1, step A, the title compound was obtained.
$^1$H NMR (300 MHz, DMSO-d$_6$) δ 1.08 (3H, d, J=6.8 Hz), 1.37 (9H, s), 3.73-4.15 (6H, m), 5.54 (2H, s), 6.86 (1H, d, J=7.9 Hz), 7.07-7.40 (5H, m).

C) methyl 1-benzyl-3-({(2S)-2-[(tert-butoxycarbonyl)amino]propyl}oxy)-4-methyl-1H-pyrazole-5-carboxylate Under an argon atmosphere, a mixture of methyl 1-benzyl-4-bromo-3-({(2S)-2-[(tert-butoxycarbonyl)amino]propyl}oxy)-1H-pyrazole-5-carboxylate (1.03 g), trimethylboroxin (552 mg), [1,1'-bis(diphenylphosphino)ferrocene]dichloropalladium(II) dichloromethane adduct (181 mg), potassium carbonate (912 mg) and DMF (20 ml) was stirred at 155° C. overnight. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound as a white powder (330 mg).
MS (ESI+): [M+H]$^+$ 404.2.

D) 1-benzyl-3-({(2S)-2-[(tert-butoxycarbonyl)amino]propyl}oxy)-4-methyl-1H-pyrazole-5-carboxylic acid Using methyl 1-benzyl-3-({(2S)-2-[(tert-butoxycarbonyl)amino]propyl}oxy)-4-methyl-1H-pyrazole-5-carboxylate, and in the same manner as in Example 2, step B, the title compound was obtained.
MS (ESI+): [M+H]$^+$ 390.2.

E) tert-butyl [(1S)-2-({1-benzyl-5-[(2,4-dihydroxyphenyl)carbamoyl]-4-methyl-1H-pyrazol-3-yl}oxy)-1-methylethyl]carbamate Using 1-benzyl-3-({(2S)-2-[(tert-butoxycarbonyl)amino]propyl}oxy)-4-methyl-1H-pyrazole-5-carboxylic acid and 4-aminobenzene-1,3-diol hydrochloride, and in the same manner as in Example 2, step C, the title compound was obtained.
MS (ESI+): [M+H]$^+$ 497.2.

F) tert-butyl [(1S)-2-{[1-benzyl-5-(6-hydroxy-1,3-benzoxazol-2-yl)-4-methyl-1H-pyrazol-3-yl]oxy}-1-methylethyl]carbamate Using tert-butyl [(1S)-2-({1-benzyl-5-[(2,4-dihydroxyphenyl)carbamoyl]-4-methyl-1H-pyrazol-3-yl}oxy)-1-methylethyl]carbamate, and in the same manner as in Example 2, step D, the title compound was obtained.
MS (ESI+): [M+H]$^+$ 479.2.

G) tert-butyl [(1S)-2-({(1-benzyl-5-[6-(cyclopropylmethoxy)-1,3-benzoxazol-2-yl]-4-methyl-1H-pyrazol-3-yl}oxy)-1-methylethyl]carbamate Using tert-butyl [(1S)-2-{[1-benzyl-5-(6-hydroxy-1,3-benzoxazol-2-yl)-4-methyl-1H-pyrazol-3-yl]oxy}-1-methylethyl]carbamate, and in the same manner as in Example 1, step A, the title compound was obtained.
$^1$H NMR (300 MHz, DMSO-d$_6$) δ 0.28-0.38 (2H, m), 0.51-0.65 (2H, m), 1.10 (3H, d, J=6.8 Hz), 1.24-1.31 (1H, m), 1.38 (9H, s), 2.22 (3H, s), 3.76-4.13 (5H, m), 5.75 (2H, s), 6.85 (1H, d, J=8.3 Hz), 6.96-7.06 (1H, m), 7.09-7.35 (5H, m), 7.40 (1H, d, J=2.3 Hz), 7.68 (1H, d, J=8.7 Hz).

H) N-[(1S)-2-({1-benzyl-5-[6-(cyclopropylmethoxy)-1,3-benzoxazol-2-yl]-4-methyl-1H-pyrazol-3-yl}oxy)-1-methylethyl]acetamide Using tert-butyl [(1S)-2-({1-benzyl-5-[6-(cyclopropylmethoxy)-1,3-benzoxazol-2-yl]-4-methyl-1H-pyrazol-3-yl}oxy)-1-methylethyl]carbamate, and in the same manner as in Example 1, step D, the title compound was obtained.
MS (ESI+): [M+H]$^+$ 475.3.

I) N-[(1S)-2-({5-[6-(cyclopropylmethoxy)-1,3-benzoxazol-2-yl]-4-methyl-1H-pyrazol-3-yl}oxy)-1-methylethyl]acetamide Using N-[(1S)-2-({1-benzyl-5-[6-(cyclopropylmethoxy)-1,3-benzoxazol-2-yl]-4-methyl-1H-pyrazol-3-yl}oxy)-1-methylethyl]acetamide, and in the same manner as in Example 8, step H, the title compound was obtained.

Example 39

N-[(1S)-2-({1-benzyl-5-[5-(cyclopropylmethoxy)-1,3-benzoxazol-2-yl]-1H-pyrazol-3-yl}oxy)-1-methylethyl]acetamide A) tert-butyl [(1S)-2-({1-benzyl-5-[(2,5-dihydroxyphenyl)carbamoyl]-1H-pyrazol-3-yl}oxy)-1-methylethyl]carbamate Using 1-benzyl-3-({(2S)-2-[(tert-butoxycarbonyl)amino]propyl}oxy)-1H-pyrazole-5-carboxylic acid, and in the same manner as in Example 2, step C, the title compound was obtained.
MS (ESI+): [M+H]$^+$ 483.4.

B) tert-butyl [(1S)-2-{[1-benzyl-5-(5-hydroxy-1,3-benzoxazol-2-yl)-1H-pyrazol-3-yl]oxy}-1-methylethyl]carbamate Using tert-butyl [(1S)-2-({1-benzyl-5-[(2,5-dihydroxyphenyl)carbamoyl]-1H-pyrazol-3-yl}oxy)-1-methylethyl] carbamate, and in the same manner as in Example 2, step D, the title compound was obtained.
MS (ESI+): [M+H]$^+$ 465.4.

C) tert-butyl [(1S)-2-({1-benzyl-5-[5-(cyclopropylmethoxy)-1,3-benzoxazol-2-yl]-1H-pyrazol-3-yl}oxy)-1-methylethyl]carbamate Using tert-butyl [(1S)-2-{[1-benzyl-5-(5-hydroxy-1,3-benzoxazol-2-yl)-1H-pyrazol-3-yl]oxy}-1-methylethyl]carbamate, and in the same manner as in Example 1, step A, the title compound was obtained.
MS (ESI+): [M+H]$^+$ 519.4.

D) N-[(1S)-2-({1-benzyl-5-[5-(cyclopropylmethoxy)-1,3-benzoxazol-2-yl]-1H-pyrazol-3-yl}oxy)-1-methylethyl]acetamide Using tert-butyl [(1S)-2-({1-benzyl-5-[5-(cyclopropylmethoxy)-1,3-benzoxazol-2-yl]-1H-pyrazol-3-yl}oxy)-1-methylethyl]carbamate, and in the same manner as in Example 1, step D, the title compound was obtained.

Example 40

N-[(1S)-2-({5-[5-(cyclopropylmethoxy)-1,3-benzoxazol-2-yl]-1H-pyrazol-3-yl}oxy)-1-methylethyl]acetamide Using N-[(1S)-2-({1-benzyl-5-[5-(cyclopropylmethoxy)-1,3-benzoxazol-2-yl]-1H-pyrazol-3-yl}oxy)-1-methylethyl]acetamide, and in the same manner as in Example 8, step H, the title compound was obtained.

Example 41

N-[(1S)-2-({5-[6-(cyclopropylmethoxy)-1,3-benzoxazol-2-yl]-4-methylisoxazol-3-yl}oxy)-1-methylethyl]acetamide A) tert-butyl [(1S)-2-({5-[(2,4-dihydroxyphenyl)carbamoyl]isoxazol-3-yl}oxy)-1-methylethyl]carbamate Using 3-({(2S)-2-[(tert-butoxycarbonyl)amino]propyl}oxy)isoxazole-5-carboxylic acid and 4-aminobenzene-1,3-diol hydrochloride, and in the same manner as in Example 2, step C, the title compound was obtained.
MS (ESI−): [M−H]$^-$ 392.3.

B) tert-butyl [(1S)-2-({5-[6-(cyclopropylmethoxy)-1,3-benzoxazol-2-yl]isoxazol-3-yl}oxy)-1-methylethyl]carbamate Using tert-butyl [(1S)-2-({5-[(2,4-dihydroxyphenyl)carbamoyl]isoxazol-3-yl}oxy)-1-methylethyl]carbamate, and in the same manner as in Example 2, step D and Example 1, step A, the title compound was obtained.
MS (ESI+): [M+H]$^+$ 430.1.

C) tert-butyl [(1S)-2-({5-[6-(cyclopropylmethoxy)-1,3-benzoxazol-2-yl]-4-methylisoxazol-3-yl}oxy)-1-methylethyl]carbamate Using tert-butyl [(1S)-2-({5-[6-(cyclopropylmethoxy)-1,3-benzoxazol-2-yl]isoxazol-3-yl}oxy)-1-methylethyl]carbamate, and in the same manner as in Example 23, step A, the title compound was obtained.

¹H NMR (300 MHz, DMSO-d₆) δ 0.27-0.43 (2H, m), 0.52-0.70 (2H, m), 1.12 (3H, d, J=6.8 Hz), 1.19-1.32 (1H, m), 1.38 (9H, s), 2.25 (3H, s), 3.79-4.02 (3H, m), 4.05-4.25 (2H, m), 6.86-7.01 (1H, m), 7.08 (1H, dd, J=8.8, 2.4 Hz), 7.47 (1H, d, J=2.4 Hz), 7.77 (1H, d, J=8.8 Hz).

D) N-[(1S)-2-({5-[6-(cyclopropylmethoxy)-1,3-benzoxazol-2-yl]-4-methylisoxazol-3-yl}oxy)-1-methylethyl]acetamide Using tert-butyl [(1S)-2-({5-[6-(cyclopropylmethoxy)-1,3-benzoxazol-2-yl]-4-methylisoxazol-3-yl}oxy)-1-methylethyl]carbamate, and in the same manner as in Example 1, step D, the title compound was obtained.

Example 42

N-[2-({5-[5-(cyclopropylmethoxy)-1,3-benzoxazol-2-yl]isoxazol-3-yl}oxy)-1-(fluoromethyl)ethyl]acetamide A) methyl 3-(3-fluoro-2-hydroxypropoxy)isoxazole-5-carboxylate A mixture of methyl 3-hydroxyisoxazole-5-carboxylate (1.88 g), 2-(fluoromethyl)oxirane (1.00 g), potassium carbonate (1.82 g) and DMF (2 mL) was stirred at room temperature for 2 hr, and then at 70° C. overnight. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound as a white powder (585 mg).
MS (ESI+): [M+H]⁺ 220.1.

B) 3-(3-fluoro-2-hydroxypropoxy)isoxazole-5-carboxylic acid

Using methyl 3-(3-fluoro-2-hydroxypropoxy)isoxazole-5-carboxylate, and in the same manner as in Example 6, step D, the title compound was obtained.
MS (ESI−): [M−H]⁻ 204.1.

C) 2-({5-[5-(cyclopropylmethoxy)-1,3-benzoxazol-2-yl]isoxazol-3-yl}oxy)-1-(fluoromethyl)ethyl methanesulfonate A mixture of 3-(3-fluoro-2-hydroxypropoxy)isoxazole-5-carboxylic acid (457 mg), methanesulfonyl chloride (0.517 mL), triethylamine (0.668 mL) and THF (20 mL) was stirred at 0° C. for 1 hr, and then at room temperature overnight. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was mixed with 2-aminobenzene-1,4-diol hydrochloride (360 mg), HATU (848 mg), N,N-diisopropylethylamine (0.769 mL) and DMF (10 mL), and the obtained mixture was stirred at room temperature overnight. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give a mixture (318 mg) of 2-({5-[(2,5-dihydroxyphenyl)carbamoyl]isoxazol-3-yl}oxy)-1-(fluoromethyl)ethyl methanesulfonate and impurity. To a solution of hexachloroethane (482 mg) and triphenylphosphine (641 mg) in acetonitrile (5 mL) was added triethylamine (0.908 mL) at room temperature, and the obtained mixture was stirred at room temperature for 10 min. A mixture of 2-({5-[(2,5-dihydroxyphenyl)carbamoyl]isoxazol-3-yl}oxy)-1-(fluoromethyl)ethyl methanesulfonate (318 mg, mixture with impurity) obtained by the aforementioned method, acetonitrile (5 mL) and THF (2 mL) was added thereto, and the obtained mixture was stirred at room temperature for 2 hr. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give a mixture (321 mg) of 2-fluoro-1-({[5-(5-hydroxy-1,3-benzoxazol-2-yl)isoxazol-3-yl]oxy}methyl)ethyl methanesulfonate and impurity. A mixture of the obtained 2-fluoro-1-({[5-(5-hydroxy-1,3-benzoxazol-2-yl)isoxazol-3-yl]oxy}methyl)ethyl methanesulfonate (321 mg, mixture with impurity), (bromomethyl)cyclopropane (128 mg), potassium carbonate (131 mg) and DMF (5 mL) was stirred at room temperature overnight. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound as a white powder (97.3 mg).
MS (ESI+): [M+H]⁺ 427.0.

D) N-[2-({5-[5-(cyclopropylmethoxy)-1,3-benzoxazol-2-yl]isoxazol-3-yl}oxy)-1-(fluoromethyl)ethyl]acetamide A mixture of 2-({5-[5-(cyclopropylmethoxy)-1,3-benzoxazol-2-yl]isoxazol-3-yl}oxy)-1-(fluoromethyl)ethyl methanesulfonate (97.3 mg), sodium azide (29.7 mg) and dimethyl sulfoxide (2 mL) was stirred at 100° C. for 4 hr. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was mixed with triphenylphosphine (71.8 mg), THF (3 mL) and water (1 mL), and the obtained mixture was stirred at 90° C. for 2 hr. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was mixed with acetic anhydride (1 mL), triethylamine (1 mL) and ethyl acetate (3 mL), and the obtained mixture was stirred at 60° C. overnight. The solvent was evaporated under reduced pressure, and the residue was purified by silica gel column chromatography (hexane/ethyl acetate). The obtained residue was separated by HPLC (C18, mobile phase: water/acetonitrile (containing 0.1% TFA)). A saturated aqueous sodium hydrogen carbonate solution was added to the obtained fraction, and the mixture was extracted with ethyl acetate. The obtained organic layer was washed with saturated brine, and dried over anhydrous magnesium sulfate, and the solvent was evaporated under reduced pressure to give the title compound as white crystals (52.3 mg).

Example 43

N-{1-[({5-[5-(cyclopropylmethoxy)-1,3-benzoxazol-2-yl]isoxazol-3-yl}oxy)methyl]-2,2-difluoroethyl}acetamide A) methyl 3-[(2-hydroxybut-3-en-1-yl)oxy]isoxazole-5-carboxylate Using 2-ethenyloxirane, and in the same manner as in Example 42, step A, the title compound was obtained.
MS (ESI+): [M+H]$^+$ 214.0.

B) methyl 3-(3,3-difluoro-2-hydroxypropoxy)isoxazole-5-carboxylate

A mixture of methyl 3-[(2-hydroxybut-3-en-1-yl)oxy]isoxazole-5-carboxylate (2.71 g), t-butyldimethylsilyl trifluoromethanesulfonate (4.03 g), 2,6-dimethylpyridine (1.64 g) and THF (30 mL) was stirred at room temperature for 2 hr. To the reaction mixture was added 1M hydrochloric acid, and the mixture was extracted with ethyl acetate. The obtained organic layer was washed with saturated aqueous sodium hydrogen carbonate solution, and then saturated brine, and dried over anhydrous magnesium sulfate, and the solvent was evaporated under reduced pressure. The residue was mixed with tetraoxide osmium (7% immobilized catalyst, 2.31 g), sodium periodate (13.6 g), acetonitrile (30 mL), acetone (30 mL) and water (20 mL), and the obtained mixture was stirred at room temperature for 3 days. The precipitate was removed by filtration, and the filtrate was extracted with ethyl acetate. The obtained organic layer was washed with saturated brine, and dried over anhydrous magnesium sulfate, and the solvent was evaporated under reduced pressure. The residue was mixed with toluene (20 mL), diethylaminosulfur trifluoride (5.04 mL) was slowly added dropwise thereto at room temperature, and the obtained mixture was stirred at room temperature for 2 hr. To the reaction mixture was added saturated aqueous sodium hydrogen carbonate solution, and the mixture was extracted with ethyl acetate. The obtained organic layer was washed with saturated brine, and dried over anhydrous magnesium sulfate, and the solvent was evaporated under reduced pressure. The residue was mixed with THF (20 mL), tetrabutylammonium fluoride (1.0M THF solution, 25.4 mL) was slowly added dropwise thereto at 0° C., and the obtained mixture was stirred at 0° C. for 30 min. To the reaction mixture was added 1M hydrochloric acid, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound as a white powder (370 mg).
MS (ESI+): [M+H]$^+$ 238.1.

C) methyl 3-{3,3-difluoro-2-[(methylsulfonyl)oxy]propoxy}isoxazole-5-carboxylate A mixture of methyl 3-(3,3-difluoro-2-hydroxypropoxy)isoxazole-5-carboxylate (370 mg), methanesulfonyl chloride (0.362 mL), triethylamine (0.652 mL) and THF (10 mL) was stirred at 0° C. for 1 hr, and then at room temperature overnight. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound as a colorless oil (432 mg).
$^1$H NMR (300 MHz, DMSO-d$_6$) δ 3.33 (3H, s), 3.89 (3H, s), 4.37-4.78 (2H, m), 5.14-5.45 (1H, m), 6.13-6.66 (1H, m), 7.20 (1H, s).

D) 1-[({5-[5-(cyclopropylmethoxy)-1,3-benzoxazol-2-yl]isoxazol-3-yl}oxy)methyl]-2,2-difluoroethyl methanesulfonate Using methyl 3-{3,3-difluoro-2-[(methylsulfonyl)oxy]propoxy}isoxazole-5-carboxylate, and in the same manner as in Example 6, step D and Example 2, steps C-E, the title compound was obtained.
MS (ESI+): [M+H]$^+$ 445.0.

E) N-{1-[({5-[5-(cyclopropylmethoxy)-1,3-benzoxazol-2-yl]isoxazol-3-yl}oxy)methyl]-2,2-difluoroethyl}acetamide Using 1-[({5-[5-(cyclopropylmethoxy)-1,3-benzoxazol-2-yl]isoxazol-3-yl}oxy)methyl]-2,2-difluoroethyl methanesulfonate, and in the same manner as in Example 42, step D, the title compound was obtained.

Example 44

1-[(1S)-2-({5-[5-(cyclopropylmethoxy)-1,3-benzoxazol-2-yl]-4-methylisoxazol-3-yl}oxy)-1-methylethyl]-3-methylurea Using tert-butyl [(1S)-2-({5-[5-(cyclopropylmethoxy)-1,3-benzoxazol-2-yl]-4-methylisoxazol-3-yl}oxy)-1-methylethyl]carbamate, and in the same manner as in Example 16 (using pyridine instead of triethylamine), the title compound was obtained.

Example 45

1-[(1S)-2-({5-[5-(cyclopropylmethoxy)-1,3-benzoxazol-2-yl]-4-methylisoxazol-3-yl}oxy)-1-methylethyl]urea Using tert-butyl [(1S)-2-({5-[5-(cyclopropylmethoxy)-1,3-benzoxazol-2-yl]-4-methylisoxazol-3-yl}oxy)-1-methylethyl]carbamate, and in the same manner as in Example 22 (using pyridine instead of triethylamine), the title compound was obtained.

Example 46

N-[(1S)-2-{[5-(5-ethoxy-1,3-benzoxazol-2-yl)isoxazol-3-yl]oxy}-1-methylethyl]acetamide A) tert-butyl [(1S)-2-{[5-(5-ethoxy-1,3-benzoxazol-2-yl)isoxazol-3-yl]oxy}-1-methylethyl]carbamate Using tert-butyl [(1S)-2-{[5-(5-hydroxy-1,3-benzoxazol-2-yl)isoxazol-3-yl]oxy}-1-methylethyl]carbamate and ethyl iodide, and in the same manner as in Example 2, step E, the title compound was obtained.
MS (ESI+): [M+H]$^+$ 404.3.

B) N-[(1S)-2-{[5-(5-ethoxy-1,3-benzoxazol-2-yl)isoxazol-3-yl]oxy}-1-methylethyl]acetamide Using tert-butyl [(1S)-2-{[5-(5-ethoxy-1,3-benzoxazol-2-yl)isoxazol-3-yl]oxy}-1-methylethyl]carbamate, and in the same manner as in Example 2, step F, the title compound was obtained.

Example 47

N-(3-{6-[6-(cyclopropylmethoxy)-1,3-benzoxazol-2-yl]pyridin-3-yl}-1-methyl-3-oxopropyl)acetamide A) tert-butyl {3-[methoxy(methyl)amino]-1-methyl-3-oxopropyl}carbamate Using 3-[(tert-butoxycarbonyl)amino]butanoic acid, and in the same manner as in Example 24, step D, the title compound was obtained.
$^1$H NMR (300 MHz, DMSO-$d_6$) δ 1.03 (3H, d, J=6.8 Hz), 1.37 (9H, s), 2.34-2.47 (1H, m), 2.52-2.61 (1H, m), 3.07 (3H, s), 3.64 (3H, s), 3.74-3.94 (1H, m), 6.71 (1H, d, J=8.3 Hz).

B) tert-butyl [3-(6-chloropyridin-3-yl)-1-methyl-3-oxopropyl]carbamate

Using tert-butyl {3-[methoxy(methyl)amino]-1-methyl-3-oxopropyl}carbamate and 5-bromo-2-chloropyridine, and in the same manner as in Example 24, step E, the title compound was obtained.
$^1$H NMR (300 MHz, DMSO-$d_6$) δ 1.11 (3H, d, J=6.8 Hz), 1.31 (9H, s), 2.90-3.09 (1H, m), 3.10-3.25 (1H, m), 3.85-4.08 (1H, m), 6.85 (1H, d, J=7.6 Hz), 7.69 (1H, d, J=8.3 Hz), 8.29 (1H, dd, J=8.3, 2.3 Hz), 8.94 (1H, d, J=2.3 Hz).

C) tert-butyl (3-{6-[6-(cyclopropylmethoxy)-1,3-benzoxazol-2-yl]pyridin-3-yl}-1-methyl-3-oxopropyl)carbamate Using tert-butyl [3-(6-chloropyridin-3-yl)-1-methyl-3-oxopropyl]carbamate, and in the same manner as in Example 1, step C, the title compound was obtained.
MS (ESI+): [M+H]$^+$ 452.0.

D) N-(3-{6-[6-(cyclopropylmethoxy)-1,3-benzoxazol-2-yl]pyridin-3-yl}-1-methyl-3-oxopropyl)acetamide Using tert-butyl (3-{6-[6-(cyclopropylmethoxy)-1,3-benzoxazol-2-yl]pyridin-3-yl}-1-methyl-3-oxopropyl)carbamate, and in the same manner as in Example 1, step D, the title compound was obtained.

Example 48 methyl [(1S)-2-({6-[6-(cyclopropylmethoxy)-1,3-benzoxazol-2-yl]-5-fluoropyridin-3-yl}oxy)-1-methylethyl]carbamate Using tert-butyl [(1S)-2-({6-[6-(cyclopropylmethoxy)-1,3-benzoxazol-2-yl]-5-fluoropyridin-3-yl}oxy)-1-methylethyl]carbamate, and in the same manner as in Example 17, step A, the title compound was obtained.

Example 49

N-[(1S)-3-{6-[6-(cyclopropylmethoxy)-1,3-benzoxazol-2-yl]pyridin-3-yl}-1-methylpropyl]acetamide A) 2-(5-bromopyridin-2-yl)-6-(cyclopropylmethoxy)-1,3-benzoxazole Using 5-bromopyridine-2-carboxylic acid and 4-aminobenzene-1,3-diol hydrochloride, and in the same manner as in Example 2, steps C-D and Example 1, step A, the title compound was obtained.
$^1$H NMR (300 MHz, DMSO-$d_6$) δ 0.21-0.45 (2H, m), 0.53-0.76 (2H, m), 1.09-1.44 (1H, m), 3.92 (2H, d, J=6.8 Hz), 7.06 (1H, dd, J=8.7, 2.3 Hz), 7.43 (1H, d, J=2.3 Hz), 7.74 (1H, d, J=8.7 Hz), 8.11-8.21 (1H, m), 8.24-8.44 (1H, m), 8.91 (1H, d, J=2.3 Hz).

B) tert-butyl [(1S)-3-{6-[6-(cyclopropylmethoxy)-1,3-benzoxazol-2-yl]pyridin-3-yl}-1-methylprop-2-yn-1-yl]carbamate Under an argon atmosphere, a mixture of 2-(5-bromopyridin-2-yl)-6-(cyclopropylmethoxy)-1,3-benzoxazole (200 mg), tert-butyl [(1S)-1-methylprop-2-yn-1-yl]carbamate (196 mg), dichlorobis(triphenylphosphine)palladium(II) (20.3 mg), copper(I) iodide (11.0 mg), triethylamine (0.081 mL) and DMF (5 mL) was stirred at 80° C. for 8 hr. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound as a yellow powder (150 mg).
MS (ESI+): [M+H]$^+$ 434.5.

C) N-[(1S)-3-{6-[6-(cyclopropylmethoxy)-1,3-benzoxazol-2-yl]pyridin-3-yl}-1-methylprop-2-yn-1-yl]acetamide Using tert-butyl [(1S)-3-{6-[6-(cyclopropylmethoxy)-1,3-benzoxazol-2-yl]pyridin-3-yl}-1-methylprop-2-yn-1-yl]carbamate, and in the same manner as in Example 1, step D, the title compound was obtained.
MS (ESI+): [M+H]$^+$ 376.1.

D) N-[(1S)-3-{6-[6-(cyclopropylmethoxy)-1,3-benzoxazol-2-yl]pyridin-3-yl}-1-methylpropyl]acetamide Under a hydrogen atmosphere, a mixture of N-[(1S)-3-{6-[6-(cyclopropylmethoxy)-1,3-benzoxazol-2-yl]pyridin-3-yl}-1-methylprop-2-yn-1-yl]acetamide (98.0 mg), 10% palladium/carbon (containing water (50%), 19.6 mg), methanol (5 mL) and THF (1 mL) was stirred at 50° C. for 4 hr. The catalyst was removed by filtration, and the obtained filtrate was concentrated under reduced pressure. The residue was purified by silica gel column chromatography (hexane/ethyl acetate/methanol) to give the title compound as yellow crystals (37.0 mg).

Example 50

N-[(1S)-2-({6-[5-(cyclopropylmethoxy)-1,3-benzoxazol-2-yl]-5-fluoropyridin-3-yl}oxy)-1-methylethyl]acetamide

A) tert-butyl [(1S)-2-({6-[(2,5-dihydroxyphenyl)carbamoyl]-5-fluoropyridin-3-yl}oxy)-1-methylethyl]carbamate Using 5-({(2S)-2-[(tert-butoxycarbonyl)amino]propyl}oxy)-3-fluoropyridine-2-carboxylic acid, and in the same manner as in Example 2, step C, the title compound was obtained.
MS (ESI+): [M+H]+ 422.3.

B) tert-butyl [(1S)-2-({6-[5-(cyclopropylmethoxy)-1,3-benzoxazol-2-yl]-5-fluoropyridin-3-yl}oxy)-1-methylethyl]carbamate Using tert-butyl [(1S)-2-({6-[(2,5-dihydroxyphenyl)carbamoyl]-5-fluoropyridin-3-yl}oxy)-1-methylethyl]carbamate, and in the same manner as in Example 2, steps D-E, the title compound was obtained.
MS (ESI+): [M+H]+ 458.2.

C) N-[(1S)-2-({6-[5-(cyclopropylmethoxy)-1,3-benzoxazol-2-yl]-5-fluoropyridin-3-yl}oxy)-1-methylethyl]acetamide Using tert-butyl [(1S)-2-({6-[5-(cyclopropylmethoxy)-1,3-benzoxazol-2-yl]-5-fluoropyridin-3-yl}oxy)-1-methylethyl]carbamate, and in the same manner as in Example 1, step D, the title compound was obtained.

Example 51

N-[(1S)-2-{[6-(6-ethoxy-1,3-benzoxazol-2-yl)-5-fluoropyridin-3-yl]oxy}-1-methylethyl]acetamide

A) tert-butyl [(1S)-2-{[6-(6-ethoxy-1,3-benzoxazol-2-yl)-5-fluoropyridin-3-yl]oxy}-1-methylethyl]carbamate Using tert-butyl [(1S)-2-({6-[(2,4-dihydroxyphenyl)carbamoyl]-5-fluoropyridin-3-yl}oxy)-1-methylethyl]carbamate and ethyl iodide, and in the same manner as in Example 2, steps D-E, the title compound was obtained.
MS (ESI+): [M+H]+ 432.1.

B) N-[(1S)-2-{[6-(6-ethoxy-1,3-benzoxazol-2-yl)-5-fluoropyridin-3-yl]oxy}-1-methylethyl]acetamide Using tert-butyl [(1S)-2-{[6-(6-ethoxy-1,3-benzoxazol-2-yl)-5-fluoropyridin-3-yl]oxy}-1-methylethyl]carbamate, and in the same manner as in Example 1, step D, the title compound was obtained.

Example 52

N-[(1S)-2-({6-[6-(2-fluoropropoxy)-1,3-benzoxazol-2-yl]pyridin-3-yl}oxy)-1-methylethyl]acetamide A mixture of tert-butyl [(1S)-2-({6-[6-(2-hydroxypropoxy)-1,3-benzoxazol-2-yl]pyridin-3-yl}oxy)-1-methylethyl]carbamate (1.02 g) (obtained using tert-butyl [(1S)-2-{[6-(6-hydroxy-1,3-benzoxazol-2-yl)pyridin-3-yl]oxy}-1-methylethyl]carbamate (4.00 g) and 1-bromopropan-2-one (1.56 g) and in the same manner as in Example 2, step E and Example 24, step F), bis(2-methoxyethyl)aminosulfur trifluoride (0.848 mL) and toluene (10 mL) was stirred at room temperature for 1 hr. To the reaction mixture was added saturated aqueous sodium hydrogen carbonate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give tert-butyl [(1S)-2-({6-[6-(2-fluoropropoxy)-1,3-benzoxazol-2-yl]pyridin-3-yl}oxy)-1-methylethyl]carbamate.
Using the obtained compound, and in the same manner as in Example 1, step D, the title compound was obtained (61.3 mg).

Example 53

N-[(1S)-2-({6-[6-(cyclopropylmethoxy)-1,3-benzoxazol-2-yl]-2-methoxypyridin-3-yl}oxy)-1-methylethyl]acetamide

A) 3-({(2S)-2-[(tert-butoxycarbonyl)amino]propyl}oxy)-6-[6-(cyclopropylmethoxy)-1,3-benzoxazol-2-yl]pyridin-2-yl acetate A mixture of tert-butyl [(1S)-2-({6-[6-(cyclopropylmethoxy)-1,3-benzoxazol-2-yl]pyridin-3-yl}oxy)-1-methylethyl]carbamate (2.34 g), m-chloroperbenzoic acid (2.66 g) and acetonitrile (30 mL) was stirred at 50° C. overnight. To the reaction mixture were added saturated sodium hydrogen carbonate and aqueous sodium thiosulfate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give a mixture (200 mg) of tert-butyl [(1S)-2-({6-[6-(cyclopropylmethoxy)-1,3-benzoxazol-2-yl]-1-oxidepyridin-3-yl}oxy)-1-methylethyl]carbamate and impurity. A mixture of the aforementioned tert-butyl [(1S)-2-({6-[6-(cyclopropylmethoxy)-1,3-benzoxazol-2-yl]-1-oxidepyridin-3-yl}oxy)-1-methylethyl]carbamate (200 mg, mixture with impurity), acetic anhydride (224 mg) and toluene (5 mL) was stirred at 110° C. overnight. The reaction mixture was purified by silica gel column chromatography (hexane/ethyl acetate) to give the title compound as a colorless oil (111 mg).
$^1$H NMR (300 MHz, DMSO-$d_6$) δ 0.26-0.42 (2H, m), 0.53-0.68 (2H, m), 1.11 (3H, d, J=6.8 Hz), 1.21-1.33 (1H, m), 1.39 (9H, s), 2.37 (3H, s), 3.78-4.03 (5H, m), 6.92 (1H, d, J=7.9 Hz), 7.02 (1H, dd, J=8.7, 2.3 Hz), 7.39 (1H, d, J=2.3 Hz), 7.68 (1H, d, J=9.0 Hz), 7.81 (1H, d, J=8.7 Hz), 8.19 (1H, d, J=8.3 Hz).

B) tert-butyl [(1S)-2-({6-[6-(cyclopropylmethoxy)-1,3-benzoxazol-2-yl]-2-methoxypyridin-3-yl}oxy)-1-methylethyl]carbamate A mixture of 3-({(2S)-2-[(tert-butoxycarbonyl)amino]propyl}oxy)-6-[6-(cyclopropylmethoxy)-1,3-benzoxazol-2-yl]pyridin-2-yl acetate (111 mg), THF (1 mL), methanol (1 mL) and 1M lithium hydroxide aqueous solution (1 mL) was stirred at 0° C. for 2 hr. The reaction mixture was neutralized with 1M hydrochloric acid at 0° C., and extracted with ethyl acetate. The obtained organic layer was washed with saturated brine, and dried over anhydrous magnesium sulfate, and the solvent was evaporated under reduced pressure. The residue was mixed with toluene (2 mL), methyl iodide (0.021 mL) and silver(I) carbonate (92 mg), and the obtained mixture was stirred at 85° C. for 3 days. To the reaction mixture were further added methyl iodide (0.021 mL) and silver(I) carbonate (92 mg), and the mixture was stirred at 85° C. for 4 hr. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound as a white powder (70.0 mg).
MS (ESI+): [M+H]$^+$ 470.3.

C) N-[(1S)-2-({6-[6-(cyclopropylmethoxy)-1,3-benzoxazol-2-yl]-2-methoxypyridin-3-yl}oxy)-1-methylethyl]acetamide Using tert-butyl [(1S)-2-({6-[6-(cyclopropylmethoxy)-1,3-benzoxazol-2-yl]-2-methoxypyridin-3-yl}oxy)-1-methylethyl]carbamate, and in the same manner as in Example 1, step D, the title compound was obtained.
MS (ESI+): [M+H]$^+$ 376.1.

Example 54

N-[(1S)-2-{[6-(6-ethoxy-1,3-benzoxazol-2-yl)pyridin-3-yl]oxy}-1-methylethyl]-2,2,2-trifluoroacetamide A mixture of tert-butyl [(1S)-2-{[6-(6-ethoxy-1,3-benzoxazol-2-yl)pyridin-3-yl]oxy}-1-methylethyl]carbamate (300 mg), ethyl acetate (10 ml) and 4M hydrogen chloride/ethyl acetate (10 mL) was stirred at room temperature overnight. The solvent was evaporated under reduced pressure, and the residue was dissolved in pyridine (3 mL), and trifluoroacetic anhydride (0.150 mL) was added thereto. The mixture was stirred at room temperature for 2 hr. To the reaction mixture was further added trifluoroacetic anhydride (0.301 mL), and the mixture was stirred at room temperature for 2 hr. To the reaction mixture were added water and 1M hydrochloric acid, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate), and recrystallized (ethyl acetate) to give the title compound as white crystals (205 mg).

Example 55

N-[(1S)-2-{[6-(6-ethoxy-1,3-benzoxazol-2-yl)pyridin-3-yl]oxy}-1-methylethyl]-2,2-difluoroacetamide A mixture of tert-butyl [(1S)-2-{[6-(6-ethoxy-1,3-benzoxazol-2-yl)pyridin-3-yl]oxy}-1-methylethyl]carbamate (300 mg), ethyl acetate (5 mL) and 4M hydrogen chloride/ethyl acetate (5 mL) was stirred at room temperature overnight. The solvent was evaporated under reduced pressure, and the residue was mixed with difluoroacetic acid (105 mg), WSC (209 mg), HOBt (167 mg), triethylamine (0.506 mL) and DMF (3 mL). The mixture was, stirred at room temperature for 3 days. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate), and recrystallized (ethyl acetate) to give the title compound as white crystals (164 mg).

Example 56

N-[(1S)-2-({6-[6-(cyclopropylmethoxy)-1,3-benzoxazol-2-yl]-1-oxidepyridin-3-yl}oxy)-1-methylethyl]acetamide A) tert-butyl [(1S)-2-({6-[6-(cyclopropylmethoxy)-1,3-benzoxazol-2-yl]-1-oxidepyridin-3-yl}oxy)-1-methylethyl]carbamate A mixture of tert-butyl [(1S)-2-({6-[6-(cyclopropylmethoxy)-1,3-benzoxazol-2-yl]pyridin-3-yl}oxy)-1-methylethyl]carbamate (529 mg), m-chloroperbenzoic acid (602 mg) and acetonitrile (10 mL) was stirred at room temperature for 8 hr. To the reaction mixture were added saturated sodium hydrogen carbonate and aqueous sodium thiosulfate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound as a pale-yellow solid (134 mg).
MS (ESI+): [M+H]$^+$ 456.4.

B) N-[(1S)-2-({6-[6-(cyclopropylmethoxy)-1,3-benzoxazol-2-yl]-1-oxidepyridin-3-yl}oxy)-1-methylethyl]acetamide Using tert-butyl [(1S)-2-({6-[6-(cyclopropylmethoxy)-1,3-benzoxazol-2-yl]-1-oxidepyridin-3-yl}oxy)-1-methylethyl]carbamate, and in the same manner as in Example 1, step D, the title compound was obtained.

Example 57

N-[(1S)-2-({6-[6-(cyclopropylmethoxy)-2-methyl-2,3-dihydro-1-benzofuran-2-yl]pyridin-3-yl}oxy)-1-methylethyl]acetamide A) 1-[2-bromo-4-(cyclopropylmethoxy)phenyl]propan-2-one To a solution (50 mL) of 2-[2-bromo-4-(cyclopropylmethoxy)phenyl]-N-methoxy-N-methylacetamide (3.00 g) in THF was added dropwise methylmagnesium bromide (19.6 mL, 1.4 M, a mixed solution of toluene-diethyl ether (3/1)) under ice-cooling. The mixture was stirred at room temperature for 3 hr, poured into saturated aqueous ammonium chloride solution, and extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound as a colorless oil (1.29 g).
$^1$H NMR (300 MHz, DMSO-d$_6$) δ 0.20-0.40 (2H, m), 0.46-0.69 (2H, m), 0.99-1.39 (1H, m), 2.14 (3H, s), 3.77-3.87 (4H, m), 6.91 (1H, dd, J=8.5, 2.5 Hz), 7.14 (1H, d, J=2.6 Hz), 7.20 (1H, d, J=8.7 Hz).

B) N-[(1S)-2-({6-[6-(cyclopropylmethoxy)-2-methyl-2,3-dihydro-1-benzofuran-2-yl]pyridin-3-yl}oxy)-1-methylethyl]acetamide Using 1-[2-bromo-4-(cyclopropylmethoxy)phenyl]propan-2-one, and in the same manner as in Example 24, steps E and G-I, the title compound was obtained.

Example 58

N-[(1S)-2-({2-[6-(cyclopropylmethoxy)-1,3-benzoxazol-2-yl]pyrimidin-5-yl}oxy)-1-methylethyl]acetamide A) 2-(5-bromopyrimidin-2-yl)-6-(cyclopropylmethoxy)-1,3-benzoxazole Using 5-bromopyrimidine-2-carboxylic acid and 4-aminobenzene-1,3-diol hydrochloride, and in the same manner as in Example 2, steps C-E, the title compound was obtained.
$^1$H NMR (300 MHz, DMSO-$d_6$) δ 0.29-0.43 (2H, m), 0.51-0.72 (2H, m), 1.15-1.40 (1H, m), 3.93 (2H, d, J=7.2 Hz), 7.09 (1H, dd, J=8.8, 2.4 Hz), 7.45 (1H, d, J=2.4 Hz), 7.79 (1H, d, J=8.8 Hz), 9.23 (2H, s).

B) 2-[5-(benzyloxy)pyrimidin-2-yl]-6-(cyclopropylmethoxy)-1,3-benzoxazole

Under an argon atmosphere, a mixture of 2-(5-bromopyrimidin-2-yl)-6-(cyclopropylmethoxy)-1,3-benzoxazole (260 mg), benzyl alcohol (812 mg), cesium carbonate (368 mg), copper(I) iodide (14.3 mg), 1,10-phenanthroline (27.0 mg) and toluene (5 mL) was stirred at 110° C. for 3 days. The precipitate was removed by filtration, and the filtrate was concentrated under reduced pressure. The residue was purified by silica gel column chromatography (hexane/ethyl acetate) to give the title compound as a pale-yellow solid (205 mg).
$^1$H NMR (300 MHz, DMSO-$d_6$) δ 0.31-0.43 (2H, m), 0.52-0.68 (2H, m), 1.16-1.34 (1H, m), 3.92 (2H, d, J=7.2 Hz), 5.40 (2H, s), 7.05 (1H, dd, J=8.9, 2.4 Hz), 7.32-7.59 (6H, m), 7.74 (1H, d, J=8.9 Hz), 8.83 (2H, s).

C) N-[(1S)-2-({2-[6-(cyclopropylmethoxy)-1,3-benzoxazol-2-yl]pyrimidin-5-yl}oxy)-1-methylethyl]acetamide Using 2-[5-(benzyloxy)pyrimidin-2-yl]-6-(cyclopropylmethoxy)-1,3-benzoxazole, and in the same manner as in Example 8, step H, Example 2, step A and Example 1, step D, the title compound was obtained.

Example 59

N-[(1S)-2-[4-(5-methoxy-2H-indazol-2-yl)phenoxy]-1-methylethyl]acetamide

N-{(1S)-2-[4-(5-methoxy-2H-indazol-2-yl)phenoxy]-1-methylethyl}acetamide

Using [4-(benzyloxy)phenyl]hydrazine hydrochloride (2.0 g) and 1-bromo-2-(bromomethyl)-4-methoxybenzene (2.23 g), and in the same manner as in Example 12, steps A-E, the title compound was obtained as colorless crystals (75.6 mg).

Example 60

N-[(1S)-2-({6-[6-(3,3-difluorobutoxy)-1,3-benzoxazol-2-yl]-5-fluoropyridin-3-yl}oxy)-1-methylethyl]acetamide A) 3,3-difluorobutyl methanesulfonate To a solution of 3,3-difluorobutan-1-ol (2.60 g) and triethylamine (6.58 mL) in THF (50 mL) was added dropwise methanesulfonyl chloride (2.74 mL) at 0° C., and the mixture was stirred at room temperature overnight. Water was added to the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound as a pale-yellow oil (2.69 g).
$^1$H NMR (300 MHz, DMSO-$d_6$) δ 1.66 (3H, t, J=19.3 Hz), 2.38 (2H, tt, J=15.8, 6.4 Hz), 3.21 (3H, s), 4.34 (2H, t, J=6.4 Hz).

B) tert-butyl [(1S)-2-({6-[6-(3,3-difluorobutoxy)-1,3-benzoxazol-2-yl]-5-fluoropyridin-3-yl}oxy)-1-methylethyl]carbamate Using tert-butyl [(1S)-2-({6-[(2,4-dihydroxyphenyl)carbamoyl]-5-fluoropyridin-3-yl}oxy)-1-methylethyl]carbamate and 3,3-difluorobutyl methanesulfonate, and in the same manner as in Example 2, steps C-D, the title compound was obtained.
MS (ESI+): [M+H]$^+$ 496.1.

C) N-[(1S)-2-({6-[6-(3,3-difluorobutoxy)-1,3-benzoxazol-2-yl]-5-fluoropyridin-3-yl}oxy)-1-methylethyl]acetamide Using tert-butyl [(1S)-2-({6-[6-(3,3-difluorobutoxy)-1,3-benzoxazol-2-yl]-5-fluoropyridin-3-yl}oxy)-1-methylethyl]carbamate, and in the same manner as in Example 1, step D, the title compound was obtained.

Example 61

1-[(1S)-2-{4-[6-(cyclopropylmethoxy)-2H-indazol-2-yl]phenoxy}-1-methylethyl]urea A mixture of tert-butyl [(1S)-2-{4-[6-(cyclopropylmethoxy)-2H-indazol-2-yl]phenoxy}-1-methylethyl]carbamate (310 mg) and 4M hydrogen chloride/ethyl acetate (5 mL) was stirred at room temperature for 1 hr. To the reaction mixture was added diethyl ether, the resultant precipitate was collected by filtration, and washed with ethyl acetate to give (2S)-1-{4-[6-(cyclopropylmethoxy)-2H-indazol-2-yl]phenoxy}propan-2-amine hydrochloride (255 mg). A mixture of (2S)-1-{4-[6-(cyclopropylmethoxy)-2H-indazol-2-yl]phenoxy}propan-2-amine hydrochloride (84 mg), (trimethyl)silyl isocyanate (78 mg), triethylamine (68 mg) and THF (1 mL) was stirred at room temperature overnight. The solvent was evaporated under reduced pressure, and the residue was diluted with ethyl acetate and THF, and the mixture was washed with water. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as colorless crystals (39.5 mg).

Example 62

1-[(1S)-2-{4-[6-(cyclopropylmethoxy)-2H-indazol-2-yl]phenoxy}-1-methylethyl]-3-methylurea A mixture of tert-butyl [(1S)-2-{4-[6-(cyclopropylmethoxy)-2H-indazol-2-yl]phenoxy}-1-methylethyl]carbamate (310 mg) and 4M hydrogen chloride/ethyl acetate (5 mL) was stirred at room temperature for 1 hr. To the reaction mixture was added diethyl ether, and the resultant precipitate was collected by filtration, and washed with ethyl acetate to give (2S)-1-{4-[6-(cyclopropylmethoxy)-2H-indazol-2-yl]phenoxy}propan-2-amine hydrochloride (255 mg). A mixture of (2S)-1-{4-[6-(cyclopropylmethoxy)-2H-indazol-2-yl]phenoxy}propan-2-amine hydrochloride (84 mg), methyl isocyanate (38.5 mg), triethylamine (68 mg) and THF (1 mL) was stirred at room temperature overnight. The solvent was evaporated under reduced pressure, and the residue was diluted with ethyl acetate, and the mixture was washed with water. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as colorless crystals (51.9 mg).

Example 63

3-[(1S)-2-{4-[6-(cyclopropylmethoxy)-2H-indazol-2-yl]phenoxy}-1-methylethyl]-1,1-dimethylurea A mixture of tert-butyl [(1S)-2-{4-[6-(cyclopropylmethoxy)-2H-indazol-2-yl]phenoxy}-1-methylethyl]carbamate (310 mg) and 4M hydrogen chloride/ethyl acetate (5 mL) was stirred at room temperature for 1 hr. To the reaction mixture was added diethyl ether, and the resultant precipitate was collected by filtration, and washed with ethyl acetate to give (2S)-1-{4-[6-(cyclopropylmethoxy)-2H-indazol-2-yl]phenoxy}propan-2-amine hydrochloride (255 mg). A mixture of (2S)-1-{4-[6-(cyclopropylmethoxy)-2H-indazol-2-yl]phenoxy}propan-2-amine hydrochloride (84 mg), dimethylcarbamoyl chloride (72.5 mg), triethylamine (68 mg) and THF (1 mL) was stirred at 50° C. overnight. The solvent was evaporated under reduced pressure, and the residue was diluted with ethyl acetate, and the mixture was washed with water. The separated aqueous layer was extracted again with ethyl acetate. The combined organic layer was washed with saturated brine, and dried over anhydrous magnesium sulfate, and the solvent is was evaporated under reduced pressure. The residue was purified by silica gel column chromatography (hexane/ethyl acetate) to give the title compound as a pale-yellow powder (42.8 mg).

Example 64

N-[(1S)-2-{4-[6-(cyclopropylmethoxy)-7-fluoro-2H-indazol-2-yl]phenoxy}-1-methylethyl]acetamide A)
4-(cyclopropylmethoxy)-2,3-difluorobenzaldehyde Using 2,3-difluoro-4-hydroxybenzaldehyde (316 mg), and in the same manner as in Example 2, step E, the title compound was obtained as a brown oil (397 mg).

$^1$H NMR (300 MHz, CDCl$_3$) δ 0.40 (2H, q), 0.66-0.75 (2H, m), 1.25-1.41 (1H, m), 3.98 (2H, d, J=6.8 Hz), 6.82 (1H, ddd, J=8.8, 6.9, 1.7 Hz), 7.54-7.65 (1H, m), 10.19 (1H, s).

B) tert-butyl [(1S)-2-{4-[6-(cyclopropylmethoxy)-7-fluoro-2H-indazol-2-yl]phenoxy}-1-methylethyl]carbamate A mixture of 4-(cyclopropylmethoxy)-2,3-difluorobenzaldehyde (397 mg), tert-butyl [(1S)-2-(4-aminophenoxy)-1-methylethyl]carbamate (498 mg) and ethanol (12 mL) was stirred under reflux overnight. The reaction mixture was concentrated under reduced pressure, sodium azide (507 mg) and DMF (8 mL) were added to the residue, and the mixture was stirred at 140° C. overnight. Water was added to the reaction mixture, and the mixture was extracted with ethyl acetate. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as a yellow solid (74.5 mg).

MS (ESI+): [M+H]$^+$ 456.0.

C) N-[(1S)-2-{4-[6-(cyclopropylmethoxy)-7-fluoro-2H-indazol-2-yl]phenoxy}-1-methylethyl]acetamide Using tert-butyl [(1S)-2-{4-[6-(cyclopropylmethoxy)-7-fluoro-2H-indazol-2-yl]phenoxy}-1-methylethyl]carbamate (75.3 mg), and in the same manner as in Example 25, step G, the title compound was obtained as colorless crystals (49 mg).

Example 65

N-[(1S)-2-{4-[6-(cyclopropylmethoxy)-4-fluoro-2H-indazol-2-yl]phenoxy}-1-methylethyl]acetamide Using 2,6-difluoro-4-hydroxybenzaldehyde (316 mg), and in the same manner as in Example 2, step E, Example 64, step B and Example 25, step G, the title compound was obtained as colorless crystals (167 mg).

Example 66

N-[(1S)-2-{4-[6-(cyclopropylmethoxy)-5-fluoro-2H-indazol-2-yl]phenoxy}-1-methylethyl]acetamide Using 2,5-difluoro-4-hydroxybenzaldehyde (316 mg), and in the same manner as in Example 2, step E, Example 64, step B and Example 25, step G, the title compound was obtained as colorless crystals (33.6 mg).

Example 67

N-[(1S)-2-{4-[6-(cyclopropylmethoxy)-2H-indazol-2-yl]-3-fluorophenoxy}-1-methylethyl]acetamide A) 4-(cyclopropylmethoxy)-2-nitrobenzaldehyde Using 4-methyl-3-nitrophenol (49.1 g) and (bromomethyl)cyclopropane (47.6 g), and in the same manner as in Example 25, steps A-C, the title compound was obtained as yellow crystals (20.89 g).

¹H NMR (300 MHz, CDCl₃) δ 0.37-0.45 (2H, m), 0.66-0.77 (2H, m), 1.22-1.39 (1H, m), 3.95 (2H, d, =7.2 Hz), 7.22 (1H, dd, J=8.7, 2.7 Hz), 7.50 (1H, d, J=2.3 Hz), 7.97 (1H, d, J=8.7 Hz), 10.29 (1H, s).

B) tert-butyl [(1S)-2-[(4-[6-(cyclopropylmethoxy)-2H-indazol-2-yl]-3-fluorophenoxy]-1-methylethyl] carbamate Using 4-(cyclopropylmethoxy)-2-nitrobenzaldehyde (547 mg) and tert-butyl [(1S)-2-(4-amino-3-fluorophenoxy)-1-methylethyl]carbamate (703 mg), and in the same manner as in Example 25, step F, the title compound was obtained as yellow solid (835 mg).
MS (ESI+): [M+H]⁺ 456.4.

C) (2S)-1-{4-[6-(cyclopropylmethoxy)-2H-indazol-2-yl]-3-fluorophenoxy}propan-2-amine A mixture of tert-butyl [(1S)-2-{4-[6-(cyclopropylmethoxy)-2H-indazol-2-yl]-3-fluorophenoxy}-1-methylethyl]carbamate (544 mg) and 4M hydrogen chloride/ethyl acetate (5 mL) was stirred at room temperature for 1 hr. The reaction mixture was concentrated under reduced pressure, to the obtained residue was added saturated aqueous sodium hydrogen carbonate solution, and the mixture was extracted twice with ethyl acetate. The combined organic layer was washed with saturated brine, and dried over anhydrous magnesium sulfate, and the solvent was evaporated under reduced pressure to give the title compound as an orange oil (424 mg).
MS (ESI+): [M+H]⁺ 356.2.

D) N-[(1S)-2-{(4-[6-(cyclopropylmethoxy)-2H-indazol-2-yl]-3-fluorophenoxy}-1-methylethyl]acetamide A mixture of (2S)-1-{4-[6-(cyclopropylmethoxy)-2H-indazol-2-yl]-3-fluorophenoxy}propan-2-amine (211 mg), acetyl chloride (70 mg), triethylamine (90 mg) and THF (4 mL) was stirred at room temperature for 1 hr. The solvent was evaporated under reduced pressure, and the residue was diluted with ethyl acetate, and the mixture was washed with water. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate), and recrystallized (hexane/ethyl acetate) to give the title compound as colorless crystals (94 mg).

Example 68

1-[(1S)-2-{(4-[6-(cyclopropylmethoxy)-2H-indazol-2-yl]-3-fluorophenoxy}-1-methylethyl]urea A mixture of (2S)-1-{4-[6-(cyclopropylmethoxy)-2H-indazol-2-yl]-3-fluorophenoxy}propan-2-amine (211 mg), (trimethyl)silyl isocyanate (137 mg) and THF (4 mL) was stirred at room temperature overnight. The solvent was evaporated under reduced pressure, and the residue was diluted with ethyl acetate, and the mixture was washed with water. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate), and recrystallized (ethanol/ethyl acetate) to give the title compound as colorless crystals (117 mg).

Example 69

N-[(1S)-2-{4-[6-(cyclopropylmethoxy)-2H-indazol-2-yl]-2-fluorophenoxy}-1-methylethyl]acetamide Using 2-fluoro-4-nitrophenol (471 mg) and 4-(cyclopropylmethoxy)-2-nitrobenzaldehyde (623 mg), and in the same manner as in Example 25, steps D-G, the title compound was obtained as colorless crystals (57 mg).

Example 70

N-[(1S)-2-{4-[6-(cyclopropylmethoxy)-2H-indazol-2-yl]-2,5-difluorophenoxy}-1-methylethyl]acetamide Using 2,5-difluoro-4-nitrophenol (525 mg) and 4-(cyclopropylmethoxy)-2-nitrobenzaldehyde (231 mg), and in the same manner as in Example 25, steps D-G, the title compound was obtained as colorless crystals (59.6 mg).

Example 71

N-[(1S)-2-{4-[7-chloro-6-(cyclopropylmethoxy)-2H-indazol-2-yl]phenoxy}-1-methylethyl]acetamide A) 6-(cyclopropylmethoxy)-2-(4-{[tris(1-methylethyl)silyl]oxy}phenyl)-2H-indazole Under a hydrogen atmosphere, a mixture of tris(1-methylethyl)(4-nitrophenoxy)silane (1.50 g), 10% palladium/carbon (containing water (50%), 150 mg) and ethyl acetate (20 mL) was stirred at room temperature for 1 hr. The catalyst was removed by filtration, and the obtained filtrate was concentrated under reduced pressure. A solution of the obtained brown oil and 4-(cyclopropylmethoxy)-2-nitrobenzaldehyde (1.12 g) in ethanol (20 ml) was stirred at 70° C. overnight. The reaction mixture was concentrated under reduced pressure, triethyl phosphite (5 mL) was added thereto, and the mixture was stirred at 130° C. for 4 hr. The reaction mixture was purified by silica gel column chromatography (hexane/ethyl acetate) to give the title compound as a yellow solid (6.53 g).
¹H NMR (300 MHz, CDCl₃) δ 0.36-0.44 (2H, m), 0.61-0.73 (2H, m), 1.09-1.16 (18H, m), 1.24-1.39 (4H, m), 3.87 (2H, d, J=6.8 Hz), 6.84 (1H, dd, J=9.0, 2.3 Hz), 6.93-7.02 (3H, m), 7.56 (1H, d, J=9.0 Hz), 7.64-7.72 (2H, m), 8.20 (1H, s).

B) 7-chloro-6-(cyclopropylmethoxy)-2-(4-{[tris(1-methylethyl)silyl]oxy}phenyl)-2H-indazole A mixture of 6-(cyclopropylmethoxy)-2-(4-[([tris(1-methylethyl)silyl]oxy]phenyl)-2H-indazole (1.23 g), N-chlorosuccinimide (389 mg) and acetic acid (10 mL) was stirred at 100° C. overnight. The reaction mixture was neutralized with saturated aqueous sodium hydrogen carbonate solution, and extracted with ethyl acetate. The separated organic layer was washed with saturated brine, and dried over anhydrous magnesium sulfate, and the solvent was evaporated under reduced pressure. The residue was purified by silica gel column chromatography (hexane/ethyl acetate) to give the title compound as a pale-yellow oil (1.20 g).
¹H NMR (300 MHz, CDCl₃) δ 0.35-0.43 (2H, m), 0.58-0.69 (2H, m), 1.10-1.14 (18H, m), 1.25-1.39 (4H, m), 4.01

(2H, d, J=7.2 Hz), 6.93-7.03 (3H, m), 7.56 (1H, d, J=9.1 Hz), 7.68-7.77 (2H, m), 8.29 (1H, s).

C) 4-[7-chloro-6-(cyclopropylmethoxy)-2H-indazol-2-yl]phenol

To a solution of 7-chloro-6-(cyclopropylmethoxy)-2-(4-{[tris(1-methylethyl)silyl]oxy}phenyl)-2H-indazole (112 mg) in THF (1 mL) was added a THF solution (1.0 M, 0.71 mL) of tetrabutylammonium fluoride at room temperature, and the mixture was stirred for 1 hr. The solvent was evaporated under reduced pressure, water was added to the residue, and the mixture was extracted with ethyl acetate. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as colorless crystals (44.6 mg).
MS (ESI+): [M+H]$^+$ 315.1.

D) N-[(1S)-2-{4-[7-chloro-6-(cyclopropylmethoxy)-2H-indazol-2-yl]phenoxy}-1-methylethyl]acetamide Using 4-[7-chloro-6-(cyclopropylmethoxy)-2H-indazol-2-yl]phenol (43 mg), and in the same manner as in Example 25, steps D and G, the title compound was obtained as colorless crystals (20.4 mg).

Example 72

N-[(1S)-2-{4-[6-(cyclopropylmethoxy)-3-methyl-2H-indazol-2-yl]phenoxy}-1-methylethyl]acetamide A) 6-(cyclopropylmethoxy)-3-methyl-2-(4-{[tris(1-methylethyl)silyl]oxy}phenyl)-2H-indazole To a solution of 6-(cyclopropylmethoxy)-2-(4-{[tris(1-methylethyl)silyl]oxy}phenyl)-2H-indazole (218 mg) in THF (5 mL) was added dropwise a THF solution (1.11 M, 0.59 mL) of lithium diisopropylamide at −78° C. under an argon atmosphere, and the mixture was stirred for 30 min. To the reaction mixture was added methyl iodide (142 mg) at −78° C., and the mixture was stirred for 1.5 hr. Water was added to the reaction mixture, and the mixture was extracted twice with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as a colorless oil (159 mg).
MS (ESI+): [M+H]$^+$ 451.3.

B) N-[(1S)-2-{4-[6-(cyclopropylmethoxy)-3-methyl-2H-indazol-2-yl]phenoxy}-1-methylethyl]acetamide Using 6-(cyclopropylmethoxy)-3-methyl-2-(4-{[tris(1-methylethyl)silyl]oxy}phenyl)-2H-indazole (271 mg), and in the same manner as in Example 71, step C, Example 25, step 0 and step G, the title compound was obtained as colorless crystals (156 mg).

Example 73

N-[(1S)-2-{4-[6-(cyclopropylmethoxy)-3-fluoro-2H-indazol-2-yl]phenoxy}-1-methylethyl]acetamide A) 6-(cyclopropylmethoxy)-3-fluoro-2-(4-{[tris(1-methylethyl)silyl]oxy}phenyl)-2H-indazole To a solution of 6-(cyclopropylmethoxy)-2-(4-{[tris(1-methylethyl)silyl]oxy}phenyl)-2H-indazole (218 mg) in THF (2.5 mL) was added dropwise a THF solution (1.11 M, 0.59 mL) of lithiumdiisopropylamide at −78° C. under an argon atmosphere, and the mixture was stirred for 30 min. To the reaction mixture was added N-fluorobenzenesulfonimide (236 mg) at −78° C., and the mixture was stirred at 0° C. for 1.5 hr. Water was added to the reaction mixture, and the mixture was extracted twice with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as colorless crystals (110 mg).
MS (ESI+): [M+H]$^+$ 455.2.

B) N-[(1S)-2-{4-[6-(cyclopropylmethoxy)-3-fluoro-2H-indazol-2-yl]phenoxy}-1-methylethyl]acetamide Using 6-(cyclopropylmethoxy)-3-fluoro-2-(4-{[tris(1-methylethyl)silyl]oxy}phenyl)-2H-indazole (165 mg), and in the same manner as in Example 71, step C and Example 25, steps D m and G, the title compound was obtained as colorless crystals (97 mg).

Example 74

N-[(1S)-2-{4-[7-bromo-6-(cyclopropylmethoxy)-2H-indazol-2-yl]phenoxy}-1-methylethyl]acetamide A) 7-bromo-6-(cyclopropylmethoxy)-2-(4-{[tris(1-methylethyl)silyl]oxy}phenyl)-2H-indazole To a solution of 6-(cyclopropylmethoxy)-2-(4-{[tris(1-methylethyl)silyl]oxy}phenyl)-2H-indazole (1.31 g) in ethyl acetate (15 mL) were added N-bromosuccinimide (0.56 g) and azobisisobutyronitrile (99 mg), and the mixture was stirred at 80° C. for 3 hr. Water was added to the reaction mixture, and the mixture was extracted twice with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as an orange oil (1.41 g).
$^1$H NMR (300 MHz, CDCl$_3$) δ 0.35-0.45 (2H, m), 0.59-0.69 (2H, m), 1.09-1.16 (18H, m), 1.21-1.41 (4H, m), 4.01 (2H, d, J=6.8 Hz), 6.94 (1H, d, J=9.1 Hz), 6.96-7.03 (2H, m), 7.59 (1H, d, J=9.1 Hz), 7.70-7.78 (2H, m), 8.33 (1H, s).

B) N-[(1S)-2-{4-[7-bromo-6-(cyclopropylmethoxy)-2H-indazol-2-yl]phenoxy}-1-methylethyl]acetamide Using 7-bromo-6-(cyclopropylmethoxy)-2-(4-{[tris(1-methylethyl)silyl]oxy}phenyl)-2H-indazole (920 mg), and in the same manner as in Example 71, step C and Example 25, steps D and G, the title compound was obtained as colorless crystals (585 mg).

Example 75

N-[(1S)-2-{4-[6-(cyclopropylmethoxy)-3-(trifluoromethyl)-2H-indazol-2-yl]phenoxy}-1-methylethyl]acetamide A) 6-(cyclopropylmethoxy)-3-iodo-2-(4-{[tris(1-methylethyl)silyl]oxy}phenyl)-2H-indazole To a solution of 6-(cyclopropylmethoxy)-2-(4-{[tris(1-methylethyl)silyl]oxy}phenyl)-2H-indazole (803 mg) in THF (6 mL) was added dropwise a THF solution (1.11 M, 3.3 mL) of lithiumdiisopropylamide at −78° C. under an argon atmosphere, and the mixture was stirred at 0° C. for 2 hr. To the reaction mixture was added a solution of iodine (933 mg) in THF (3 mL), and the mixture was stirred at 0° C. for 1 hr. To the reaction mixture was added saturated aqueous sodium thiosulfate solution, and the mixture was extracted twice with ethyl acetate. The combined organic layer was washed with saturated brine, and dried over anhydrous magnesium sulfate, and the solvent was evaporated under reduced pressure. The obtained crystals were recrystallized from methanol to give the title compound as colorless crystals (782 mg).

MS (ESI+): [M+H]$^+$ 563.3.

B) methyl ({4-[6-(cyclopropylmethoxy)-3-(trifluoromethyl)-2H-indazol-2-yl]phenoxy}sulfonyl)(difluoro)acetate A mixture of 6-(cyclopropylmethoxy)-3-iodo-2-(4-{[tris(1-methylethyl)silyl]oxy}phenyl)-2H-indazole (500 mg), copper(I) iodide (169 mg), methyl difluoro(fluorosulfonyl)acetate (1.71 g) and DMF (4 mL) was stirred at 80° C. for 1 hr under an argon atmosphere. The reaction mixture was filtered through celite, and the filtrate was concentrated under reduced pressure. Saturated aqueous ammonium chloride solution was added to the residue, and the mixture was extracted twice with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as colorless crystals (365 mg).

MS (ESI+): [M+H]$^+$ 521.0.

C) 4-[6-(cyclopropylmethoxy)-3-(trifluoromethyl)-2H-indazol-2-yl]phenol

To a solution of methyl ({4-[6-(cyclopropylmethoxy)-3-(trifluoromethyl)-2H-indazol-2-yl]phenoxy}sulfonyl)(difluoro)acetate (365 mg) in methanol (4 mL) was added dropwise 27% sodium methoxide methanol solution (1 mL) at room temperature, and the mixture was stirred for 3 hr. The reaction mixture was neutralized with saturated aqueous ammonium chloride solution, and extracted twice with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as a colorless powder (179 mg).

MS (ESI+): [M+H]$^+$ 349.3.

D) N-[(1S)-2-{4-[6-(cyclopropylmethoxy)-3-(trifluoromethyl)-2H-indazol-2-yl]phenoxy}-1-methylethyl]acetamide Using 4-[6-(cyclopropylmethoxy)-3-(trifluoromethyl)-2H-indazol-2-yl]phenol (179 mg), and in the same manner as in Example 25, steps D and G, the title compound was obtained as colorless crystals (117 mg).

Example 76

N-[(1S)-2-{4-[3-cyano-6-(cyclopropylmethoxy)-2H-indazol-2-yl]phenoxy}-1-methylethyl]acetamide

A) 6-(cyclopropylmethoxy)-2-(4-{[tris(1-methylethyl)silyl]oxy}phenyl)-2H-indazole-3-carbonitrile A mixture of 6-(cyclopropylmethoxy)-3-iodo-2-(4-{[tris(1-methylethyl)silyl]oxy}phenyl)-2H-indazole (281 mg), tris(dibenzylideneacetone)dipalladium(0) (92 mg), 1,1'-bis(diphenylphosphino)ferrocene (111 mg), zinc cyanide (88 mg), zinc powder (33 mg) and N,N-dimethylacetamide (3 mL) was stirred at 120° C. for 1.5 hr under an argon atmosphere. The reaction mixture was filtered through silica gel, and the filtrate was concentrated under reduced pressure. To the residue was added water, and the mixture was extracted with ethyl acetate. The combined organic layer was washed three times with saturated brine, and dried over anhydrous magnesium sulfate, and the solvent was evaporated under reduced pressure. The residue was purified by silica gel column chromatography (hexane/ethyl acetate) to give the title compound as colorless crystals (189 mg).

$^1$H NMR (300 MHz, CDCl$_3$) δ 0.36-0.45 (2H, m), 0.64-0.75 (2H, m), 1.10-1.16 (18H, m), 1.23-1.38 (4H, m), 3.88 (2H, d, J=6.8 Hz), 6.99-7.07 (3H, m), 7.07-7.12 (1H, m), 7.63-7.73 (3H, m).

B) N-[(1S)-2-{4-[3-cyano-6-(cyclopropylmethoxy)-2H-indazol-2-yl]phenoxy}-1-methylethyl]acetamide Using 6-(cyclopropylmethoxy)-2-(4-{[tris(1-methylethyl)silyl]oxy}phenyl)-2H-indazole-3-carbonitrile (187 mg), and in the same manner as in Example 71, step C and Example 25, steps D and G, the title compound was obtained as colorless crystals (76.7 mg).

Example 77

N-[(1S)-2-{4-[7-cyano-6-(cyclopropylmethoxy)-2H-indazol-2-yl]phenoxy}-1-methylethyl]acetamide A mixture of N-[(1S)-2-{4-[7-bromo-6-(cyclopropylmethoxy)-2H-indazol-2-yl]phenoxy}-1-methylethyl]acetamide (150 mg), tris(dibenzylideneacetone)dipalladium(0) (45 mg), 1,1'-bis(diphenylphosphino)ferrocene (54.4 mg), zinc cyanide (57.7 mg), zinc powder (10.7 mg) and N,N-dimethylacetamide (3 mL) was stirred at 120° C. for 1.5 hr under an argon atmosphere. The reaction mixture was filtered through silica gel, and the filtrate was concentrated under reduced pressure. To the residue was added water, and the mixture was extracted with ethyl acetate. The combined organic layer was washed three times with saturated brine, and dried over anhydrous magnesium sulfate, and the solvent was evaporated under reduced pressure. The residue was purified by silica gel column chromatography (hexane/ethyl acetate) to give the title compound as colorless crystals (54.5 mg).

Example 78

N-[1S)-2-{4-[6-(cyclopropylmethoxy)-7-methyl-2H-indazol-2-yl]phenoxy}-1-methylethyl]acetamide A mixture of N-[(1S)-2-{4-[7-bromo-6-(cyclopropylmethoxy)-2H-indazol-2-yl]phenoxy}-1-methylethyl]acetamide (200 mg), tetrakis(triphenylphosphine)palladium(0) (101 mg), methylboronic acid (131 mg), aqueous sodium carbonate solution (2M, 0.66 mL) and toluene (1 mL) was stirred at 120° C. for 1 hr under an argon atmosphere. The reaction mixture was purified by silica gel column chromatography (hexane/ethyl acetate), and separated by HPLC (C18, mobile phase: water/acetonitrile (containing 0.1% TFA)). To the obtained fraction was added saturated aqueous sodium hydrogen carbonate solution, and the mixture was extracted with ethyl acetate. The obtained organic layer was dried over anhydrous magnesium sulfate, and concentrated under reduced pressure to give the title compound as colorless crystals (22.5 mg).

Example 79

N-[(1S)-2-{4-[6-(cyclopropylmethoxy)-2H-indazol-2-yl]-2-methylphenoxy}-1-methylethyl]acetamide Using 2-methyl-4-nitrophenol (306 mg), and in the same manner as in Example 25, steps D-G, the title compound was obtained as colorless crystals (115 mg).

Example 80

N-[(1S)-2-{4-[6-(cyclopropylmethoxy)-2H-indazol-2-yl]-3-methylphenoxy}-1-methylethyl]acetamide Using 3-methyl-4-nitrophenol (306 mg), and in the same manner as in Example 25, steps D-G, the title compound was obtained as colorless crystals (137 mg).

Example 81

N-[(1S)-2-{4-[6-(cyclopropylmethoxy)-2H-indazol-2-yl]-3,5-difluorophenoxy}-1-methylethyl]acetamide A) 2,6-difluoro-4-{[tris(1-methylethyl)silyl]oxy}aniline A mixture of 4-amino-3,5-difluorophenol (580 mg), imidazole (354 mg), triisopropylsilane chloride (848 mg) and DMF (12 mL) was stirred at room temperature overnight. The solvent was evaporated under reduced pressure, water was added to the residue, and the mixture was extracted with ethyl acetate. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as a pale-brown oil (1.0 g).
$^1$H NMR (300 MHz, CDCl$_3$) δ 1.06-1.11 (18H, m), 1.14-1.32 (3H, m), 3.38 (2H, brs), 6.28-6.53 (2H, m).

B) N-[(1S)-2-{4-[6-(cyclopropylmethoxy)-2H-indazol-2-yl]-3,5-difluorophenoxy}-1-methylethyl]acetamide Using 2,6-difluoro-4-{[tris(1-methylethyl)silyl]oxy}aniline (1.0 g) and 4-(cyclopropylmethoxy)-2-nitrobenzaldehyde (734 mg), and in the same manner as in Example 25, step F, Example 71, step C and Example 25, steps D and G, the title compound was obtained as colorless crystals (27.6 mg).

Example 82

N-[(1S)-2-{3-chloro-4-[6-(cyclopropylmethoxy)-2H-indazol-2-yl]phenoxy}-1-methylethyl]acetamide Using 4-amino-3-chlorophenol hydrochloride (580 mg) and 4-(cyclopropylmethoxy)-2-nitrobenzaldehyde (353 mg), and in the same manner as in Example 81, step A, Example 25, step F, Example 71, step C and Example 25, steps D and G, the title compound was obtained as colorless crystals (263 mg).

Example 83

N-[(1S)-2-{4-[6-(cyclopropylmethoxy)imidazo[1,2-a]pyridin-2-yl]phenoxy}-1-methylethyl]acetamide A) 2-bromo-5-(cyclopropylmethoxy)pyridine Using 6-bromopyridin-3-ol (5.22 g), and in the same manner as in Example 2, step E, the title compound was obtained as a colorless oil (6.82 g).
MS (ESI+): [M+H]$^+$ 228.1.

3) 5-(cyclopropylmethoxy)pyridin-2-amine

A mixture of 2-bromo-5-(cyclopropylmethoxy)pyridine (5.65 g), tris(dibenzylideneacetone)dipalladium(0) (454 mg), 1,1'-binaphthalene-2,2'-diylbis(diphenylphosphine) (925 mg), 1,1-diphenylmethanimine (5.42 g), sodium t-butoxide (3.33 g) and toluene (50 mL) was stirred at 80° C. for 3 hr under an argon atmosphere. The reaction mixture was concentrated under reduced pressure, and the residue was diluted with THF (15 mL). 1M Hydrochloric acid (15 mL) was added thereto, and the mixture was stirred at room temperature for 30 min. 6M Hydrochloric acid (6 mL) was added thereto, and the organic layer was separated from the aqueous layer. The separated organic layer was extracted with 1M hydrochloric acid. The combined aqueous layer was neutralized with 8M aqueous sodium hydroxide solution, and extracted twice with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate), and recrystallized (hexane/diethyl ether) to give the title compound as colorless crystals (3.67 g).
MS (ESI+): [M+H]$^+$ 165.1.

C) 4-[6-(cyclopropylmethoxy)imidazo[1,2-a]pyridin-2-yl]phenol

A mixture of 5-(cyclopropylmethoxy)pyridin-2-amine (328 mg), 2-bromo-1-(4-hydroxyphenyl)ethanone (430 mg) and ethanol (10 mL) was stirred at 80° C. for 4 hr. The reaction mixture was allowed to cool to room temperature, and the resulting crystals were collected by filtration. The obtained crystals were dissolved in saturated aqueous sodium hydrogen carbonate solution and THF, and the solution was extracted twice with ethyl acetate. The combined organic layer was washed with saturated brine, and dried over anhydrous magnesium sulfate, and the solvent was evaporated under reduced pressure to give the title compound as a brown solid (561 mg).
MS (ESI+): [M+H]$^+$ 281.2.

D) N-[(1S)-2-{4-[6-(cyclopropylmethoxy)imidazo[1,2-a]pyridin-2-yl]phenoxy}-1-methylethyl]acetamide Using 4-[6-(cyclopropylmethoxy)imidazo[1,2-a]pyridin-2-yl]phenol (561 mg), and in the same manner as in Example 25, steps D and G, the title compound was obtained as colorless crystals (39.8 mg).

Example 84

N-[(1S)-2-{4-[6-(cyclopropylmethoxy)pyrazolo[1,5-a]pyridin-2-yl]phenoxy}-1-methylethyl]acetamide

A) tert-butyl [(1S)-2-(4-iodophenoxy)-1-methylethyl]carbamate

Using 4-iodophenol (5.50 g), and in the same manner as in Example 1, step B, the title compound was obtained as colorless crystals (4.71 g).

MS (ESI+): [M+H-Boc]$^+$ 278.0.

B) 5-(cyclopropylmethoxy)-2-[(trimethylsilyl)ethynyl]pyridine

A mixture of 2-bromo-5-(cyclopropylmethoxy)pyridine (1.145 g), bis(triphenylphosphine)palladium(II) dichloride (175 mg), copper(I) iodide (48 mg), trimethylsilylacetylene (737 mg), triethylamine (759 mg) and DMF (15 mL) was stirred at room temperature overnight under an argon atmosphere. The reaction mixture was concentrated under reduced pressure, and the residue was diluted with ethyl acetate and water, and the mixture was filtered through celite. The aqueous layer was separated from the organic layer. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as a yellow oil (774 mg).

MS (ESI+): [M+H]$^+$ 246.1.

C) 5-(cyclopropylmethoxy)-2-ethynylpyridine

To a solution of 5-(cyclopropylmethoxy)-2-[(trimethylsilyl)ethynyl]pyridine (773 mg) in THF (15 mL) was added a THF solution (1.0 M, 4.1 mL) of tetrabutylammonium fluoride at room temperature, and the reaction mixture was concentrated under reduced pressure. The residue was diluted with ethyl acetate and water, and the aqueous layer was separated from the organic layer. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as a colorless oil (591 mg).

MS (ESI+): [M+H]$^+$ 174.2.

D) tert-butyl [(1S)-2-(4-{[5-(cyclopropylmethoxy)pyridin-2-yl]ethynyl}phenoxy)-1-methylethyl]carbamate A mixture of 5-(cyclopropylmethoxy)-2-ethynylpyridine (591 mg), tert-butyl [(1S)-2-(4-iodophenoxy)-1-methylethyl]carbamate (1.67 g), bis(triphenylphosphine)palladium (II) dichloride (120 mg), copper(I) iodide (32.5 mg), triethylamine (518 mg) and DMF (10 mL) was stirred at 60° C. overnight under an argon atmosphere. The reaction mixture was concentrated under reduced pressure, and the residue was diluted with ethyl acetate and water, filtered through celite, and the aqueous layer was separated from the organic layer. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as a yellow solid (1.40 g).

MS (ESI+): [M+H]$^+$ 423.2.

E) tert-butyl [(1S)-2-{4-[6-(cyclopropylmethoxy)pyrazolo[1,5-a]pyridin-2-yl]phenoxy}-1-methylethyl]carbamate (Aminooxy)(hydroxy)sulfane dioxide (679 mg) was dissolved in water (3 mL), and saturated aqueous sodium hydrogen carbonate solution was added dropwise thereto at 0° C. to neutralize the solution. To the obtained mixture was added a solution of tert-butyl [(1S)-2-(4-{[5-(cyclopropylmethoxy)pyridin-2-yl]ethynyl}phenoxy)-1-methylethyl]carbamate (845 mg) in methanol (5 mL) at room temperature, and the mixture was stirred at 60° C. overnight, and concentrated under reduced pressure. To the residue were added DMF (8 mL) and potassium carbonate (829 mg), and the mixture was stirred at room temperature for 4 hr. The reaction mixture was concentrated under reduced pressure, the residue was diluted with ethyl acetate and water, and the aqueous layer was separated from the organic layer. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as a colorless solid (134 mg).

MS (ESI+): [M+H]$^+$ 438.2.

F) N-[(1S)-2-{4-[6-(cyclopropylmethoxy)pyrazolo[1,5-a]pyridin-2-yl]phenoxy}-1-methylethyl]acetamide Using tert-butyl [(1S)-2-{4-[6-(cyclopropylmethoxy)pyrazolo[1,5-a]pyridin-2-yl]phenoxy}-1-methylethyl]carbamate (134 mg), and in the same manner as in Example 25, step G, the title compound was obtained as colorless crystals (89.8 mg).

Example 85

N-{(1S)-2-[4-(6-ethoxypyrazolo[1,5-a]pyridin-2-yl)phenoxy]-1-methylethyl}acetamide

A) 5-ethoxy-2-[(trimethylsilyl)ethynyl]pyridine

Using 6-bromopyridin-3-ol (3.48 g), and in the same manner as in Example 25, step A and Example 84, step B, the title compound was obtained as a yellow oil (2.74 g).

MS (ESI+): [M+H]$^+$ 220.1.

B) 5-ethoxy-2-ethynylpyridine

To a solution of 5-ethoxy-2-[(trimethylsilyl)ethynyl]pyridine (2.74 g) in methanol (40 mL) was added 8M aqueous sodium hydroxide solution (3.73 mL) at room temperature, and the reaction mixture was concentrated under reduced pressure. The residue was diluted with ethyl acetate and water, and the aqueous layer was separated from the organic layer. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as a pale-brown powder (1.72 g).
MS (ESI+): [M+H]$^+$ 148.3.

C) tert-butyl [(1S)-2-{4-[(5-ethoxypyridin-2-yl)ethynyl]phenoxy}-1-methylethyl]carbamate Using 5-ethoxy-2-ethynylpyridine (1.63 g), and in the same manner as in Example 84, step D, the title compound was obtained as a yellow powder (2.22 g).
MS (ESI+): [M+H]$^+$ 397.3.

D) tert-butyl {(1S)-2-[4-(6-ethoxypyrazolo[1,5-a]pyridin-2-yl)phenoxy]-1-methylethyl}carbamate To a solution of tert-butyl [(1S)-2-{4-[(5-ethoxypyridin-2-yl)ethynyl]phenoxy}-1-methylethyl]carbamate (2.25 g) in THF (30 mL) was added 2-[(aminooxy)sulfonyl]-1,3,5-trimethylbenzene (1.75 g, containing water) at room temperature, and the mixture was stirred for 1 hr, and concentrated under reduced pressure. To the residue were added DMF (20 mL) and potassium carbonate (1.18 g), and the mixture was stirred at room temperature for 2 hr. The reaction mixture was concentrated under reduced pressure, and the residue was diluted with ethyl acetate and water, and the aqueous layer was separated from the organic layer. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as colorless crystals (1.18 g).
MS (ESI+): [M+H]$^+$ 412.3.

E) N-{(1S)-2-[4-(6-ethoxypyrazolo[1,5-a]pyridin-2-yl)phenoxy]-1-methylethyl}acetamide Using tert-butyl {(1S)-2-[4-(6-ethoxypyrazolo[1,5-a]pyridin-2-yl)phenoxy]-1-methylethyl}carbamate (200 mg), and in the same manner as in Example 25, step G, the title compound was obtained as colorless crystals (75 mg).

Example 86

N-{(1S)-2-[4-(6-ethoxy-3-fluoropyrazolo[1,5-a]pyridin-2-yl)phenoxy]-1-methylethyl}acetamide A) tert-butyl {(1S)-2-[4-(6-ethoxy-3-fluoropyrazolo[1,5-a]pyridin-2-yl)phenoxy]-1-methylethyl}carbamate A mixture of tert-butyl {(1S)-2-[4-(6-ethoxypyrazolo[1,5-a]pyridin-2-yl)phenoxy]-1-methylethyl}carbamate (400 mg), 1,1'-difluoro-2,2'-bipyridinium bis(tetrafluoroborate) (358 mg) and acetonitrile (3 mL) was stirred at room temperature for 3 hr. The reaction mixture was neutralized with saturated aqueous sodium hydrogen carbonate solution, and extracted with ethyl acetate. The separated organic layer was washed with water and saturated brine, and dried over anhydrous magnesium sulfate, and the solvent was evaporated under reduced pressure. The residue was purified by silica gel column chromatography (hexane/ethyl acetate) to give the title compound as colorless crystals (129 mg).
$^1$H NMR (300 MHz, CDCl$_3$) δ 1.31 (3H, d, J=6.8 Hz), 1.41-1.51 (12H, m), 3.92-4.14 (5H, m), 4.78 (1H, brs), 6.88 (1H, dd, J=9.6, 2.1 Hz), 6.95-7.03 (2H, m), 7.36 (1H, d, J=9.4 Hz), 7.87 (1H, s), 7.88-7.95 (2H, m).

B) N-{(1S)-2-[4-(6-ethoxy-3-fluoropyrazolo[1,5-a]pyridin-2-yl)phenoxy]-1-methylethyl}acetamide Using tert-butyl {(1S)-2-[4-(6-ethoxy-3-fluoropyrazolo[1,5-a]pyridin-2-yl)phenoxy]-1-methylethyl}carbamate (128 mg), and in the same manner as in Example 25, step G, the title compound was obtained as colorless crystals (66 mg).

Example 87

1-[(1S)-2-({6-[6-(3,3-difluorobutoxy)-1,3-benzoxazol-2-yl]-5-fluoropyridin-3-yl}oxy)-1-methylethyl]urea Using tert-butyl [(1S)-2-({6-[6-(3,3-difluorobutoxy)-1,3-benzoxazol-2-yl]-5-fluoropyridin-3-yl}oxy)-1-methylethyl]carbamate, and in the same manner as in Example 22, the title compound was obtained.

Example 88

N-{(1S)-2-[4-(6-ethoxy-7-fluoropyrazolo[1,5-a]pyridin-2-yl)phenoxy]-1-methylethyl}acetamide A) tert-butyl {(1S)-2-[4-(6-ethoxy-7-fluoropyrazolo[1,5-a]pyridin-2-yl)phenoxy]-1-methylethyl}carbamate To a solution of tert-butyl {(1S)-2-[4-(6-ethoxypyrazolo[1,5-a]pyridin-2-yl)phenoxy]-1-methylethyl}carbamate (580 mg) in THF (10 mL) was added dropwise a hexane solution (1.6 M, 2.2 mL) of n-butyllithium at −78° C. under an argon atmosphere, and the mixture was stirred for 1.5 hr. To the reaction mixture was added N-fluorobenzenesulfonimide (578 mg) at −78° C., and the mixture was stirred at room temperature for 1 hr. Water was added to the reaction mixture, and the mixture was extracted twice with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as a pale-yellow solid (187 mg).
MS (ESI+): [M+H]$^+$ 430.3.

B) N-{(1S)-2-[4-(6-ethoxy-7-fluoropyrazolo[1,5-a]pyridin-2-yl)phenoxy]-1-methylethyl}acetamide Using tert-butyl {(1S)-2-[4-(6-ethoxy-7-fluoropyrazolo[1,5-a]pyridin-2-yl)phenoxy]-1-methylethyl}carbamate (187 mg), and in the same manner as in Example 25, step G, the title compound was obtained as colorless crystals (108 mg).

Example 89

N-[(1S)-2-{4-[6-(cyclopropylmethoxy)[1,2,4]triazolo[1,5-a]pyridin-2-yl]phenoxy}-1-methylethyl]acetamide A) 2-[4-(benzyloxy)phenyl]-6-(cyclopropylmethoxy)[1,2,4]triazolo[1,5-a]pyridine (Aminooxy)(hydroxy)sulfane dioxide (3.39 g) was dissolved in water (10 mL), and saturated aqueous sodium hydrogen carbonate solution was added dropwise thereto at 0° C. to neutralize the solution. To the obtained mixture was added a solution of 5-(cyclopropylmethoxy)pyridin-2-amine (1.64 g) in ethanol (25 ml) at 0° C., and the mixture was stirred at 70° C. for 3 days. To the reaction mixture were added 4-(benzyloxy)benzaldehyde (2.12 g) and potassium carbonate (4.15 g), and the mixture was stirred at 70° C. for 2 hr. The reaction mixture was concentrated under reduced pressure, and the residue was diluted with ethyl acetate and water, and the aqueous layer was separated from the organic layer. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as a yellow solid (134 mg).

MS (ESI+): [M+H]$^+$ 372.2.

B) N-[(1S)-2-{4-[6-(cyclopropylmethoxy)[1,2,4]triazolo[1,5-a]pyridin-2-yl]phenoxy}-1-methylethyl]acetamide Using 2-[4-(benzyloxy)phenyl]-6-(cyclopropylmethoxy)[1,2,4]triazolo[1,5-a]pyridine (453 mg), and in the same manner as in Example 12, step C and Example 25, steps D and G, the title compound was obtained as colorless crystals (124 mg).

Example 90

N-[(1S)-2-({6-[6-(cyclopropylmethoxy)[1,2,4]triazolo[1,5-a]pyridin-2-yl]pyridin-3-yl}oxy)-1-methylethyl]acetamide A) methyl 5-({(2S)-2-[(tert-butoxycarbonyl)amino]propyl}oxy)pyridine-2-carboxylate Using methyl 5-hydroxypyridine-2-carboxylate (2.60 g), and in the same manner as in Example 1, step B, the title compound was obtained as a white solid (4.78 g).

MS (ESI+): [M+H]$^+$ 311.2.

B) tert-butyl {(1S)-2-[(6-formylpyridin-3-yl)oxy]-1-methylethyl}carbamate

To a solution of methyl 5-({(2S)-2-[(tert-butoxycarbonyl)amino]propyl}oxy)pyridine-2-carboxylate (4.78 g) in THF (75 mL) was added a toluene solution (1.0 M, 30.8 mL) of diisobutylaluminum hydride at −78° C., and the mixture was stirred at −20° C. for 2 hr under an argon atmosphere. Sodium sulfate decahydrate (22.7 g) was added thereto at −78° C., and the mixture was stirred at room temperature overnight. The reaction mixture was filtered through celite, and the solvent of the filtrate was evaporated under reduced pressure to give the title compound as a pale-yellow solid (4.30 g).

MS (ESI+): [M+H]$^+$ 281.2.

C) tert-butyl [(1S)-2-({6-[6-(cyclopropylmethoxy)[1,2,4]triazolo[1,5-a]pyridin-2-yl]pyridin-3-yl}oxy)-1-methylethyl]carbamate To a solution of 5-(cyclopropylmethoxy)pyridin-2-amine (821 mg) in THF (30 mL) was added 2-[(aminooxy)sulfonyl]-1,3,5-trimethylbenzene (800 mg, containing water) at room temperature, and the mixture was stirred overnight and concentrated under reduced pressure. To the residue were added DMF (20 mL), tert-butyl {(1S)-2-[(6-formylpyridin-3-yl)oxy]-1-methylethyl}carbamate (1.40 g) and potassium carbonate (1.04 g), and the mixture was stirred at 60° C. for 3 days. The reaction mixture was concentrated under reduced pressure, and the residue was diluted with ethyl acetate and water, and the aqueous layer was separated from the organic layer. The separated aqueous layer was extracted again with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate) to give the title compound as a colorless solid (700 mg).

MS (ESI+): [M+H]$^+$ 440.2.

D) (2S)-1-({6-[6-(cyclopropylmethoxy)[1,2,4]triazolo[1,5-a]pyridin-2-yl]pyridin-3-yl}oxy)propan-2-amine Using tert-butyl [(1S)-2-({6-[6-(cyclopropylmethoxy)[1,2,4]triazolo[1,5-a]pyridin-2-yl]pyridin-3-yl}oxy)-1-methylethyl]carbamate (700 mg), and in the same manner as in Example 67, step C, the title compound was obtained as a yellow gum (491 mg).

MS (ESI+): [M+H]$^+$ 340.1.

E) N-[(1S)-2-({6-[6-(cyclopropylmethoxy)[1,2,4]triazolo[1,5-a]pyridin-2-yl]pyridin-3-yl}oxy)-1-methylethyl]acetamide Using (2S)-1-({6-[6-(cyclopropylmethoxy)[1,2,4]triazolo[1,5-a]pyridin-2-yl]pyridin-3-yl}oxy)propan-2-amine (245 mg), and in the same manner as in Example 67, step D, the title compound was obtained as colorless crystals (224 mg).

Example 91

1-[(1S)-2-({6-[6-(cyclopropylmethoxy)[1,2,4]triazolo[1,5-a]pyridin-2-yl]pyridin-3-yl}oxy)-1-methylethyl]urea Using (2S)-1-({6-[6-(cyclopropylmethoxy)[1,2,4]triazolo[1,5-a]pyridin-2-yl]pyridin-3-yl}oxy)propan-2-amine (245 mg), and in the same manner as in Example 68, the title compound was obtained as colorless crystals (157 mg).

Example 92

N-[(1S)-2-{4-[6-(cyclopropylmethoxy)-3-fluoroimidazo[1,2-a]pyridin-2-yl]phenoxy}-1-methylethyl]acetamide A) 4-[6-(cyclopropylmethoxy)imidazo[1,2-a]pyridin-2-yl]phenyl acetate Using 4-[6-(cyclopropylmethoxy)imidazo[1,2-a]pyridin-2-yl]phenol (487 mg), and in the same manner as in Example 67, step D, the title compound was obtained as a pale-brown powder (494 mg).

MS (ESI+): [M+H]$^+$ 323.2.

B) 4-[6-(cyclopropylmethoxy)-3-fluoroimidazo[1,2-a]pyridin-2-yl]phenol

A mixture of 4-[6-(cyclopropylmethoxy)imidazo[1,2-a]pyridin-2-yl]phenyl acetate (425 mg), 2,6-dichloro-1-fluoropyridinium trifluoromethanesulfonate (1.25 g) and acetonitrile (6 mL) was stirred at room temperature for 4 hr. To the reaction mixture was added saturated aqueous sodium hydrogen carbonate solution, and the mixture was extracted twice with ethyl acetate. The combined organic layer was washed with saturated brine, and dried over anhydrous magnesium sulfate, and the solvent was evaporated under reduced pressure. The residue was purified by silica gel column chromatography (hexane/ethyl acetate), and the obtained compound was dissolved in methanol (6 mL). 1M Aqueous sodium hydroxide solution (0.66 mL) was added at room temperature, and the mixture was stirred for 1 hr, and concentrated under reduced pressure. The residue was diluted with ethyl acetate and water, and the mixture was neutralized with 1M hydrochloric acid, and the aqueous layer was separated from the organic layer. The separated aqueous layer was extracted again with ethyl acetate. The combined organic layer was washed with saturated brine, and dried over anhydrous magnesium sulfate, and the solvent was evaporated under reduced pressure. The residue was purified by basic silica gel column chromatography (hexane/ethyl acetate) to give the title compound as a pale-brown powder (54 mg).

MS (ESI+): [M+H]$^+$ 299.2.

C) N-[(1S)-2-{4-[6-(cyclopropylmethoxy)-3-fluoroimidazo[1,2-a]pyridin-2-yl]phenoxy}-1-methylethyl]acetamide Using 4-[6-(cyclopropylmethoxy)-3-fluoroimidazo[1,2-a]pyridin-2-yl]phenol (53.6 mg), and in the same manner as in Example 25, steps D and G, the title compound was obtained as a dark-yellow solid (9.4 mg).

Example 93

N-{(1S)-2-[4-(6-ethoxypyrazolo[1,5-a]pyridin-2-yl)-3-fluorophenoxy]-1-methylethyl}acetamide Using 4-bromo-3-fluorophenol (5.0 g) and 2-bromo-5-ethoxypyridine (2.74 g), and in the same manner as in Example 1, step B, Example 84, step B, Example 85, step B, Example 84, step D, Example 85, step D and Example 25, step G, the title compound was obtained as pale-pink crystals (91.4 mg).

Example 94

N-[(1S)-2-({6-[7-(cyclopropylmethoxy)[1,2,4]triazolo[1,5-a]pyridin-2-yl]pyridin-3-yl}oxy)-1-methylethyl]acetamide Using 4-(benzyloxy)pyridin-2-amine (360 mg), and in the same manner as in Example 90, step C, Example 12, step C, Example 2, step E and Example 25, step G, the title compound was obtained as colorless crystals (42.9 mg).

Example 95

N-[(1S)-2-{4-[7-(cyclopropylmethoxy) [1,2,4]triazolo[1,5-a]pyridin-2-yl]phenoxy}-1-methylethyl] acetamide

A) methyl 4-({(2S)-2-[(tert-butoxycarbonyl)amino]propyl}oxy)benzoate

Using methyl 4-hydroxybenzoate (1.52 g), and in the same manner as in Example 1, step B, the title compound was obtained as a colorless solid (2.36 g).

$^1$H NMR (300 MHz, CDCl$_3$) δ 1.30 (3H, d, J=6.4 Hz), 1.45 (9H, s), 3.89 (3H, s), 3.98 (2H, d, J=4.2 Hz), 4.07 (1H, brs), 4.71 (1H, brs), 6.78-7.01 (2H, m), 7.84-8.14 (2H, m).

B) tert-butyl [(1S)-2-(4-formylphenoxy)-1-methylethyl]carbamate

To a solution of methyl 4-({(2S)-2-[(tert-butoxycarbonyl)amino]propyl}oxy)benzoate (816 mg) in THF (10 mL) was added a toluene solution (1.0 M, 5.28 mL) of diisobutylaluminum hydride at −78° C., and the mixture was stirred at room temperature for 30 min under an argon atmosphere. Sodium sulfate decahydrate (22.7 g) was added thereto at −78° C., and the mixture was stirred at room temperature for 3 hr. The reaction mixture was filtered through celite, and the solvent of the filtrate was evaporated under reduced pressure to give a mixture of tert-butyl {(1S)-2-[4-(hydroxymethyl)phenoxy]-1-methylethyl}carbamate and methyl 4-({(2S)-2-[(tert-butoxycarbonyl)amino]propyl}oxy)benzoate as a pale-yellow oil (813 mg). A mixture of the aforementioned mixture (813 mg) of tert-butyl {(1S)-2-[4-(hydroxymethyl)phenoxy]-1-methylethyl}carbamate and methyl 4-({(2S)-2-[(tert-butoxycarbonyl)amino]propyl}oxy)benzoate, sulfur trioxide pyridine complex (657 mg), DMSO (7 mL) and triethylamine (3 mL) was stirred at room temperature for 2 hr. Water was added to the reaction mixture, and the mixture was extracted twice with ethyl acetate. The combined organic layer was washed with water and saturated brine, and dried over anhydrous magnesium sulfate, and the solvent was evaporated under reduced pressure. The residue was purified by silica gel column chromatography (hexane/ethyl acetate) to give the title compound as a colorless oil (504 mg).

$^1$H NMR (300 MHz, CDCl$_3$) δ 1.31 (3H, d, J=6.8 Hz), 1.45 (9H, s), 3.95-4.13 (3H, m), 4.70 (1H, brs), 6.97-7.08 (2H, m), 7.79-7.88 (2H, m), 9.89 (1H, s).

C) N-[(1S)-2-{4-[7-(cyclopropylmethoxy)[1,2,4]triazolo[1,5-a]pyridin-2-yl]phenoxy}-1-methylethyl] acetamide Using tert-butyl [(1S)-2-(4-formylphenoxy)-1-methylethyl]carbamate (502 mg) and 4-(benzyloxy)pyridin-2-amine (360 mg), and in the same manner as in Example 90, step C, Example 12, step C, Example 2, step E and Example 25, step G, the title compound was obtained as colorless crystals (53.6 mg).

Example 96

N-{(1S)-2-[(6-{6-[(2,2-difluorocyclopropyl)methoxy]-1,3-benzoxazol-2-yl}-5-fluoropyridin-3-yl)oxy]-1-methylethyl}acetamide

A) (2,2-difluorocyclopropyl)methyl methanesulfonate

Methanesulfonyl chloride (1.43 mL) was added to a solution of (2,2-difluorocyclopropyl)methanol (1.00 g) and triethylamine (2.58 mL) in THF (10 mL) dropwise at 0° C. The mixture was stirred at room temperature overnight. Water was added, and the mixture was extracted with ethyl acetate. The organic layer was washed with brine, dried over anhydrous magnesium sulfate and concentrated in vacuo. The residue was purified by silica gel column chromatography (hexane/ethyl acetate) to give the title compound (1.47 g) as a colorless oil.

$^1$H NMR (300 MHz, CDCl$_3$) δ 1.24-1.43 (1H, m), 1.57-1.79 (1H, m), 1.96-2.24 (1H, m), 3.05 (3H, s), 4.16-4.45 (2H, m).

B) tert-butyl {(1S)-2-[(6-{6-[(2,2-difluorocyclopropyl)methoxy]-1,3-benzoxazol-2-yl}-5-fluoropyridin-3-yl)oxy]-1-methylethyl}carbamate Triethylamine (14.1 mL) was added to a solution of hexachloroethane (7.46 g) and triphenylphosphine (9.91 g) in acetonitrile (50 mL) at room temperature, and the mixture was stirred at room temperature for 10 min. Then a mixture of tert-butyl [(1S)-2-({6-[(2,4-dihydroxyphenyl)carbamoyl]-5-fluoropyridin-3-yl}oxy)-1-methylethyl]carbamate (5.31 g) and acetonitrile (50 mL) was added, and the mixture was stirred at room temperature for 2 hr. Water was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) to give tert-butyl [(1S)-2-{[5-fluoro-6-(6-hydroxy-1,3-benzoxazol-2-yl)pyridin-3-yl]oxy}-1-methylethyl]carbamate (10.7 g) as a mixture with impurities. A mixture of [(1S)-2-{[5-fluoro-6-(6-hydroxy-1,3-benzoxazol-2-yl)pyridin-3-yl]oxy}-1-methylethyl]carbamate (4.28 g, a mixture with impurities), (2,2-difluorocyclopropyl)methyl methanesulfonate (0.494 g), potassium carbonate (0.367 g), and DMF (30 mL) was stirred at 60° C. for 1 hr. Then additional (2,2-difluorocyclopropyl)methyl methanesulfonate (0.494 g) and potassium carbonate (0.367 g) were added, and the mixture was stirred at 60° C. for 1 hr. Then additional (2,2-difluorocyclopropyl)methyl methanesulfonate (0.494 g) and potassium carbonate (0.367 g) were added, and the mixture was stirred at 60° C. for 1 hr. Water was added, and the mixture was extracted with ethyl acetate. The organic layer was separated, washed with brine, dried over anhydrous magnesium sulfate and concentrated under reduced pressure. The residue was purified by silica gel column chromatography (hexane/ethyl acetate) to give the title compound (1.39 g) as a pale yellow solid.

MS (ESI+): [M+H]$^+$ 494.2.

C) N-{(1S)-2-[(6-{6-[(2,2-difluorocyclopropyl)methoxy]-1,3-benzoxazol-2-yl}-5-fluoropyridin-3-yl)oxy]-1-methylethyl}acetamide A mixture of tert-butyl {(1S)-2-[(6-{6-[(2,2-difluorocyclopropyl)methoxy]-1,3-benzoxazol-2-yl}-5-fluoropyridin-3-yl)oxy]-1-methylethyl}carbamate (690 mg), 4 M hydrogen chloride/ethyl acetate (10 mL), and ethyl acetate (10 mL) was stirred at room temperature overnight. The mixture was concentrated under reduced pressure. The residue was mixed with pyridine (10 mL) and acetic anhydride (5 mL). The mixture was stirred at room temperature overnight. 1 M hydrochloric acid was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) and recrystallization (ethyl acetate) to give the title compound (496 mg) as white crystals.

$^1$H NMR (300 MHz, DMSO-d$_6$) δ 1.18 (3H, d, J=6.3 Hz), 1.40-1.60 (1H, m), 1.66-1.81 (1H, m), 1.82 (3H, s), 2.18-2.41 (1H, m), 3.95-4.33 (5H, m), 7.07 (1H, dd, J=8.8, 2.4 Hz), 7.49 (1H, d, J=2.4 Hz), 7.69-7.82 (2H, m), 8.00 (1H, d, J=6.8 Hz), 8.34-8.43 (1H, m).

mp 163-164° C.

Example 97

1-{(1S)-2-[(6-{(6-[(2,2-difluorocyclopropyl)methoxy]-1,3-benzoxazol-2-yl}-5-fluoropyridin-3-yl)oxy]-1-methylethyl}urea A mixture of tert-butyl {(1S)-2-[(6-{6-[(2,2-difluorocyclopropyl)methoxy]-1,3-benzoxazol-2-yl}-5-fluoropyridin-3-yl)oxy]-1-methylethyl}carbamate (690 mg), 4 M hydrogen chloride/ethyl acetate (10 mL), and ethyl acetate (10 mL) was stirred at room temperature overnight. The mixture was concentrated under reduced pressure. The residue was mixed with THF (10 mL) and triethylamine (1.559 mL), and then trimethylsilyl isocyanate (193 mg) was added. The mixture was stirred at room temperature overnight. Water was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate/methanol) and recrystallization (ethyl acetate) to give the title compound (315 mg) as pale yellow crystals.

$^1$H NMR (300 MHz, DMSO-d$_6$) δ 1.10-1.19 (3H, m), 1.43-1.61 (1H, m), 1.65-1.87 (1H, m), 2.15-2.38 (1H, m), 3.76-4.43 (5H, m), 5.50 (2H, s), 6.12 (1H, d, J=7.4 Hz), 7.07 (1H, dd, J=8.7, 2.4 Hz), 7.49 (1H, d, J=2.4 Hz), 7.67-7.87 (2H, m), 8.32-8.46 (1H, m).

Example 98

N-{(1S)-2-[(6-{6-[2-(2,2-difluorocyclopropyl)ethoxy]-1,3-benzoxazol-2-yl}-5-fluoropyridin-3-yl)oxy]-1-methylethyl}acetamide A) 2-(2,2-difluorocyclopropyl)ethyl methanesulfonate Methanesulfonyl chloride (1.35 mL) was added to a solution of 2-(2,2-difluorocyclopropyl)ethanol (1.42 g) and triethylamine (3.24 mL) in THF (20 mL) dropwise at 0° C. The mixture was stirred at room temperature overnight. Water was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) to give the title compound (1.31 g) as a pale yellow oil.

$^1$H NMR (300 MHz, DMSO-d$_6$) δ 1.17-1.30 (1H, m), 1.44-1.98 (4H, m), 3.19 (3H, s), 4.16-4.36 (2H, m).

B) tert-butyl {(1S)-2-[(6-{6-[2-(2,2-difluorocyclopropyl)ethoxy]-1,3-benzoxazol-2-yl}-5-fluoropyridin-3-yl)oxy]-1-methylethyl}carbamate Triethylamine (14.1 mL) was added to a solution of hexachloroethane (7.46 g) and triphenylphosphine (9.91 g) in acetonitrile (50 mL) at room temperature, and the mixture was stirred at room temperature for 10 min. Then a mixture of tert-butyl [(1S)-2-({6-[(2,4-dihydroxyphenyl)carbamoyl]-5-fluoropyridin-3-yl}oxy)-1-methylethyl]carbamate (5.31 g) and acetonitrile (50 mL) was added, and the mixture was stirred at room temperature for 2 hr. Water was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) to give tert-butyl [(1S)-2-{[5-fluoro-6-(6-hydroxy-1,3-benzoxazol-2-yl)pyridin-3-yl]oxy}-1-methylethyl]carbamate (10.7 g) as a mixture with impurities. A mixture of tert-butyl [(1S)-2-{[5-fluoro-6-(6-hydroxy-1,3-benzoxazol-2-yl)pyridin-3-yl]oxy}-1-methylethyl]carbamate (4.28 g, a mixture with impurities), 2-(2,2-difluorocyclopropyl)ethyl methanesulfonate (0.531 g), potassium carbonate (0.367 g), and DMF (30 mL) was stirred at 60° C. for 1 hr. Then additional 2-(2,2-difluorocyclopropyl)ethyl methanesulfonate (0.531 g) and potassium carbonate (0.367 g) were added, and the mixture was stirred at 60° C. for 1 hr. Then additional 2-(2,2-difluorocyclopropyl)ethyl methanesulfonate (1.06 g) and potassium carbonate (0.733 g) were added, and the mixture was stirred at 60° C. for 1 hr. Water was added, and the mixture was extracted with ethyl acetate. The organic layer was separated, washed with brine, dried over anhydrous magnesium sulfate and concentrated under reduced pressure. The residue was purified by silica gel column chromatography (hexane/ethyl acetate) to give the title compound (1.83 g) as a colorless oil.

MS (ESI+): [M+H]$^+$ 508.1.

C) N-{(1S)-2-[(6-{6-[2-(2,2-difluorocyclopropyl)ethoxy]-1,3-benzoxazol-2-yl}-5-fluoropyridin-3-yl)oxy]-1-methylethyl}acetamide A mixture of tert-butyl {(1S)-2-[(6-{6-[2-(2,2-difluorocyclopropyl)ethoxy]-1,3-benzoxazol-2-yl}-5-fluoropyridin-3-yl)oxy]-1-methylethyl}carbamate (910 mg), 4 M hydrogen chloride/ethyl acetate (10 mL), and ethyl acetate (10 mL) was stirred at room temperature overnight. The mixture was concentrated under reduced pressure. The residue was mixed with pyridine (10 mL) and acetic anhydride (5 mL). The mixture was stirred at room temperature overnight. 1 M hydrochloric acid was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) and recrystallization (ethyl acetate/hexane) to give the title compound (475 mg) as white crystals.

$^1$H NMR (300 MHz, DMSO-d$_6$) δ 1.13-1.39 (4H, m), 1.48-1.69 (1H, m), 1.73-2.10 (6H, m), 3.94-4.27 (5H, m), 7.05 (1H, dd, J=8.8, 2.4 Hz), 7.46 (1H, d, J=2.3 Hz), 7.67-7.86 (2H, m), 7.99 (1H, d, J=6.9 Hz), 8.33-8.44 (1H, m).

Example 99

1-{(1S)-2-[(6-{6-[2-(2,2-difluorocyclopropyl)ethoxy]-1,3-benzoxazol-2-yl}-5-fluoropyridin-3-yl)oxy]-1-methylethyl}urea A mixture of tert-butyl {(1S)-2-[(6-{6-[2-(2,2-difluorocyclopropyl)ethoxy]-1,3-benzoxazol-2-yl}-5-fluoropyridin-3-yl)oxy]-1-methylethyl}carbamate (910 mg), 4 M hydrogen chloride/ethyl acetate (10 mL), and EtOAc (10 mL) was stirred at room temperature overnight. The mixture was concentrated under reduced pressure. The residue was mixed with THF (10 mL) and triethylamine (1.999 mL), and then trimethylsilyl isocyanate (248 mg) was added. The mixture was stirred at room temperature overnight. Water was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate/methanol) and recrystallization (ethyl acetate) to give the title compound (145 mg) as pale yellow crystals.

$^1$H NMR (300 MHz, DMSO-d$_6$) δ 1.07-2.01 (8H, m), 3.86-4.26 (5H, m), 5.51 (2H, s), 6.14 (1H, d, J=7.4 Hz), 7.05 (1H, dd, J=8.8, 2.4 Hz), 7.46 (1H, d, J=2.3 Hz), 7.69-7.86 (2H, m), 8.30-8.48 (1H, m).

Example 100

N-{(1S)-2-[4-(6-ethoxy-3-fluoropyrazolo[1,5-a]pyridin-2-yl)-3-fluorophenoxy]-1-methylethyl}acetamide A) tert-butyl [(1S)-2-(4-bromo-3-fluorophenoxy)-1-methylethyl]carbamate Diisopropyl azodicarboxylate (1.9 M solution in toluene, 83 mL) was added to a mixture of 4-bromo-3-fluorophenol (25.0 g), tert-butyl [(1S)-2-hydroxy-1-methylethyl]carbamate (25.2 g), triphenylphosphine (41.2 g), and THF (250 mL) dropwise at 0° C. The mixture was stirred at 0° C. for 30 min, and then at room temperature for 3 hr. The mixture was concentrated under reduced pressure. The residue was purified by silica gel column chromatography (hexane/ethyl acetate) to give the title compound (33.7 g) as a pale yellow solid.

$^1$H NMR (300 MHz, DMSO-d$_5$) δ 1.10 (3H, d, J=6.3 Hz), 1.37 (9H, s), 3.64-3.99 (3H, m), 6.78 (1H, ddd, J=8.9, 2.8, 0.9 Hz), 6.89 (1H, d, J=7.0 Hz), 7.03 (1H, dd, J=11.1, 2.8 Hz), 7.50-7.69 (1H, m).

B) 2-bromo-5-ethoxypyridine

A mixture of 6-bromopyridin-3-ol (7.58 g), iodoethane (5.23 mL), potassium carbonate (9.03 g), and DMF (80 mL) was stirred at 60° C. for 3 hr. Water was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) to give the title compound (7.58 g) as a pale yellow solid.

$^1$H NMR (300 MHz, DMSO-d$_6$) δ 1.33 (3H, t, J=6.9 Hz), 4.10 (2H, q, J=7.0 Hz), 7.37 (1H, dd, J=8.7, 3.2 Hz), 7.47-7.62 (1H, m), 8.10 (1H, d, J=2.9 Hz).

C) tert-butyl [(1S)-2-(4-ethynyl-3-fluorophenoxy)-1-methylethyl]carbamate

Under nitrogen, a mixture of tert-butyl [(1S)-2-(4-bromo-3-fluorophenoxy)-1-methylethyl]carbamate (23.3 g), ethynyl(trimethyl)silane (13.1 g), bis(triphenylphosphine)palladium(II) dichloride (4.70 g), cuprous iodide (1.27 g), triethylamine (14.0 mL), and toluene (20 mL) was stirred at 100° C. overnight. The precipitate was filtered, and the filtrate was concentrated under reduced pressure. The residue was dissolved in THF (200 mL), and tetrabutylammonium fluoride (1.0 M solution in THF, 201 mL) was added dropwise at room temperature. The mixture was stirred at room temperature for 2 hr. 1 M hydrochloric acid was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) and washed with hexane to give the title compound (12.2 g) as a light brown solid.

$^1$H NMR (300 MHz, DMSO-d$_6$) δ 1.10 (3H, d, J=6.4 Hz), 1.37 (9H, s), 3.72-4.00 (3H, m), 4.30 (1H, s), 6.79 (1H, dd, J=8.6, 2.4 Hz), 6.83-7.00 (2H, m), 7.39-7.54 (1H, m).

D) tert-butyl [(1S)-2-{4-[(5-ethoxypyridin-2-yl)ethynyl]-3-fluorophenoxy}-1-methylethyl]carbamate Under nitrogen, a mixture of tert-butyl [(1S)-2-(4-ethynyl-3-fluorophenoxy)-1-methylethyl]carbamate (9.36 g), 2-bromo-5-ethoxypyridine (5.86 g), bis(triphenylphosphine)palladium(II) dichloride (2.04 g), cuprous iodide (0.552 g), triethylamine (6.06 mL), and toluene (20 mL) was stirred at 100° C. overnight. The precipitate was filtered, and the filtrate was concentrated under reduced pressure. The residue was purified by silica gel column chromatography (hexane/ethyl acetate) to give the title compound (7.00 g) as a yellow solid.

MS (ESI+): [M+H]$^+$ 415.1.

E) tert-butyl {(1S)-2-[4-(6-ethoxypyrazolo[1,5-a]pyridin-2-yl)-3-fluorophenoxy]-1-methylethyl}carbamate Perchloric acid (6.39 mL) was added to a solution of ethyl N-{[(2,4,6-trimethylphenyl)sulfonyl]oxy}ethanimidoate (10.60 g) in THF (10 mL) dropwise at 0° C. The mixture was stirred at 0° C. for 20 min. The mixture was poured into iced-water. The precipitate was filtered and washed with water. The residue was added to a solution of tert-butyl [(1S)-2-{4-[(5-ethoxypyridin-2-yl)ethynyl]-3-fluorophenoxy}-1-methylethyl]carbamate (7.00 g) in THF (70 mL) at room temperature. The mixture was stirred at room temperature for 30 min. The solvent was removed under reduced pressure, and the residue was dissolved in DMF (70 mL). Potassium carbonate (4.67 g) was added at room temperature, and the mixture was stirred at room temperature overnight. Water was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) to give the title compound (4.12 g) as a light brown oil.

MS (ESI+): [M+H]$^+$ 430.1.

F) tert-butyl {(1S)-2-[4-(6-ethoxy-3-fluoropyrazolo[1,5-a]pyridin-2-yl)-3-fluorophenoxy]-1-methylethyl}carbamate 1-Fluoro-4-hydroxy-1,4-diazabicyclo[2.2.2]octane bis(tetrafluoroborate) (0.975 g) was added to a solution of tert-butyl {(1S)-2-[4-(6-ethoxypyrazolo[1,5-a]pyridin-2-yl)-3-fluorophenoxy]-1-methylethyl}carbamate (1.37 g) in acetonitrile (20 mL) at room temperature. The mixture was stirred at room temperature for 30 min. Then additional 1-fluoro-4-hydroxy-1,4-diazabicyclo[2.2.2]octane bis(tetrafluoroborate) (0.975 g) was added, and the mixture was stirred at room temperature for 30 min. saturated sodium hydrogen carbonate solution was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) to give the title compound (0.105 g) as a colorless oil.

MS (ESI+): [M+H]$^+$ 448.1.

G) N-{(1S)-2-[4-(6-ethoxy-3-fluoropyrazolo[1,5-a]pyridin-2-yl)-3-fluorophenoxy]-1-methylethyl}acetamide A mixture of tert-butyl {(1S)-2-[4-(6-ethoxy-3-fluoropyrazolo[1,5-a]pyridin-2-yl)-3-fluorophenoxy]-1-methylethyl}carbamate (52 mg), 4 M hydrogen chloride/ethyl acetate (2 mL), and ethyl acetate (1 mL) was stirred at room temperature for 6 hr. The mixture was concentrated under reduced pressure. The residue was mixed with pyridine (1 mL) and acetic anhydride (1 mL). The mixture was stirred at room temperature overnight. 1 M hydrochloric acid was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) to give the title compound (18.7 mg) as white crystals.

$^1$H NMR (300 MHz, DMSO-d$_6$) δ 1.16 (3H, d, J=6.7 Hz), 1.36 (3H, t, J=6.9 Hz), 1.82 (3H, s), 3.74-4.22 (5H, m), 6.88-7.16 (3H, m), 7.53-7.74 (2H, m), 7.96 (1H, d, J=7.6 Hz), 8.34 (1H, s).

Example 101

1-{(1S)-2-[4-(6-ethoxy-3-fluoropyrazolo[1,5-a]pyridin-2-yl)-3-fluorophenoxy]-1-methylethyl}urea A mixture of tert-butyl {(1S)-2-[4-(6-ethoxy-3-fluoropyrazolo[1,5-a]pyridin-2-yl)-3-fluorophenoxy]-1-methylethyl}carbamate (52 mg), 4 M hydrogen chloride/ethyl acetate (2 mL), and ethyl acetate (1 mL) was stirred at room temperature for 6 hr. The mixture was concentrated under reduced pressure. The residue was mixed with THF (1 mL) and triethylamine (0.130 mL), and then trimethylsilyl isocyanate (16.1 mg) was added. The mixture was stirred at room temperature overnight. Water was added, and the mixture was extracted with ethyl acetate. The organic layer was washed with brine, dried over anhydrous magnesium sulfate and concentrated under reduced pressure. The residue was purified by silica gel column chromatography (NH, hexane/ethyl acetate/methanol) and by preparative HPLC (C18, water/acetonitrile (containing 0.1% trifluoroacetic acid)). The desired fraction was neutralized with saturated sodium hydrogen carbonate solution and extracted with ethyl acetate. The organic layer was separated, washed with brine, dried over anhydrous magnesium sulfate and concentrated under reduced pressure to give the title compound (4.00 mg) as white crystals.

$^1$H NMR (300 MHz, DMSO-d$_6$) δ 1.15 (3H, d, J=6.4 Hz), 1.36 (3H, t, J=6.9 Hz), 3.76-4.17 (5H, m), 5.49 (2H, s), 5.93-6.17 (1H, m), 6.88-7.18 (3H, m), 7.56-7.70 (2H, m), 8.34 (1H, s).

Example 102

N-[(1S)-2-{4-[6-(cyclopropylmethoxy)-3-fluoropyrazolo[1,5-a]pyridin-2-yl]-3-fluorophenoxy}-1-methylethyl]acetamide A) 2-bromo-5-(cyclopropylmethoxy)pyridine A mixture of 6-bromopyridin-3-ol (10.0 g), (bromomethyl)cyclopropane (7.76 g), potassium carbonate (11.9 g), and DMF (100 mL) was stirred at 60° C. overnight. Water was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) to give the title compound (12.0 g) as a colorless oil.

$^1$H NMR (300 MHz, DMSO-d$_6$) δ 0.25-0.40 (2H, m), 0.52-0.68 (2H, m), 1.02-1.40 (1H, m), 3.89 (2H, d, J=7.1 Hz), 7.37 (1H, dd, J=8.7, 3.2 Hz), 7.52 (1H, d, J=8.7 Hz), 8.10 (1H, d, J=3.0 Hz).

B) tert-butyl [(1S)-2-(4-{([5-(cyclopropylmethoxy)pyridin-2-yl]ethynyl}-3-fluorophenoxy)-1-methylethyl]carbamate Under nitrogen, a mixture of 2-bromo-5-(cyclopropylmethoxy)pyridine (3.11 g), tert-butyl [(1S)-2-(4-ethynyl-3-fluorophenoxy)-1-methylethyl]carbamate (4.00 g), bis(triphenylphosphine)palladium(II) dichloride (0.957 g), cuprous iodide (0.260 g), triethylamine (2.85 mL), and toluene (10 mL) was stirred at 100° C. overnight. The precipitate was filtered, and the filtrate was concentrated under reduced pressure. The residue was purified by silica gel column chromatography (hexane/ethyl acetate) to give the title compound (5.13 g) as a light brown oil.

MS (ESI+): [M+H]$^+$ 441.2.

C) tert-butyl [(1S)-2-{4-[6-(cyclopropylmethoxy)pyrazolo[1,5-a]pyridin-2-yl]-3-fluorophenoxy}-1-methylethyl]carbamate Perchloric acid (4.40 mL) was added to a solution of ethyl N-{[(2,4,6-trimethylphenyl)sulfonyl]oxy}ethanimidoate (7.31 g) in THF (7 mL) dropwise at 0° C. The mixture was stirred at 0° C. for 20 min. The mixture was poured into iced-water. The precipitate was filtered and washed with water. The residue was added to a solution of tert-butyl [(1S)-2-(4-{[5-(cyclopropylmethoxy)pyridin-2-yl]ethynyl}-3-fluorophenoxy)-1-methylethyl]carbamate (5.13 g) in THF (50 mL) at room temperature. The mixture was stirred at room temperature for 30 min. The solvent was removed under reduced pressure, and the residue was dissolved in DMF (50 mL). Potassium carbonate (3.22 g) was added at room temperature, and the mixture was stirred at room temperature overnight. Water was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) to give the title compound (2.05 g) as a light brown solid.

MS (ESI+): [M+H]$^+$ 456.2.

D) tert-butyl [(1S)-2-{4-[6-(cyclopropylmethoxy)-3-fluoropyrazolo[1,5-a]pyridin-2-yl]-3-fluorophenoxy}-1-methylethyl]carbamate 1-Fluoro-4-hydroxy-1,4-diazabicyclo[2.2.2]octane bis(tetrafluoroborate) (0.919 g) was added to a solution of tert-butyl [(1S)-2-{4-[6-(cyclopropylmethoxy)pyrazolo[1,5-a]pyridin-2-yl]-3-fluorophenoxy}-1-methylethyl]carbamate (1.37 g) in acetonitrile (20 mL) at room temperature. The mixture was stirred at room temperature for 30 min. Then additional 1-fluoro-4-hydroxy-1,4-diazabicyclo[2.2.2]octane bis(tetrafluoroborate) (0.919 g) was added, and the mixture was stirred at room temperature for 30 min. Saturated sodium hydrogen carbonate solution was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) to give the title compound (0.134 g) as a colorless oil.

MS (ESI+): [M+H]$^+$ 474.2.

E) N-[(1S)-2-{4-[6-(cyclopropylmethoxy)-3-fluoropyrazolo[1,5-a]pyridin-2-yl]-3-fluorophenoxy}-1-methylethyl]acetamide A mixture of tert-butyl [(1S)-2-{4-[6-(cyclopropylmethoxy)-3-fluoropyrazolo[1,5-a]pyridin-2-yl]-3-fluorophenoxy}-1-methylethyl]carbamate (67 mg), 4 M hydrogen chloride/ethyl acetate (2 mL), and ethyl acetate (1 mL) was stirred at room temperature for 6 hr. The mixture was concentrated under reduced pressure. The residue was mixed with pyridine (1 mL) and acetic anhydride (1 mL). The mixture was stirred at room temperature overnight. 1 M hydrochloric acid was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) to give the title compound (33.4 mg) as white crystals.

$^1$H NMR (300 MHz, DMSO-d$_6$) δ 0.25-0.41 (2H, m), 0.52-0.70 (2H, m), 1.16 (3H, d, J=6.7 Hz), 1.21-1.32 (1H, m), 1.82 (3H, s), 3.76-4.33 (5H, m), 6.89-7.15 (3H, m), 7.57-7.70 (2H, m), 7.96 (1H, d, J=7.9 Hz), 8.29 (1H, s).

Example 103

1-[(1S)-2-{4-[6-(cyclopropylmethoxy)-3-fluoropyrazolo[1,5-a]pyridin-2-yl]-3-fluorophenoxy}-1-methylethyl]urea A mixture of tert-butyl [(1S)-2-{4-[6-(cyclopropylmethoxy)-3-fluoropyrazolo[1,5-a]pyridin-2-yl]-3-fluorophenoxy}-1-methylethyl]carbamate (67 mg), 4 M hydrogen chloride/ethyl acetate (2 mL), and ethyl acetate (1 mL) was stirred at room temperature for 6 hr. The mixture was concentrated under reduced pressure. The residue was mixed with THF (1 mL) and triethylamine (0.158 mL), and then trimethylsilyl isocyanate (19.6 mg) was added. The mixture was stirred at room temperature overnight. Water was added, and the mixture was extracted with ethyl acetate. The organic layer was washed with brine, dried over anhydrous magnesium sulfate and concentrated under reduced pressure. The residue was purified by silica gel column chromatography (NH, hexane/ethyl acetate/methanol) to give the title compound (4.40 mg) as white crystals.

$^1$H NMR (300 MHz, DMSO-d$_6$) δ 0.28-0.39 (2H, m), 0.60 (2H, d, J=7.9 Hz), 1.10-1.32 (4H, m), 3.77-4.09 (5H, m), 5.49 (2H, s), 6.00-6.16 (1H, m), 6.92-7.16 (3H, m), 7.56-7.72 (2H, m), 8.30 (1H, s).

Example 104

N-[(1S)-2-{4-[6-(cyclopropylmethoxy)pyrazolo[1,5-a]pyridin-2-yl]-3-fluorophenoxy}-1-methylethyl]acetamide A mixture of tert-butyl [(1S)-2-{4-[6-(cyclopropylmethoxy)pyrazolo[1,5-a]pyridin-2-yl]-3-fluorophenoxy}-1-methylethyl]carbamate (200 mg), 4 M hydrogen chloride/ethyl acetate (2 mL), and ethyl acetate (2 mL) was stirred at room temperature for 2 hr. The mixture was concentrated under reduced pressure. The residue was mixed with pyridine (2 mL) and acetic anhydride (2 ml). The mixture was stirred at room temperature overnight. 1 M hydrochloric acid was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) and by preparative HPLC (C18, water/acetonitrile (containing 0.1% trifluoroacetic acid)). The desired fraction was neutralized with saturated sodium hydrogen carbonate solution and extracted with ethyl acetate. The organic layer was separated, dried over anhydrous magnesium sulfate and concentrated under reduced pressure to give the title compound (60.6 mg) as off-white crystals.

$^1$H NMR (300 MHz, DMSO-$d_6$) δ 0.24-0.40 (2H, m), 0.54-0.68 (2H, m), 1.16 (3H, d, J=6.7 Hz), 1.19-1.35 (1H, m), 1.82 (3H, s), 3.79-4.22 (5H, m), 6.83 (1H, d, J=3.8 Hz), 6.87-7.11 (3H, m), 7.62 (1H, d, J=9.6 Hz), 7.87-8.03 (2H, m), 8.36 (1H, s).

Example 105

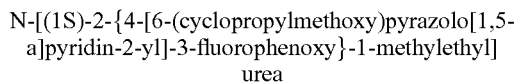

N-[(1S)-2-{4-[6-(cyclopropylmethoxy)pyrazolo[1,5-a]pyridin-2-yl]-3-fluorophenoxy}-1-methylethyl]urea A mixture of tert-butyl [(1S)-2-{4-[6-(cyclopropylmethoxy)pyrazolo[1,5-a]pyridin-2-yl]-3-fluorophenoxy}-1-methylethyl]carbamate (200 mg), 4 M hydrogen chloride/ethyl acetate (2 mL), and ethyl acetate (2 mL) was stirred at room temperature for 2 hr. The mixture was concentrated under reduced pressure. The residue was mixed with THF (2 mL) and triethylamine (0.490 mL), and then trimethylsilyl isocyanate (76 mg) was added. The mixture was stirred at room temperature overnight. Water was added, and the mixture was extracted with ethyl acetate. The organic layer was washed with brine, dried over anhydrous magnesium sulfate and concentrated under reduced pressure. The residue was purified by silica gel column chromatography (NH, hexane/ethyl acetate/methanol) and by preparative HPLC (C18, water/acetonitrile (containing 0.1% trifluoroacetic acid)). The desired fraction was neutralized with saturated sodium hydrogen carbonate solution and extracted with ethyl acetate. The organic layer was separated, washed with brine, dried over anhydrous magnesium sulfate and concentrated under reduced pressure. The residue was recrystallized (ethyl acetate) to give the title compound (56.9 mg) as off-white crystals.

$^1$H NMR (300 MHz, DMSO-$d_6$) δ 0.27-0.41 (2H, m), 0.52-0.66 (2H, m), 1.15 (3H, d, J=6.4 Hz), 1.19-1.33 (1H, m), 3.72-4.11 (5H, m), 5.48 (2H, s), 6.05 (1H, d, J=7.3 Hz), 6.83 (1H, d, J=3.6 Hz), 6.86-7.16 (3H, m), 7.62 (1H, d, J=9.4 Hz), 7.85-8.03 (1H, m), 8.36 (1H, s).

Example 106

1-[(1S)-2-({6-[6-(2,2-difluoropropoxy)-1,3-benzoxazol-2-yl]pyridin-3-yl}oxy)-1-methylethyl]urea A) tert-butyl [(1S)-2-({6-[(2,4-dihydroxyphenyl)carbamoyl]pyridin-3-yl}oxy)-1-methylethyl]carbamate Diisopropyl azodicarboxylate (1.9 M solution in toluene, 9.52 mL) was added to a mixture of methyl 5-hydroxypyridine-2-carboxylate (5.00 g), tert-butyl [(1S)-2-hydroxy-1-methylethyl]carbamate (8.58 g), triphenylphosphine (12.9 g), and THF (50 mL) at 0° C. dropwise. The mixture was stirred at room temperature for 3 days. The mixture was concentrated under reduced pressure. The residue was purified by silica gel column chromatography (hexane/ethyl acetate) to give methyl 5-({(2S)-2-[(tert-butoxycarbonyl)amino]propyl}oxy)pyridine-2-carboxylate (810 mg) as a mixture with impurities. A mixture of methyl 5-({(2S)-2-[(tert-butoxycarbonyl)amino]propyl}oxy)pyridine-2-carboxylate (810 mg, a mixture with impurities), THF (8 mL), methanol (8 mL), and 1 M sodium hydroxide (8 mL) was stirred at room temperature for 4 hr. The mixture was neutralized with 1 M hydrochloric acid at 0° C., and brine was added. The mixture was extracted with ethyl acetate. The organic layer was separated, washed with water and brine, dried over anhydrous magnesium sulfate and concentrated under reduced pressure to give 5-({(2S)-2-[(tert-butoxycarbonyl)amino]propyl}oxy)pyridine-2-carboxylic acid (765 mg) as a mixture with impurities. A mixture of 5-({(2S)-2-[(tert-butoxycarbonyl)amino]propyl}oxy)pyridine-2-carboxylic acid (765 mg, a mixture with impurities), 4-aminobenzene-1,3-diol hydrochloride (417 mg), HATU (982 mg), N,N-diisopropylethylamine (0.902 ml), and DMF (7 mL) was stirred at room temperature overnight. Water was added, and the mixture was extracted with ethyl acetate. The organic layer was separated, washed with brine, dried over anhydrous magnesium sulfate and concentrated under reduced pressure. The residue was purified by silica gel column chromatography (hexane/ethyl acetate) to give the title compound (442 mg) as a pale yellow oil.

MS (ESI+): [M+H]$^+$ 404.2.

B) tert-butyl [(1S)-2-({6-[6-(2,2-difluoropropoxy)-1,3-benzoxazol-2-yl]pyridin-3-yl}oxy)-1-methylethyl]carbamate Triethylamine (1.22 ml) was added to a solution of hexachloroethane (648 mg) and triphenylphosphine (862 mg) in acetonitrile (5 mL) at room temperature. The mixture was stirred at room temperature for 10 min. Then a mixture of tert-butyl [(1S)-2-({6-[(2,4-dihydroxyphenyl)carbamoyl]pyridin-3-yl}oxy)-1-methylethyl]carbamate (442 mg) and acetonitrile (5 mL) was added, and the mixture was stirred at room temperature overnight. Water was added, and the mixture was extracted with ethyl acetate. The organic layer was separated, washed with brine, dried over anhydrous magnesium sulfate and concentrated under reduced pressure. The residue was purified by silica gel column chromatography (hexane/ethyl acetate) to give a mixture of tert-butyl [(1S)-2-{[6-(6-hydroxy-1,3-benzoxazol-2-yl)pyridin-3-yl]oxy}-1-methylethyl]carbamate and tert-butyl [(1S)-2-({6-[(2,4-dihydroxyphenyl)carbamoyl]pyridin-3-yl}oxy)-1-methylethyl]carbamate. Triethylamine (1.22 ml) was added to a solution of hexachloroethane (648 mg) and triphenylphosphine (862 mg) in acetonitrile (5 mL) at room temperature. The mixture was stirred at room temperature for 10 min. Then a mixture of tert-butyl [(1S)-2-{[6-(6-hydroxy-1,3-benzoxazol-2-yl)pyridin-3-yl]oxy}-1-methylethyl]carbamate and tert-butyl [(1S)-2-({6-[(2,4-dihydroxyphenyl)carbamoyl]pyridin-3-yl}oxy)-1-methylethyl]carbamate, and acetonitrile (5 mL) were added, and the mixture was stirred at room temperature overnight. Water was added, and the mixture was extracted with ethyl acetate. The organic layer was separated, washed with brine, dried over anhydrous magnesium sulfate and concentrated under reduced pressure. The residue was purified by silica gel column chromatography (hexane/ethyl acetate) to give tert-butyl [(1S)-2-{[6-(6-hydroxy-1,3-benzoxazol-2-yl)pyridin-3-yl]oxy}-1-methylethyl]carbamate (640 mg) as a mixture with impurities. A mixture of tert-butyl [(1S)-2-{[6-(6-hydroxy-1,3-benzox-

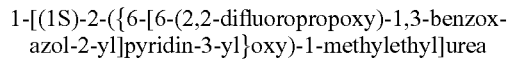

azol-2-yl)pyridin-3-yl]oxy}-1-methylethyl]carbamate (640 mg, a mixture with impurities), 1-bromopropan-2-one (455 mg), potassium carbonate (459 mg), and DMF (10 mL) was stirred at 60° C. for 1 hr. Water was added, and the mixture was extracted with ethyl acetate. The organic layer was separated, washed with brine, dried over anhydrous magnesium sulfate and concentrated under reduced pressure. The residue was purified by silica gel column chromatography (hexane/ethyl acetate) to give tert-butyl [(1S)-1-methyl-2-({6-[6-(2-oxopropoxy)-1,3-benzoxazol-2-yl]pyridin-3-yl}oxy)ethyl]carbamate (630 mg) as a mixture with impurities. Bis(2-methoxyethyl)aminosulfur trifluoride (0.789 mL) was added to a mixture of tert-butyl [(1S)-1-methyl-2-({6-[6-(2-oxopropoxy)-1,3-benzoxazol-2-yl]pyridin-3-yl}oxy)ethyl]carbamate (630 mg, a mixture with impurities) and toluene (10 mL) at room temperature. The mixture was stirred at 80° C. for 2 hr. Saturated sodium hydrogen carbonate solution was added, and the mixture was extracted with ethyl acetate. The organic layer was separated, washed with brine, dried over anhydrous magnesium sulfate and concentrated under reduced pressure. The residue was purified by silica gel column chromatography (hexane/ethyl acetate) to give the title compound (111 mg) as a white solid.

MS (ESI+): [M+H]$^+$ 464.2.

C) 1-[(1S)-2-({6-[6-(2,2-difluoropropoxy)-1,3-benzoxazol-2-yl]pyridin-3-yl}oxy)-1-methylethyl]urea A mixture of tert-butyl [(1S)-2-({6-[6-(2,2-difluoropropoxy)-1,3-benzoxazol-2-yl]pyridin-3-yl}oxy)-1-methylethyl]carbamate (111 mg), 4 M hydrogen chloride/ethyl acetate (1 mL), and ethyl acetate (2 mL) was stirred at room temperature for 4 hr. The mixture was concentrated under reduced pressure. The residue was mixed with THF (2 mL) and triethylamine (0.267 mL), and then trimethylsilyl isocyanate (27.6 mg) was added. The mixture was stirred at room temperature overnight. Water was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate/methanol) and recrystallization (ethyl acetate) to give the title compound (38.8 mg) as white crystals.

$^1$H NMR (300 MHz, DMSO-d$_6$) δ 1.17 (3H, d, J=6.5 Hz), 1.78 (3H, t, J=19.3 Hz), 3.86-4.23 (3H, m), 4.40 (2H, t, J=12.7 Hz), 5.49 (2H, s), 6.10 (1H, d, J=7.3 Hz), 7.11 (1H, dd, J=8.8, 2.5 Hz), 7.54 (1H, d, J=2.4 Hz), 7.65 (1H, dd, J=8.8, 2.9 Hz), 7.73 (1H, d, J=8.9 Hz), 8.22 (1H, d, J=8.9 Hz), 8.49 (1H, d, J=2.7 Hz).

Example 107

N-{(1S)-2-[(6-{6-[(3,3-difluorocyclobutyl)methoxy]-1,3-benzoxazol-2-yl}-5-fluoropyridin-3-yl)oxy]-1-methylethyl}acetamide A) tert-butyl [(1S)-2-{[5-fluoro-6-(6-hydroxy-1,3-benzoxazol-2-yl)pyridin-3-yl]oxy}-1-methylethyl]carbamate A mixture of 5-({(2S)-2-[(tert-butoxycarbonyl)amino]propyl}oxy)-3-fluoropyridine-2-carboxylic acid (5.00 g), 4-aminobenzene-1,3-diol hydrochloride (2.57 g), HATU (6.05 g), N,N-diisopropylethylamine (5.56 mL), and DMF (50 mL) was stirred at room temperature overnight. Water was added, and the mixture was extracted with ethyl acetate. The organic layer was separated, washed with brine, dried over anhydrous magnesium sulfate and concentrated under reduced pressure. The residue was purified by silica gel column chromatography (hexane/ethyl acetate) to give tert-butyl [(1S)-2-({6-[(2,4-dihydroxyphenyl)carbamoyl]-5-fluoropyridin-3-yl}oxy)-1-methylethyl]carbamate (2.51 g) as a mixture with impurities. Triethylamine (6.64 mL) was added to a solution of hexachloroethane (3.53 g) and triphenylphosphine (4.69 g) in acetonitrile (25 mL) at room temperature. The mixture was stirred at room temperature for 10 min. Then a mixture of tert-butyl [(1S)-2-({6-[(2,4-dihydroxyphenyl)carbamoyl]-5-fluoropyridin-3-yl}oxy)-1-methylethyl]carbamate (2.51 g, a mixture with impurities) and acetonitrile (25 mL) was added, and the mixture was stirred at room temperature overnight. Water was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) to give the title compound (0.770 g) as a pale yellow solid.

MS (ESI+): [M+H]$^+$ 404.2.

B) tert-butyl {(1S)-2-[(6-{6-[(3,3-difluorocyclobutyl)methoxy]-1,3-benzoxazol-2-yl}-5-fluoropyridin-3-yl)oxy]-1-methylethyl}carbamate A mixture of tert-butyl [(1S)-2-{[5-fluoro-6-(6-hydroxy-1,3-benzoxazol-2-yl)pyridin-3-yl]oxy}-1-methylethyl]carbamate (770 mg), (3,3-difluorocyclobutyl)methyl methanesulfonate (459 mg), potassium carbonate (317 mg), and DMF (10 mL) was stirred at 60° C. for 2 hr. Then additional (3,3-difluorocyclobutyl)methyl methanesulfonate (459 mg) and potassium carbonate (317 mg) were added, and the mixture was stirred at 60° C. overnight. Water was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate) to give the title compound (780 mg) as a white solid.

MS (ESI+): [M+H]$^+$ 508.1.

C) N-{(1S)-2-[(6-{6-[(3,3-difluorocyclobutyl)methoxy]-1,3-benzoxazol-2-yl}-5-fluoropyridin-3-yl)oxy]-1-methylethyl}acetamide A mixture of tert-butyl {(1S)-2-[(6-{6-[(3,3-difluorocyclobutyl)methoxy]-1,3-benzoxazol-2-yl}-5-fluoropyridin-3-yl)oxy]-1-methylethyl}carbamate (390 mg), 4 M hydrogen chloride/ethyl acetate (3 mL), and ethyl acetate (3 mL) was stirred at room temperature for 4 hr. The mixture was concentrated under reduced pressure. The residue was mixed with pyridine (3 mL) and acetic anhydride (1 mL). The mixture was stirred at room temperature for 3 days. 1 M hydrochloric acid was added, and the mixture was extracted with ethyl is acetate. The organic layer was washed with brine, dried over anhydrous magnesium sulfate and concentrated under reduced pressure. The residue was purified by silica gel column chromatography (hexane/ethyl acetate/methanol) and recrystallization (ethyl acetate) to give the title compound (218 mg) as white crystals.

$^1$H NMR (300 MHz, DMSO-d$_6$) δ 1.18 (3H, d, J=6.3 Hz), 1.82 (3H, s), 2.35-2.86 (5H, m), 3.94-4.24 (5H, m), 7.05 (1H, dd, J=8.8, 2.4 Hz), 7.46 (1H, d, J=2.4 Hz), 7.65-7.81 (2H, m), 8.01 (1H, d, J=7.4 Hz), 8.34-8.44 (1H, m).

Example 108

1-{(1S)-2-[(6-{6-[(3,3-difluorocyclobutyl)methoxy]-1,3-benzoxazol-2-yl}-5-fluoropyridin-3-yl)oxy]-1-methylethyl}urea A mixture of tert-butyl {(1S)-2-[(6-{6-[(3,3-difluorocyclobutyl)methoxy]-1,3-benzoxazol-2-yl}-5-fluoropyridin-3-yl)oxy]-1-methylethyl}carbamate (390 mg), 4 M hydrogen chloride/ethyl acetate (3 ml), and ethyl acetate (3 ml) was stirred at room temperature for 4 hr. The mixture was concentrated under reduced pressure. The residue was mixed with THF (3 mL) and triethylamine (0.857 mL), and then trimethylsilyl isocyanate (89 mg) was added. The mixture was stirred at room temperature for 3 days. Water was added, and the mixture was extracted with ethyl acetate. The organic layer was washed with brine, dried over anhydrous magnesium sulfate and concentrated under reduced pressure. The residue was purified by silica gel column chromatography (hexane/ethyl acetate/methanol) and recrystallization (ethyl acetate) to give the title compound (227 mg) as white crystals.
$^1$H NMR (300 MHz, DMSO-$d_6$) δ 1.13-1.20 (3H, m), 2.40-2.90 (5H, m), 3.80-4.23 (5H, m), 5.51 (2H, s), 6.13 (1H, d, J=7.1 Hz), 7.05 (1H, dd, J=8.8, 2.4 Hz), 7.46 (1H, d, J=2.4 Hz), 7.69-7.86 (2H, m), 8.36-8.45 (1H, m).

Example 109

Diastereomer of N-{(1S)-2-[(6-{6-[(2,2-difluorocyclopropyl)methoxy]-1,3-benzoxazol-2-yl}-5-fluoropyridin-3-yl)oxy]-1-methylethyl}acetamide (retention time: short)

The diastereomeric mixture (186 mg) of the title compound obtained in Example 96 was resolved by preparative HPLC (CHIRALPAK AD, 50 mmID×500 mL, manufactured by Daicel Corporation, mobile phase: methanol=100%). The residue was recrystallized (ethyl acetate) to give the title compound (47.4 mg, >99.9% de, retention time: short) as white crystals.
$^1$H NMR (300 MHz, DMSO-$d_6$) δ 1.18 (3H, d, J=6.3 Hz), 1.42-1.59 (1H, m), 1.65-1.89 (4H, m), 2.16-2.39 (1H, m), 3.96-4.33 (5H, m), 7.07 (1H, dd, J=8.8, 2.4 Hz), 7.49 (1H, d, J=2.3 Hz), 7.69-7.81 (2H, m), 8.01 (1H, d, J=6.8 Hz), 8.34-8.42 (1H, m).

Example 110

Diastereomer of N-{(1S)-2-[(6-{6-[(2,2-difluorocyclopropyl)methoxy]-1,3-benzoxazol-2-yl}-5-fluoropyridin-3-yl)oxy]-1-methylethyl}acetamide (retention time: long)

The diastereomeric mixture (186 mg) of the title compound obtained in Example 96 was resolved by preparative HPLC (CHIRALPAK AD, 50 mmID×500 mL, manufactured by Daicel Corporation, mobile phase: methanol=100%). The residue was recrystallized (ethyl acetate) to give the title compound (45.8 mg, 99.7% de, retention time: long) as white crystals.
$^1$H NMR (300 MHz, DMSO-$d_6$) δ 1.18 (3H, d, J=6.4 Hz), 1.42-1.59 (1H, m), 1.67-1.88 (4H, m), 2.16-2.39 (1H, m), 4.00-4.33 (5H, m), 7.07 (1H, dd, J=8.8, 2.4 Hz), 7.49 (1H, d, J=2.4 Hz), 7.70-7.82 (2H, m), 8.01 (1H, d, J=7.0 Hz), 8.35-8.41 (1H, m).

Example 111

Diastereomer of 1-{(1S)-2-[(6-{6-[(2,2-difluorocyclopropyl)methoxy]-1,3-benzoxazol-2-yl}-5-fluoropyridin-3-yl)oxy]-1-methylethyl}urea (retention time: short)

The diastereomeric mixture (200 mg) of the title compound obtained in Example 97 was resolved by preparative HPLC (CHIRALPAK AD, 50 mmID×500 mL, manufactured by Daicel Corporation, mobile phase: ethanol/2-propanol=500/500). The residue was recrystallized (ethyl acetate) to give the title compound (81.4 mg, >99.9% de, retention time: short) as yellow crystals.
$^1$H NMR (300 MHz, DMSO-$d_6$) δ 1.17 (3H, d, J=6.5 Hz), 1.38-1.61 (1H, m), 1.67-1.85 (1H, m), 2.11-2.40 (1H, m), 3.83-4.41 (5H, m), 5.50 (2H, s), 6.11 (1H, d, J=7.1 Hz), 7.07 (1H, dd, J 8.7, 2.4 Hz), 7.49 (1H, d, J=2.3 Hz), 7.66-7.89 (2H, m), 8.32-8.47 (1H, m).

Example 112

Diastereomer of 1-{(1S)-2-[(6-{6-[(2,2-difluorocyclopropyl)methoxy]-1,3-benzoxazol-2-yl}-5-fluoropyridin-3-yl)oxy]-1-methylethyl}urea (retention time: long)

The diastereomeric mixture (200 mg) of the title compound obtained in Example 97 was resolved by preparative HPLC (CHIRALPAK AD, 50 mmID×500 mL, manufactured by Daicel Corporation, mobile phase: ethanol/2-propanol=500/500). The residue was recrystallized (ethyl acetate) to give the title compound (66.1 mg, >99.9% de, retention time: long) as white crystals.
$^1$H NMR (300 MHz, DMSO-$d_6$) δ 1.17 (3H, d, J=6.5 Hz), 1.40-1.58 (1H, m), 1.66-1.85 (1H, m), 2.15-2.42 (1H, m), 3.74-4.36 (5H, m), 5.50 (2H, s), 6.11 (1H, d, J=7.3 Hz), 7.07 (1H, dd, J=8.8, 2.4 Hz), 7.49 (1H, d, J=2.3 Hz), 7.67-7.86 (2H, m), 8.34-8.46 (1H, m).

Example 113

Diastereomer of N-{(1S)-2-[(6-{6-[2-(2,2-difluorocyclopropyl)ethoxy]-1,3-benzoxazol-2-yl}-5-fluoropyridin-3-yl)oxy]-1-methylethyl}acetamide (retention time: short)

The diastereomeric mixture (200 mg) of the title compound obtained in Example 98 was resolved by preparative HPLC (CHIRALPAK AD, 50 mmID×500 mL, manufactured by Daicel Corporation, mobile phase: methanol=100%). The residue was recrystallized (ethyl acetate) to give the title compound (57.2 mg, >99.9% de, retention time: short) as white crystals.
$^1$H NMR (300 MHz, DMSO-$d_6$) δ 1.11-1.35 (4H, m), 1.45-2.11 (7H, m), 3.94-4.23 (5H, m), 7.05 (1H, dd, J=8.8, 2.4 Hz), 7.46 (1H, d, J=2.3 Hz), 7.67-7.82 (2H, m), 8.01 (1H, d, J=6.9 Hz), 8.33-8.45 (1H, m).

Example 114

Diastereomer of N-{(1S)-2-[(6-{6-[2-(2,2-difluoro-cyclopropyl)ethoxy]-1,3-benzoxazol-2-yl}-5-fluoro-pyridin-3-yl)oxy]-1-methylethyl}acetamide (retention time: long)

The diastereomeric mixture (200 mg) of the title compound obtained in Example 98 was resolved by preparative HPLC (CHIRALPAK AD, 50 mmID×500 mL, manufactured by Daicel Corporation, mobile phase: methanol=100%). The residue was recrystallized (ethyl acetate) to give the title compound (57.4 mg, >99.9% de, retention time: long) as white crystals.
$^1$H NMR (300 MHz, DMSO-$d_6$) δ 1.11-1.35 (4H, m), 1.47-2.14 (7H, m), 3.96-4.27 (5H, m), 7.05 (1H, dd, J=8.8, 2.4 Hz), 7.46 (1H, d, J=2.3 Hz), 7.69-7.87 (2H, m), 8.01 (1H, d, J=6.9 Hz), 8.31-8.45 (1H, m).

Example 115

Diastereomer of 1-{(1S)-2-[(6-{6-[2-(2,2-difluorocyclopropyl)ethoxy]-1,3-benzoxazol-2-yl}-5-fluoropyridin-3-yl)oxy]-1-methylethyl}urea (retention time: short)

The diastereomeric mixture (100 mg) of the title compound obtained in Example 99 was resolved by preparative HPLC (CHIRALPAK AD, 50 mmID×500 mL, manufactured by Daicel Corporation, mobile phase: ethanol=100%). The residue was recrystallized (ethyl acetate) to give the title compound (44.0 mg, >99.9% de, retention time: short) as white crystals.
$^1$H NMR (300 MHz, DMSO-$d_6$) δ 1.10-2.03 (8H, m), 3.81-4.27 (5H, m), 5.52 (2H, s), 6.13 (1H, d, J=7.2 Hz), 6.97-7.12 (1H, m), 7.46 (1H, d, J=2.3 Hz), 7.63-7.84 (2H, m), 8.36-8.45 (1H, m).

Example 116

Diastereomer of 1-{(1S)-2-[(6-{6-[2-(2,2-difluorocyclopropyl)ethoxy]-1,3-benzoxazol-2-yl}-5-fluoropyridin-3-yl)oxy]-1-methylethyl}urea (retention time: long)

The diastereomeric mixture (100 mg) of the title compound obtained in Example 99 was resolved by preparative HPLC (CHIRALPAK AD, 50 mmID×500 mL, manufactured by Daicel Corporation, mobile phase: ethanol=100%). The residue was recrystallized (ethyl acetate) to give the title compound (24.5 mg, >99.9% de, retention time: long) as white crystals.
$^1$H NMR (300 MHz, DMSO-$d_6$) δ 1.05-2.15 (8H, m), 3.87-4.23 (5H, m), 5.51 (2H, s), 6.13 (1H, d, J=7.6 Hz), 7.05 (1H, dd, J 8.8, 2.5 Hz), 7.46 (1H, d, J=2.3 Hz), 7.66-7.83 (2H, m), 8.35-8.44 (1H, m).

Example 117

Diastereomer of N-[(1S)-2-({6-[6-(cyclopropyl-methoxy)-2-methyl-2,3-dihydro-1-benzofuran-2-yl]pyridin-3-yl}oxy)-1-methylethyl]acetamide A) 2-(2-Bromo-4-hydroxyphenyl)acetic acid To a solution of (2-bromo-4-methoxyphenyl)acetic acid (0.49 g) in dichloromethane (5 mL) was added a solution of tribromoborane (5 mL) dropwise at room temperature. The mixture was refluxed for 3 hr. After cooling to room temperature, the mixture was poured into iced water. The organic layer was separated, and the water layer was extracted by ethyl acetate (30 mL×3). The combined organic layer was dried over anhydrous sodium sulfate, filtered and evaporated to dryness. The residue was washed with ether to give the title compound (0.45 g).
MS (ESI+): [M+H]$^+$ 230.9

B) 2-(2-Bromo-4-hydroxyphenyl)-N-methoxy-N-methylacetamide

A mixture of 2-(2-bromo-4-hydroxyphenyl)acetic acid (0.67 g), HATU (1.33 g), triethylamine (0.35 g) and N,O-dimethylhydroxylamine hydrochloride (0.34 g) in dichloromethane (30 mL) was stirred overnight, to which water (30 mL) was added. The organic layer was separated. The water layer was extracted by ethyl acetate (20 mL×3). The combined organic layer was dried over anhydrous sodium sulfate, filtered and evaporated to dryness. The residue was purified by silica gel column chromatography (petroleum ether/ethyl acetate) to afford the title compound (773 mg).
$^1$H NMR (CDCl$_3$, 400 MHz): δ 3.27 (3H, s), 3.79 (3H, s), 3.85 (2H, s), 6.56 (1H, d, J=8.0 Hz), 6.77 (1H, s), 6.87 (1H, s), 7.01 (1H, d, J=8.4 Hz).

C) 2-(2-Bromo-4-(methoxymethoxy)phenyl)-N-methoxy-N-methylacetamide

A solution of 2-(2-bromo-4-hydroxyphenyl)-N-methoxy-N-methylacetamide (1.37 g) in THF (5 mL) was slowly added to a suspension of sodium hydride (0.22 g) in THF (30 mL) at 0° C. After stirring for 10 min, bromo(methoxy)methane (1.25 g) was added dropwise at 0° C. The mixture was stirred at 0° C. for 2 hr. The mixture was poured into water and extracted with ethyl acetate (30 mL×3). The organic layer was dried over anhydrous sodium sulfate, filtered and evaporated to dryness. The residue was purified by silica gel column chromatography (petroleum ether/ethyl acetate) to afford the title compound (1.34 g).
$^1$H NMR (DMSO, 400 MHz): δ 3.12 (3H, s), 3.38 (3H, s), 3.73 (3H, s), 3.82 (2H, s), 5.20 (2H, s), 7.00 (1H, q), 7.26 (2H, q).

D) 1-(2-Bromo-4-(methoxymethoxy)phenyl)propan-2-one

To a mixture of 2-(2-bromo-4-(methoxymethoxy)phenyl)-N-methoxy-N-methylacetamide (4.30 g) in ether (93 ml) was added methyl magnesium bromide (3 M in ether, 63 mL) dropwise at 0° C. After addition, the solution was stirred at 0° C. for 1.5 hr. The mixture was poured into saturated aqueous ammonium chloride, and extracted with ethyl acetate (100 mL×2). The organic phase was dried over anhydrous sodium sulfate, The solvent was removed under reduced pressure, and the residue was purified by silica gel column chromatography (petroleum ether/ethyl acetate) to afford the title compound (23 g).
$^1$H NMR (CDCl$_3$, 400 MHz): δ 2.13 (3H, s), 3.40 (3H, s), 3.73 (2H, s), 5.07 (2H, d, J=3.6 Hz), 6.91 (1H, d, J=2.8 Hz), 7.05 (1H, d, J=8.4 Hz), 7.22 (1H, d, J=2.4 Hz).

E) 1-(2-Bromo-4-(methoxymethoxy)phenyl)-2-(5-(triisopropylsilyloxy)pyridin-2-yl)propan-2-ol To a solution of 2-bromo-5-(triisopropylsilyloxy)pyridine (26.6 g) in ether (80 mL) at −78° C. was added n-butyllithium (2.5 M in hexane, 32.2 mL) dropwise. After being stirred at the same temperature for 10 min, a solution of 1-(2-bromo-4-(methoxymethoxy)phenyl)propan-2-one (11 g) in diethylether (40 mL) was added dropwise. The mixture was stirred at −78° C. for 5 hr, and poured into iced saturated ammonium chloride and extracted with ethyl acetate. The combined organic layer was washed with brine, dried over anhydrous magnesium sulfate, and concentrated under reduced pressure. The residue was purified by silica gel column chromatography (petroleum ether/ethyl acetate) to afford the title compound (9.6 g).

$^1$H NMR (CDCl$_3$, 400 MHz): δ 1.07-1.10 (18H, d, J=8.8 Hz), 1.23-1.31 (6H, m), 3.12-3.27 (2H, q, J=7.2 Hz), 3.45 (3H, s), 4.89 (1H, s), 5.11 (2H, s), 6.83 (1H, dd, J=8.4 Hz and 2.4 Hz), 7.09 (1H, d, J=8.8 Hz), 7.16-7.22 (3H, m), 8.10-8.12 (1H, m).

F) 2-(6-(Methoxymethoxy)-2-methyl-2,3-dihydrobenzofuran-2-yl)-5-(triisopropylsilyloxy)pyridine A mixture of 1-(2-bromo-4-(methoxymethoxy)phenyl)-2-(5-(triisopropylsilyloxy)pyridin-2-yl)propan-2-ol (9.6 g), copper iodide(I) (3.5 g), cesium carbonate (5.1 g) in toluene (60 mL, containing ca. 0.6 mL DMF) was heated to reflux overnight. The mixture was filtrated and the solid was washed with ethyl acetate. The filtrate was concentrated under reduced pressure and the residue was purified by silica gel column chromatography (petroleum ether/ethyl acetate) to afford the title compound (8 g).

MS (ESI+): [M+H]$^+$ 444.2

G) 6-(6-(Methoxymethoxy)-2-methyl-2,3-dihydrobenzofuran-2-yl)pyridin-3-ol

A mixture of 2-(6-(methoxymethoxy)-2-methyl-2,3-dihydrobenzofuran-2-yl)-5-(triisopropylsilyloxy)pyridine (8 g) and tetrabutylammonium fluoride (5.66 g) in THF (30 mL) was stirred at ambient temperature for 30 min. The mixture was concentrated under reduced pressure. The residue was purified by silica gel column chromatography (dichloromethane/methanol) to afford the title compound (4.66 g).

MS (ESI+): [M+H]$^+$ 288.0

H) Diastereomer of 6-(6-(methoxymethoxy)-2-methyl-2,3-dihydrobenzofuran-2-yl)pyridin-3-ol The diastereomeric mixture of 6-(6-(methoxymethoxy)-2-methyl-2,3-dihydrobenzofuran-2-yl)pyridin-3-ol was separated by preparative HPLC (column: CHIRALPAK AD-H, 4.6×250 mm, 5 μm, mobile phase: methanol) to afford the more polar isomer (shorter retention time).

MS (ESI+): [M+H]$^+$ 288.0.
100% de

I) Diastereomer of tert-Butyl [(1S)-2-({6-[6-(methoxymethoxy)-2-methyl-2,3-dihydro-1-benzofuran-2-yl]pyridin-3-yl}oxy)-1-methylethyl]carbamate A solution of diisopropyl azodicarboxylate (1.9 M in toluene, 2.20 mL) was added dropwise to a solution of diastereomer of 6-(6-(methoxymethoxy)-2-methyl-2,3-dihydrobenzofuran-2-yl)pyridin-3-ol (shorter retention time, 800 mg), (S)-tert-butyl (1-hydroxypropan-2-yl)carbamate (976 mg), and triphenylphosphine (1100 mg) in toluene (20 mL) at ambient temperature. The mixture was stirred at room temperature for 2 hr. The mixture was concentrated under reduced pressure. The residue was partitioned between ethyl acetate and water. The separated organic layer was washed with brine, dried over anhydrous magnesium sulfate, and concentrated under reduced pressure. The residue was purified by column chromatography (hexane/ethyl acetate) to give the title compound (1100 mg).

$^1$H NMR (300 MHz, DMSO-d$_6$) δ 0.98 (3H, d, J=6.7 Hz), 1.37 (9H, so s), 1.68 (3H, s), 3.07-3.22 (2H, m), 3.26-3.34 (2H, m), 3.36 (3H, s), 3.37-3.60 (2H, m), 5.12 (2H, s), 6.40-6.58 (2H, m), 7.03 (1H, d, J=8.0 Hz), 7.13 (1H, dd, J=8.6, 2.8 Hz), 7.36 (1H, d, J=8.6 Hz), 8.09 (1H, d, J=2.4 Hz).

J) Diastereomer of 2-(5-{[(2S)-2-aminopropyl]oxy}pyridin-2-yl)-2-methyl-2,3-dihydro-1-benzofuran-6-ol dihydrochloride A solution of 4 M hydrogen chloride/ethyl acetate (10 mL) was added dropwise to a solution of diastereomer of tert-butyl [(1S)-2-({6-[6-(methoxymethoxy)-2-methyl-2,3-dihydro-1-benzofuran-2-yl]pyridin-3-yl}oxy)-1-methylethyl]carbamate (1000 mg) in ethyl acetate (20 mL) at room temperature. The mixture was stirred at room temperature for 3 hr. The resulting precipitate was collected by filtration to give the title compound (650 mg).

$^1$H NMR (300 MHz, DMSO-d$_6$) δ 1.29 (3H, d, J=6.7 Hz), 1.72 (3H, s), 3.20 (1H, d, J=15.5 Hz), 3.47 (1H, d, J=15.4 Hz), 3.53-3.71 (1H, m), 4.08-4.18 (1H, m), 4.20-4.30 (1H, m), 6.25 (1H, dd, J=7.9, 2.2 Hz), 6.33 (1H, d, J=2.1 Hz), 6.90 (1H, d, J=7.9 Hz), 7.43-7.65 (2H, m), 8.24-8.48 (4H, m).

K) Diastereomer of N-[(1S)-2-{[6-(6-hydroxy-2-methyl-2,3-dihydro-1-benzofuran-2-yl)pyridin-3-yl]oxy}-1-methylethyl]acetamide A solution of acetic anhydride (0.126 mL) was added dropwise to a solution of diastereomer of 2-(5-{[(2S)-2-aminopropyl]oxy}pyridin-2-yl)-2-methyl-2,3-dihydro-1-benzofuran-6-ol (500 mg) in pyridine (15 mL) at ambient temperature. After being stirred at ambient temperature for 2 hr, the mixture was diluted with methanol (15 mL) and 4 M sodium hydroxide (10 mL). The mixture was stirred at ambient temperature for 15 hr. The organic solvent was removed under reduced pressure, and the aqueous solution was acidified with 4 M hydrochloric acid and extracted with ethyl acetate. The organic layer was separated, washed with water and brine, dried over anhydrous magnesium sulfate and concentrated under reduced pressure. The residue was purified by silica gel column chromatography (hexane/ethyl acetate) to give the title compound (350 mg).

MS (ESI+): [M+H]$^+$ 343.1

L) Diastereomer of N-[(1S)-2-({6-[6-(cyclopropylmethoxy)-2-methyl-2,3-dihydro-1-benzofuran-2-yl]pyridin-3-yl}oxy)-1-methylethyl]acetamide A mixture of (bromomethyl)cyclopropane (177 mg), diastereomer of N-[(1S)-2-{[6-(6-hydroxy-2-methyl-2,3-dihydro-1-benzofuran-2-yl)pyridin-3-yl]oxy}-1-methylethyl]acetamide (150 mg) and potassium carbonate (72.7 mg) in DMF (3 mL) was stirred at 80° C. for 3 hr. After cooling to room temperature, the mixture was concentrated under reduced pressure. The residue was partitioned between ethyl acetate and water. The separated organic layer was washed with brine, dried over anhydrous magnesium sulfate, and concentrated under reduced pressure. The residue was purified by silica gel column chromatography (NH, hexane/ethyl acetate) to give the title compound (150 mg).

Example 118

Diastereomer of N-[(1S)-2-({6-[6-(cyclopropyl-methoxy)-2-methyl-2,3-dihydro-1-benzofuran-2-yl]pyridin-3-yl}oxy)-1-methylethyl]acetamide

A) Diastereomer of 6-(6-(methoxymethoxy)-2-methyl-2,3-dihydrobenzofuran-2-yl)pyridin-3-ol The diastereomeric mixture of 6-(6-(methoxymethoxy)-2-methyl-2,3-dihydrobenzofuran-2-yl)pyridin-3-ol was separated by preparative HPLC (column: CHIRALPAK AD-H, 4.6×250 mm, 5 μm, mobile phase: methanol) to afford the less polar isomer (longer retention time).
MS (ESI+): [M+H]+ 288.0.
100% de

B) Diastereomer of N-[(1S)-2-({6-[6-(cyclopropyl-methoxy)-2-methyl-2,3-dihydro-1-benzofuran-2-yl]pyridin-3-yl}oxy)-1-methylethyl]acetamide By a method similar to Example 117, steps I, J, K and L, and using diastereomer of 6-(6-(methoxymethoxy)-2-methyl-2,3-dihydrobenzofuran-2-yl)pyridin-3-ol (longer retention time), the title compound was obtained.

Example 119

Diastereomer of N-[(1S)-2-({6-[6-(cyclopropyl-methoxy)-2-ethyl-2,3-dihydro-1-benzofuran-2-yl]pyridin-3-yl}oxy)-1-methylethyl]acetamide

A) 1-(2-Bromo-4-(methoxymethoxy)phenyl)butan-2-one

By a method similar to Example 117, step D, and using ethylmagnesium bromide instead of methyl magnesium bromide, the title compound was obtained.
$^1$H NMR (DMSO, 400 MHz): δ 0.95 (3H, t), 2.38 (2H, m), 3.32 (3H, s), 3.84 (2H, s), 5.20 (2H, s), 6.99 (1H, s), 7.22 (2H, s).

B) 6-(2-Ethyl-6-(methoxymethoxy)-2,3-dihydro-1-benzofuran-2-yl)pyridin-3-ol

By a method similar to Example 117, step E to G, and using 1-(2-bromo-4-(methoxymethoxy)phenyl)butan-2-one, the title compound was obtained.
MS (ESI+): [M+H]+ 302.1.

C) Diastereomer of 6-(2-ethyl-6-(methoxymethoxy)-2,3-dihydro-1-benzofuran-2-yl)pyridin-3-ol The diastereomeric mixture of 6-(2-ethyl-6-(methoxymethoxy)-2,3-dihydro-1-benzofuran-2-yl)pyridin-3-ol was separated by preparative HPLC (column: CHIRALPAK AD-H, 4.6×250 mm, 5 μm, mobile phase: ethanol) to afford the more polar isomer (shorter retention time).
MS (ESI+): [M+]+ 302.0.
100% de

D) Diastereomer of N-[(1S)-2-({6-[6-(cyclopropyl-methoxy)-2-ethyl-2,3-dihydro-1-benzofuran-2-yl]pyridin-3-yl}oxy)-1-methylethyl]acetamide By a method similar to Example 117, steps I, J, K and L, and using diastereomer of 6-(2-ethyl-6-(methoxymethoxy)-2,3-dihydro-1-benzofuran-2-yl)pyridin-3-ol (shorter retention time), the title compound was obtained.

Example 120

Diastereomer of N-[(1S)-2-({6-[6-(cyclopropyl-methoxy)-2-ethyl-2,3-dihydro-1-benzofuran-2-yl]pyridin-3-yl}oxy)-1-methylethyl]acetamide

A) Diastereomer of 6-(2-ethyl-6-(methoxymethoxy)-2,3-dihydro-1-benzofuran-2-yl)pyridin-3-ol The diastereomeric mixture of 6-(2-ethyl-6-(methoxymethoxy)-2,3-dihydro-1-benzofuran-2-yl)pyridin-3-ol was separated by preparative HPLC (column: CHIRALPAK AD-H, 4.6×250 mm, 5 μm, mobile phase: ethanol) to afford the less polar isomer (longer retention time).
MS (ESI+): [M+H]+ 302.0.
100% de

B) Diastereomer of N-[(1S)-2-({6-[6-(cyclopropyl-methoxy)-2-ethyl-2,3-dihydro-1-benzofuran-2-yl]pyridin-3-yl}oxy)-1-methylethyl]acetamide By a method similar to Example 117, steps I, J, K and L, and using diastereomer of 6-(2-ethyl-6-(methoxymethoxy)-2,3-dihydro-1-benzofuran-2-yl)pyridin-3-ol (longer retention time), the title compound was obtained.

Example 121

Diastereomer of N-[(1S)-2-({6-[2-cyclopropyl-6-(cyclopropylmethoxy)-2,3-dihydro-1-benzofuran-2-yl]pyridin-3-yl}oxy)-1-methylethyl]acetamide

A) 2-(2-Bromo-4-(methoxymethoxy)phenyl)-1-cyclopropylethanone

By a method similar to Example 117, step D, and using ethylmagnesium bromide instead of cyclopropylmethyl magnesium bromide, the title compound was obtained.
MS (ESI+): [M+H]+ 298.9.

B) 6-(2-Cyclopropyl-6-(methoxymethoxy)-2,3-dihydro-1-benzofuran-2-yl)pyridin-3-ol By a method similar to Example 117, step E to G, and using 2-(2-bromo-4-(methoxymethoxy)phenyl)-1-cyclopropylethanone, the title compound was obtained.
MS (ESI+): [M+H]+ 314.1.

C) Diastereomer of 6-(2-cyclopropyl-6-(methoxymethoxy)-2,3-dihydro-1-benzofuran-2-yl)pyridin-3-ol The diastereomeric mixture of 6-(2-cyclopropyl-6-(methoxymethoxy)-2,3-dihydro-1-benzofuran-2-yl)pyridin-3-ol was separated by preparative HPLC (column: CHIRALPAK AD-H, 4.6×250 mm, 5 μm, mobile phase: ethanol) to afford the more polar isomer (shorter retention time).
MS (ESI+): [M+H]+ 314.0.
100% de

D) Diastereomer of N-[(1S)-2-({6-[2-cyclopropyl-6-(cyclopropylmethoxy)-2,3-dihydro-1-benzofuran-2-yl]pyridin-3-yl}oxy)-1-methylethyl]acetamide By a method similar to Example 117, steps I, J, K and L, and using diastereomer of 6-(2-cyclopropyl-6-(methoxymethoxy)-2,3-dihydro-1-benzofuran-2-yl)pyridin-3-ol (shorter retention time), the title compound was obtained.

Example 122

Diastereomer of N-[(1S)-2-({6-[2-cyclopropyl-6-(cyclopropylmethoxy)-2,3-dihydro-1-benzofuran-2-yl]pyridin-3-yl}oxy)-1-methylethyl]acetamide A) Diastereomer of 6-(2-cyclopropyl-6-(methoxymethoxy)-2,3-dihydro-1-benzofuran-2-yl)pyridin-3-ol The diastereomeric mixture of 6-(2-cyclopropyl-6-(methoxymethoxy)-2,3-dihydro-1-benzofuran-2-yl)pyridin-3-ol was separated by preparative HPLC (column: CHIRALPAK AD-H, 4.6×250 mm, 5 μm, mobile phase: ethanol) to afford the less polar isomer (longer retention time).
MS (ESI+): [M+H]$^+$ 314.0.
100% de B) Diastereomer of N-[(1S)-2-({6-[2-cyclopropyl-6-(cyclopropylmethoxy)-2,3-dihydro-1-benzofuran-2-yl]pyridin-3-yl}oxy)-1-methylethyl]acetamide By a method similar to Example 117, steps I, J, K and L, and using diastereomer of 6-(2-cyclopropyl-6-(methoxymethoxy)-2,3-dihydro-1-benzofuran-2-yl)pyridin-3-ol (longer retention time), the title compound was obtained.

Example 123

N-[(1S)-2-{4-[6-(cyclopropylmethoxy)pyrazolo[1,5-a]pyridin-2-yl]-3,5-difluorophenoxy}-1-methylethyl]acetamide A) tert-butyl [(1S)-2-(4-bromo-3,5-difluorophenoxy)-1-methylethyl]carbamate To a solution of 4-bromo-3,5-difluorophenol (5.0 g), tert-butyl [(1S)-2-hydroxy-1-methylethyl]carbamate (5 g) and triphenylphosphine (7.5 g) in THF (50 mL) was added diisopropyl azodicarboxylate (1.9 M in toluene, 14 mL) dropwise at room temperature. The reaction mixture was stirred at 60° C. overnight and concentrated under reduced pressure. The residue was purified by silica gel column chromatography (hexane/ethyl acetate) to afford the title compound (5.1 g).
$^1$H NMR (300 MHz, DMSO-d$_6$) δ 1.10 (3H, d, J=6.5 Hz), 1.33-1.42 (9H, m), 3.71-3.99 (3H, m), 6.80-7.03 (3H, m).
MS (ESI+): [M+H]$^+$ 266.9.

B) tert-butyl [(1S)-2-(4-ethynyl-3,5-difluorophenoxy)-1-methylethyl]carbamate

A mixture of text-butyl [(1S)-2-(4-bromo-3,5-difluorophenoxy)-1-methylethyl]carbamate (5.1 g), ethynyl(trimethyl)silane (3.9 mL), copper iodide (I) (0.26 g), dichloropalladium triphenylphosphine (1:2) (0.98 g) and triethylamine (3.9 ml) in toluene (50 ml) was stirred at 100° C. overnight under Ar atmosphere. After cooling to room temperature, the mixture was filtered through a pad of Celite. The filtrate was concentrated under reduced pressure. The residue was dissolved in THF (50 mL) and tetrabutylammonium fluoride (1.0 M in THF, 28 ml) was added to the mixture. After stirring at room temperature for 1 hr, the mixture was extracted with ethyl acetate and water. The organic layer was washed with brine, dried over anhydrous magnesium sulfate and concentrated under reduced pressure. The residue was purified by silica gel column chromatography (hexane/ethyl acetate) to afford the title compound (2.5 g).
$^1$H NMR (300 MHz, DMSO-d$_6$) δ 1.10 (3H, d, J=6.6 Hz), 1.37 (9H, s), 3.68-3.99 (3H, m), 4.59 (1H, s), 6.78-7.03 (3H, m).

C) tert-butyl [(1S)-2-(4-{[5-(cyclopropylmethoxy)pyridin-2-yl]ethynyl}-3,5-difluorophenoxy)-1-methylethyl]carbamate A mixture of tert-butyl [(1S)-2-(4-ethynyl-3,5-difluorophenoxy)-1-methylethyl]carbamate (2.5 g), 2-bromo-5-(cyclopropylmethoxy)pyridine (1.8 g), copper iodide (I) (0.15 g), dichloropalladium-triphenylphosphine (1:2) (0.56 g) and triethylamine (2.2 mL) in toluene (20 mL) was stirred at 100° C. overnight under argon atmosphere. After cooling to room temperature, the mixture was filtered through a pad of Celite. The filtrate was concentrated under reduced pressure. The residue was purified by silica gel column chromatography (hexane/ethyl acetate) to afford the title compound (1.3 g).
$^1$H NMR (300 MHz, DMSO-d$_6$) δ 0.29-0.42 (2H, m), 0.53-0.66 (2H, m), 1.11 (3H, dd, J=6.7, 1.7 Hz), 1.21-1.30 (1H, m), 1.37 (9H, d, J=1.4 Hz), 3.77-3.99 (5H, m), 6.85-7.02 (3H, m), 7.35-7.48 (1H, m), 7.51-7.64 (1H, m), 8.22-8.38 (1H, m).
MS (ESI+): [M+H]$^+$ 459.2.

D) tert-butyl [(1S)-2-{4-[6-(cyclopropylmethoxy)pyrazolo[1,5-a]pyridin-2-yl]-3,5-difluorophenoxy}-1-methylethyl]carbamate To an ice cold stirred solution of ethyl N-((mesitylsulfonyl)oxy)ethanimidoate (1.794 g) in THF (2 mL) was added perchloric acid (0.759 ml) dropwise. After stirring at 0° C. for 20 min, the mixture was poured into ice water. The precipitated solid was collected by filtration and washed with water. The solid was added to the solution of tert-butyl [(1S)-2-(4-{[5-(cyclopropylmethoxy)pyridin-2-yl]ethynyl}-3,5-difluorophenoxy)-1-methylethyl]carbamate (1.31 g) in THF (13 mL) at room temperature. The mixture was stirred at room temperature for 30 min. The mixture was concentrated under reduced pressure and the residue was dissolved in DMF (13 ml). Potassium carbonate (0.790 g) was added to the mixture at room temperature and the reaction mixture was stirred at room temperature overnight. The mixture was extracted with ethyl acetate and water. The organic layer was washed with brine, dried over anhydrous magnesium sulfate and concentrated under reduced pressure. The residue was purified by silica gel column chromatography (hexane/ethyl acetate) to afford the title compound (130 mg).
$^1$H NMR (300 MHz, DMSO-d$_6$) δ 0.24-0.41 (2H, m), 0.52-0.67 (2H, m), 1.12 (3H, d, J=6.6 Hz), 1.19-1.31 (1H, m), 1.39 (9H, s), 3.76-4.06 (5H, m), 6.69-6.78 (1H, m), 6.80-6.99 (3H, m), 7.01-7.13 (1H, m), 7.58-7.70 (1H, m), 8.34-8.42 (1H, m).
MS (ESI+): [M+H]$^+$ 474.2.

E) N-[(1S)-2-{4-[6-(cyclopropylmethoxy)pyrazolo[1,5-a]pyridin-2-yl]-3,5-difluorophenoxy}-1-methylethyl]acetamide A mixture of tert-butyl [(1S)-2-{4-[6-(cyclopropylmethoxy)pyrazolo[1,5-a]pyridin-2-yl]-3,5-difluorophenoxy}-1-methylethyl]carbamate (130 mg) and 4 M hydrogen chloride-ethyl acetate (2 mL) was stirred at room temperature for 30 min. The mixture was concentrated under reduced pressure. To the residue were added pyridine (2 mL) and acetic anhydride (0.26 mL). The mixture was stirred at room temperature for 30 min and concentrated under reduced pressure. The residue was purified by silica gel column chromatography (NH, hexane/ethyl acetate) to afford the title compound (40 mg).

$^1$H NMR (300 MHz, DMSO-$d_6$) δ 0.29-0.39 (2H, m), 0.53-0.64 (2H, m), 1.15 (3H, d, J=6.7 Hz), 1.20-1.33 (1H, m), 1.82 (3H, s), 3.83-3.94 (3H, m), 3.96-4.16 (2H, m), 6.70-6.78 (1H, m), 6.89 (2H, d, J=10.5 Hz), 7.08 (1H, dd, J=9.6, 2.1 Hz), 7.64 (1H, d, J=9.5 Hz), 7.94 (1H, d, J=7.5 Hz), 8.33-8.43 (1H, m).

Anal. Calcd for $C_{22}H_{23}N_3O_3F_2$: C, 63.60; H, 5.58; N, 10.11. Found: C, 63.47; H, 5.59; N, 9.95.

Table 1-1 to Table 1-16 show compound names, structural formulas and measured values of MS of the Example compounds.

The measured values of MS generally show those in a positive mode (ESI+), and those in a negative mode (ESI−) are accompanied by [M−H]$^−$. In addition, when a fragment peak wherein a sodium ion (+Na) is added to a molecular ion peak is observed in the positive mode (ESI+), [M+Na]$^+$ is also shown.

TABLE 1-1

| Ex. No. | compound name | structural formula | MS |
|---|---|---|---|
| 1 | N-[(1S)-2-({6-[6-(cyclopropylmethoxy)-1,3-benzoxazol-2-yl]pyridin-3-yl}oxy)-1-methylethyl]-acetamide | | 382.3 |
| 2 | N-[(1S)-2-({5-[5-(cyclopropylmethoxy)-1,3-benzoxazol-2-yl]isoxazol-3-yl}oxy)-1-methylethyl]-acetamide | | 372.1 |
| 3 | N-[(1S)-2-{4-[6-(cyclopropylmethoxy)-1,3-benzoxazol-2-yl]phenoxy}-1-methylethyl]acetamide | | 381.1 |
| 4 | N-[(1S)-2-({6-[6-(cyclopropylmethoxy)-1,3-benzoxazol-2-yl]-5-methylpyridin-3-yl}oxy)-1-methylethyl]acetamide | | 396.1 |

TABLE 1-1-continued

| Ex. No. | compound name | structural formula | MS |
|---|---|---|---|
| 5 | N-[(1S)-2-({5-chloro-6-[6-(cyclopropylmethoxy)-1,3-benzoxazol-2-yl]pyridin-3-yl}oxy)-1-methylethyl]-acetamide | | 416.3 |
| 6 | N-[(1S)-2-({6-[6-(cyclopropylmethoxy)-1,3-benzoxazol-2-yl]-5-fluoropyridin-3-yl}oxy)-1-methylethyl]acetamide | | 400.1 |
| 7 | N-[(1S)-2-({5-[6-(cyclopropylmethoxy)-1,3-benzoxazol-2-yl]isoxazol-3-yl}oxy)-1-methylethyl]-acetamide | | 372.4 |
| 8 | N-[(1S)-2-({5-[6-(cyclopropylmethoxy)-1,3-benzoxazol-2-yl]-1H-pyrazol-3-yl}oxy)-1-methylethyl]-acetamide | | 371.2 |

TABLE 1-2

| Ex. No. | compound name | structural formula | MS |
|---|---|---|---|
| 9 | N-[(1S)-2-({5-[6-(cyclopropylmethoxy)-1,3-benzoxazol-2-yl]-4-fluoro-1H-pyrazol-3-yl}oxy)-1-methylethyl]acetamide | | 389.3 |
| 10 | N-[(1S)-2-({5-[6-(cyclopropylmethoxy)-1,3-benzoxazol-2-yl]-1-methyl-1H-pyrazol-3-yl}oxy)-1-methylethyl]acetamide | | 385.1 |
| 11 | N-[(1S)-2-({5-[6-(cyclopropylmethoxy)-1,3-benzoxazol-2-yl]-4-fluoro-1-methyl-1H-pyrazol-3-yl}oxy)-1-methylethyl]acetamide | | 403.1 |

TABLE 1-2-continued

| Ex. No. | compound name | structural formula | MS |
|---|---|---|---|
| 12 | N-[(1S)-2-{4-[5-(cyclopropylmethoxy)-2H-indazol-2-yl]phenoxy}-1-methylethyl]acetamide | | 380.2 |
| 13 | N-[(1S)-2-{4-[6-(cyclopropylmethoxy)-2H-indazol-2-yl]phenoxy}-1-methylethyl]acetamide | | 380.2 |
| 14 | N-[(1S)-2-({6-[6-(cyclopropylmethoxy)-2H-indazol-2-yl]pyridin-3-yl}oxy)-1-methylethyl]acetamide | | 381.1 |
| 15 | 1-[(1S)-2-({6-[6-(cyclopropylmethoxy)-1,3-benzoxazol-2-yl]pyridin-3-yl}oxy)-1-methylethyl]urea | | 383.2 |
| 16 | 1-[(1S)-2-({6-[6-(cyclopropylmethoxy)-1,3-benzoxazol-2-yl]pyridin-3-yl}oxy)-1-methylethyl]-3-methylurea | | 397.1 |

TABLE 1-3

| Ex. No. | compound name | structural formula | MS |
|---|---|---|---|
| 17 | methyl [(1S)-2-({6-[6-(cyclopropylmethoxy)-1,3-benzoxazol-2-yl]pyridin-3-yl}oxy)-1-methylethyl]carbamate | | 398.2 |
| 18 | 1-[(1S)-2-({6-[6-(cyclopropylmethoxy)-1,3-benzoxazol-2-yl]-5-fluoropyridin-3-yl}oxy)-1-methylethyl]urea | | 401.2 |
| 19 | 1-[(1S)-2-({6-[6-(cyclopropylmethoxy)-1,3-benzoxazol-2-yl]-5-fluoropyridin-3-yl}oxy)-1-methylethyl]-3-methylurea | | 415.2 |
| 20 | 1-[(1S)-2-({5-[5-(cyclopropylmethoxy)-1,3-benzoxazol-2-yl]isoxazol-3-yl}oxy)-1-methylethyl]-3-methylurea | | 387.3 |
| 21 | methyl [(1S)-2-({5-[5-(cyclopropylmethoxy)-1,3-benzoxazol-2-yl]isoxazol-3-yl}oxy)-1-methylethyl]carbamate | | 388.2 |
| 22 | 1-[(1S)-2-({5-[5-(cyclopropylmethoxy)-1,3-benzoxazol-2-yl]isoxazol-3-yl}oxy)-1-methylethyl]urea | | 373.2 |
| 23 | N-[(1S)-2-({5-[5-(cyclopropylmethoxy)-1,3-benzoxazol-2-yl]-4-methylisoxazol-3-yl}oxy)-1-methylethyl]acetamide | | 386.3 |

TABLE 1-3-continued

| Ex. No. | compound name | structural formula | MS |
|---|---|---|---|
| 24 | N-[(1S)-2-({6-[6-(cyclopropylmethoxy)-2,3-dihydro-1-benzofuran-2-yl]pyridin-3-yl}oxy)-1-methylethyl]acetamide | | 383.2 |

TABLE 1-4

| Ex. No. | compound name | structural formula | MS |
|---|---|---|---|
| 25 | N-{(1S)-2-[4-(6-ethoxy-2H-indazol-2-yl)-3-fluorophenoxy]-1-methylethyl}acetamide monohydrate | | 372.2 |
| 26 | N-{(1S)-2-[4-(6-ethoxy-2H-indazol-2-yl)phenoxy]-1-methylethyl}acetamide | | 354.2 |
| 27 | N-[(1S)-2-{4-[5-(cyclopropylmethoxy)-2H-benzotriazol-2-yl]phenoxy}-1-methylethyl]acetamide | | 381.1 |
| 28 | N-[(1S)-2-{[6-(6-ethoxy-1,3-benzoxazol-2-yl)pyridin-3-yl]oxy}-1-methylethyl]acetamide | | 356.2 |

TABLE 1-4-continued

| Ex. No. | compound name | structural formula | MS |
|---|---|---|---|
| 29 | N-{(1S)-2-[(6-{6-[(3,3-difluorocyclobutyl)methoxy]-1,3-benzoxazol-2-yl}pyridin-3-yl)oxy]-1-methylethyl}acetamide | | 432.1 |
| 30 | N-[(1S)-2-({6-[6-(2,2-difluoropropoxy)-1,3-benzoxazol-2-yl]pyridin-3-yl}oxy)-1-methylethyl]acetamide | | 406.1 |
| 31 | N-[(1S)-2-({6-[5-(cyclopropylmethoxy)-1,3-benzoxazol-2-yl]pyridin-3-yl}oxy)-1-methylethyl]acetamide | | 382.4 |
| 32 | N-[(1S)-2-({6-[5-(2-cyclopropylethoxy)-1,3-benzoxazol-2-yl]pyridin-3-yl}oxy)-1-methylethyl]acetamide | | 396.2 |
| 33 | N-[(1S)-1-methyl-2-({5-[5-(1-methylethoxy)-1,3-benzoxazol-2-yl]isoxazol-3-yl}oxy)ethyl]acetamide | | 360.2 |
| 34 | N-[(1S)-2-({5-[5-(cyclopropylmethoxy)-1,3-benzoxazol-2-yl]-4-fluoroisoxazol-3-yl}oxy)-1-methylethyl]acetamide | | 390.1 |

TABLE 1-5

| Ex. No. | compound name | structural formula | MS |
|---|---|---|---|
| 35 | N-[(1S)-2-{4-[6-(cyclopropylmethoxy)-1,3-benzothiazol-2-yl]phenoxy}-1-methylethyl]acetamide | | NT |
| 36 | N-[(1S)-2-({5-[6-(cyclopropylmethoxy)-1,3-benzothiazol-2-yl]isoxazol-3-yl}oxy)-1-methylethyl]-acetamide | | 388.1 |
| 37 | N-[(1S)-2-({5-[5-(cyclopropylmethoxy)-1,3-benzothiazol-2-yl]isoxazol-3-yl}oxy)-1-methylethyl]-acetamide | | 388.1 |
| 38 | N-[(1S)-2-({5-[6-(cyclopropylmethoxy)-1,3-benzoxazol-2-yl]-4-methyl-1H-pyrazol-3-yl}oxy)-1-methylethyl]acetamide | | 385.2 |
| 39 | N-[(1S)-2-({1-benzyl-5-[5-(cyclopropylmethoxy)-1,3-benzoxazol-2-yl]-1H-pyrazol-3-yl}oxy)-1-methylethyl]acetamide | | 461.5 |
| 40 | N-[(1S)-2-({5-[5-(cyclopropylmethoxy)-1,3-benzoxazol-2-yl]-1H-pyrazol-3-yl}oxy)-1-methylethyl]acetamide | | 371.3 |
| 41 | N-[(1S)-2-({5-[6-(cyclopropylmethoxy)-1,3-benzoxazol-2-yl]-4-methylisoxazol-3-yl}oxy)-1-methylethyl]acetamide | | 386.2 |
| 42 | N-[2-({5-[5-(cyclopropylmethoxy)-1,3-benzoxazol-2-yl]isoxazol-3-yl}oxy)-1-(fluoromethyl)-ethyl]acetamide | | 390.1 |

TABLE 1-6

| Ex. No. | compound name | structural formula | MS |
|---|---|---|---|
| 43 | N-{1-[({5-[5-(cyclopropylmethoxy)-1,3-benzoxazol-2-yl]isoxazol-3-yl}oxy)methyl]-2,2-difluoroethyl}acetamide | | 408.1 |
| 44 | 1-[(1S)-2-({5-[5-(cyclopropylmethoxy)-1,3-benzoxazol-2-yl]-4-methylisoxazol-3-yl}oxy)-1-methylethyl]-3-methylurea | | 401.3 |
| 45 | 1-[(1S)-2-({5-[5-(cyclopropylmethoxy)-1,3-benzoxazol-2-yl]-4-methylisoxazol-3-yl}oxy)-1-methylethyl]urea | | 387.2 |
| 46 | N-[(1S)-2-{[5-(5-ethoxy-1,3-benzoxazol-2-yl)isoxazol-3-yl]oxy}-1-methylethyl]acetamide | | 346.2 |
| 47 | N-(3-{6-[6-(cyclopropylmethoxy)-1,3-benzoxazol-2-yl]pyridin-3-yl}-1-methyl-3-oxopropyl)acetamide | | 394.1 |
| 48 | methyl [(1S)-2-({6-[6-(cyclopropylmethoxy)-1,3-benzoxazol-2-yl]-5-fluoropyridin-3-yl}oxy)-1-methylethyl]carbamate | | 416.1 |
| 49 | N-[(1S)-3-{6-[6-(cyclopropylmethoxy)-1,3-benzoxazol-2-yl]pyridin-3-yl}-1-methylpropyl]acetamide | | 380.2 |

TABLE 1-6-continued

| Ex. No. | compound name | structural formula | MS |
|---|---|---|---|
| 50 | N-[(1S)-2-({6-[5-(cyclopropylmethoxy)-1,3-benzoxazol-2-yl]-5-fluoropyridin-3-yl}oxy)-1-methylethyl]acetamide | | 400.3 |

TABLE 1-7

| Ex. No. | compound name | structural formula | MS |
|---|---|---|---|
| 51 | N-[(1S)-2-{[6-(6-ethoxy-1,3-benzoxazol-2-yl)-5-fluoropyridin-3-yl]oxy}-1-methylethyl]acetamide | | 374.3 |
| 52 | N-[(1S)-2-({6-[6-(2-fluoropropoxy)-1,3-benzoxazol-2-yl]pyridin-3-yl}oxy)-1-methylethyl]acetamide | | 388.1 |
| 53 | N-[(1S)-2-({6-[6-(cyclopropylmethoxy)-1,3-benzoxazol-2-yl]-2-methoxypyridin-3-yl}oxy)-1-methylethyl]acetamide | | 412.4 |
| 54 | N-[(1S)-2-{[6-(6-ethoxy-1,3-benzoxazol-2-yl)pyridin-3-yl]oxy}-1-methylethyl]-2,2,2-trifluoroacetamide | | 410.2 |

TABLE 1-7-continued

| Ex. No. | compound name | structural formula | MS |
|---|---|---|---|
| 55 | N-[(1S)-2-{[6-(6-ethoxy-1,3-benzoxazol-2-yl)pyridin-3-yl]oxy}-1-methylethyl]-2,2-difluoroacetamide | | 392.3 |
| 56 | N-[(1S)-2-({6-[6-(cyclopropylmethoxy)-1,3-benzoxazol-2-yl]-1-oxidepyridin-3-yl}oxy)-1-methylethyl]acetamide | | 398 |
| 57 | N-[(1S)-2-({6-[6-(cyclopropylmethoxy)-2-methyl-2,3-dihydro-1-benzofuran-2-yl]pyridin-3-yl}oxy)-1-methylethyl]acetamide | | 397.3 |
| 58 | N-[(1S)-2-({2-[6-(cyclopropyl-methoxy)-1,3-benzoxazol-2-yl]pyrimidin-5-yl}oxy)-1-methylethyl]acetamide | | 383.2 |

TABLE 1-8

| Ex. No. | compound name | structural formula | MS |
|---|---|---|---|
| 59 | N-{(1S)-2-[4-(5-methoxy-2H-indazol-2-yl)phenoxy]-1-methylethyl}acetamide | | 340.1 |

TABLE 1-8-continued

| Ex. No. | compound name | structural formula | MS |
|---|---|---|---|
| 60 | N-[(1S)-2-({6-[6-(3,3-difluorobutoxy)-1,3-benzoxazol-2-yl]-5-fluoropyridin-3-yl}oxy)-1-methylethyl]acetamide | | 438.2 |
| 61 | 1-[(1S)-2-{4-[6-(cyclopropylmethoxy)-2H-indazol-2-yl]phenoxy}-1-methylethyl]urea | | 381.2 |
| 62 | 1-[(1S)-2-{4-[6-(cyclopropylmethoxy)-2H-indazol-2-yl]phenoxy}-1-methylethyl]-3-methylurea | | 395.2 |
| 63 | 3-[(1S)-2-{4-[6-(cyclopropylmethoxy)-2H-indazol-2-yl]phenoxy}-1-methylethyl]-1,1-dimethylurea | | 409.3 |
| 64 | N-[(1S)-2-{4-[6-(cyclopropylmethoxy)-7-fluoro-2H-indazol-2-yl]phenoxy}-1-methylethyl]acetamide | | 398.2 |
| 65 | N-[(1S)-2-{4-[6-(cyclopropylmethoxy)-4-fluoro-2H-indazol-2-yl]phenoxy}-1-methylethyl]acetamide | | 398.2 |

TABLE 1-8-continued

| Ex. No. | compound name | structural formula | MS |
|---|---|---|---|
| 66 | N-[(1S)-2-{4-[6-(cyclopropylmethoxy)-5-fluoro-2H-indazol-2-yl]phenoxy}-1-methylethyl]acetamide | | 398.2 |

TABLE 1-9

| Ex. No. | compound name | structural formula | MS |
|---|---|---|---|
| 67 | N-[(1S)-2-{4-[6-(cyclopropylmethoxy)-2H-indazol-2-yl]-3-fluorophenoxy}-1-methylethyl]acetamide | | 398.2 |
| 68 | 1-[(1S)-2-{4-[6-(cyclopropylmethoxy)-2H-indazol-2-yl]-3-fluorophenoxy}-1-methylethyl]urea | | 399.2 |
| 69 | N-[(1S)-2-{4-[6-(cyclopropylmethoxy)-2H-indazol-2-yl]-2-fluorophenoxy}-1-methylethyl]acetamide | | 398.2 |
| 70 | N-[(1S)-2-{4-[6-(cyclopropylmethoxy)-2H-indazol-2-yl]-2,5-difluorophenoxy}-1-methylethyl]acetamide | | 416.2 |

TABLE 1-9-continued

| Ex. No. | compound name | structural formula | MS |
|---|---|---|---|
| 71 | N-[(1S)-2-{4-[7-chloro-6-(cyclopropylmethoxy)-2H-indazol-2-yl]phenoxy}-1-methylethyl]acetamide | | 414.1 |
| 72 | N-[(1S)-2-{4-[6-(cyclopropylmethoxy)-3-methyl-2H-indazol-2-yl]phenoxy}-1-methylethyl]acetamide | | 394.3 |
| 73 | N-[(1S)-2-{4-[6-(cyclopropylmethoxy)-3-fluoro-2H-indazol-2-yl]phenoxy}-1-methylethyl]acetamide | | 398.2 |
| 74 | N-[(1S)-2-{4-[7-bromo-6-(cyclopropylmethoxy)-2H-indazol-2-yl]phenoxy}-1-methylethyl]acetamide | | 458 |

TABLE 1-10

| Ex. No. | compound name | structural formula | MS |
|---|---|---|---|
| 75 | N-[(1S)-2-{4-[6-(cyclopropylmethoxy)-3-(trifluoromethyl)-2H-indazol-2-yl]phenoxy}-1-methylethyl]acetamide | | 448.1 |

TABLE 1-10-continued

| Ex. No. | compound name | structural formula | MS |
|---|---|---|---|
| 76 | N-[(1S)-2-{4-[3-cyano-6-(cyclopropylmethoxy)-2H-indazol-2-yl]phenoxy}-1-methylethyl]acetamide | 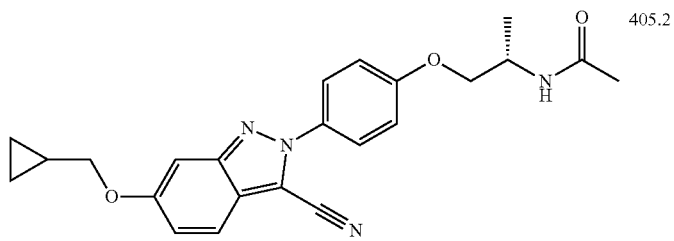 | 405.2 |
| 77 | N-[(1S)-2-{4-[7-cyano-6-(cyclopropylmethoxy)-2H-indazol-2-yl]phenoxy}-1-methylethyl]acetamide | 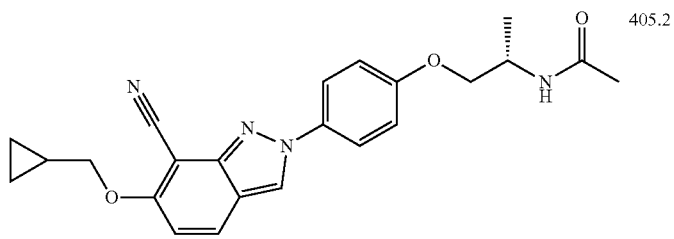 | 405.2 |
| 78 | N-[(1S)-2-{4-[6-(cyclopropylmethoxy)-7-methyl-2H-indazol-2-yl]phenoxy}-1-methylethyl]acetamide | 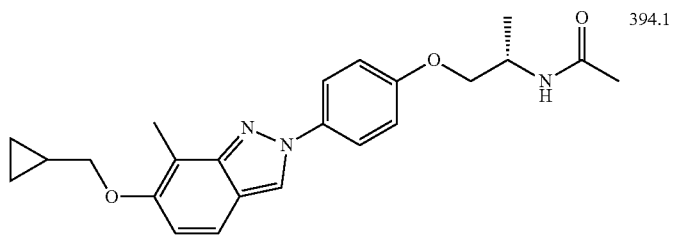 | 394.1 |
| 79 | N-[(1S)-2-{4-[6-(cyclopropylmethoxy)-2H-indazol-2-yl]-2-methylphenoxy}-1-methylethyl]acetamide | 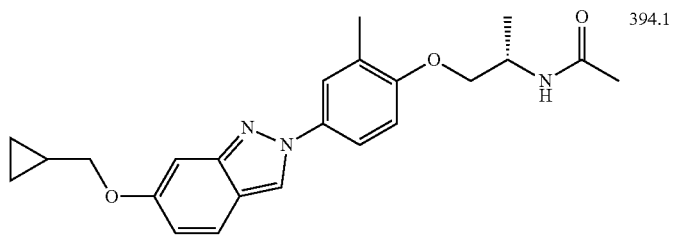 | 394.1 |
| 80 | N-[(1S)-2-{4-[6-(cyclopropylmethoxy)-2H-indazol-2-yl]-3-methylphenoxy}-1-methylethyl]acetamide | 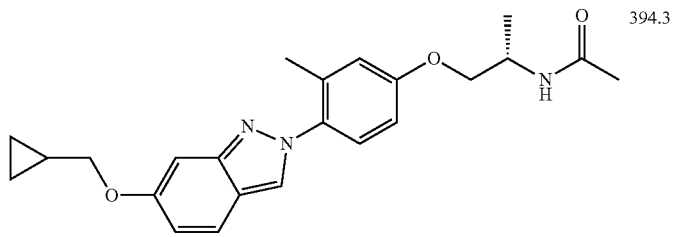 | 394.3 |
| 81 | N-[(1S)-2-{4-[6-(cyclopropylmethoxy)-2H-indazol-2-yl]-3,5-difluorophenoxy}-1-methylethyl]acetamide | 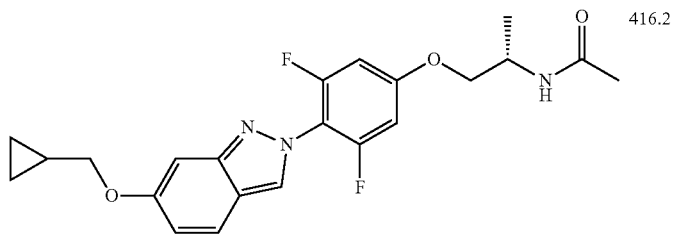 | 416.2 |

TABLE 1-10-continued

| Ex. No. | compound name | structural formula | MS |
|---|---|---|---|
| 82 | N-[(1S)-2-{3-chloro-4-[6-(cyclopropylmethoxy)-2H-indazol-2-yl]phenoxy}-1-methylethyl]acetamide | | 414.2 |

TABLE 1-11

| Ex. No. | compound name | structural formula | MS |
|---|---|---|---|
| 83 | N-[(1S)-2-{4-[6-(cyclopropylmethoxy)imidazo-[1,2-a]pyridin-2-yl]phenoxy}-1-methylethyl]acetamide | | 380.2 |
| 84 | N-[(1S)-2-{4-[6-(cyclopropylmethoxy)pyrazolo[1,5-a]pyridin-2-yl]phenoxy}-1-methylethyl]acetamide | | 380.2 |
| 85 | N-{(1S)-2-[4-(6-ethoxypyrazolo[1,5-a]pyridin-2-yl)phenoxy]-1-methylethyl}acetamide | | 354.2 |
| 86 | N-{(1S)-2-[4-(6-ethoxy-3-fluoropyrazolo[1,5-a]pyridin-2-yl)phenoxy]-1-methylethyl}acetamide | | 372.2 |

TABLE 1-11-continued

| Ex. No. | compound name | structural formula | MS |
|---|---|---|---|
| 87 | 1-[(1S)-2-({6-[6-(3,3-difluorobutoxy)-1,3-benzoxazol-2-yl]-5-fluoropyridin-3-yl}oxy)-1-methylethyl]urea | | 439.1 |
| 88 | N-{(1S)-2-[4-(6-ethoxy-7-fluoropyrazolo[1,5-a]pyridin-2-yl)phenoxy]-1-methylethyl}acetamide | | 372.2 |
| 89 | N-[(1S)-2-{4-[6-(cyclopropylmethoxy)[1,2,4]triazolo[1,5-a]pyridin-2-yl]phenoxy}-1-methylethyl]acetamide | | 381.2 |
| 90 | N-[(1S)-2-({6-[6-(cyclopropylmethoxy)[1,2,4]triazolo[1,5-a]pyridin-2-yl]pyridin-3-yl}oxy)-1-methylethyl]acetamide | | 382.3 |

TABLE 1-12

| Ex. No. | compound name | structural formula | MS |
|---|---|---|---|
| 91 | 1-[(1S)-2-({6-[6-(cyclopropylmethoxy)[1,2,4]triazolo[1,5-a]pyridin-2-yl]pyridin-3-yl}oxy)-1-methylethyl]urea | | 383.2 |

TABLE 1-12-continued

| Ex. No. | compound name | structural formula | MS |
|---|---|---|---|
| 92 | N-[(1S)-2-{4-[6-(cyclopropylmethoxy)-3-fluoroimidazo[1,2-a]pyridin-2-yl]phenoxy}-1-methylethyl]acetamide | | 398.2 |
| 93 | N-{(1S)-2-[4-(6-ethoxypyrazolo[1,5-a]pyridin-2-yl)-3-fluorophenoxy]-1-methylethyl}acetamide | | 372.2 |
| 94 | N-[(1S)-2-({6-[7-(cyclopropylmethoxy)[1,2,4]triazolo[1,5-a]pyridin-2-yl]pyridin-3-yl}oxy)-1-methylethyl]acetamide | | 382.1 |
| 95 | N-[(1S)-2-{4-[7-(cyclopropylmethoxy)[1,2,4]triazolo[1,5-a]pyridin-2-yl]phenoxy}-1-methylethyl]acetamide | | 381.2 |

TABLE 1-13

| Ex. No. | compound name | structural formula | MS |
|---|---|---|---|
| 96 | N-{(1S)-2-[(6-{6-[(2,2-difluorocyclopropyl)methoxy]-1,3-benzoxazol-2-yl}-5-fluoropyridin-3-yl)oxy]-1-methylethyl}acetamide | | 436.1 |

TABLE 1-13-continued

| Ex. No. | compound name | structural formula | MS |
|---|---|---|---|
| 97 | 1-{(1S)-2-[(6-{6-[(2,2-difluorocyclopropyl)methoxy]-1,3-benzoxazol-2-yl}-5-fluoropyridin-3-yl)oxy]-1-methylethyl}urea | 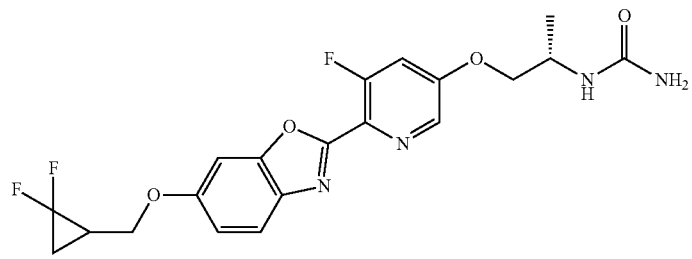 [SMILES: C[C@@H](COc1cnc(-c2nc3ccc(OCC4CC4(F)F)cc3o2)c(F)c1)NC(N)=O] | 437.2 |
| 98 | N-{(1S)-2-[(6-{6-[2-(2,2-difluorocyclopropyl)ethoxy]-1,3-benzoxazol-2-yl}-5-fluoropyridin-3-yl)oxy]-1-methylethyl}acetamide | 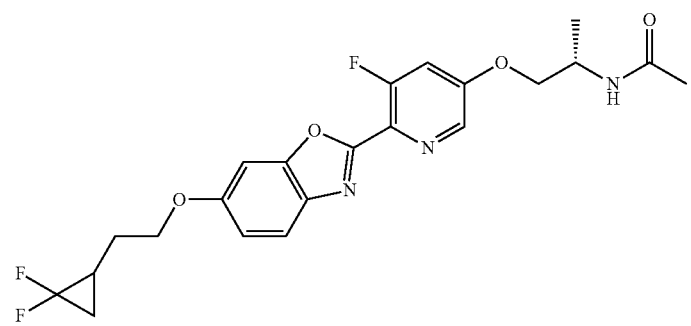 [SMILES: CC(=O)N[C@@H](C)COc1cnc(-c2nc3ccc(OCCC4CC4(F)F)cc3o2)c(F)c1] | 450.2 |
| 99 | 1-{(1S)-2-[(6-{6-[2-(2,2-difluorocyclopropyl)ethoxy]-1,3-benzoxazol-2-yl}-5-fluoropyridin-3-yl)oxy]-1-methylethyl}urea | 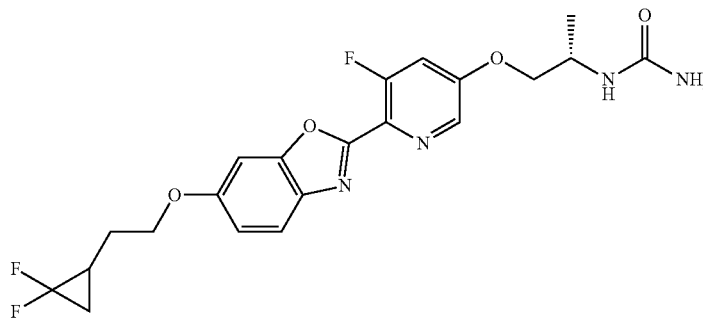 [SMILES: C[C@@H](COc1cnc(-c2nc3ccc(OCCC4CC4(F)F)cc3o2)c(F)c1)NC(N)=O] | 451.1 |
| 100 | N-{(1S)-2-[4-(6-ethoxy-3-fluoropyrazolo[1,5-a]pyridin-2-yl)-3-fluorophenoxy]-1-methylethyl}acetamide | 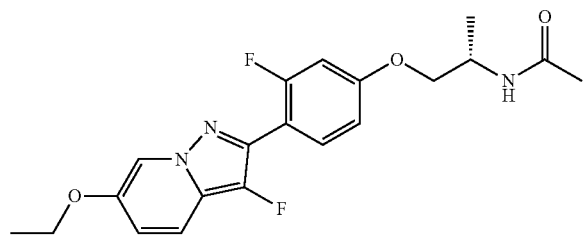 [SMILES: CCOc1ccc2c(F)c(-c3ccc(OC[C@H](C)NC(C)=O)cc3F)nn2c1] | 390.2 |
| 101 | 1-{(1S)-2-[4-(6-ethoxy-3-fluoropyrazolo[1,5-a]pyridin-2-yl)-3-fluorophenoxy]-1-methylethyl}urea | 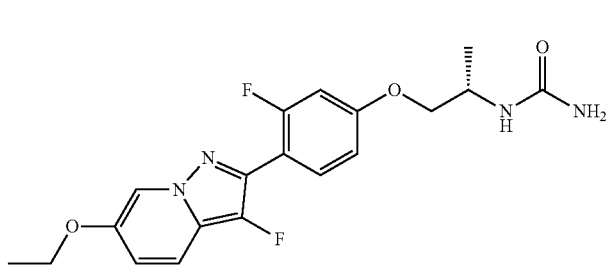 [SMILES: CCOc1ccc2c(F)c(-c3ccc(OC[C@H](C)NC(N)=O)cc3F)nn2c1] | 391.1 |

TABLE 1-13-continued

| Ex. No. | compound name | structural formula | MS |
|---|---|---|---|
| 102 | N-[(1S)-2-{4-[6-(cyclopropylmethoxy)-3-fluoropyrazolo[1,5-a]pyridin-2-yl]-3-fluorophenoxy}-1-methylethyl]acetamide | | 416.2 |
| 103 | 1-[(1S)-2-{4-[6-(cyclopropylmethoxy)-3-fluoropyrazolo[1,5-a]pyridin-2-yl]-3-fluorophenoxy}-1-methylethyl]urea | | 417.2 |

TABLE 1-14

| Ex. No. | compound name | structural formula | MS |
|---|---|---|---|
| 104 | N-[(1S)-2-{4-[6-(cyclopropylmethoxy)pyrazolo-[1,5-a]pyridin-2-yl]-3-fluorophenoxy}-1-methylethyl]acetamide | | 398.2 |
| 105 | 1-[(1S)-2-{4-[6-(cyclopropylmethoxy)pyrazolo-[1,5-a]pyridin-2-yl]-3-fluorophenoxy}-1-methylethyl]urea | | 399.2 |
| 106 | 1-[(1S)-2-({6-[6-(2,2-difluoropropoxy)-1,3-benzoxazol-2-yl]pyridin-3-yl}oxy)-1-methylethyl]urea | | 407.2 |

TABLE 1-14-continued

| Ex. No. | compound name | structural formula | MS |
|---|---|---|---|
| 107 | N-{(1S)-2-[(6-{6-[(3,3-difluorocyclobutyl)methoxy]-1,3-benzoxazol-2-yl}-5-fluoropyridin-3-yl)oxy]-1-methylethyl}acetamide | | 450.2 |
| 108 | 1-{(1S)-2-[(6-{6-[(3,3-difluorocyclobutyl)methoxy]-1,3-benzoxazol-2-yl}-5-fluoropyridin-3-yl)oxy]-1-methylethyl}urea | | 451.1 |
| 109 | Diastereomer of N-{(1S)-[(6-{6-[(2,2-difluorocyclopropyl)methoxy]-1,3-benzoxazol-2-yl}-5-fluoropyridin-3-yl)oxy]-1-methylethyl}acetamide (retention time: short) | | 436.1 |
| 110 | Distereomer of N-{(1S)-2-[(6-{6-[(2,2-difluorocyclopropyl)methoxy]-1,3-benzoxazol-2-yl}-5-fluoropyridin-3-yl)oxy]-1-methylethyl}acetamide (retention time: long) | | 436.1 |
| 111 | Distereomer of 1-{(1S)-2-[(6-{6-[(2,2-difluorocyclopropyl)methoxy]-1,3-benzoxazol-2-yl}-5-fluoropyridin-3-yl)oxy]-1-methylethyl}urea (retention time: short) | | 437.2 |

TABLE 1-15

| Ex. No. | compound name | structural formula | MS |
|---|---|---|---|
| 112 | Diastereomer of 1-{(1S)-2-[(6-{6-[(2,2-difluorocyclopropyl)methoxy]-1,3-benzoxazol-2-yl}-5-fluoropyridin-3-yl)oxy]-1-methylethyl}urea (retention time: long) | | 437.2 |
| 113 | Diastereomer of N-{(1S)-2-[(6-{6-[2-(2,2-difluorocyclopropyl)ethoxy]-1,3-benzoxazol-2-yl}-5-fluoropyridin-3-yl)oxy]-1-methylethyl}acetamide (retention time: short) | | 450.1 |
| 114 | Diastereomer of N-{(1S)-2-[(6-{6-[2-(2,2-difluorocyclopropyl)ethoxy]-1,3-benzoxazol-2-yl}-5-fluoropyridin-3-yl)oxy]-1-methylethyl}acetamide (retention time: long) | | 450.1 |
| 115 | Diastereomer of 1-{(1S)-2-[(6-{6-[2-(2,2-difluorocyclopropyl)ethoxy]-1,3-benzoxazol-2-yl}-5-fluoropyridin-3-yl)oxy]-1-methylethyl}urea (retention time: short) | | 451.1 |
| 116 | Diastereomer of 1-{(1S)-2-[(6-{6-[2-(2,2-difluorocyclopropyl)ethoxy]-1,3-benzoxazol-2-yl}-5-fluoropyridin-3-yl)oxy]-1-methylethyl}urea (retention time: long) | | 451.1 |

TABLE 1-15-continued

| Ex. No. | compound name | structural formula | MS |
|---|---|---|---|
| 117 | Diastereomer of N-[(1S)-2-({6-[6-(cyclopropylmethoxy)-2-methyl-2,3-dihydro-1-benzofuran-2-yl]pyridin-3-yl}oxy)-1-methylethyl]acetamide | | 397.1 |
| 118 | Diastereomer of N-[(1S)-2-({6-[6-(cyclopropylmethoxy)-2-methyl-2,3-dihydro-1-benzofuran-2-yl]pyridin-3-yl}oxy)-1-methylethyl]acetamide | | 397.3 |
| 119 | Diastereomer of N-[(1S)-2-({6-[6-(cyclopropylmethoxy)-2-ethyl-2,3-dihydro-1-benzofuran-2-yl]pyridin-3-yl}oxy)-1-methylethyl]acetamide | | 411.2 |

TABLE 1-16

| Ex. No. | compound name | structural formula | MS |
|---|---|---|---|
| 120 | Diastereomer of N-[(1S)-2-({6-[6-(cyclopropylmethoxy)-2-ethyl-2,3-dihydro-1-benzofuran-2-yl]pyridin-3-yl}oxy)-1-methylethyl]acetamide | | 411.2 |
| 121 | Diastereomer of N-[(1S)-2-({6-[2-cyclopropyl-6-(cyclopropylmethoxy)-2,3-dihydro-1-benzofuran-2-yl]pyridin-3-yl}oxy)-1-methylethyl]acetamide | | 423.2 |

TABLE 1-16-continued

| Ex. No. | compound name | structural formula | MS |
|---|---|---|---|
| 122 | Diastereomer of N-[(1S)-2-({6-[2-cyclopropyl-6-(cyclopropylmethoxy)-2,3-dihydro-1-benzofuran-2-yl]pyridin-3-yl}oxy)-1-methylethyl]acetamide | 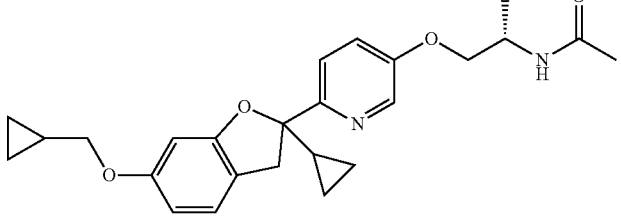 | 423.2 |
| 123 | N-[(1S)-2-{4-[6-(cyclopropylmethoxy)pyrazolo-[1,5-a]pyridin-2-yl]-3,5-difluorophenoxy}-1-methylethyl]acetamide | 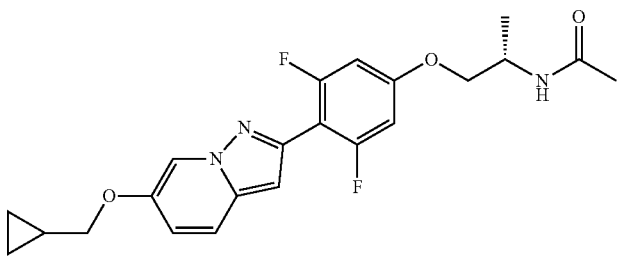 [SMILES: CC(=O)N[C@@H](C)COc1cc(F)c(-c2cc3ccc(OCC4CC4)cn3n2)c(F)c1] | 416.1 |

Experimental Example 1

The ACC2 inhibitory action of the compound of the present invention was evaluated by the following method.

(1) Cloning of Human ACC2 Gene and Preparation of Recombinant Baculovirus

Human ACC2 gene was cloned by PCR using a human skeletal muscle cDNA library (Clontech) as a template and Primer 1 and Primer 2 shown below. Primer 1 and Primer 2 were prepared by adding SalI, XbaI restriction enzyme recognition sequences based on the information of the base sequence of human ACC2 gene (Genbank Accession U89344).

Primer 1:
(SEQ ID NO: 1)
5'-AAAAGTCGACCCACCATGGTCTTGCTTCTTTGTCTATCTTG-3'

Primer 2:
(SEQ ID NO: 2)
5'-TTTTTCTAGATCAGGTAGAGGCCGGGCTGTCCATG-3'

PCR was performed using Pyrobest DNA polymerase (TAKARA BIO INC.). The obtained PCR product was cloned to pT7 Blue vector (Novagen) and after confirmation of the base sequence, digested with restriction enzymes SalI and XbaI. The obtained DNA fragment was inserted into pFAST-BacHTa (Invitrogen) digested with restriction enzymes SalI and XbaI to give expression plasmid ACC2/pFAST-BacHTa.

A plasmid for expression of ACC2 without a mitochondrial targeting sequence was prepared by PCR using the expression plasmid as a template, and Primer 3 (salI restriction enzyme recognition sequence was added) and Primer 4, which are prepared by reference to the information of human ACC2 gene base sequence (Genbank Accession U89344).

Primer 3:
(SEQ ID NO: 3)
5'-CCAGGTCGACCCGCCAACGGGACTGGGACACAAGG-3'

Primer 4:
(SEQ ID NO: 4)
5r-CGCACTCTCAGTTTCCCGGATTCCC-3'

PCR was performed using Pyrobest-DNA polymerase (TAKARA BIO INC.). The obtained PCR product was cloned to pT7 Blue vector (Novagen) and after confirmation of the base sequence, digested with restriction enzymes SalI and AflII. The obtained DNA fragment was inserted into ACC2/pFAST-BacHTa digested with restriction enzymes SalI and AfiII to give expression plasmid ACC2mito7/pFAST-BacHTa.

Using the expression plasmid ACC2mito7/pFAST-BacHTa and BAC-TO-BAC Baculovirus Expression System (Invitrogen), virus stock BAC-ACC2 of recombinant Baculovirus (N terminal deleted (hereinafter Nd)) was prepared.

(2) Preparation of ACC2 (Nd) Protein

SF-9 cells (Invitrogen) were inoculated to a medium (2 L) for insect cells (Sf-900IISFM medium (Invitrogen) containing 10% fetal bovine serum (Trace), 50 mg/L Gentamicin (Invitrogen), 0.1% Pluronic F-68 (Invitrogen)) at $0.5 \times 10^6$ cells/mL, and cultured with shaking in Wave Bioreactor (Wave) at 27° C., 20 rpm, rocking angle 6°, oxygen concentration 30%.

On day 4 of the culture, 3 L of the medium for insect cells was added, the rocking angle was set to 8°, and the cells were further cultured. On day 5 of the culture, 100 mL of recombinant Baculovirus BAC-ACC2 (Nd) was added, 5 L of the medium for insect cells was further added, the rocking angle was set to 11°, and the cells were cultured for 3 days. The culture medium was centrifuged at 1000×g for 10 min to give virus-infected cells. The cells were washed with phosphate buffered saline (Invitrogen) and centrifuged under the same conditions. The obtained cells were cryopreserved at −80° C.

The cryopreserved cells were thawed in ice and suspended in 900 mL of 25 mM HEPES buffer (pH 7.5) containing 10% Glycerol, 0.13 M NaCl, 1 mM EDTA, 25 mM Sodium β-Glycerophosphate and 1 mM Sodium Orthovanadate, and supplemented with Complete Protease Inhibitor (Nippon Boehringer Ingelheim Co., Ltd.). The obtained suspension was homogenized three times in a polytron homogenizer (Kinematica) at 20,000 rpm for 30 sec. The obtained cell disruption solution was clarified by centrifugation at 31000×g for 60 min, and filtered through a 0.45 μm filter. The filtrate was passed through a column packed with 60 mL of Ni-NTA Super Flow Gel (QUIAGEN) at a flow rate of about 5 mL/min. The column was washed with buffer A (50 mM HEPES (pH 7.5) containing 0.3 M NaCl), further washed with buffer A containing 20 mM Imidazole, and eluted with buffer A containing 100 mM Imidazole. The eluate was concentrated with Vivaspin 20 (Vivascience) with a molecular weight cut off of 30K. The obtained concentrate was dialyzed against 50 mM HEPES (pH 7.5) containing 10 mM $MgCl_2$, 2 mM Dithiothreitol, 10 mM Tripotassium Citrate and 0.3 M NaCl. The inner dialysate was filtered through a 0.22 μm filter to give ACC2 (Nd). The obtained ACC2 (Nd) was cryopreserved at −80° C.

(3) Measurement of ACC2 Inhibitory Activity

ACC2 (Nd) (1.1 mg/ml) obtained in the above-mentioned (2) was diluted with an enzyme reaction buffer (50 mM HEPES (pH 7.5), 10 mM $MgCl_2$, 10 mM Tripotassium Citrate, 2 mM Dithiothreitol, 0.75 mg/ml Fatty acid free BSA) to a concentration of 6.4 μg/ml, and the mixture was added to each well of a 384 well assay plate (Nunc 265196) by 10 μl. A test compound dissolved in dimethyl sulfoxide (DMSO) was diluted with an enzyme reaction buffer and the resulting solution (5 μl) was added to each well. The mixture was incubated at 30° C. for 20 min. Then, a substrate solution (50 mM $KHCO_3$, 200 μM ATP, 200 μM Acetyl-CoA, 5 μl) was added to each well, and the mixture was reacted at 30° C. for 20 min (test compound addition group).

In addition, a reaction was performed in the same manner as above and without adding the test compound (test compound non-addition group).

Furthermore, a reaction was performed in the same manner as above and without adding the test compound and Acetyl-CoA (control group).

The reaction was quenched by adding a malachite green solution to each of the obtained reaction mixtures by 5 μl and stirring the mixtures. The obtained reaction mixture was left standing at room temperature for 20 min, and absorbance (620 nm) was measured using wallac1420 (PerkinElmer Japan Co., Ltd.). The above-mentioned malachite green solution was prepared by mixing Solution A (0.12% malachite green solution, prepared with $5NH_2SO_4$, preserved at 4° C. in shading), Solution B (7.5% aqueous ammonium molybdate solution, prepared when in use) and Solution C (11% aqueous Tween 20 solution, preserved at room temperature) at a ratio of Solution A:Solution B:Solution C=100:25:2 (volume ratio).

ACC2 inhibitory rate (%) was determined according to the following calculation formula.

(1−(absorbance of test compound addition group−
absorbance of control group)÷(absorbance of test
compound non-addition group−absorbance of
control group))×100

The inhibitory rates (%) against ACC2 at 10 μl of the test compound are shown in Table 2-1 and Table 2-2.

TABLE 2-1

| Example No. | ACC2 inhibitory rate at 10 μM (%) |
|---|---|
| 1 | 101 |
| 2 | 92 |
| 3 | 99 |
| 6 | 95 |
| 9 | 98 |
| 12 | 103 |
| 13 | 94 |
| 15 | 92 |
| 16 | 93 |
| 17 | 90 |
| 24 | 90 |
| 25 | 90 |
| 26 | 95 |
| 28 | 83 |
| 30 | 100 |
| 33 | 85 |

TABLE 2-2

| Example No. | ACC2 inhibitory rate at 10 μM (%) |
|---|---|
| 63 | 93 |
| 70 | 93 |
| 73 | 99 |
| 85 | 93 |
| 89 | 94 |
| 92 | 93 |
| 95 | 94 |
| 97 | 95 |
| 100 | 90 |
| 102 | 99 |
| 104 | 102 |
| 109 | 95 |
| 110 | 91 |
| 111 | 100 |
| 112 | 100 |
| 119 | 97 |

Experimental Example 2

Male F344/Jcl rats (CLEA Japan, Inc., Tokyo) purchased at 5 weeks of age were acclimated to the rearing environment, and used for an experiment of malonyl CoA content measurement at 10 weeks of age. In the experiment of malonyl CoA content measurement, the body weight was measured in the morning (8:00-11:00) 3 days before administration of a test compound, and the rats were divided into groups free of dispersion in the body weight between administration groups. The test compound was prepared as a 0.5% methyl cellulose (Wako) suspension to a dose of 5 mL/kg, in the afternoon (12:00-17:00) of one day before administration by gavage, and administered by gavage according to the body weight on the day of test compound administration. The vehicle group was administered with a solvent (0.5% methyl cellulose) alone by gavage. The femoral muscle was rapidly removed 2 hr after the test compound administration, sliced into thin pieces (80-150 mg), placed in an eppendorf tube, rapidly frozen in liquid nitrogen, and preserved at −80° C. until use for the measurement of malonyl CoA content.

A sample homogenate for the malonyl CoA measurement was prepared by disrupting a frozen tissue with a measured weight in a Multi-beads shocker (MB400U, Yasui Kikai Corporation), adding an extract (6% perchloric acid:aqueous di-n-butylammonium acetate solution (IPC-DBAA, 0.5 mol/L, TOKYO CHEMICAL INDUSTRY CO., LTD.)=1000:1, 500 μL) containing an internal standard substance ($[^{13}C_3]$-malonyl CoA lithium salt (100 pmol/mL, Sigma-Aldrich)), and applying the mixture to the Multi-beads shocker again. The entire amount of the extract was centrifuged (13,000 rpm, 2 min), and the supernatant was added to a solid phase extraction cartridge (OASIS HLB 1 cc/30 mg, WAT05882, Waters) to perform a solid phase extraction. The solid phase extraction cartridge used had previously undergone activation with solution A (500 μL, 50% acetonitrile), and further, two times of equilibration with solution B (1 mL, 6% perchloric acid:IPC-DBAA=1000:1). The sample was added to the solid phase cartridge, washed twice with ultrapure water (1 mL), and eluted with solution A (500 μL). This eluate was directly used for the LC/MS/MS analysis. The sample for analytical curve was added with malonyl CoA lithium salt with a known concentration (Sigma-Aldrich), while regarding 100 μL of 4% aqueous BSA (w/v) solution as 100 mg of a tissue, added with an internal standard substance, like the tissue sample, and subjected to a solid phase extraction.

The HPLC for LC/MS/MS analysis was performed by using Prominence (SHIMADZU Corporation), and CAPCELL PAK C18 AQ (particle size; 3 μm, inner diameter; 2.0 mm, length; 35 mm, Shiseido Co., Ltd.) as a separation column, and gradient mode of mobile phase (A) 10 mmol/L ammonium acetate/IPC-DBAA (100:1, v/v, pH 9.0), and mobile phase (B) acetonitrile. The gradient program included linear increase of mobile phase (B) concentration from 5% at 0 min (start of analysis) to 35% in 2 min, and thereafter to 100% until 2.1 min, liquid supply at 100% until 6 min, decrease to 5% by 6.1 min, and liquid supply under the same conditions until the end of analysis (10 min). Using a switching valve, the eluate of analysis time 2.0-6.0 min was introduced into MS/MS. The analysis was performed at a column temperature of 40° C. and a sample injection volume of 10 μL. The mass spectrometer used was API5000 (AB Sciex) and, using turboion spray as an ionization mode, ion was detected by selected reaction monitoring (SRM) in an anion mode. As the ion spray, zero air was used, and the ionization was performed at 4.5 kV. Nitrogen was used for collision-induced decomposition of ion. As a monitor ion, a precursor ion and a fragment ion were set to malonyl CoA; m/z 852.0→m/z 808.0 and $[^{13}C_3]$-malonyl CoA; m/z 855.0→m/z 810.0 Da, respectively. For quantitative calculation, a peak area ratio of internal standard ($[^{13}C_3]$-malonyl CoA) and malonyl CoA was used, and a malonyl CoA concentration of each sample was calculated from the regression formula of standard analytical curve at each concentration (1/concentration weighted). All values are shown in mean±standard deviation, and Steel test was used for statistical analysis. The results are shown in Table 3.

TABLE 3

Malonyl-CoA content of femoral muscle at 2 hours after dosing

| Compounds | dose | malonyl-CoA (nmol/g-tissue) | No. of animals |
|---|---|---|---|
| vehicle | 0 | 1.955 ± 0.496 | 6 |
| Example 6 | 10 mg/kg | 0.513 ± 0.048 * | 4 |
| Example 28 | 10 mg/kg | 0.663 ± 0.119 * | 4 |

Mean ± S.D., N = 4–6,
* P ≤ 0.05 (Steel test)

| Formulation Example 1 (production of capsule) | |
|---|---|
| 1) compound of Example 1 | 30 mg |
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

| Formulation Example 2 (production of tablets) | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention has ACC (acetyl-CoA carboxylase) inhibitory action, and is useful for the prophylaxis or treatment of obesity, diabetes, hypertension, hyperlipidemia, cardiac failure, diabetic complications, metabolic syndrome, sarcopenia, cancer and the like.

This application is based on patent application Nos. 266097/2010 and 175330/2011 filed in Japan, the contents of which are hereby incorporated by reference.

The invention claimed is:

1. A compound represented by the formula (I):

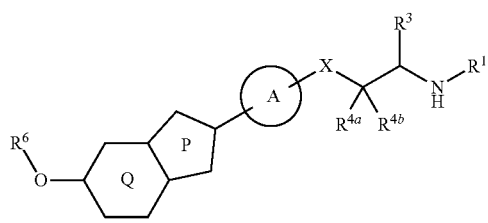

wherein
$R^1$ is a group represented by the formula: —$COR^2$ wherein $R^2$ is methyl;
$R^3$ is methyl;
$R^{4a}$ and $R^{4b}$ are each a hydrogen atom;
X is O;
ring A is pyridin-3-yl optionally substituted by 1 to 3 halogen atoms;
ring P and ring Q are fused to form

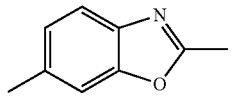

; and
$R^6$ is cyclopropylmethyl or ethyl,
or a salt thereof.

2. N-[(1S)-2-({6-[6-(cyclopropylmethoxy)-1,3-benzoxazol-2-yl]pyridin-3-yl}oxy)-1-methylethyl]acetamide or a salt thereof.

3. N-[(1S)-2-({6-[6-(cyclopropylmethoxy)-1,3-benzoxazol-2-yl]-5-fluoropyridin-3-yl}oxy)-1-methylethyl]acetamide or a salt thereof.

4. N-[(1S)-2-{[6-(6-ethoxy-1,3-benzoxazol-2-yl)pyridin-3-yl]oxy}-1-methylethyl]acetamide or a salt thereof.

5. A pharmaceutical composition comprising the compound or salt of claim 1 and a pharmacologically acceptable carrier.

* * * * *

UNITED STATES PATENT AND TRADEMARK OFFICE
CERTIFICATE OF CORRECTION

PATENT NO. : 8,729,102 B2  
APPLICATION NO. : 13/306069  
DATED : May 20, 2014  
INVENTOR(S) : Tsuneo Yasuma et al.

Page 1 of 1

It is certified that error appears in the above-identified patent and that said Letters Patent is hereby corrected as shown below:

Title Page, correct Item (75) Inventors, to read:

-- (75)  Inventors:  Tsuneo Yasuma, Osaka (JP); Tohru Yamashita, Kanagawa (JP); Takuya Fujimoto, Kanagawa (JP); Zenichi Ikeda, Kanagawa (JP); Ryo Mizojiri, Kanagawa (JP) --.

Signed and Sealed this
Thirteenth Day of January, 2015

Michelle K. Lee
*Deputy Director of the United States Patent and Trademark Office*

SEQUENCE LISTING

```
<160> NUMBER OF SEQ ID NOS: 4

<210> SEQ ID NO 1
<211> LENGTH: 41
<212> TYPE: DNA
<213> ORGANISM: Artificial
<220> FEATURE:
<223> OTHER INFORMATION: PCR primer for hACC2 gene cloning

<400> SEQUENCE: 1
aaaagtcgac ccaccatggt cttgcttctt tgtctatctt g                41
```

```
<210> SEQ ID NO 2
<211> LENGTH: 35
<212> TYPE: DNA
<213> ORGANISM: Artificial
<220> FEATURE:
<223> OTHER INFORMATION: PCR primer for hACC2 gene cloning

<400> SEQUENCE: 2
tttttctaga tcaggtagag gccgggctgt ccatg                              35

<210> SEQ ID NO 3
<211> LENGTH: 35
<212> TYPE: DNA
<213> ORGANISM: Artificial
<220> FEATURE:
<223> OTHER INFORMATION: PCR primer for construction of ACC2-expressing
      plasmid

<400> SEQUENCE: 3
ccaggtcgac ccgccaacgg gactgggaca caagg                              35

<210> SEQ ID NO 4
<211> LENGTH: 25
<212> TYPE: DNA
<213> ORGANISM: Artificial
<220> FEATURE:
<223> OTHER INFORMATION: PCR primer for construction of ACC2-expressing
      plasmid

<400> SEQUENCE: 4
cgcactctca gtttcccgga ttccc                                         25
```